United States Patent
Gray et al.

(10) Patent No.: US 10,342,798 B2
(45) Date of Patent: Jul. 9, 2019

(54) FUSED BICYCLIC PYRIMIDINE DERIVATIVES AND USES THEREOF

(71) Applicant: Dana-Farber Cancer Institute, Inc., Boston, MA (US)

(72) Inventors: Nathanael S. Gray, Boston, MA (US); Tinghu Zhang, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/737,683

(22) PCT Filed: Jun. 24, 2016

(86) PCT No.: PCT/US2016/039302
§ 371 (c)(1),
(2) Date: Dec. 18, 2017

(87) PCT Pub. No.: WO2016/210291
PCT Pub. Date: Dec. 29, 2016

(65) Prior Publication Data
US 2018/0153894 A1 Jun. 7, 2018
US 2018/0369243 A9 Dec. 27, 2018

Related U.S. Application Data

(60) Provisional application No. 62/185,366, filed on Jun. 26, 2015.

(51) Int. Cl.
| | |
|---|---|
| C07D 491/048 | (2006.01) |
| A61K 31/519 | (2006.01) |
| A61K 45/06 | (2006.01) |
| A61K 31/437 | (2006.01) |
| C07D 495/04 | (2006.01) |
| C07D 519/00 | (2006.01) |
| A61K 31/166 | (2006.01) |
| A61K 31/167 | (2006.01) |
| A61K 31/34 | (2006.01) |
| A61K 31/381 | (2006.01) |
| A61P 35/02 | (2006.01) |

(52) U.S. Cl.
CPC .......... *A61K 31/519* (2013.01); *A61K 31/166* (2013.01); *A61K 31/167* (2013.01); *A61K 31/34* (2013.01); *A61K 31/381* (2013.01); *A61K 31/437* (2013.01); *A61K 45/06* (2013.01); *A61P 35/02* (2018.01); *C07D 491/048* (2013.01); *C07D 495/04* (2013.01); *C07D 519/00* (2013.01)

(58) Field of Classification Search
None
See application file for complete search history.

(56) References Cited

U.S. PATENT DOCUMENTS

| 10,047,070 B2 * | 8/2018 | Gray ................ C07D 401/04 |
| 2013/0040949 A1 | 2/2013 | Gray et al. |

(Continued)

FOREIGN PATENT DOCUMENTS

| CN | 103242341 A | 8/2013 |
| CN | 104177363 A | 12/2014 |
| WO | WO 2014/063068 A1 | 4/2014 |

(Continued)

OTHER PUBLICATIONS

International Search Report and Written Opinion for PCT/US2016/39312, dated Sep. 27, 2016.

(Continued)

*Primary Examiner* — Heidi Reese
(74) *Attorney, Agent, or Firm* — Wolf, Greenfield & Sacks, P.C.

(57) ABSTRACT

The present invention provides novel compounds of Formula (I), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating or preventing proliferative diseases (e.g., cancers (e.g., lung cancer, breast cancer, leukemia, lymphoma, melanoma, multiple myeloma, Ewing's sarcoma, osteosarcoma, brain cancer, neuroblastoma), benign neoplasms, angiogenesis, inflammatory diseases, autoinflammatory diseases, and autoimmune diseases) in a subject. Treatment of a subject with a proliferative disease using a compound or composition of the invention may inhibit the aberrant activity of a kinase (e.g. a protein kinase (e.g. a cyclin-dependent kinase (CDK) (e.g. CDK7, CDK12, or CDK13) or a lipid kinase such as a phosphatidylinositol-5-phosphate 4-kinase (PIP4K) (e.g., PI5P4Kα, PI5P4Kβ, or PI5P4Kγ)) in the subject.

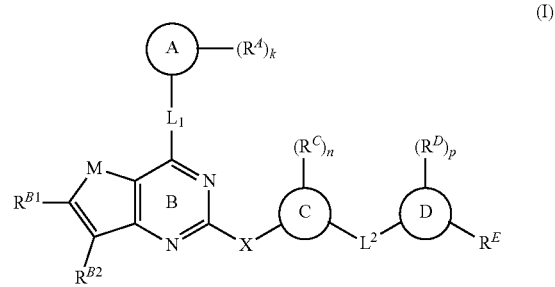

42 Claims, 3 Drawing Sheets
Specification includes a Sequence Listing.

(56) References Cited

U.S. PATENT DOCUMENTS

2015/0166532 A1 6/2015 Gray et al.
2017/0044111 A1 2/2017 Gray et al.

FOREIGN PATENT DOCUMENTS

WO WO 2015/058126 A1 4/2015
WO WO 2015/058140 A1 4/2015

OTHER PUBLICATIONS

International Preliminary Report on Patentability for PCT/US2016/39312, dated Jan. 4, 2018.
International Search Report and Written Opinion for PCT/US2016/39302, dated Sep. 27, 2016.
International Preliminary Report on Patentability for PCT/US2016/39302, dated Jan. 4, 2018.
[No Author Listed] GenBank: M80629.1. Human cdc2-related protein kinase (CHED) mRNA, complete cds.
[No Author Listed] NCBI Reference Sequence: NP_001790.1. cyclin-dependent kinase 7 isoform 1 [*Homo sapiens*].
[No Author Listed] Uniprot No. Q9NYV4. Cyclin-dependent kinase 12. Gene CDK12. *Homo sapiens* (Human).
Camilli et al., Phosphoinositides as regulators in membrane traffic. Science. Mar. 15, 1996;271(5255):1533-9.
Emerling et al., Depletion of a putatively druggable class of phosphatidylinositol kinases inhibits growth of p53-null tumors. Cell. Nov. 7, 2013;155(4):844-57. doi: 10.1016/j.cell.2013.09.057.
Fruman et al., Phosphoinositide Kinases. Annual Review of Biochemistry 1998;67(1):481-507.
Liu et al., Targeting the phosphoinositide 3-kinase pathway in cancer. Nat Rev Drug Discov. Aug. 2009;8(8):627-44. doi: 10.1038/nrd2926.
Martin, Phosphoinositide lipids as signaling molecules: common themes for signal transduction, cytoskeletal regulation, and membrane trafficking. Annu Rev Cell Dev Biol. 1998;14:231-64.
Rameh et al., A new pathway for synthesis of phosphatidylinositol-4,5-bisphosphate. Nature. Nov. 13, 1997;390(6656):192-6.
Schramp et al., Phosphoinositides I: Enzymes of Synthesis and Degradation, 2012, Chapter 2, PIP Kinases from the Cell Membrane to the Nucleus, p. 25.
Extended European Search Report for EP 16815397.1, dated Nov. 22, 2018.

* cited by examiner

```
                             SEQUENCE LISTING

<160> NUMBER OF SEQ ID NOS: 9

<210> SEQ ID NO 1
<211> LENGTH: 346
<212> TYPE: PRT
<213> ORGANISM: Homo sapiens

<400> SEQUENCE: 1

Met Ala Leu Asp Val Lys Ser Arg Ala Lys Arg Tyr Glu Lys Leu Asp
1               5                   10                  15

Phe Leu Gly Glu Gly Gln Phe Ala Thr Val Tyr Lys Ala Arg Asp Lys
                20                  25                  30

Asn Thr Asn Gln Ile Val Ala Ile Lys Lys Ile Lys Leu Gly His Arg
            35                  40                  45

Ser Glu Ala Lys Asp Gly Ile Asn Arg Thr Ala Leu Arg Glu Ile Lys
        50                  55                  60

Leu Leu Gln Glu Leu Ser His Pro Asn Ile Ile Gly Leu Leu Asp Ala
65                  70                  75                  80

Phe Gly His Lys Ser Asn Ile Ser Leu Val Phe Asp Phe Met Glu Thr
                85                  90                  95

Asp Leu Glu Val Ile Ile Lys Asp Asn Ser Leu Val Leu Thr Pro Ser
                100                 105                 110

His Ile Lys Ala Tyr Met Leu Met Thr Leu Gln Gly Leu Glu Tyr Leu
            115                 120                 125

His Gln His Trp Ile Leu His Arg Asp Leu Lys Pro Asn Asn Leu Leu
        130                 135                 140

Leu Asp Glu Asn Gly Val Leu Lys Leu Ala Asp Phe Gly Leu Ala Lys
145                 150                 155                 160

Ser Phe Gly Ser Pro Asn Arg Ala Tyr Thr His Gln Val Val Thr Arg
                165                 170                 175

Trp Tyr Arg Ala Pro Glu Leu Leu Phe Gly Ala Arg Met Tyr Gly Val
            180                 185                 190

Gly Val Asp Met Trp Ala Val Gly Cys Ile Leu Ala Glu Leu Leu Leu
        195                 200                 205

Arg Val Pro Phe Leu Pro Gly Asp Ser Asp Leu Asp Gln Leu Thr Arg
    210                 215                 220

Ile Phe Glu Thr Leu Gly Thr Pro Thr Glu Glu Gln Trp Pro Asp Met
```

```
               225                 230                 235                 240

Cys Ser Leu Pro Asp Tyr Val Thr Phe Lys Ser Phe Pro Gly Ile Pro
                        245                 250                 255

Leu His His Ile Phe Ser Ala Ala Gly Asp Asp Leu Leu Asp Leu Ile
                        260                 265                 270

Gln Gly Leu Phe Leu Phe Asn Pro Cys Ala Arg Ile Thr Ala Thr Gln
                        275                 280                 285

Ala Leu Lys Met Lys Tyr Phe Ser Asn Arg Pro Gly Pro Thr Pro Gly
                        290                 295                 300

Cys Gln Leu Pro Arg Pro Asn Cys Pro Val Glu Thr Leu Lys Glu Gln
        305                 310                 315                 320

Ser Asn Pro Ala Leu Ala Ile Lys Arg Lys Arg Thr Glu Ala Leu Glu
                        325                 330                 335

Gln Gly Gly Leu Pro Lys Lys Leu Ile Phe
                        340                 345

<210> SEQ ID NO 2
<211> LENGTH: 1490
<212> TYPE: PRT
<213> ORGANISM: Homo sapiens

<400> SEQUENCE: 2

Met Pro Asn Ser Glu Arg His Gly Gly Lys Lys Asp Gly Ser Gly Gly
1               5                   10                  15

Ala Ser Gly Thr Leu Gln Pro Ser Gly Gly Gly Ser Ser Asn Ser
                20                  25                  30

Arg Glu Arg His Arg Leu Val Ser Lys His Lys Arg His Lys Ser Lys
                35                  40                  45

His Ser Lys Asp Met Gly Leu Val Thr Pro Glu Ala Ala Ser Leu Gly
                50                  55                  60

Thr Val Ile Lys Pro Leu Val Glu Tyr Asp Asp Ile Ser Ser Asp Ser
65              70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
                100                 105                 110

His His Gln His Arg Arg Ser Arg Asp Leu Leu Lys Ala Lys Gln Thr
                115                 120                 125

Glu Lys Glu Lys Ser Gln Glu Val Ser Ser Lys Ser Gly Ser Met Lys
                130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
                180                 185                 190

Gly His Lys Asp Arg Ser Lys Ser His Arg Lys Arg Glu Thr Pro Lys
                195                 200                 205

Ser Tyr Lys Thr Val Asp Ser Pro Lys Arg Arg Ser Arg Ser Pro His
                210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255
```

-continued

```
Ser Asn Tyr Asp Ser Tyr Lys Lys Ser Pro Gly Ser Thr Ser Arg Arg
                260                 265                 270

Gln Ser Val Ser Pro Pro Tyr Lys Glu Pro Ser Ala Tyr Gln Ser Ser
            275                 280                 285

Thr Arg Ser Pro Ser Pro Tyr Ser Arg Arg Gln Arg Ser Val Ser Pro
        290                 295                 300

Tyr Ser Arg Arg Arg Ser Ser Tyr Glu Arg Ser Gly Ser Tyr Ser
305                 310                 315                 320

Gly Arg Ser Pro Ser Pro Tyr Gly Arg Arg Ser Ser Ser Pro Phe
                325                 330                 335

Leu Ser Lys Arg Ser Leu Ser Arg Ser Pro Leu Pro Ser Arg Lys Ser
            340                 345                 350

Met Lys Ser Arg Ser Arg Ser Pro Ala Tyr Ser Arg His Ser Ser Ser
        355                 360                 365

His Ser Lys Lys Lys Arg Ser Ser Ser Arg Ser Arg His Ser Ser Ile
    370                 375                 380

Ser Pro Val Arg Leu Pro Leu Asn Ser Ser Leu Gly Ala Glu Leu Ser
385                 390                 395                 400

Arg Lys Lys Lys Glu Arg Ala Ala Ala Ala Ala Ala Lys Met Asp
                405                 410                 415

Gly Lys Glu Ser Lys Gly Ser Pro Val Phe Leu Pro Arg Lys Glu Asn
            420                 425                 430

Ser Ser Val Glu Ala Lys Asp Ser Gly Leu Glu Ser Lys Lys Leu Pro
        435                 440                 445

Arg Ser Val Lys Leu Glu Lys Ser Ala Pro Asp Thr Glu Leu Val Asn
    450                 455                 460

Val Thr His Leu Asn Thr Glu Val Lys Asn Ser Ser Asp Thr Gly Lys
465                 470                 475                 480

Val Lys Leu Asp Glu Asn Ser Glu Lys His Leu Val Lys Asp Leu Lys
                485                 490                 495

Ala Gln Gly Thr Arg Asp Ser Lys Pro Ile Ala Leu Lys Glu Glu Ile
            500                 505                 510

Val Thr Pro Lys Glu Thr Glu Thr Ser Glu Lys Glu Thr Pro Pro Pro
        515                 520                 525

Leu Pro Thr Ile Ala Ser Pro Pro Pro Leu Pro Thr Thr Thr Pro
    530                 535                 540

Pro Pro Gln Thr Pro Pro Leu Pro Pro Leu Pro Ile Pro Ala Leu
545                 550                 555                 560

Pro Gln Gln Pro Pro Leu Pro Pro Ser Gln Pro Ala Phe Ser Gln Val
                565                 570                 575

Pro Ala Ser Ser Thr Ser Thr Leu Pro Pro Ser Thr His Ser Lys Thr
            580                 585                 590

Ser Ala Val Ser Ser Gln Ala Asn Ser Gln Pro Pro Val Gln Val Ser
        595                 600                 605

Val Lys Thr Gln Val Ser Val Thr Ala Ala Ile Pro His Leu Lys Thr
    610                 615                 620

Ser Thr Leu Pro Pro Leu Pro Leu Pro Leu Leu Pro Gly Asp Asp
625                 630                 635                 640

Asp Met Asp Ser Pro Lys Glu Thr Leu Pro Ser Lys Pro Val Lys Lys
                645                 650                 655

Glu Lys Glu Gln Arg Thr Arg His Leu Leu Thr Asp Leu Pro Leu Pro
            660                 665                 670

Pro Glu Leu Pro Gly Gly Asp Leu Ser Pro Pro Asp Ser Pro Glu Pro
```

```
            675                 680                 685
Lys Ala Ile Thr Pro Gln Gln Pro Tyr Lys Lys Arg Pro Lys Ile
    690                 695                 700
Cys Cys Pro Arg Tyr Gly Glu Arg Arg Gln Thr Glu Ser Asp Trp Gly
705                 710                 715                 720
Lys Arg Cys Val Asp Lys Phe Asp Ile Ile Gly Ile Gly Glu Gly
                725                 730                 735
Thr Tyr Gly Gln Val Tyr Lys Ala Lys Asp Lys Asp Thr Gly Glu Leu
            740                 745                 750
Val Ala Leu Lys Lys Val Arg Leu Asp Asn Glu Lys Glu Gly Phe Pro
        755                 760                 765
Ile Thr Ala Ile Arg Glu Ile Lys Ile Leu Arg Gln Leu Ile His Arg
        770                 775                 780
Ser Val Val Asn Met Lys Glu Ile Val Thr Asp Lys Gln Asp Ala Leu
785                 790                 795                 800
Asp Phe Lys Lys Asp Lys Gly Ala Phe Tyr Leu Val Phe Glu Tyr Met
                805                 810                 815
Asp His Asp Leu Met Gly Leu Leu Glu Ser Gly Leu Val His Phe Ser
            820                 825                 830
Glu Asp His Ile Lys Ser Phe Met Lys Gln Leu Met Glu Gly Leu Glu
            835                 840                 845
Tyr Cys His Lys Lys Asn Phe Leu His Arg Asp Ile Lys Cys Ser Asn
        850                 855                 860
Ile Leu Leu Asn Asn Ser Gly Gln Ile Lys Leu Ala Asp Phe Gly Leu
865                 870                 875                 880
Ala Arg Leu Tyr Asn Ser Glu Glu Ser Arg Pro Tyr Thr Asn Lys Val
                885                 890                 895
Ile Thr Leu Trp Tyr Arg Pro Pro Glu Leu Leu Leu Gly Glu Glu Arg
            900                 905                 910
Tyr Thr Pro Ala Ile Asp Val Trp Ser Cys Gly Cys Ile Leu Gly Glu
            915                 920                 925
Leu Phe Thr Lys Lys Pro Ile Phe Gln Ala Asn Leu Glu Leu Ala Gln
        930                 935                 940
Leu Glu Leu Ile Ser Arg Leu Cys Gly Ser Pro Cys Pro Ala Val Trp
945                 950                 955                 960
Pro Asp Val Ile Lys Leu Pro Tyr Phe Asn Thr Met Lys Pro Lys Lys
                965                 970                 975
Gln Tyr Arg Arg Arg Leu Arg Glu Glu Phe Ser Phe Ile Pro Ser Ala
            980                 985                 990
Ala Leu Asp Leu Leu Asp His Met Leu Thr Leu Asp Pro Ser Lys Arg
        995                 1000                1005
Cys Thr Ala Glu Gln Thr Leu Gln Ser Asp Phe Leu Lys Asp Val
        1010                1015                1020
Glu Leu Ser Lys Met Ala Pro Pro Asp Leu Pro His Trp Gln Asp
        1025                1030                1035
Cys His Glu Leu Trp Ser Lys Lys Arg Arg Arg Gln Arg Gln Ser
        1040                1045                1050
Gly Val Val Val Glu Glu Pro Pro Ser Lys Thr Ser Arg Lys
        1055                1060                1065
Glu Thr Thr Ser Gly Thr Ser Thr Glu Pro Val Lys Asn Ser Ser
        1070                1075                1080
Pro Ala Pro Pro Gln Pro Ala Pro Gly Lys Val Glu Ser Gly Ala
        1085                1090                1095
```

-continued

```
Gly Asp Ala Ile Gly Leu Ala Asp Ile Thr Gln Gln Leu Asn Gln
    1100            1105                1110
Ser Glu Leu Ala Val Leu Leu Asn Leu Leu Gln Ser Gln Thr Asp
    1115            1120                1125
Leu Ser Ile Pro Gln Met Ala Gln Leu Leu Asn Ile His Ser Asn
    1130            1135                1140
Pro Glu Met Gln Gln Leu Glu Ala Leu Asn Gln Ser Ile Ser
    1145            1150                1155
Ala Leu Thr Glu Ala Thr Ser Gln Gln Gln Asp Ser Glu Thr Met
    1160            1165                1170
Ala Pro Glu Glu Ser Leu Lys Glu Ala Pro Ser Ala Pro Val Ile
    1175            1180                1185
Leu Pro Ser Ala Glu Gln Thr Thr Leu Glu Ala Ser Ser Thr Pro
    1190            1195                1200
Ala Asp Met Gln Asn Ile Leu Ala Val Leu Leu Ser Gln Leu Met
    1205            1210                1215
Lys Thr Gln Glu Pro Ala Gly Ser Leu Glu Glu Asn Asn Ser Asp
    1220            1225                1230
Lys Asn Ser Gly Pro Gln Gly Pro Arg Arg Thr Pro Thr Met Pro
    1235            1240                1245
Gln Glu Glu Ala Ala Ala Cys Pro Pro His Ile Leu Pro Pro Glu
    1250            1255                1260
Lys Arg Pro Pro Glu Pro Pro Gly Pro Pro Pro Pro Pro Pro Pro
    1265            1270                1275
Pro Pro Leu Val Glu Gly Asp Leu Ser Ser Ala Pro Gln Glu Leu
    1280            1285                1290
Asn Pro Ala Val Thr Ala Ala Leu Leu Gln Leu Leu Ser Gln Pro
    1295            1300                1305
Glu Ala Glu Pro Pro Gly His Leu Pro His Glu His Gln Ala Leu
    1310            1315                1320
Arg Pro Met Glu Tyr Ser Thr Arg Pro Arg Pro Asn Arg Thr Tyr
    1325            1330                1335
Gly Asn Thr Asp Gly Pro Glu Thr Gly Phe Ser Ala Ile Asp Thr
    1340            1345                1350
Asp Glu Arg Asn Ser Gly Pro Ala Leu Thr Glu Ser Leu Val Gln
    1355            1360                1365
Thr Leu Val Lys Asn Arg Thr Phe Ser Gly Ser Leu Ser His Leu
    1370            1375                1380
Gly Glu Ser Ser Ser Tyr Gln Gly Thr Gly Ser Val Gln Phe Pro
    1385            1390                1395
Gly Asp Gln Asp Leu Arg Phe Ala Arg Val Pro Leu Ala Leu His
    1400            1405                1410
Pro Val Val Gly Gln Pro Phe Leu Lys Ala Glu Gly Ser Ser Asn
    1415            1420                1425
Ser Val Val His Ala Glu Thr Lys Leu Gln Asn Tyr Gly Glu Leu
    1430            1435                1440
Gly Pro Gly Thr Thr Gly Ala Ser Ser Ser Gly Ala Gly Leu His
    1445            1450                1455
Trp Gly Gly Pro Thr Gln Ser Ser Ala Tyr Gly Lys Leu Tyr Arg
    1460            1465                1470
Gly Pro Thr Arg Val Pro Pro Arg Gly Gly Arg Gly Arg Gly Val
    1475            1480                1485
```

-continued

Pro Tyr
    1490

<210> SEQ ID NO 3
<211> LENGTH: 1512
<212> TYPE: PRT
<213> ORGANISM: Homo sapiens

<400> SEQUENCE: 3

```
Met Pro Ser Ser Ser Asp Thr Ala Leu Gly Gly Gly Gly Leu Ser
1               5                   10                  15

Trp Ala Glu Lys Lys Leu Glu Glu Arg Arg Lys Arg Arg Phe Leu
                20                  25                  30

Ser Pro Gln Gln Pro Leu Leu Leu Pro Leu Leu Gln Pro Gln Leu
            35                  40                  45

Leu Gln Pro Pro Pro Pro Pro Pro Leu Leu Phe Leu Ala Ala Pro
        50                  55                  60

Gly Thr Ala Ala Ala Ala Ala Ala Ala Ala Ser Ser Ser Cys
65                  70                  75                  80

Phe Ser Pro Gly Pro Pro Leu Glu Val Lys Arg Leu Ala Arg Gly Lys
                85                  90                  95

Arg Arg Ala Gly Gly Arg Gln Lys Arg Arg Gly Pro Arg Ala Gly
                100                 105                 110

Gln Glu Ala Glu Lys Arg Val Phe Ser Leu Pro Gln Pro Gln Gln
            115                 120                 125

Asp Gly Gly Gly Ala Ser Ser Gly Gly Val Thr Pro Leu Val
        130                 135                 140

Glu Tyr Glu Asp Val Ser Ser Gln Ser Glu Gln Gly Leu Leu Leu Gly
145                 150                 155                 160

Gly Ala Ser Ala Ala Thr Ala Ala Thr Ala Ala Gly Thr Gly Gly
                165                 170                 175

Ser Gly Gly Ser Pro Ala Ser Ser Ser Gly Thr Gln Arg Arg Gly Glu
                180                 185                 190

Gly Ser Glu Arg Arg Pro Arg Arg Asp Arg Arg Ser Ser Gly Arg
            195                 200                 205

Ser Lys Glu Arg His Arg Glu His Arg Arg Arg Asp Gly Gln Arg Gly
        210                 215                 220

Gly Ser Glu Ala Ser Lys Ser Arg Ser Arg His Ser His Ser Gly Glu
225                 230                 235                 240

Glu Arg Ala Glu Val Ala Lys Ser Gly Ser Ser Ser Ser Gly Gly
                245                 250                 255

Arg Arg Lys Ser Ala Ser Ala Thr Ser Ser Ser Ser Ser Arg Lys
            260                 265                 270

Asp Arg Asp Ser Lys Ala His Arg Ser Arg Thr Lys Ser Ser Lys Glu
        275                 280                 285

Pro Pro Ser Ala Tyr Lys Glu Pro Lys Ala Tyr Arg Glu Asp Lys
    290                 295                 300

Thr Glu Pro Lys Ala Tyr Arg Arg Arg Ser Leu Ser Pro Leu Gly
305                 310                 315                 320

Gly Arg Asp Asp Ser Pro Val Ser His Arg Ala Ser Gln Ser Leu Arg
                325                 330                 335

Ser Arg Lys Ser Pro Ser Pro Ala Gly Gly Gly Ser Ser Pro Tyr Ser
            340                 345                 350

Arg Arg Leu Pro Arg Ser Pro Ser Pro Tyr Ser Arg Arg Arg Ser Pro
        355                 360                 365
```

```
Ser Tyr Ser Arg His Ser Ser Tyr Glu Arg Gly Gly Asp Val Ser Pro
370                 375                 380

Ser Pro Tyr Ser Ser Ser Ser Trp Arg Arg Ser Arg Ser Pro Tyr Ser
385                 390                 395                 400

Pro Val Leu Arg Arg Ser Gly Lys Ser Arg Ser Arg Ser Pro Tyr Ser
            405                 410                 415

Ser Arg His Ser Arg Ser Arg Ser Arg His Arg Leu Ser Arg Ser Arg
            420                 425                 430

Ser Arg His Ser Ser Ile Ser Pro Ser Thr Leu Thr Leu Lys Ser Ser
            435                 440                 445

Leu Ala Ala Glu Leu Asn Lys Asn Lys Lys Ala Arg Ala Ala Glu Ala
450                 455                 460

Ala Arg Ala Ala Glu Ala Ala Lys Ala Ala Glu Ala Thr Lys Ala Ala
465                 470                 475                 480

Glu Ala Ala Ala Lys Ala Ala Lys Ala Ser Asn Thr Ser Thr Pro Thr
                485                 490                 495

Lys Gly Asn Thr Glu Thr Ser Ala Ser Ala Ser Gln Thr Asn His Val
            500                 505                 510

Lys Asp Val Lys Lys Ile Lys Ile Glu His Ala Pro Ser Pro Ser Ser
            515                 520                 525

Gly Gly Thr Leu Lys Asn Asp Lys Ala Lys Thr Lys Pro Pro Leu Gln
530                 535                 540

Val Thr Lys Val Glu Asn Asn Leu Ile Val Asp Lys Ala Thr Lys Lys
545                 550                 555                 560

Ala Val Ile Val Gly Lys Glu Ser Lys Ser Ala Ala Thr Lys Glu Glu
                565                 570                 575

Ser Val Ser Leu Lys Glu Lys Thr Lys Pro Leu Thr Pro Ser Ile Gly
            580                 585                 590

Ala Lys Glu Lys Glu Gln His Val Ala Leu Val Thr Ser Thr Leu Pro
        595                 600                 605

Pro Leu Pro Leu Pro Pro Met Leu Pro Glu Asp Lys Glu Ala Asp Ser
610                 615                 620

Leu Arg Gly Asn Ile Ser Val Lys Ala Val Lys Lys Glu Val Glu Lys
625                 630                 635                 640

Lys Leu Arg Cys Leu Leu Ala Asp Leu Pro Leu Pro Pro Glu Leu Pro
                645                 650                 655

Gly Gly Asp Asp Leu Ser Lys Ser Pro Glu Glu Lys Lys Thr Ala Thr
            660                 665                 670

Gln Leu His Ser Lys Arg Arg Pro Lys Ile Cys Gly Pro Arg Tyr Gly
            675                 680                 685

Glu Thr Lys Glu Lys Asp Ile Asp Trp Gly Lys Arg Cys Val Asp Lys
690                 695                 700

Phe Asp Ile Ile Gly Ile Ile Gly Glu Gly Thr Tyr Gly Gln Val Tyr
705                 710                 715                 720

Lys Ala Arg Asp Lys Asp Thr Gly Glu Met Val Ala Leu Lys Lys Val
            725                 730                 735

Arg Leu Asp Asn Glu Lys Glu Gly Phe Pro Ile Thr Ala Ile Arg Glu
            740                 745                 750

Ile Lys Ile Leu Arg Gln Leu Thr His Gln Ser Ile Ile Asn Met Lys
            755                 760                 765

Glu Ile Val Thr Asp Lys Glu Asp Ala Leu Asp Phe Lys Lys Asp Lys
770                 775                 780
```

```
Gly Ala Phe Tyr Leu Val Phe Glu Tyr Met Asp His Asp Leu Met Gly
785                 790                 795                 800

Leu Leu Glu Ser Gly Leu Val His Phe Asn Glu Asn His Ile Lys Ser
            805                 810                 815

Phe Met Arg Gln Leu Met Glu Gly Leu Asp Tyr Cys His Lys Lys Asn
            820                 825                 830

Phe Leu His Arg Asp Ile Lys Cys Ser Asn Ile Leu Leu Asn Asn Arg
            835                 840                 845

Gly Gln Ile Lys Leu Ala Asp Phe Gly Leu Ala Arg Leu Tyr Ser Ser
    850                 855                 860

Glu Glu Ser Arg Pro Tyr Thr Asn Lys Val Ile Thr Leu Trp Tyr Arg
865                 870                 875                 880

Pro Pro Glu Leu Leu Leu Gly Glu Arg Tyr Thr Pro Ala Ile Asp
            885                 890                 895

Val Trp Ser Cys Gly Cys Ile Leu Gly Glu Leu Phe Thr Lys Lys Pro
            900                 905                 910

Ile Phe Gln Ala Asn Gln Glu Leu Ala Gln Leu Glu Leu Ile Ser Arg
            915                 920                 925

Ile Cys Gly Ser Pro Cys Pro Ala Val Trp Pro Asp Val Ile Lys Leu
            930                 935                 940

Pro Tyr Phe Asn Thr Met Lys Pro Lys Lys Gln Tyr Arg Arg Lys Leu
945                 950                 955                 960

Arg Glu Glu Phe Val Phe Ile Pro Ala Ala Ala Leu Asp Leu Phe Asp
                965                 970                 975

Tyr Met Leu Ala Leu Asp Pro Ser Lys Arg Cys Thr Ala Glu Gln Ala
            980                 985                 990

Leu Gln Cys Glu Phe Leu Arg Asp Val Glu Pro Ser Lys Met Pro Pro
    995                 1000                1005

Pro Asp Leu Pro Leu Trp Gln Asp Cys His Glu Leu Trp Ser Lys
    1010                1015                1020

Lys Arg Arg Arg Gln Lys Gln Met Gly Met Thr Asp Asp Val Ser
    1025                1030                1035

Thr Ile Lys Ala Pro Arg Lys Asp Leu Ser Leu Gly Leu Asp Asp
    1040                1045                1050

Ser Arg Thr Asn Thr Pro Gln Gly Val Leu Pro Ser Ser Gln Leu
    1055                1060                1065

Lys Ser Gln Gly Ser Ser Asn Val Ala Pro Val Lys Thr Gly Pro
    1070                1075                1080

Gly Gln His Leu Asn His Ser Glu Leu Ala Ile Leu Leu Asn Leu
    1085                1090                1095

Leu Gln Ser Lys Thr Ser Val Asn Met Ala Asp Phe Val Gln Val
    1100                1105                1110

Leu Asn Ile Lys Val Asn Ser Glu Thr Gln Gln Gln Leu Asn Lys
    1115                1120                1125

Ile Asn Leu Pro Ala Gly Ile Leu Ala Thr Gly Glu Lys Gln Thr
    1130                1135                1140

Asp Pro Ser Thr Pro Gln Gln Glu Ser Ser Lys Pro Leu Gly Gly
    1145                1150                1155

Ile Gln Pro Ser Ser Gln Thr Ile Gln Pro Lys Val Glu Thr Asp
    1160                1165                1170

Ala Ala Gln Ala Ala Val Ser Ala Phe Ala Val Leu Leu Thr
    1175                1180                1185

Gln Leu Ile Lys Ala Gln Gln Ser Lys Gln Lys Asp Val Leu Leu
```

```
                1190                1195                1200
Glu Glu Arg Glu Asn Gly Ser Gly His Glu Ala Ser Leu Gln Leu
    1205                1210                1215
Arg Pro Pro Glu Pro Ser Thr Pro Val Ser Gly Gln Asp Asp
    1220                1225                1230
Leu Ile Gln His Gln Asp Met Arg Ile Leu Glu Leu Thr Pro Glu
    1235                1240                1245
Pro Asp Arg Pro Arg Ile Leu Pro Pro Asp Gln Arg Pro Pro Glu
    1250                1255                1260
Pro Pro Glu Pro Pro Val Thr Glu Glu Asp Leu Asp Tyr Arg
    1265                1270                1275
Thr Glu Asn Gln His Val Pro Thr Thr Ser Ser Leu Thr Asp
    1280                1285                1290
Pro His Ala Gly Val Lys Ala Ala Leu Leu Gln Leu Leu Ala Gln
    1295                1300                1305
His Gln Pro Gln Asp Asp Pro Lys Arg Glu Gly Gly Ile Asp Tyr
    1310                1315                1320
Gln Ala Gly Asp Thr Tyr Val Ser Thr Ser Asp Tyr Lys Asp Asn
    1325                1330                1335
Phe Gly Ser Ser Ser Phe Ser Ser Ala Pro Tyr Val Ser Asn Asp
    1340                1345                1350
Gly Leu Gly Ser Ser Ser Ala Pro Pro Leu Glu Arg Arg Ser Phe
    1355                1360                1365
Ile Gly Asn Ser Asp Ile Gln Ser Leu Asp Asn Tyr Ser Thr Ala
    1370                1375                1380
Ser Ser His Ser Gly Gly Pro Pro Gln Pro Ser Ala Phe Ser Glu
    1385                1390                1395
Ser Phe Pro Ser Ser Val Ala Gly Tyr Gly Asp Ile Tyr Leu Asn
    1400                1405                1410
Ala Gly Pro Met Leu Phe Ser Gly Asp Lys Asp His Arg Phe Glu
    1415                1420                1425
Tyr Ser His Gly Pro Ile Ala Val Leu Ala Asn Ser Ser Asp Pro
    1430                1435                1440
Ser Thr Gly Pro Glu Ser Thr His Pro Leu Pro Ala Lys Met His
    1445                1450                1455
Asn Tyr Asn Tyr Gly Gly Asn Leu Gln Glu Asn Pro Ser Gly Pro
    1460                1465                1470
Ser Leu Met His Gly Gln Thr Trp Thr Ser Pro Ala Gln Gly Pro
    1475                1480                1485
Gly Tyr Ser Gln Gly Tyr Arg Gly His Ile Ser Thr Ser Thr Gly
    1490                1495                1500
Arg Gly Arg Gly Arg Gly Leu Pro Tyr
    1505                1510

<210> SEQ ID NO 4
<211> LENGTH: 406
<212> TYPE: PRT
<213> ORGANISM: Homo sapiens

<400> SEQUENCE: 4

Met Ala Thr Pro Gly Asn Leu Gly Ser Ser Val Leu Ala Ser Lys Thr
1               5                   10                  15

Lys Thr Lys Lys Lys His Phe Val Ala Gln Lys Val Leu Phe Arg
            20                  25                  30
```

```
Ala Ser Asp Pro Leu Leu Ser Val Leu Met Trp Gly Val Asn His Ser
     35                  40                  45

Ile Asn Glu Leu Ser His Val Gln Ile Pro Val Met Leu Met Pro Asp
 50                  55                  60

Asp Phe Lys Ala Tyr Ser Lys Ile Lys Val Asp Asn His Leu Phe Asn
 65                  70                  75                  80

Lys Glu Asn Met Pro Ser His Phe Lys Phe Glu Tyr Cys Pro Met
                 85                  90                  95

Val Phe Arg Asn Leu Arg Glu Arg Phe Gly Ile Asp Asp Gln Asp Phe
                100                 105                 110

Gln Asn Ser Leu Thr Arg Ser Ala Pro Leu Pro Asn Asp Ser Gln Ala
                115                 120                 125

Arg Ser Gly Ala Arg Phe His Thr Ser Tyr Asp Lys Arg Tyr Ile Ile
130                 135                 140

Lys Thr Ile Thr Ser Glu Asp Val Ala Glu Met His Asn Ile Leu Lys
145                 150                 155                 160

Lys Tyr His Gln Tyr Ile Val Glu Cys His Gly Ile Thr Leu Leu Pro
                165                 170                 175

Gln Phe Leu Gly Met Tyr Arg Leu Asn Val Asp Gly Val Glu Ile Tyr
                180                 185                 190

Val Ile Val Thr Arg Asn Val Phe Ser His Arg Leu Ser Val Tyr Arg
                195                 200                 205

Lys Tyr Asp Leu Lys Gly Ser Thr Val Ala Arg Glu Ala Ser Asp Lys
                210                 215                 220

Glu Lys Ala Lys Glu Leu Pro Thr Leu Lys Asp Asn Asp Phe Ile Asn
225                 230                 235                 240

Glu Gly Gln Lys Ile Tyr Ile Asp Asp Asn Asn Lys Lys Val Phe Leu
                245                 250                 255

Glu Lys Leu Lys Lys Asp Val Glu Phe Leu Ala Gln Leu Lys Leu Met
                260                 265                 270

Asp Tyr Ser Leu Leu Val Gly Ile His Asp Val Glu Arg Ala Glu Gln
                275                 280                 285

Glu Glu Val Glu Cys Glu Glu Asn Asp Gly Glu Glu Gly Glu Ser
290                 295                 300

Asp Gly Thr His Pro Val Gly Thr Pro Pro Asp Ser Pro Gly Asn Thr
305                 310                 315                 320

Leu Asn Ser Ser Pro Pro Leu Ala Pro Gly Glu Phe Asp Pro Asn Ile
                325                 330                 335

Asp Val Tyr Gly Ile Lys Cys His Glu Asn Ser Pro Arg Lys Glu Val
                340                 345                 350

Tyr Phe Met Ala Ile Ile Asp Ile Leu Thr His Tyr Asp Ala Lys Lys
                355                 360                 365

Lys Ala Ala His Ala Ala Lys Thr Val Lys His Gly Ala Gly Ala Glu
                370                 375                 380

Ile Ser Thr Val Asn Pro Glu Gln Tyr Ser Lys Arg Phe Leu Asp Phe
385                 390                 395                 400

Ile Gly His Ile Leu Thr
                405

<210> SEQ ID NO 5
<211> LENGTH: 416
<212> TYPE: PRT
<213> ORGANISM: Homo sapiens

<400> SEQUENCE: 5
```

```
Met Ser Ser Asn Cys Thr Ser Thr Ala Val Ala Val Ala Pro Leu
1               5                   10                  15

Ser Ala Ser Lys Thr Lys Thr Lys Lys His Phe Val Cys Gln Lys
                20                  25                  30

Val Lys Leu Phe Arg Ala Ser Glu Pro Ile Leu Ser Val Leu Met Trp
            35                  40                  45

Gly Val Asn His Thr Ile Asn Glu Leu Ser Asn Val Pro Val Pro Val
        50                  55                  60

Met Leu Met Pro Asp Asp Phe Lys Ala Tyr Ser Lys Ile Lys Val Asp
65                  70                  75                  80

Asn His Leu Phe Asn Lys Glu Asn Leu Pro Ser Arg Phe Lys Phe Lys
                85                  90                  95

Glu Tyr Cys Pro Met Val Phe Arg Asn Leu Arg Glu Arg Phe Gly Ile
                100                 105                 110

Asp Asp Gln Asp Tyr Gln Asn Ser Val Thr Arg Ser Ala Pro Ile Asn
            115                 120                 125

Ser Asp Ser Gln Gly Arg Cys Gly Thr Arg Phe Leu Thr Thr Tyr Asp
        130                 135                 140

Arg Arg Phe Val Ile Lys Thr Val Ser Ser Glu Asp Val Ala Glu Met
145                 150                 155                 160

His Asn Ile Leu Lys Lys Tyr His Gln Phe Ile Val Glu Cys His Gly
                165                 170                 175

Asn Thr Leu Leu Pro Gln Phe Leu Gly Met Tyr Arg Leu Thr Val Asp
                180                 185                 190

Gly Val Glu Thr Tyr Met Val Val Thr Arg Asn Val Phe Ser His Arg
            195                 200                 205

Leu Thr Val His Arg Lys Tyr Asp Leu Lys Gly Ser Thr Val Ala Arg
        210                 215                 220

Glu Ala Ser Asp Lys Glu Lys Ala Lys Asp Leu Pro Thr Phe Lys Asp
225                 230                 235                 240

Asn Asp Phe Leu Asn Glu Gly Gln Lys Leu His Val Gly Glu Glu Ser
                245                 250                 255

Lys Lys Asn Phe Leu Glu Lys Leu Lys Arg Asp Val Glu Phe Leu Ala
                260                 265                 270

Gln Leu Lys Ile Met Asp Tyr Ser Leu Leu Val Gly Ile His Asp Val
        275                 280                 285

Asp Arg Ala Glu Gln Glu Glu Met Glu Val Glu Glu Arg Ala Glu Asp
290                 295                 300

Glu Glu Cys Glu Asn Asp Gly Val Gly Gly Asn Leu Leu Cys Ser Tyr
305                 310                 315                 320

Gly Thr Pro Pro Asp Ser Pro Gly Asn Leu Leu Ser Phe Pro Arg Phe
                325                 330                 335

Phe Gly Pro Gly Glu Phe Asp Pro Ser Val Asp Val Tyr Ala Met Lys
            340                 345                 350

Ser His Glu Ser Ser Pro Lys Lys Glu Val Tyr Phe Met Ala Ile Ile
        355                 360                 365

Asp Ile Leu Thr Pro Tyr Asp Thr Lys Lys Ala Ala His Ala Ala
        370                 375                 380

Lys Thr Val Lys His Gly Ala Gly Ala Glu Ile Ser Thr Val Asn Pro
385                 390                 395                 400

Glu Gln Tyr Ser Lys Arg Phe Asn Glu Phe Met Ser Asn Ile Leu Thr
                405                 410                 415
```

<210> SEQ ID NO 6
<211> LENGTH: 421
<212> TYPE: PRT
<213> ORGANISM: Homo sapiens

<400> SEQUENCE: 6

```
Met Ala Ser Ser Val Pro Pro Ala Thr Val Ser Ala Thr Ala
1               5                   10                  15

Gly Pro Gly Pro Gly Phe Gly Phe Ala Ser Lys Thr Lys Lys Lys His
                20                  25                  30

Phe Val Gln Gln Lys Val Lys Val Phe Arg Ala Ala Asp Pro Leu Val
                35                  40                  45

Gly Val Phe Leu Trp Gly Val Ala His Ser Ile Asn Glu Leu Ser Gln
            50                  55                  60

Val Pro Pro Pro Val Met Leu Leu Pro Asp Asp Phe Lys Ala Ser Ser
65                  70                  75                  80

Lys Ile Lys Val Asn Asn His Leu Phe His Arg Glu Asn Leu Pro Ser
                    85                  90                  95

His Phe Lys Phe Lys Glu Tyr Cys Pro Gln Val Phe Arg Asn Leu Arg
                100                 105                 110

Asp Arg Phe Gly Ile Asp Asp Gln Asp Tyr Leu Val Ser Leu Thr Arg
                115                 120                 125

Asn Pro Pro Ser Glu Ser Glu Gly Ser Asp Gly Arg Phe Leu Ile Ser
            130                 135                 140

Tyr Asp Arg Thr Leu Val Ile Lys Glu Val Ser Ser Glu Asp Ile Ala
145                 150                 155                 160

Asp Met His Ser Asn Leu Ser Asn Tyr His Gln Tyr Ile Val Lys Cys
                    165                 170                 175

His Gly Asn Thr Leu Leu Pro Gln Phe Leu Gly Met Tyr Arg Val Ser
                180                 185                 190

Val Asp Asn Glu Asp Ser Tyr Met Leu Val Met Arg Asn Met Phe Ser
                195                 200                 205

His Arg Leu Pro Val His Arg Lys Tyr Asp Leu Lys Gly Ser Leu Val
            210                 215                 220

Ser Arg Glu Ala Ser Asp Lys Glu Lys Val Lys Glu Leu Pro Thr Leu
225                 230                 235                 240

Lys Asp Met Asp Phe Leu Asn Lys Asn Gln Lys Val Tyr Ile Gly Glu
                    245                 250                 255

Glu Glu Lys Lys Ile Phe Leu Glu Lys Leu Lys Arg Asp Val Glu Phe
                260                 265                 270

Leu Val Gln Leu Lys Ile Met Asp Tyr Ser Leu Leu Leu Gly Ile His
            275                 280                 285

Asp Ile Ile Arg Gly Ser Glu Pro Glu Glu Ala Pro Val Arg Glu
        290                 295                 300

Asp Glu Ser Glu Val Asp Gly Asp Cys Ser Leu Thr Gly Pro Ala
305                 310                 315                 320

Leu Val Gly Ser Tyr Gly Thr Ser Pro Glu Gly Ile Gly Tyr Ile
                325                 330                 335

His Ser His Arg Pro Leu Gly Pro Gly Glu Phe Glu Ser Phe Ile Asp
            340                 345                 350

Val Tyr Ala Ile Arg Ser Ala Glu Gly Ala Pro Gln Lys Glu Val Tyr
        355                 360                 365

Phe Met Gly Leu Ile Asp Ile Leu Thr Gln Tyr Asp Ala Lys Lys Lys
370                 375                 380
```

| Ala | Ala | His | Ala | Ala | Lys | Thr | Val | Lys | His | Gly | Ala | Gly | Ala | Glu | Ile |
|-----|-----|-----|-----|-----|-----|-----|-----|-----|-----|-----|-----|-----|-----|-----|-----|
| 385 | | | | 390 | | | | | 395 | | | | | 400 | |

| Ser | Thr | Val | His | Pro | Glu | Gln | Tyr | Ala | Lys | Arg | Phe | Leu | Asp | Phe | Ile |
|-----|-----|-----|-----|-----|-----|-----|-----|-----|-----|-----|-----|-----|-----|-----|-----|
| | | | 405 | | | | | 410 | | | | 415 | | | |

| Thr | Asn | Ile | Phe | Ala |
|-----|-----|-----|-----|-----|
| | 420 | | | |

<210> SEQ ID NO 7
<211> LENGTH: 1221
<212> TYPE: DNA
<213> ORGANISM: Homo sapiens

<400> SEQUENCE: 7

```
atggcgaccc ccggcaacct agggtcctct gtcctggcga gcaagaccaa gaccaagaag    60
aagcacttcg tagcgcagaa agtgaagctg tttcgggcca gcgacccgct gctcagcgtc   120
ctcatgtggg gggtaaacca ctcgatcaat gaactgagcc atgttcaaat ccctgttatg   180
ttgatgccag atgacttcaa agcctattca aaaataaagg tggacaatca cctttttaac   240
aaagaaaaca tgccgagcca tttcaagttt aaggaatact gcccgatggt cttccgtaac   300
ctgcgggaga ggtttggaat tgatgatcaa gatttccaga attccctgac caggagcgca   360
cccctcccca cgactcccca ggcccgcagt ggagctcgtt tcacacttc ctacgacaaa   420
agatacatca tcaagactat taccagtgaa acgtggccg aaatgcacaa catcctgaag   480
aaataccacc agtacatagt ggaatgtcat gggatcaccc ttcttcccca gttcttgggc   540
atgtaccggc ttaatgttga tggagttgaa atatatgtga tagttacaag aaatgtattc   600
agccaccgtt tgtctgtgta taggaaatac gacttaaagg gctctacagt ggctagagaa   660
gctagtgaca agaaaaaggc caagaactg ccaactctga agataatga tttcattaat   720
gagggccaaa agatttatat tgatgacaac aacaagaagg tcttcctgga aaaactaaaa   780
aaggatgttg agtttctggc ccagctgaag ctcatggact acagtctgct ggtgggaatt   840
catgatgtgg agagagccga acaggaggaa gtggagtgtg aggagaacga tggggaggag   900
gagggcgaga gcgatggcac ccacccggtg gaaccccc cagatagccc cgggaataca   960
ctgaacagct caccaccct ggctcccggg gagttcgatc cgaacatcga cgtctatgga  1020
attaagtgcc atgaaaactc gcctaggaag gaggtgtact tcatggcaat tattgacatc  1080
cttactcatt atgatgcaaa aagaaagct gcccatgctg caaaactgt taaacatggc  1140
gctggcgcgg agatctccac cgtgaaccca gaacagtatt caaagcgctt tttggactt  1200
attggccaca tcttgacgta a                                            1221
```

<210> SEQ ID NO 8
<211> LENGTH: 1251
<212> TYPE: DNA
<213> ORGANISM: Homo sapiens

<400> SEQUENCE: 8

```
atgtcgtcca actgcaccag caccacggcg gtggcggtgg cgccgctcag cgccagcaag    60
accaagacca agaagaagca tttcgtgtgc cagaaagtga agctattccg ggccagcgag   120
ccgatcctca gcgtcctgat gtgggggtg aaccacacga tcaatgagct gagcaatgtt   180
cctgttcctg tcatgctaat gccagatgac ttcaaagcct acagcaagat caaggtggac   240
aatcatctct tcaataagga gaacctgccc agccgcttta gtttaagga gtattgcccc   300
atggtgttcc gaaaccttcg ggagaggttt ggaattgatg atcaggatta ccagaattca   360
```

```
gtgacgcgca gcgcccccat caacagtgac agccagggtc ggtgtggcac gcgtttcctc      420
accacctacg accggcgctt tgtcatcaag actgtgtcca gcgaggacgt ggcggagatg      480
cacaacatct taaagaaata ccaccagttt atagtggagt gtcatggcaa cacgcttttg      540
ccacagttcc tgggcatgta ccgcctgacc gtggatggtg tggaaaccta catggtggtt      600
accaggaacg tgttcagcca tcggctcact gtgcatcgca agtatgacct caagggttct      660
acggttgcca gagaagcgag cgacaaggag aaggccaagg acttgccaac attcaaagac      720
aatgacttcc tcaatgaagg gcagaagctg catgtgggag aggagagtaa aagaacttc       780 ctggagaaac tgaagcggga cgttgagttc ttggcacagc tgaagatcat ggactacagc      840
ctgctggtgg gcatccacga cgtggaccgg gcagagcagg aggagatgga ggtggaggag      900
cgggcagagg acgaggagtg tgagaatgat ggggtgggtg gcaacctact ctgctcctat      960
ggcacacctc cggacagccc tggcaacctc ctcagctttc ctcggttctt tggtcctggg     1020
gaattcgacc cctctgttga cgtctatgcc atgaaaagcc atgaaagttc ccccaagaag     1080
gaggtgtatt tcatggccat cattgatatc ctcacgccat acgatacaaa gaagaaagct     1140
gcacatgctg ccaaaacggt gaaacacggg gcaggggccg agatctcgac tgtgaaccct     1200
gagcagtact ccaaacgctt caacgagttt atgtccaaca tcctgacgta g              1251

<210> SEQ ID NO 9
<211> LENGTH: 1266
<212> TYPE: DNA
<213> ORGANISM: Homo sapiens

<400> SEQUENCE: 9
atggcgtcct cctcggtccc accagccacg gtatcggcgg cgacagcagg ccccggccca       60
ggtttcggct tcgcctccaa gaccaagaag aagcatttcg tgcagcagaa ggtgaaggtg      120
ttccgggcgg ccgacccgct ggtgggtgtg ttcctgtggg gcgtagccca ctcgatcaat      180
gagctcagcc aggtgcctcc cccggtgatg ctgctgccag atgactttaa ggccagctcc      240
aagatcaagg tcaacaatca cctttccac agggaaaatc tgcccagtca tttcaagttc       300
aaggagtatt gtccccaggt cttcaggaac ctccgtgatc gatttggcat tgatgaccaa      360
gattacttgg tgtcccttac ccgaaacccc ccagcgaaa gtgaaggcag tgatggtcgc       420
ttccttatct cctacgatcg gactctggtc atcaaagaag tatccagtga ggacattgct      480
gacatgcata gcaacctctc caactatcac cagtacattg tgaagtgcca tggcaacacg      540
cttctgcccc agttcctggg gatgtaccga gtcagtgtgg acaacgaaga cagctacatg      600
cttgtgatgc gcaatatgtt tagccaccgt cttcctgtgc acaggaagta tgacctcaag      660
ggttccctag tgtcccggga agccagcgat aaggaaaagg ttaaagaatt gcccacctt       720 aaggatatgg actttctcaa caagaaccag aaagtatata ttggtgaaga ggagaagaaa      780
atatttctgg agaagctgaa gagagatgtg gagtttctag tgcagctgaa gatcatggac      840
tacagccttc tgctaggcat ccacgacatc attcggggct ctgaaccaga ggaggaagcg      900
cccgtgcggg aggatgagtc agaggtggat ggggactgca gcctgactgg acctcctgct      960
ctggtgggct cctatggcac ctccccagag ggtatcggag ctacatcca ttcccatcgg     1020 ccctgggcc caggagagtt tgagtccttc attgatgtct atgccatccg gagtgctgaa     1080 ggagccccc agaaggaggt ctacttcatg ggcctcattg atatcctac acagtatgat      1140 gctaagaaga aagcagctca tgcagccaaa actgtcaagc atggggctgg ggcagagatc    1200
```

```
tctactgtcc atccggagca gtatgctaag cgattcctgg attttattac caacatcttt  1260
gcctaa                                                             1266
```

FUSED BICYCLIC PYRIMIDINE DERIVATIVES AND USES THEREOF

RELATED APPLICATIONS

The present application is a national stage filing under 35 U.S.C. § 371 of international PCT application, PCT/US2016/039302, filed Jun. 24, 2016, which claims priority under 35 U.S.C. § 119(e) to U.S. provisional application, U.S. Ser. No. 62/185,366, filed Jun. 26, 2015, each of which is incorporated herein by reference.

GOVERNMENT SUPPORT

This invention was made with government support under grant number R01CA197329 awarded by The National Institutes of Health. The government has certain rights in the invention.

BACKGROUND OF THE INVENTION

Lung cancer is the leading cancer killer worldwide accounting for 1.37 million deaths annually. In the United States, lung cancer causes more deaths than the next three most common cancers combined (colon, breast and pancreatic) and in 2014, an estimated 159,260 Americans will die from lung cancer. Lung cancer arises as a result of environmental exposures, such as smoking, combined with genetic alterations such as deregulation of oncoproteins, including Myc and RAS, and loss of tumor suppressors, such as p53. The vast majority of patients that develop lung cancer will have non-small cell lung cancer (NSCLC), and 50% of patients will initially present with advanced NSCLC, which is incurable using currently available therapies. The median survival of patients with advanced NSCLC treated with chemotherapy is 8-10 months.

A major therapeutic goal in lung cancer is to identify agents against targets that are critical to the growth of lung cancers. This has been clinically achieved for patients that harbor activating mutations in EGFR or chromosomal translocations such as EML4-ALK using selective ATP-competitive kinase inhibitors. Unfortunately the duration of response to targeted kinase inhibitors is typically less than 2 years, and most lung tumors do not express an oncogene that is targeted by an available drug. For example, loss of p53 is a common event in lung cancer, but there are currently limited drugs that can exploit its loss.

Phosphatidylinositol 4,5-bisphosphate ($PIP_2$) is a membrane bound lipid molecule with the ability to affect a wide array of signaling pathways that regulate different cellular processes (Camilli et al., *Science*, 1996, 271: 1533-1539). $PIP_2$ is used as a precursor to generate the second messengers $PIP_3$, DAG, and $IP_3$, indispensable molecules for signaling events generated by membrane receptors. However, $PIP_2$ can also directly regulate a vast array of proteins and is emerging as a crucial messenger with the potential to distinctly modulate biological processes critical for both normal and pathogenic cell physiology (Martin, T. F. J. (1998) *Annu. Rev. Cell Dev. Biol.* 14, 231-264). $PIP_2$ directly associates with effector proteins via unique phosphoinositide binding domains, altering their localization and/or enzymatic activity. The spatial and temporal generation of $PIP_2$ synthesized by the phosphatidylinositol phosphate kinases (PIPKs) tightly regulates the activation of receptor signaling pathways, endocytosis and vesicle trafficking, cell polarity, focal adhesion dynamics, actin assembly, and 3' mRNA processing (Balla et al., Phosphoinositides I: Enzymes of Synthesis and Degradation, 2012, Chapter 2, PIP Kinases from the Cell Membrane to the Nucleus, p 25). Two types of PIP kinases have been identified, type I and type II PI(4)P 5-kinases (Fruman et al., *Annu. Rev. Biochem.*, 1998, 67: 481-507). Type I phosphorylates PI(4)P at the 5-position to make PI(4,5)P2 and type II can phosphorylate PI(5)P and PI(3)P at the 4-position to make PI(4,5)P2 and PI(3,4)P2.

Recently, it has been discovered that RNAi-mediated depletion of two type II PIP kinases, PIP4K2A and PIP4K2B, selectively inhibited the proliferation of TP53 mutant breast cancer cell line (BT474 cells) while cells that were wild-type for TP53 were unaffected (Emerling et al., *Cell*, 2013, 155: 844-857). These kinases phosphorylate the lipid phosphatidylinositol-5-phosphate (PI-5-P) at the 4-position of the inositol ring to generate phosphatidylinositol-4,5-bisphosphate (PI-4,5-P2) and are in the same kinase family as the PI3 kinases which are now targeted by a number of clinical stage drugs. Genetic studies in mice demonstrate that homozygous germline deletion of PIP4K2B results in healthy mice with a normal life span, while combined deletion of PIP4K2B and TP53 results in early embryonic lethality (FIG. 1) (Rameh et al., *Nature*, 1997, 390: 192-196). Mice expressing one allele of PIP4K2B and homozygous deletion of PIP4K2A and TP53 are viable and exhibit a dramatic reduction in cancers and an extended lifespan compared to their littermates that were TP53 deleted with wild type PIP4K2A. These studies suggest that PIP4K2A/B becomes essential when TP53 function is lost. Therefore, small molecule inhibitors of PIP4K2A/B may hold promise as a therapeutic agent for treating cancer.

SUMMARY OF THE INVENTION

The phosphoinositide family of lipids includes seven derivatives of phosphatidylinositol (PI) that are formed through the phosphorylation of the 3-, 4-, and 5-positions on the inositol ring (Emerling et al., *Cell*, 2013, 155: 844-857). Phosphoinositides have distinct biological roles and regulate many cellular processes, including proliferation survival, glucose uptake, and migration. Phosphoinositide kinases, phosphatases and phospholipases, spatially and temporally regulate the generation of the different phosphoinositide species, which localize to different subcellular compartments. phosphorylation of lipid phosphatidylinositol-5-phosphate (PI-5-P) at the 4-position to generate phosphatidylinositol-4,5-bisphosphate (PI-4,5-$P_2$) is catalyzed by the enzymes PIP4K2A, B and C. Germ line deletion of PIP4K2A and PIP4K2B in mice suppresses tumor formation in the context of TP53 deletion (Rameh et al., Nature, 1997, 390: 192-196). Loss or mutations in the tumor suppressor gene TP53 (encoding p53) is one of the most frequent events in cancer. Clinical and functional studies have unequivocally validated the functional importance of the loss of p53 in cancer. Therefore, it is advantageous to develop PIP4K2A and/or PIP4K2B inhibitors to provide therapeutic benefit in cancers, for example, TP53-deleted tumors.

The present invention provides compounds of Formula (I), and pharmaceutically acceptable salts, solvates, hydrates, polymorphs, co-crystals, tautomers, stereoisomers, isotopically labeled derivatives, prodrugs, and compositions thereof. The compounds of Formula (I), and pharmaceutically acceptable salts, solvates, hydrates, polymorphs, co-crystals, tautomers, stereoisomers, isotopically labeled derivatives, prodrugs, and compositions thereof, may inhibit the activity of a kinase. In certain embodiments, the kinase is a protein kinase. In certain embodiments, the protein kinase is a CDK (e.g., cyclin-dependent kinases (CDKs)). In certain embodiments, the kinase is a lipid kinase. In certain embodiments, the lipid kinase is a phosphatidylinositol phosphate kinase (PIPK). In certain embodiments, the PIPK is PIP4K, catalyzing phosphorylation of lipid phosphatidylinositol-5-phosphate (PI-5-P) at the 4-position to generate phosphatidylinositol-4,5-bisphosphate (PI-4,5-P$_2$). In some embodiments, the PIP4K is class I PIP4K, i.e., PIP4K1. In some embodiments, the PIP4K is class II PIP4K, i.e., PIP4K2. In some embodiments, the PIP4K2 is PIP4K2A protein. In some embodiments, the PIP4K2 is PIP4K2B protein. In some embodiments, the PIP4K2 is PIP4K2C protein. In certain embodiments, the compound of Formula (I) is selective for a lipid kinase compared to other kinases. In certain embodiments, the compound of Formula (I) is selective for PIP4K compared to other kinases.

The present invention further provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., PIP4K) and as therapeutics for the prevention and/or treatment of diseases associated with overexpression and/or aberrant activity of a kinase (e.g., PIP4K). In certain embodiments, the inventive compounds are used for the prevention and/or treatment of proliferative diseases (e.g., cancers (e.g., lung cancer, breast cancer, leukemia, lymphoma, melanoma, multiple myeloma, Ewing's sarcoma, osteosarcoma, brain cancer, neuroblastoma), benign neoplasms, angiogenesis, inflammatory diseases, autoinflammatory diseases, and autoimmune diseases) in a subject.

In one aspect, the present invention provides compounds of Formula (I):

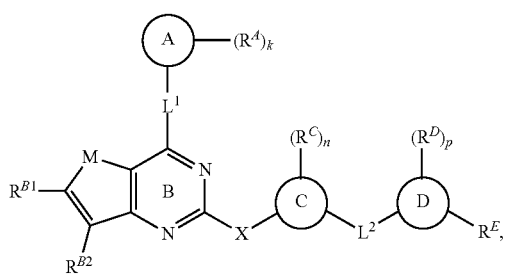

(I)

and pharmaceutically acceptable salts, solvates, hydrates, polymorphs, co-crystals, tautomers, stereoisomers, isotopically labeled derivatives, and prodrugs thereof, wherein Ring A, $L^1$, $L^2$, $R^{B1}$, $R^{B2}$, M, X, $R^A$, $R^C$, $R^D$, $R^E$, n, and p are as defined herein.

In certain embodiments, a compound of Formula (I) is of Formula (I-a):

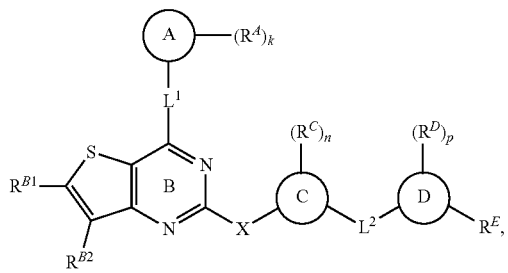

(I-a)

or a pharmaceutically acceptable salt, solvate, hydrate, polymorph, co-crystal, tautomer, stereoisomer, isotopically labeled derivative, or prodrug thereof.

In certain embodiments, a compound of Formula (I) is Formula (I-b):

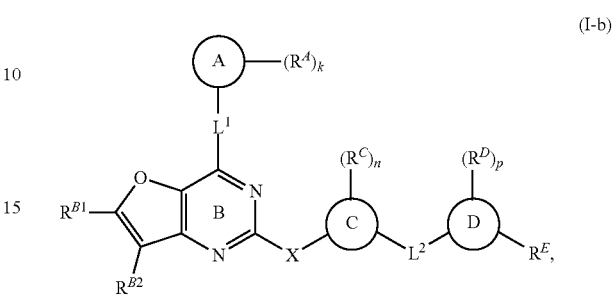

(I-b)

or a pharmaceutically acceptable salt, solvate, hydrate, polymorph, co-crystal, tautomer, stereoisomer, isotopically labeled derivative, or prodrug thereof.

In certain embodiments, a compound of Formula (I) is Formula (I-c):

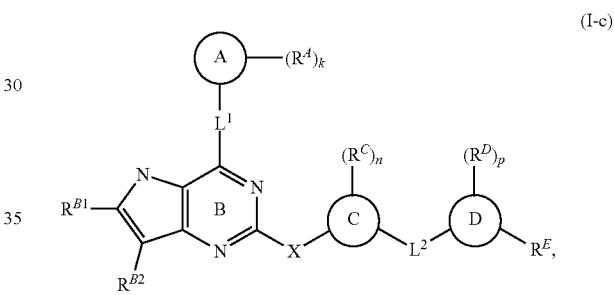

(I-c)

or a pharmaceutically acceptable salt, solvate, hydrate, polymorph, co-crystal, tautomer, stereoisomer, isotopically labeled derivative, or prodrug thereof.

In another aspect, the present invention provides pharmaceutical compositions comprising a compound of Formula (I), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of Formula (I), or a pharmaceutically acceptable salt, solvate, hydrate, polymorph, co-crystal, tautomer, stereoisomer, isotopically labeled derivative, or prodrug thereof. The pharmaceutical composition may be useful for treating and/or preventing a proliferative disease (e.g., cancer) or an infectious disease.

In another aspect, the present invention provides methods for treating and/or preventing proliferative diseases. Exemplary proliferative diseases include cancer (e.g., lung cancer, breast cancer, leukemia, lymphoma, melanoma, multiple myeloma, Ewing's sarcoma, osteosarcoma, brain cancer, neuroblastoma), benign neoplasm, angiogenesis, inflammatory diseases, autoinflammatory diseases, and autoimmune diseases. In certain embodiments, the cancer has one or more mutations. In certain embodiments, the cancer is TP53-deleted cancer. In other embodiments, the present invention provides methods for treating and/or preventing an infectious disease (e.g., a viral infection).

Another aspect of the invention relates to methods of modulating the activity of a kinase (e.g., PIP4K (e.g., PIP4K2) enzyme) in a biological sample or subject. In certain embodiments, the method involves the selective inhibition of the PIP4K enzyme over other kinases. In certain embodiments, the method involves the selective inhibition of the PIP4K2 enzyme over other kinases.

The present invention also provides methods of inhibiting cell growth in a biological sample or subject.

Another aspect of the invention relates to methods of screening a library of compounds (e.g., compounds of Formula (I)) to identify one or more compounds useful in the treatment of a proliferative disease (e.g., cancer (e.g., lung cancer, breast cancer, leukemia, lymphoma, melanoma, multiple myeloma, Ewing's sarcoma, osteosarcoma, brain cancer, neuroblastoma), benign neoplasm, angiogenesis, inflammatory diseases, autoinflammatory diseases, and autoimmune diseases) or an infectious disease (e.g., viral infection) in a subject, in inhibiting a kinase (e.g., PIP4K enzyme), or in inhibiting cell growth.

In yet another aspect, the present invention provides compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment of a proliferative disease in a subject.

In yet another aspect, the present invention provides compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment or prevention of an infectious disease in a subject. In certain embodiments, the infectious disease is a viral infection.

Another aspect of the present invention relates to kits comprising a container with a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment and/or prevention of a proliferative disease (e.g., cancer (e.g., lung cancer, breast cancer, leukemia, lymphoma, melanoma, multiple myeloma, Ewing's sarcoma, osteosarcoma, brain cancer, neuroblastoma), benign neoplasm, angiogenesis, inflammatory diseases, autoinflammatory diseases, and autoimmune diseases) or an infectious disease in a subject. In certain embodiments, the kits described herein further include instructions for administering the compound of Formula (I), or the pharmaceutically acceptable salt, solvate, hydrate, polymorph, co-crystal, tautomer, stereoisomer, isotopically labeled derivative, or prodrug thereof, or the pharmaceutical composition thereof.

The details of one or more embodiments of the invention are set forth herein. Other features, objects, and advantages of the invention will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are substituted or unsubstituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., benzyl (Bn) or —CF$_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

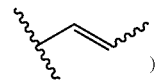

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered, non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a C$_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups, wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" refers to a substituted or unsubstituted alkyl group substituted by a substituted or unsubstituted aryl group. In certain embodiments, the aralkyl is substituted or unsubstituted benzyl. In certain embodiments, the aralkyl is benzyl. In certain embodiments, the aralkyl is substituted or unsubstituted phenethyl. In certain embodiments, the aralkyl is phenethyl.

"Heteroaryl" refers to a radical of a 5-10 membered, monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to a substituted or unsubstituted alkyl group substituted by a substituted or unsubstituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent linking groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is substituted or unsubstituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are substituted or unsubstituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

In certain embodiments, the carbon atom substituents are independently halogen, substituted or unsubstituted $C_{1-6}$ alkyl, or —OR$^{aa}$.

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$))$_2$, wherein R$^{aa}$, R$^{bb}$, and R$^{cc}$ are as defined herein.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like). Further exemplary counterions include, but are not limited to, BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes "Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is Bn, BOC, Cbz, Fmoc, trifluoroacetyl, triphenylmethyl, acetyl, or Ts.

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)

$(R^{aa})_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the substituent present on a sulfur atom is a sulfur protecting group (also referred to as a "thiol protecting group"). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

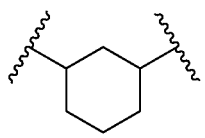 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form a substituted or unsubstituted carbocyclyl, substituted or unsubstituted heterocyclyl, substituted or unsubstituted aryl, or substituted or unsubstituted heteroaryl ring. For instance,

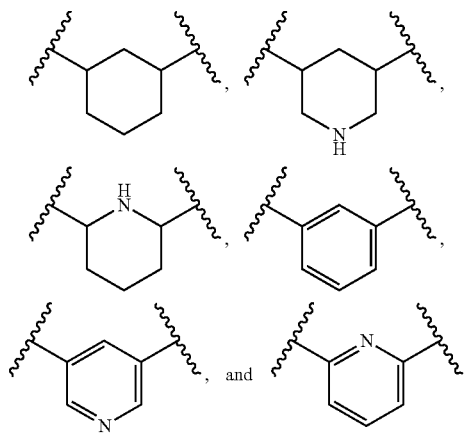

and are all examples of a hydrocarbon chain. In contrast, in certain embodiments,

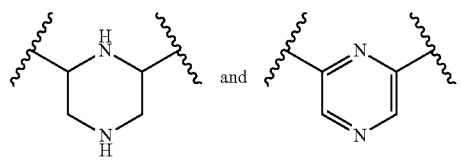 [SMILES: *C1CNCC(*)N1 ; *c1cncc(*)n1]

H and N are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

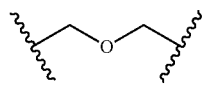 [SMILES: *COC*]

is a $C_3$ hydrocarbon chain wherein one chain atom is replaced with an oxygen atom.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R, —OC(=O)N(R$^{bb}$)$_2$, —OC(=NR$^{bb}$)R, —OC(=NR$^{bb}$)OR$^{aa}$, —OC(=NR$^{bb}$)N(R$^{bb}$)$_2$, —OS(=O)R$^{aa}$, —OSO$_2$R, —OP(R$^{cc}$)$_2$, —OP(R$^{cc}$)$_3$, —OP(=O)$_2$R, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

Other Definitions

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal may contain a compound of the present invention and one or more other component, including but not limited to, atoms, ions, molecules, or solvent molecules. In certain embodiments, a co-crystal may contain a compound of the present invention and one or more components related to said compound, including not limited to, an isomer, tautomer, salt, solvate, hydrate, synthetic precursor, synthetic derivative, fragment or impurity of said compound.

The term "isotopically labeled derivative" or "isotopically labeled" refers to a compound wherein one or more atoms in the compound (or in an associated ion or molecule of a salt, hydrate, or solvate) has been replaced with an isotope of the same element. For the given element or position in the molecule the isotope will be enriched, or present in a higher percentage of all atoms of the element or of all atoms at the position in the molecule in a sample, relative to an unlabeled variant. In certain embodiments, the enriched isotope will be a stable isotope. In certain embodiments, the enriched isotope will be an unstable or radioactive isotope (e.g., a radionuclide). In certain embodiments, the enriched isotope may be detected by a measurement technique, including but not limited to nuclear magnetic resonance, mass spectrometry, infrared spectroscopy, or a technique that measures radioactive decay.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce, slow, halt or prevent activity of a particular biological process (e.g., activity of a bromodomain and/or a bromodomain-containing protein) in a cell relative to vehicle.

When a compound, pharmaceutical composition, method, use, or kit is referred to as "selectively," "specifically," or "competitively" binding a first protein or a first chromatin, the compound, pharmaceutical composition, method, use, or kit binds the first protein or the first chromatin with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or second chromatin that is different from the first protein and the first chromatin. When a compound, pharmaceutical composition, method, use, or kit is referred to as "selectively," "specifically," or "competitively" modulating (e.g., increasing or inhibiting) the activity of a bromodomain-containing protein, the compound, pharmaceutical composition, method, use, or kit modulates the activity of the bromodomain-containing protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the bromodomain-containing protein.

The term "aberrant activity" refers to activity deviating from normal activity, that is, abnormal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from another biological sample.

The terms "administer," "administering," or "administration" refers to implanting, absorbing, ingesting, injecting, inhaling, or otherwise introducing a compound described herein, or a composition thereof, into, in, or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology;* Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated as in the growth of normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC)); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "hematological malignancy" refers to tumors that affect blood, bone marrow, and/or lymph nodes. Exemplary hematological malignancies include, but are not limited to, leukemia, such as acute lymphoblastic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt's lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hay fever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "kinase" is a type of enzyme that transfers phosphate groups from high energy donor molecules, such as ATP, to specific substrates, referred to as phosphorylation. Kinases are part of the larger family of phosphotransferases. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. In some embodiments, the kinase is a protein kinase. A protein kinase is a kinase enzyme that modifies other proteins by chemically adding phosphate groups to them (phosphorylation). In some embodiments, the protein kinase is Cyclin dependent kinases (CDKs). CDKs are a group of several different kinases involved in regulation of the cell cycle. They phosphorylate other proteins on their serine or threonine residues, but CDKs must first bind to a cyclin protein in order to be active. In some embodiments, the protein kinase is mitogen-activated protein kinases (MAPKs). MAP kinases (MAPKs) are a family of serine/threonine kinases that respond to a variety of extracellular growth signals. In some embodiments, the kinase is a lipid kinases that phosphorylate lipids in the cell, both on the plasma membrane as well as on the membranes of the organelles. The addition of phosphate groups can change the reactivity and localization of the lipid and can be used in signal transmission. In some embodiments, the lipid kinase is a phosphatidylinositol kinase that phosphorylates phosphatidylinositol species, to create species such as phosphatidylinositol 3,4-bisphosphate (PI(3,4)P2), phosphatidylinositol 3,4,5-trisphosphate (PIP3), and phosphatidylinositol 3-phosphate (PI3P). In some embodiments, the lipid kinase is sphingosine kinase (SK), a lipid kinase that catalyzes the conversion of sphingosine to sphingosine-1-phosphate (S1P). In certain embodiments, the SK is SK1 or SK2. Exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIKIL, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PIP4K2A, PIP4K2B, PIPK□, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The term "CDK" refers to a cyclin-dependent kinase. A CDK binds a cyclin (e.g., Cyclin H), which is a regulatory protein. CDKs phosphorylate their substrates at serines and threonines. The consensus sequence for the phosphorylation site in the amino acid sequence of a CDK substrate is [S/T*]PX[K/R], where S/T* is the phosphorylated serine or threonine, P is proline, X is any amino acid, K is lysine, and R is arginine. CDKs include CDK1, CDK2, CDK3, CDK4, CDK5, CDK6, CDK7, CDK8, CDK9, CDK10, CDK11, CDK12, CDK13, CDK14, CDK15, CDK16, CDK17, CDK18, CDK19 and CDK20.

CDK7, cyclin-dependent kinase 7, is a CDK, wherein the substrate is Cyclin H, MAT1 (e.g., MNAT1), or Cyclin H and MAT1. CDK7 is alternatively referred to as CAK1, HCAK, MO15, STK1, CDKN7, and p39MO15. Non-limiting examples of the nucleotide and protein sequences for human CDK7 are described in GenBank Accession Number NP_001790, incorporated herein by reference. The amino acid sequence of this CDK7 is as follows:

```
MALDVKSRAKRYEKLDFLGEGQFATVYKARDKNTNQIVAIKKIKLGHRSE
AKDGINRTALREIKLLQELSHPNIIGLLDAFGHKSNISLVFDFMETDLEV
IIKDNSLVLTPSHIKAYMLMTLQGLEYLHQHWILHRDLKPNNLLLDENGV
LKLADFGLAKSFGSPNRAYTHQVVTRWYRAPELLFGARMYGVGVDMWAVG
CILAELLLRVPFLPGDSDLDQLTRIFETLGTPTEEQWPDMCSLPDYVTFK
SFPGIPLHHIFSAAGDDLLDLIQGLFLFNPCARITATQALKMKYFSNRPG
PTPGCQLPRPNCPVETLKEQSNPALAIKRKRTEALEQGGLPKKLIF
```

CDK12, cyclin-dependent kinase 12, is a CDK, wherein the substrate is Cyclin K or Flavopiridol. CDK12 is alternatively referred to as Cdc2-related kinase, CDC2-related protein kinase 7, Cell division cycle 2-related protein kinase 7, Cell division protein kinase 12, CRK7, CRKR, CRKRS, cyclin-dependent kinase 12, or KIAA0904. Non-limiting examples of the nucleotide and protein sequences for human CDK12 are described in Uniprot Number Q9NYV4, which is incorporated herein by reference. The amino acid sequence of this CDK12 is as follows:

```
MPNSERHGGKKDGSGGASGTLQPSSGGGSSNSRERHRLVSKHKRHKSKHS
KDMGLVTPEAASLGTVIKPLVEYDDISSDSDTFSDDMAFKLDRRENDERR
GSDRSDRLHKHRHHQHRRSRDLLKAKQTEKEKSQEVSSKSGSMKDRISGS
SKRSNEETDDYGKAQVAKSSSKESRSSKLHKEKTRKERELKSGHKDRSKS
HRKRETPKSYKTVDSPKRRSRSPHRKWSDSSKQDDSPSGASYGQDYDLSP
SRSHTSSNYDSYKKSPGSTSRRQSVSPPYKEPSAYQSSTRSPSPYSRRQR
SVSPYSRRRSSSYERSGSYSGRSPSPYGRRRSSSPFLSKRSLSRSPLPSR
KSMKSRSRSPAYSRHSSSHSKKKRSSSRSRHSSISPVRLPLNSSLGAELS
RKKKERAAAAAAKMDGKESKGSPVFLPRKENSSVEAKDSGLESKKLPRS
VKLEKSAPDTELVNVTHLNTEVKNSSDTGKVKLDENSEKHLVKDLKAQGT
RDSKPIALKEEIVTPKETETSEKETPPPLPTIASPPPPLPTTTPPPQTPP
LPPPLPPIPALPQQPPLPPSQPAFSQVPASSTSTLPPSTHSKTSAVSSQAN
SQPPVQVSVKTQVSVTAAIPHLKTSTLPPLPLPPLLPGDDDMDSPKETLP
SKPVKKEKEQRTRHLLTDLPLPPELPGGDLSPPDSPEPKAITPPQQPYKK
RPKICCPRYGERRQTESDWGKRCVDKFDIIGIIGEGTYGQVYKAKDKDTG
ELVALKKVRLDNEKEGFPITAIREIKILRQLIHRSVVNMKEIVTDKQDAL
DFKKDKGAFYLVFEYMDHDLMGLLESGLVHFSEDHIKSFMKQLMEGLEYC
HKKNFLHRDIKCSNILLNNSGQIKLADFGLARLYNSEESRPYTNKVITLW
YRPPELLLGEERYTPAIDVWSCGCILGELFTKKPIFQANLELAQLELISR
LCGSPCPAVWPDVIKLPYFNTMKPKKQYRRRLREEFSFIPSAALDLLDHM
LTLDPSKRCTAEQTLQSDFLKDVELSKMAPPDLPHWQDCHELWSKKRRRQ
RQSGVVVEEPPPSKTSRKETTSGTSTEPVKNSSPAPPQPAPGKVESGAGD
AIGLADITQQLNQSELAVLLNLLQSQTDLSIPQMAQLLNIHSNPEMQQQL
EALNQSISALTEATSQQQDSETMAPEESLKEAPSAPVILPSAEQTTLEAS
STPADMQNILAVLLSQLMKTQEPAGSLEENNSDKNSGPQGPRRTPTMPQE
EAAACPPHILPPEKRPPEPPGPPPPPPPPPLVEGDLSSAPQELNPAVTAA
LLQLLSQPEAEPPGHLPEHQALRPMEYSTRPRPNRTYGNTDGPETGFSA
IDTDERNSGPALTESLVQTLVKNRTFSGSLSHLGESSSYQGTGSVQFPGD
QDLRFARVPLALHPVVGQPFLKAEGSSNSVVHAETKLQNYGELGPGTTGA
SSSGAGLHWGGPTQSSAYGKLYRGPTRVPPRGGRGRGVPY
```

CDK13, cyclin-dependent kinase 13, is a CDK, wherein the relevant cyclin is cyclin K and a reference inhibitor is the pan-CDK inhibitor Flavopiridol and the c-terminal domain (CTD) of RNA-polymerase II is a physiological substrate. CDK13 is alternatively referred to as CHED; CDC2L; CDC2L5; or hCDK13. Non-limiting examples of the nucleotide and protein sequences for human CDK12 are described in GenBank Accession Number M80629, which is incorporated herein by reference. The amino acid sequence of this CDK13 is as follows:

```
MPSSSDTALGGGGGLSWAEKKLEERRKRRRFLSPQQPPLLLPLLQPQLLQ
PPPPPPPLLFLAAPGTAAAAAAAAASSSCFSPGPPLEVKRLARGKRRAG
GRQKRRRGPRAGQEAEKRRVFSLPQPQQDGGGGASSGGGVTPLVEYEDVS
SQSEQGLLLGGASAATAATAAGGTGGSGGSPASSSGTQRRGEGSERRPRR
DRRSSSGRSKERHREHRRRDGQRGGSEASKSRSRHSHSGEERAEVAKSGS
SSSSGGRRKSASATSSSSSSRKDRDSKAHRSRTKSSKEPPSAYKEPPKAY
REDKTEPKAYRRRRSLSPLGGRDDSPVSHRASQSLRSRKSPSPAGGGSSP
YSRRLPRSPSPYSRRRSPSYSRHSSYERGGDVSPSPYSSSSWRRSRSPYS
PVLRRSGKSRSRSPYSSRHSRSRSRHRLSRSRSRHSSISPSTLTLKSSLA
AELNKNKKARAAEEAARAAEAAKAAEATKAAEAAAKAAKASNTSTPTKGNT
ETSASASQTNHVKDVKKIKIEHAPSPSSGGTLKNDKAKTKPPLQVTKVEN
NLIVDKATKKAVIVGKESKSAATKEESVSLKEKTKPLTPSIGAKEKEQHV
ALVTSTLPPLPLPPMLPEDKEADSLRGNISVKAVKKEVEKKLRCLLADLP
LPPELPGGDDLSKSPEEKKTATQLHSKRRPKICGPRYGETKEKDIDWGKR
CVDKFDIIGIIGEGTYGQVYKARDKDTGEMVALKKVRLDNEKEGFPITAI
REIKILRQLTHQSIINMKEIVTDKEDALDFKKDKGAFYLVFEYMDHDLMG
LLESGLVHFNENHIKSFMRQLMEGLDYCHKKNFLHRDIKCSNILLNNRGQ
IKLADFGLARLYSSEESRPYTNKVITLWYRPPELLLGEERYTPAIDVWSC
GCILGELFTKKPIFQANQELAQLELISRICGSPCPAVWPDVIKLPYFNTM
KPKKQYRRKLREEFVFIPAAALDLFDYMLALDPSKRCTAEQALQCEFLRD
VEPSKMPPPDLPLWQDCHELWSKKRRRQKQMGMTDDVSTIKAPRKDLSLG
LDDSRTNTPQGVLPSSQLKSQGSSNVAPVKTGPGQHLNHSELAILLNLLQ
SKTSVNMADFVQVLNIKVNSETQQQLNKINLPAGILATGEKQTDPSTPQQ
ESSKPLGGIQPSSQTIQPKVETDAAQAAVQSAFAVLLTQLIKAQQSKQKD
VLLEERENGSGHEASLQLRPPPEPSTPVSGQDDLIQHQDMRILELTPEPD
RPRILPPDQRPPEPPEPPPVTEEDLDYRTENQHVPTTSSSLTDPHAGVKA
ALLQLLAQHQPQDDPKREGGIDYQAGDTYVSTSDYKDNFGSSSFSSAPYV
SNDGLGSSSAPPLERRSFIGNSDIQSLDNYSTASSHSGGPPQPSAFSESF
PSSVAGYGDIYLNAGPMLFSGDKDHRFEYSHGPIAVLANSSDPSTGPEST
HPLPAKMHNYNYGGNLQENPSGPSLMHGQTWTSPAQGPGYSQGYRGHIST
STGRGRGRGLPY
```

The term "PIP kinases", also known as "PIPKs," refers to phosphatidylinositol phosphate kinases or phosphatidylinositol-5-phosphate 4-kinases, a class of enzymes that catalyzes the chemical reaction: ATP+1-phosphatidyl-1D-myo-inositol 4-phosphate ⇌ADP+1-phosphatidyl-1D-myo-inositol 4,5-bisphosphate. PIP kinases are divided into two classes, type I and type II. The type I and type II PIP kinases are 35% identical at the kinase domain. Their sequences are significantly divergent for a stretch of about 25 amino acids in the region of the kinase domain that corresponds to the activation loop of protein kinases. There are three isoforms of type II PIP4-kinase in mammalian cells, namely α (PIP4K2A), β (PIP4K2B), and γ (PIP4K2C) isoforms (Liu et al., Nat. Rev. Drug. Discov., 2009, 8(8): 627-644). At the protein level, the α and β isoforms are 83% identical and the γ isoform is about 60% identical to either one of them. All isoforms are ubiquitously expressed, but the α isoform is found predominantly in brain and platelets, the β isoform in brain and muscle, and the γ isoform in brain and kidney. Although the type II PIP4-kinase isoforms are ubiquitously expressed, changes in protein levels may play a role in the regulation of their cellular function. The type II PIP4-kinase β isoform gene, which localizes to the chromosome 17q11-12, was found to be amplified in primary breast cancer samples with Heregulin 2 gene amplifications and in a subset of breast cancer cell lines. These gene amplifications resulted in increased protein expression, which correlated with increased breast cancer cell proliferation and anchorage-independent growth (Emerling et al., Cell, 2013, 155(4): 844-857). In certain embodiments, the PIPK is PI5P4Kα (i.e. PIP4K2A enzyme) encoded by PIP4K2A gene. In certain embodiments, the PIPK is PI5P4Kβ (i.e. PIP4K2B enzyme) encoded by PIP4K2B gene. In certain embodiments, the PIPK is PI5P4Kγ (i.e. PIP4K2C enzyme) encoded by PIP4K2C gene. As used herein, type II PIP4Ks enzymes are referred as follows: PI5P4K is interchangeable with PIP4K; PI5P4Kα is interchangeable with PIP4Kα, PIP4K2A, PIP4K2A enzyme, and PIP4K2A protein; PI5P4Kβ is interchangeable with PIP4Kβ, PIP4K2B, PIP4K2B enzyme, and PIP4K2B protein; PI5P4Kγ is interchangeable with PIP4Kγ, PIP4K2C, PIP4K2C enzyme, and PIP4K2C protein.

In certain embodiments, the PIP4K2A enzyme is sp|P48426|PI42A_HUMAN Phosphatidylinositol 5-phosphate 4-kinase type-2 alpha (OS=*Homo sapiens*, GN=PIP4K2A, PE=1, and SV=2) and of the following sequence:

```
MATPGNLGSSVLASKTKTKKKHFVAQKVKLFRASDPLLSVLMWGVNHSIN

ELSHVQIPVMLMPDDFKAYSKIKVDNHLFNKENMPSHFKFKEYCPMVFRN

LRERFGIDDQDFQNSLTRSAPLPNDSQARSGARFHTSYDKRYIIKTITSE

DVAEMHNILKKYHQYIVECHGITLLPQFLGMYRLNVDGVEIYVIVTRNVF

SHRLSVYRKYDLKGSTVAREASDKEKAKELPTLKDNDFINEGQKIYIDDN

NKKVFLEKLKKDVEFLAQLKLMDYSLLVGIHDVERAEQEEVECEENDGEE

EGESDGTHPVGTPPDSPGNTLNSSPPLAPGEFDPNIDVYGIKCHENSPRK

EVYFMAIIDILTHYDAKKKAAHAAKTVKHGAGAEISTVNPEQYSKRFLDF

IGHILT
```

In certain embodiments, the PIP4K2B enzyme is sp|P78356|PI42B_HUMAN Phosphatidylinositol 5-phosphate 4-kinase type-2 beta (OS=*Homo sapiens*, GN=PIP4K2B, PE=1, and SV=1) and of the following sequence:

```
MSSNCTSTTAVAVAPLSASKTKTKKKHFVCQKVKLFRASEPILSVLMWGV

NHTINELSNVPVPVMLMPDDFKAYSKIKVDNHLFNKENLPSRFKFKEYCP

MVFRNLRERFGIDDQDYQNSVTRSAPINSDSQGRCGTRFLTTYDRRFVIK

TVSSEDVAEMHNILKKYHQFIVECHGNTLLPQFLGMYRLTVDGVETYMVV

TRNVFSHRLTVHRKYDLKGSTVAREASDKEKAKDLPTFKDNDFLNEGQKL

HVGEESKKNFLEKLKRDVEFLAQLKIMDYSLLVGIHDVDRAEQEEMEVEE

RAEDEECENDGVGGNLLCSYGTPPDSPGNLLSFPRFFGPGEFDPSVDVYA

MKSHESSPKKEVYFMAIIDILTPYDTKKKAAHAAKTVKHGAGAEISTVNP

EQYSKRFNEFMSNILT
```

In certain embodiments, the PIP4K2C enzyme is sp|Q8TBX8|PI42C_HUMAN Phosphatidylinositol 5-phosphate 4-kinase type-2 gamma (OS=*Homo sapiens*, GN=PIP4K2C, PE=1, and SV=3) and of the following sequence:

```
MASSSVPPATVSAATAGPGPGFGFASKTKKKHFVQQKVKVFRAADPLVGV

FLWGVAHSINELSQVPPPVMLLPDDFKASSKIKVNNHLFHRENLPSHFKF

KEYCPQVFRNLRDRFGIDDQDYLVSLTRNPPSESEGSDGRFLISYDRTLV

IKEVSSEDIADMHSNLSNYHQYIVKCHGNTLLPQFLGMYRVSVDNEDSYM

LVMRNMFSHRLPVHRKYDLKGSLVSREASDKEKVKELPTLKDMDFLNKNQ

KVYIGEEEKKIFLEKLKRDVEFLVQLKIMDYSLLLGIHDIIRGSEPEEEA

PVREDESEVDGDCSLTGPPALVGSYGTSPEGIGGYIHSHRPLGPGEFESF

IDVYAIRSAEGAPQKEVYFMGLIDILTQYDAKKKAAHAAKTVKHGAGAEI

STVHPEQYAKRFLDFITNIFA
```

In certain embodiments, the PIP4K2A gene of Gene ID: 5305 and HGNC:8997 and has the cDNA sequence as follows:

```
ATGGCGACCCCCGGCAACCTAGGGTCCTCTGTCCTGGCGAGCAAGACCAA

GACCAAGAAGAAGCACTTCGTAGCGCAGAAAGTGAAGCTGTTTCGGGCCA

GCGACCCGCTGCTCAGCGTCCTCATGTGGGGGGTAAACCACTCGATCAAT

GAACTGAGCCATGTTCAAATCCCTGTTATGTTGATGCCAGATGACTTCAA

AGCCTATTCAAAAATAAAGGTGGACAATCACCTTTTTAACAAAGAAAACA

TGCCAAGCCATTTCAAGTTTAAGGAATACTGCCCGATGGTCTTCCGTAAC

CTGCGGGAGAGGTTTGGAATTGATGATCAAGATTTCCAGAATTCCCTGAC

CAGGAGCGCACCCCTCCCCAACGACTCCCAGGCCCGCAGTGGAGCTCGTT

TTCACACTTCCTACGACAAAAGATACATCATCAAGACTATTACCAGTGAA

GACGTGGCCGAAATGCACAACATCCTGAAGAAATACCACCAGTACATAGT

GGAATGTCATGGGATCACCCTTCTTCCCCAGTTCTTGGGCATGTACCGGC

TTAATGTTGATGGAGTTGAAATATATGTGATAGTTACAAGAAATGTATTC

AGCCACCGTTTGTCTGTGTATAGGAAATACGACTTAAAGGGCTCTACAGT
```

-continued
GGCTAGAGAAGCTAGTGACAAAGAAAAGGCCAAAGAACTGCCAACTCTGA

AAGATAATGATTTCATTAATGAGGGCCAAAAGATTTATATTGATGACAAC

AACAAGAAGGTCTTCCTGGAAAAACTAAAAAAGGATGTTGAGTTTCTGGC

CCAGCTGAAGCTCATGGACTACAGTCTGCTGGTGGGAATTCATGATGTGG

AGAGAGCCGAACAGGAGGAAGTGGAGTGTGAGGAGAACGATGGGGAGGAG

GAGGGCGAGAGCGATGGCACCCACCCGGTGGGAACCCCCCCAGATAGCCC

CGGGAATACACTGAACAGCTCACCACCCCTGGCTCCCGGGGAGTTCGATC

CGAACATCGACGTCTATGGAATTAAGTGCCATGAAAACTCGCCTAGGAAG

GAGGTGTACTTCATGGCAATTATTGACATCCTTACTCATTATGATGCAAA

AAAGAAAGCTGCCCATGCTGCAAAAACTGTTAAACATGGCGCTGGCGCGG

AGATCTCCACCGTGAACCCAGAACAGTATTCAAAGCGCTTTTTGGACTTT

ATTGGCCACATCTTGACGTAA

In certain embodiments, the PIP4K2B gene of Gene ID: 8396 and HGNC:8998, and has the cDNA sequence as follows:

ATGTCGTCCAACTGCACCAGCACCACGGCGGTGGCGGTGGCGCCGCTCAG

CGCCAGCAAGACCAAGACCAAGAAGAAGCATTTCGTGTGCCAGAAAGTGA

AGCTATTCCGGGCCAGCGAGCCGATCCTCAGCGTCCTGATGTGGGGGGTG

AACCACACGATCAATGAGCTGAGCAATGTTCCTGTTCCTGTCATGCTAAT

GCCAGATGACTTCAAAGCCTACAGCAAGATCAAGGTGGACAATCATCTCT

TCAATAAGGAGAACCTGCCCAGCCGCTTTAAGTTTAAGGAGTATTGCCCC

ATGGTGTTCCGAAACCTTCGGGAGAGGTTTGGAATTGATGATCAGGATTA

CCAGAATTCAGTGACGCGCAGCGCCCCCATCAACAGTGACAGCCAGGGTC

GGTGTGGCACGCGTTTCCTCACCACCTACGACCGGCGCTTTGTCATCAAG

ACTGTGTCCAGCGAGGACGTGGCGGAGATGCACAACATCTTAAAGAAATA

CCACCAGTTTATAGTGGAGTGTCATGGCAACACGCTTTTGCCACAGTTCC

TGGGCATGTACCGCCTGACCGTGGATGGTGTGGAAACCTACATGGTGGTT

ACCAGGAACGTGTTCAGCCATCGGCTCACTGTGCATCGCAAGTATGACCT

CAAGGGTTCTACGGTTGCCAGAGAAGCGAGCGACAAGGAGAAGGCCAAGG

ACTTGCCAACATTCAAAGACAATGACTTCCTCAATGAAGGGCAGAAGCTG

CATGTGGGAGAGGAGAGTAAAAAGAACTTCCTGGAGAAACTGAAGCGGGA

CGTTGAGTTCTTGGCACAGCTGAAGATCATGGACTACAGCCTGCTGGTGG

GCATCCACGACGTGGACCGGGCAGAGCAGGAGGAGATGGAGGTGGAGGAG

CGGGCAGAGGACGAGGAGTGTGAGAATGATGGGGTGGGTGGCAACCTACT

CTGCTCCTATGGCACACCTCCGGACAGCCCTGGCAACCTCCTCAGCTTTC

CTCGGTTCTTTGGTCCTGGGGAATTCGACCCCTCTGTTGACGTCTATGCC

ATGAAAAGCCATGAAAGTTCCCCCAAGAAGGAGGTGTATTTCATGGCCAT

CATTGATATCCTCACGCCATACGATACAAAGAAGAAAGCTGCACATGCTG

CCAAAACGGTGAAACACGGGGCAGGGGCCGAGATCTCGACTGTGAACCCT

GAGCAGTACTCCAAACGCTTCAACGAGTTTATGTCCAACATCCTGACGTA

G

In certain embodiments, the PIP4K2C gene of Gene ID: 79837 and HGNC:23786, and has the cDNA sequence as follows:

ATGGCGTCCTCCTCGGTCCCACCAGCCACGGTATCGGCGGCGACAGCAGG

CCCCGGCCCAGGTTTCGGCTTCGCCTCCAAGACCAAGAAGAAGCATTTCG

TGCAGCAGAAGGTGAAGGTGTTCCGGGCGGCCGACCCGCTGGTGGGTGTG

TTCCTGTGGGGCGTAGCCCACTCGATCAATGAGCTCAGCCAGGTGCCTCC

CCCGGTGATGCTGCTGCCAGATGACTTTAAGGCCAGCTCCAAGATCAAGG

TCAACAATCACCTTTTCCACAGGGAAAATCTGCCCAGTCATTTCAAGTTC

AAGGAGTATTGTCCCCAGGTCTTCAGGAACCTCCGTGATCGATTTGGCAT

TGATGACCAAGATTACTTGGTGTCCCTTACCCGAAACCCCCCAGCGAAA

GTGAAGGCAGTGATGGTCGCTTCCTTATCTCCTACGATCGGACTCTGGTC

ATCAAAGAAGTATCCAGTGAGGACATTGCTGACATGCATAGCAACCTCTC

CAACTATCACCAGTACATTGTGAAGTGCCATGGCAACACGCTTCTGCCCC

AGTTCCTGGGGATGTACCGAGTCAGTGTGGACAACGAAGACAGCTACATG

CTTGTGATGCGCAATATGTTTAGCCACCGTCTTCCTGTGCACAGGAAGTA

TGACCTCAAGGGTTCCCTAGTGTCCCGGGAAGCCAGCGATAAGGAAAAGG

TTAAAGAATTGCCCACCCTTAAGGATATGGACTTTCTCAACAAGAACCAG

AAAGTATATATTGGTGAAGAGGAGAAGAAAATATTTCTGGAGAAGCTGAA

GAGAGATGTGGAGTTTCTAGTGCAGCTGAAGATCATGGACTACAGCCTTC

TGCTAGGCATCCACGACATCATTCGGGGCTCTGAACCAGAGGAGGAAGCG

CCCGTGCGGGAGGATGAGTCAGAGGTGGATGGGGACTGCAGCCTGACTGG

ACCTCCTGCTCTGGTGGGCTCCTATGGCACCTCCCCAGAGGGTATCGGAG

GCTACATCCATTCCCATCGGCCCCTGGGCCCAGGAGAGTTTGAGTCCTTC

ATTGATGTCTATGCCATCCGGAGTGCTGAAGGAGCCCCCCAGAAGGAGGT

CTACTTCATGGGCCTCATTGATATCCTTACACAGTATGATGCTAAGAAGA

AAGCAGCTCATGCAGCCAAAACTGTCAAGCATGGGGCTGGGGCAGAGATC

TCTACTGTCCATCCGGAGCAGTATGCTAAGCGATTCCTGGATTTTATTAC

CAACATCTTTGCCTAA

BRIEF DESCRIPTION OF THE DRAWINGS

FIG. 3A: THZ-CE-A7 inhibited the kinase activity of both PI5P4Kα and PI5P4Kβ. Radiometric kinase assay was performed using $C^{32}P$-ATP and PI5P. The radiolabeled product, PI(4,5)P$_2$, was measured after the separation by thin layer chromatography. FIG. 3B: THZ-CE-A7 inhibited the proliferation of TP53 mutant BT474 cells at 1 µM (left panel). The inhibition stayed effective after 6 hours of treatment and washout (middle panel). THZ-CE-A7 did not inhibit TP53 wild type MCF7 cells at 1 µM (right panel).

DETAILED DESCRIPTION OF CERTAIN EMBODIMENTS OF THE INVENTION

Figure 1:
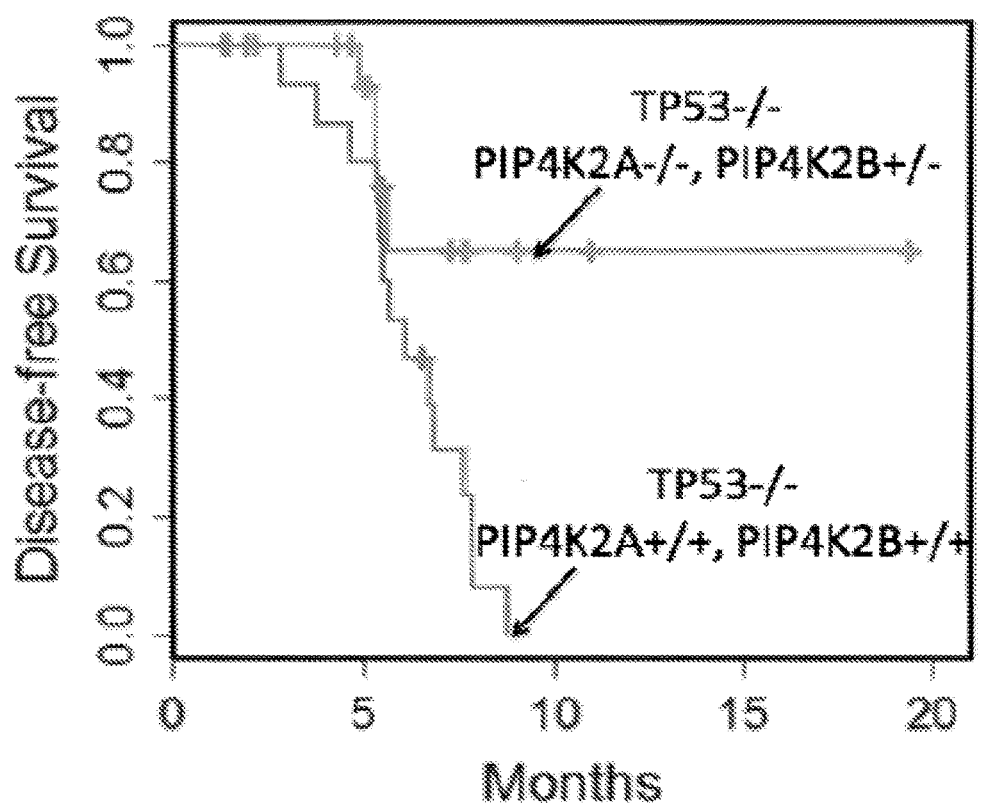
FIG. 1 shows that loss of PIP4K2α/β restricts tumor death after p53 deletion. Kaplan-Meier plot analysis was conducted for tumor free survival after p53 deletion. 15 TP53$^{-/-}$PIP4K2A$^{+/+}$PIP4K2B$^{+/+}$ and 20 TP53$^{-/-}$PIP4K2A$^{-/-}$PIP4K2B$^{+/-}$ mice were tested. *p<0.05 with two-tailed Student's t test. TP53$^{-/-}$PIP4K2A$^{-/-}$PIP4K2B$^{+/-}$ mice had a great increase of tumor free survival compared to TP53$^{-/-}$PIP4K2A$^{+/+}$PIP4K2B$^{+/+}$ mice. (Emerling et al., Cell, 2013, 155(4):844-57).

Recent studies have shown that lipid kinases play an essential role in inhibiting cancer cell growth when the TP53 function is absent. Depletion of two lipid kinases, PIP4K2A and PIP4K2B, selectively inhibited the proliferation of TP53 mutant breast cancer cell line (BT474 cells) while cells that were wild-type for TP53 were unaffected (Emerling et al., Cell, 2013, 155: 844-857). Further research has shown that mice expressing one allele of PIP4K2B and homozygous deletion of PIP4K2A and TP53 are viable and exhibit a dramatic reduction in cancers and extended lifespan compared to their littermates that were TP53 deleted with wild type PIP4K2A. Therefore, small molecule inhibitors of lipid kinases may hold promise as a therapeutic agent for treating proliferative diseases.

The present invention provides compounds, which inhibit the activity of a kinase, for the prevention and/or treatment of a proliferative disease of a subject. In certain embodiments, the inventive compounds inhibit the activity of a lipid kinase, such as PIP4K. The present invention further provides methods of using the compounds described herein, e.g., as biological probes to study the modulation of the activity of a kinase (e.g., a lipid kinase such as PIP4K), and as therapeutics, e.g., in the prevention and/or treatment of diseases associated with the overexpression and/or aberrant activity of the kinase (e.g., a lipid kinase such as PIP4K). In certain embodiments, the disease being treated and/or prevented is a proliferative disease. Exemplary proliferative diseases include, but are not limited to, cancers (e.g., lung cancer, breast cancer, leukemia, melanoma, multiple myeloma), benign neoplasms, angiogenesis, inflammatory diseases, autoinflammatory diseases, and autoimmune diseases. In certain embodiments, the cancer is associated with the overexpression and/or aberrant activity of a kinase (e.g., a lipid kinase such as PIP4K).

Compounds

In one aspect of the present invention, provided are compounds of Formula (I):

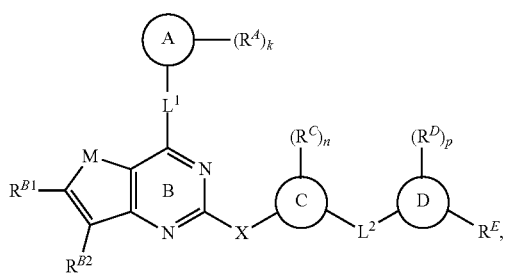

or a pharmaceutically acceptable salt thereof, wherein:

Ring A is a substituted or unsubstituted, monocyclic or bicyclic heteroaryl ring or a substituted or unsubstituted, monocyclic heterocyclic ring;

each instance of $R^A$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

k is 0, 1, 2, 3, 4, 5, or 6;

M is $NR^M$, O, or S;

$R^M$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$L^1$ is a bond, —C($R^b$)$_2$—, —C(=O)—, —O—, —S—, —S(=O)—, —S(=O)$_2$—, or —$NR^c$—;

each instance of $R^b$ is independently hydrogen, halogen, or substituted or unsubstituted $C_{1-6}$ alkyl;

each instance of $R^c$ is independently hydrogen, substituted or unsubstituted $C_{1-6}$ alkyl, or a nitrogen protecting group;

$R^{B1}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

$R^{B2}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

X is —C($R^b$)$_2$—, —C(=O)—, —O—, —S—, —S(=O)—, —S(=O)$_2$—, —$NR^c$—, —C($R^b$)$_2$C($R^b$)$_2$—, —C($R^b$)$_2$C(=O)—, —C(=O)C($R^b$)$_2$—, (E)-C$R^b$=C$R^b$—, (Z)—C$R^b$=C$R^b$—, —C≡C—, —OC(=O)—, —C(=O)O—, —SC(=O)—, —C(=O)S—, —$NR^cC$(=O)—, —C(=O)$NR^c$—, —OC($R^b$)$_2$—, —C($R^b$)$_2$O—, —SC($R^b$)$_2$—, —C($R^b$)$_2$S—, —$NR^cC$($R^b$)$_2$—, —C($R^b$)$_2NR^c$—, —S(=O)O—, —OS(=O)—, —S(=O)$NR^c$—, —$NR^cS$(=O)—, —S(=O)$_2$O—, —OS(=O)$_2$—, —S(=O)$_2NR^c$—, or —$NR^cS$(=O)$_2$—;

Ring C is a substituted or unsubstituted phenyl ring;

Ring D is a substituted or unsubstituted phenyl ring;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

n is 0, 1, 2, 3, or 4;

$L^2$ is —C($R^b$)$_2$—, —C(=O)—, —O—, —S—, —S(=O)—, —S(=O)$_2$—, —$NR^c$—, —C($R^b$)$_2$C($R^b$)$_2$—, —C($R^b$)$_2$C(=O)—, —C(=O)C($R^b$)$_2$—, (E)-C$R^b$=C$R^b$—, (Z)—C$R^b$=C$R^b$—, —C≡C—, —OC(=O)—, —C(=O)O—, —SC(=O)—, —C(=O)S—, —$NR^c$C(=O)—, —C(=O)$NR^c$—, —OC($R^b$)$_2$—, —C($R^b$)$_2$O—, —SC($R^b$)$_2$—, —C($R^b$)$_2$S—, —$NR^c$C($R^b$)$_2$—, —C($R^b$)$_2$$NR^c$—, —S(=O)O—, —OS(=O)—, —S(=O)$NR^c$—, —$NR^c$S(=O)—, —S(=O)$_2$O—, —OS(=O)$_2$—, —S(=O)$_2$$NR^c$—, —$NR^c$S(=O)$_2$—, —OC(=O)O—, —$NR^c$C(=O)O—, —OC(=O)$NR^c$—, —$NR^c$C(=O)$NR^c$—, —C($R^b$)$_2$C(=O)C($R^b$)$_2$—, —OC(=O)C($R^b$)$_2$—, —C($R^b$)$_2$C(=O)O—, —$NR^c$C(=O)C($R^b$)$_2$—, —C($R^b$)$_2$C(=O)$NR^c$—, or a substituted or unsubstituted $C_{1-4}$ hydrocarbon chain, optionally wherein one or more carbon units of the hydrocarbon chain are independently replaced with —C(=O)—, —O—, —S—, —S(=O)—, —S(=O)$_2$—, or —$NR^c$—;

each instance of $R^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

p is 0, 1, 2, 3, or 4;

$R^E$ is of the formula:

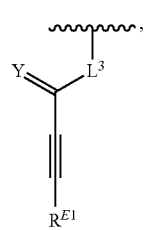
(i-1)

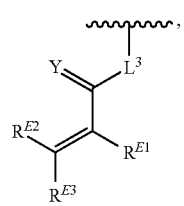
(i-2)

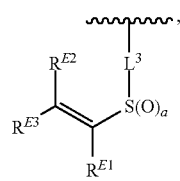
(i-3)

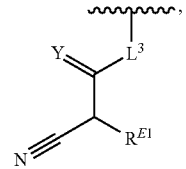
(i-4)

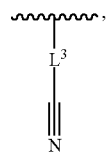
(i-5)

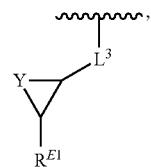
(i-6)

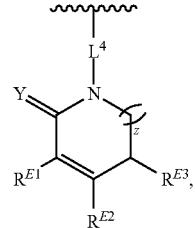
(i-7)

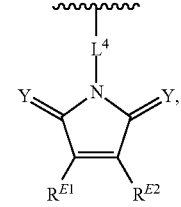
(i-8)

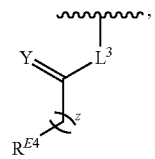
(i-9)

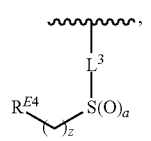
(i-10)

(i-11) 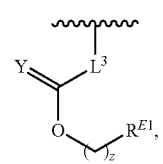
(i-12) 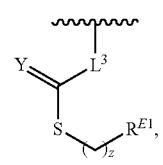
(i-13) 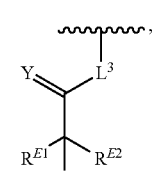
(i-14) 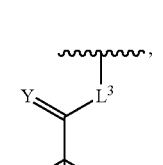
(i-15) 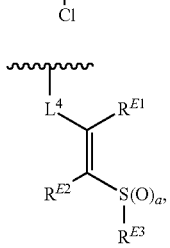
(i-16) 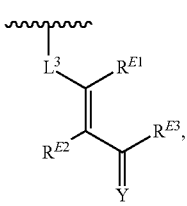
(i-17) 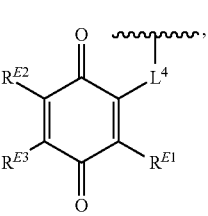
(i-18) 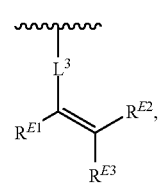
(i-19) 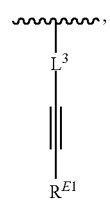
(i-20) 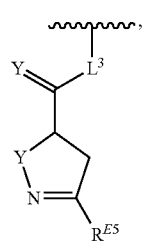
(i-21) 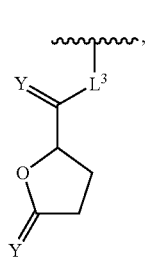
(i-22) 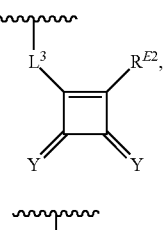
(i-23) 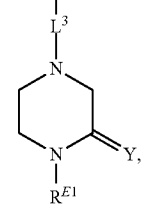
(i-24) 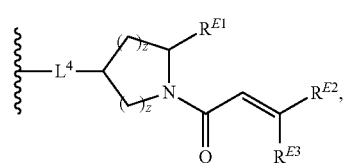
(i-25) 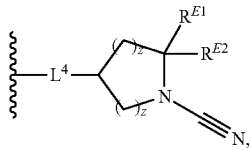

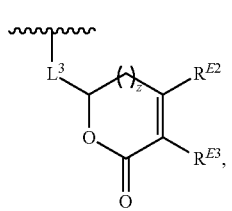 (i-26)

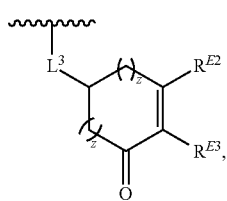 (i-27)

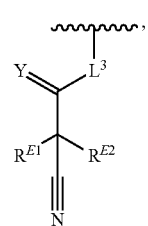 (i-28)

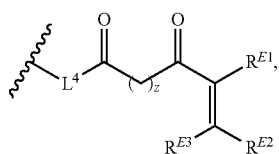 (i-29)

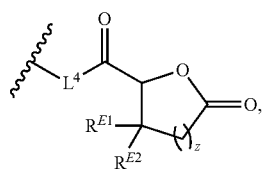 (i-30)

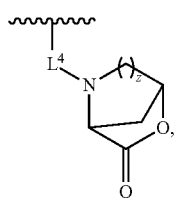 (i-31)

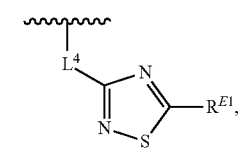 (i-32)

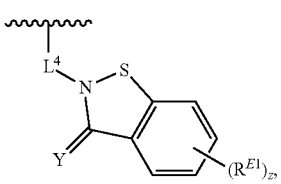 (i-33)

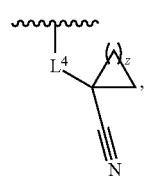 (i-34)

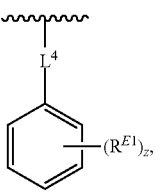 (i-35)

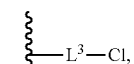 (i-36)

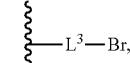 (i-37)

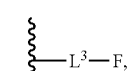 (i-38)

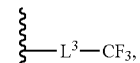 (i-39)

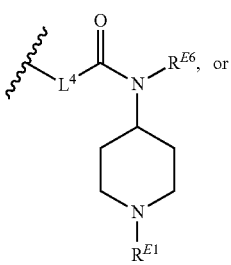 (i-40)

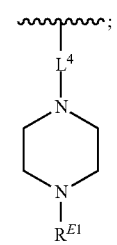 (i-41)

$L^3$ is —$C(R^b)_2$—, —C(=O)—, —O—, —S—, —S(O)—, —S(=O)—, —S(=O)$_2$—, —NR$^c$—, —$C(R^b)_2C(R^b)_2$—, —$C(R^b)_2$C(=O)—, —C(=O)$C(R^b)_2$—, (E)-CR$^b$=CR$^b$—, (Z)—CR$^b$=CR$^b$—, —C≡C—, —OC(=O)—, —C(=O)O—, —SC(=O)—, —C(=O)S—, —NR$^c$C(=O)—, —C(=O)NR$^c$—, —OC$(R^b)_2$—, —$C(R^b)_2$O—, —SC$(R^b)_2$—, —$C(R^b)_2$S—, —NR$^c$C$(R^b)_2$—, —$C(R^b)_2$NR$^c$—, —S(=O)O—, —OS(=O)—, —S(=O)NR$^c$—, —NR$^c$S(=O)—, —S(=O)$_2$O—, —OS(=O)$_2$—, —S(=O)$_2$NR$^c$—, —NR$^c$S(=O)$_2$—, —OC(=O)O—, —NR$^c$C(=O)O—, —OC(=O)NR$^c$—, —NR$^c$C(=O)NR$^c$—, —$C(R^b)_2$C(=)C$(R^b)_2$—,

—OC(=O)C($R^b$)$_2$—, —C($R^b$)$_2$C(=O)—, —N$R^c$C(=O)C($R^b$)$_2$—, —C($R^b$)$_2$C(=O)N$R^c$—, or a substituted or unsubstituted C$_{1-4}$ hydrocarbon chain, optionally wherein one or more carbon units of the hydrocarbon chain are independently replaced with —C(=O)—, —O—, —S—, —S(=O)—, —S(=O)$_2$—, or —N$R^c$—;

$L^4$ is a bond or substituted or unsubstituted C$_{1-6}$ hydrocarbon chain;

each of $R^{E1}$, $R^{E2}$, and $R^{E3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —CH$_2$O$R^a$, —CH$_2$N($R^a$)$_2$, —CH$_2$S$R^a$, —O$R^a$, —N($R^a$)$_2$, —S$R^a$, or —Si($R^a$)$_3$; or $R^{E1}$ and $R^{E3}$, or $R^{E2}$ and $R^{E3}$, or $R^{E1}$ and $R^{E2}$ are joined to form a substituted or unsubstituted, carbocyclic ring, or substituted or unsubstituted, heterocyclic ring;

$R^{E4}$ is a leaving group;

$R^{E5}$ is halogen;

$R^{E6}$ is hydrogen, substituted or unsubstituted C$_{1-6}$ alkyl, or a nitrogen protecting group;

each instance of Y is independently O, S, or N$R^c$;

a is 1 or 2; and each instance of z is independently 0, 1, 2, 3, 4, 5, or 6.

In certain embodiments, the compound described herein is of Formula (I), or a pharmaceutically acceptable salt thereof, wherein:

Ring A is a substituted or unsubstituted, bicyclic heteroaryl ring or a substituted or unsubstituted, monocyclic heterocyclic ring;

each instance of $R^A$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

k is 0, 1, 2, 3, 4, 5, or 6;

M is N$R^M$, O, or S;

$R^M$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$L^1$ is a bond, —C($R^b$)$_2$—, —C(=O)—, —O—, —S—, —S(=O)—, —S(=O)$_2$—, or —N$R^c$—;

each instance of $R^b$ is independently hydrogen, halogen, or substituted or unsubstituted C$_{1-6}$ alkyl;

each instance of $R^c$ is independently hydrogen, substituted or unsubstituted C$_{1-6}$ alkyl, or a nitrogen protecting group;

$R^{B1}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

$R^{B2}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

X is —C($R^b$)$_2$—, —C(=O)—, —O—, —S—, —S(=O)—, —S(=O)$_2$—, —N$R^c$—, —C($R^b$)$_2$C($R^b$)$_2$—, —C($R^b$)$_2$C(=O)—, —C(=O)C($R^b$)$_2$—, (E)-C$R^b$=C$R^b$—, (Z)—C$R^b$=C$R^b$—, —C≡C—, —OC(=O)—, —C(=O)O—, —SC(=O)—, —C(=O)S—, —N$R^c$C(=O)—, —C(=O)N$R^c$—, —OC($R^b$)$_2$—, —C($R^b$)$_2$O—, —SC($R^b$)$_2$—, —C($R^b$)$_2$S—, —N$R^c$C($R^b$)$_2$—, —C($R^b$)$_2$N$R^c$—, —S(=O)O—, —OS(=O)—, —S(=O)N$R^c$—, —N$R^c$S(=O)—, —S(=O)$_2$O—, —OS(=O)$_2$—, —S(=O)$_2$N$R^c$—, or —N$R^c$S(=O)$_2$—;

Ring C is a substituted or unsubstituted phenyl ring;

Ring D is a substituted or unsubstituted phenyl ring;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

n is 0, 1, 2, 3, or 4;

$L^2$ is —C($R^b$)$_2$—, —C(=O)—, —O—, —S—, —S(O)—, —S(=O)—, —S(=O)$_2$—, —N$R^c$—, —C($R^b$)$_2$C($R^b$)$_2$—, —C($R^b$)$_2$C(=O)—, —C(=O)C($R^b$)$_2$—, (E)-C$R^b$=C$R^b$—, (Z)—C$R^b$=C$R^b$—, —C≡C—, —OC(=O)—, —C(=O)O—, —SC(=O)—, —C(=O)S—, —N$R^c$C(=O)—, —C(=O)N$R^c$—, —OC($R^b$)$_2$—, —C($R^b$)$_2$O—, —SC($R^b$)$_2$—, —C($R^b$)$_2$S—, —N$R^c$C($R^b$)$_2$—, —C($R^b$)$_2$N$R^c$—, —S(=O)O—, —OS(=O)—, —S(=O)N$R^c$—, N$R^c$S(=O)—, —S(=O)$_2$O—, —OS(=O)$_2$—, —S(=O)$_2$N$R^c$—, —N$R^c$S(=O)$_2$—, —OC(=O)O—, —N$R^c$C(=O)O—, —OC(=O)N$R^c$—, —N$R^c$C(=O)N$R^c$—, —C($R^b$)$_2$C(=)C($R^b$)$_2$—, —OC(=O)C($R^b$)$_2$—, —C($R^b$)$_2$C(=O)O—, —N$R^c$C(=O)C($R^b$)$_2$—, —C($R^b$)$_2$C(=O)N$R^c$—, or a substituted or unsubstituted C$_{1-4}$ hydrocarbon chain, optionally wherein one or more carbon units of the hydrocarbon chain are independently replaced with —C(=O)—, —O—, —S—, —S(=O)—, —S(=O)$_2$—, or —N$R^c$—;

each instance of $R^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

p is 0, 1, 2, 3, or 4;

R$^E$ is of the formula:

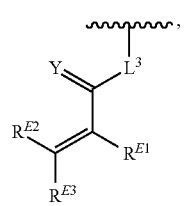 (i-1)

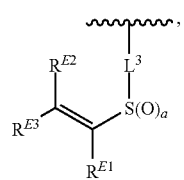 (i-2)

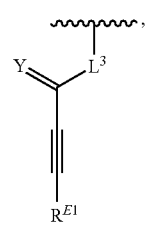 (i-3)

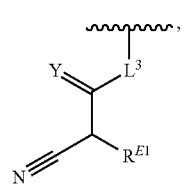 (i-4)

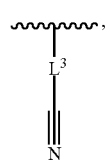 (i-5)

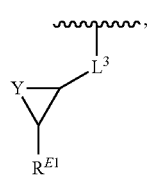 (i-6)

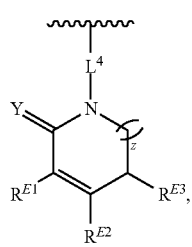 (i-7)

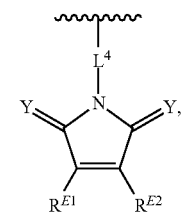 (i-8)

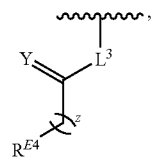 (i-9)

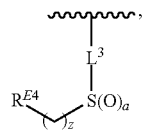 (i-10)

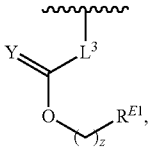 (i-11)

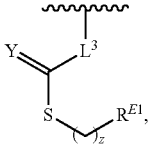 (i-12)

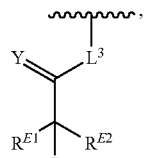 (i-13)

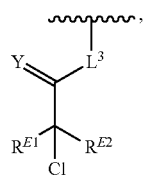 (i-14)

-continued
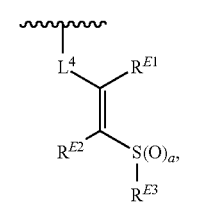 (i-15)
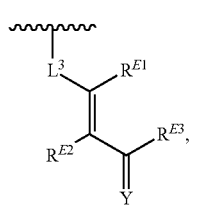 (i-16)
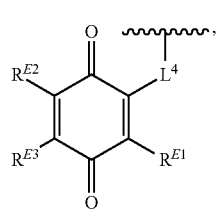 (i-17)
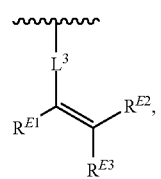 (i-18)
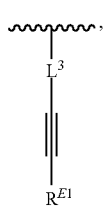 (i-19)
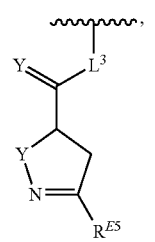 (i-20)
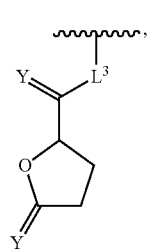 (i-21)
-continued
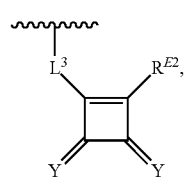 (i-22)
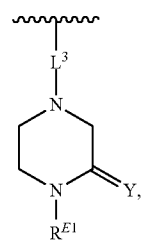 (i-23)
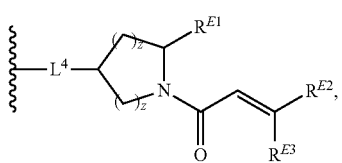 (i-24)
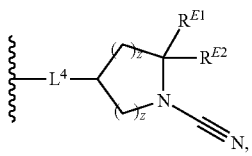 (i-25)
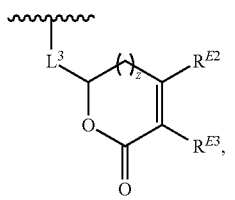 (i-26)
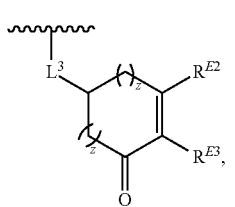 (i-27)
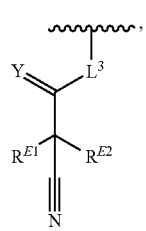 (i-28)
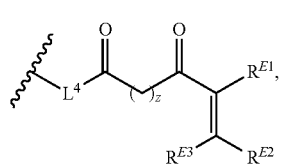 (i-29)

(i-30) 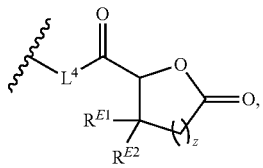

(i-31) 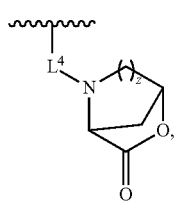

(i-32) 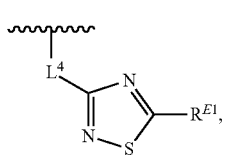

(i-33) 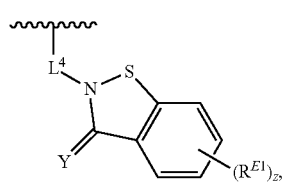

(i-34) 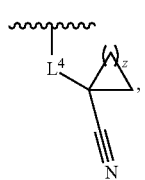

(i-35) 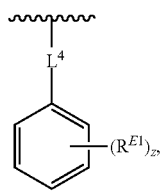

(i-36) 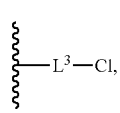

(i-37) 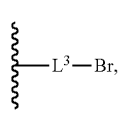

(i-38) 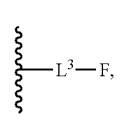

(i-39) 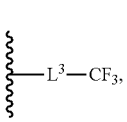

(i-40) 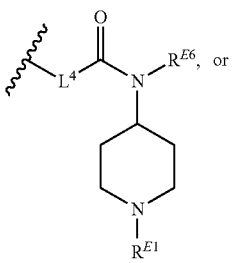

(i-41) 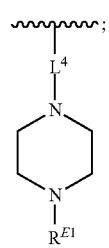

$L^3$ is —C($R^b$)$_2$—, —C(=O)—, —O—, —S—, —S(=O)—, —S(=O)$_2$—, —N$R^c$—, —C($R^b$)$_2$C($R^b$)$_2$—, —C($R^b$)$_2$C(=O)—, —C(=O)C($R^b$)$_2$—, (E)-C$R^b$=C$R^b$—, (Z)—C$R^b$=C$R^b$—, —C≡C—, —OC(=O)—, —C(=O)O—, —SC(=O)—, —C(=O)S—, —N$R^c$C(=O)—, —C(=O)N$R^c$—, —OC($R^b$)$_2$—, —C($R^b$)$_2$O—, —SC($R^b$)$_2$—, —C($R^b$)$_2$S—, —N$R^c$C($R^b$)$_2$—, —C($R^b$)$_2$N$R^c$—, —S(=O)O—, —OS(=O)—, —S(=O)N$R^c$—, —N$R^c$S(=O)—, —S(=O)$_2$O—, —OS(=O)$_2$—, —S(=O)$_2$N$R^c$—, —N$R^c$S(=O)$_2$—, —OC(=O)O—, —N$R^c$C(=O)O—, —OC(=O)N$R^c$—, —N$R^c$C(=O)N$R^c$—, —C($R^b$)$_2$C(=)C($R^b$)$_2$—, —OC(=O)C($R^b$)$_2$—, —C($R^b$)$_2$C(=)O—, —N$R^c$C(=O)C($R^b$)$_2$—, —C($R^b$)$_2$C(=O)N$R^c$—, or a substituted or unsubstituted $C_{1-4}$ hydrocarbon chain, optionally wherein one or more carbon units of the hydrocarbon chain are independently replaced with —C(=O)—, —O—, —S—, —S(=O)—, —S(=O)$_2$—, or —N$R^c$—;

$L^4$ is a bond or substituted or unsubstituted $C_{1-6}$ hydrocarbon chain;

each of $R^{E1}$, $R^{E2}$, and $R^{E3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —CH$_2$O$R^a$, —CH$_2$N($R^a$)$_2$, —CH$_2$S$R^a$, —O$R^a$, —N($R^a$)$_2$, —S$R^a$, or —Si($R^a$)$_3$; or $R^{E1}$ and $R^{E3}$, or $R^{E2}$ and $R^{E3}$, or $R^{E1}$ and $R^{E2}$ are joined to form a substituted or unsubstituted, carbocyclic ring, or substituted or unsubstituted, heterocyclic ring;

$R^{E4}$ is a leaving group;

$R^{E5}$ is halogen;

$R^{E6}$ is hydrogen, substituted or unsubstituted $C_{1-6}$ alkyl, or a nitrogen protecting group;

each instance of Y is independently O, S, or N$R^c$;

a is 1 or 2; and each instance of z is independently 0, 1, 2, 3, 4, 5, or 6.

As generally defined herein, M is N$R^M$, O, or S. In certain embodiments, M is N$R^M$, wherein $R^M$ is as defined herein. In certain embodiments, M is N$R^M$, wherein $R^M$ is hydrogen, substituted or unsubstituted alkenyl, or a nitrogen protecting group. In certain embodiments, M is NH. In certain embodiments, M is O. In certain embodiments, M is S.

Compounds of Formula (I) include Ring A attached to Ring B through linker $L^1$. In certain embodiments, Ring A is a substituted or unsubstituted bicyclic heteroaryl ring. In certain embodiments, Ring A is a substituted or unsubstituted, 9- or 10-membered, bicyclic heteroaryl ring, wherein one, two, three, or four atoms in the heteroaryl ring system are independently oxygen, nitrogen, or sulfur, as valency permits. In certain embodiments, Ring A is a substituted or unsubstituted bicyclic heteroaryl ring with one nitrogen. In certain embodiments, Ring A is a substituted or unsubstituted bicyclic heteroaryl ring with two nitrogen. In certain embodiments, Ring A is a substituted or unsubstituted monocyclic heteroaryl ring fused with a substituted or unsubstituted monocyclic aryl ring. In certain embodiments, Ring A is a substituted or unsubstituted monocyclic heteroaryl ring fused with another substituted or unsubstituted monocyclic heteroaryl ring. Ring A may be a substituted or unsubstituted 6,5-membered heteroaryl ring or a substituted or unsubstituted 5,6-membered heteroaryl ring. In certain embodiments, Ring A is a substituted or unsubstituted monocyclic 5-membered heteroaryl ring fused with a substituted or unsubstituted monocyclic 6-membered aryl ring. In certain embodiments, Ring A is a substituted or unsubstituted monocyclic 5-membered heteroaryl ring fused with a substituted or unsubstituted monocyclic 6-membered heteroaryl ring. The point of attachment of Ring A to Ring B may be at any atom of Ring A, as valency permits. In certain embodiments, Ring A is of Formula (i-1):

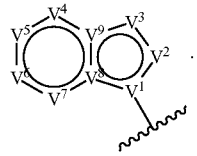
(i-1)

In certain embodiments, Ring A is of Formula (i-2):

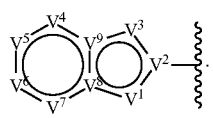
(i-2)

In certain embodiments, Ring A is of Formula (i-3)

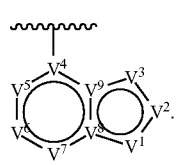
(i-3)

In certain embodiments, Ring A is of Formula (i-4):

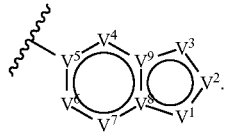
(i-4)

In compounds of Formula (I), $V^1$, $V^2$, $V^3$, $V^4$, $V^5$, $V^6$, $V^7$, $V^8$, and $V^9$ of Ring A may each independently be O, S, N, $NR^{41}$, C, or $CR^{42}$, as valency permits. In certain embodiments, $V^1$ is O, S, N or $NR^{41}$. In certain embodiments, $V^1$ is N or $NR^{41}$. In certain embodiments, Ring A is of the formula:

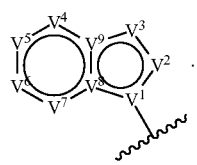

In certain embodiments, Ring A is of the formula:

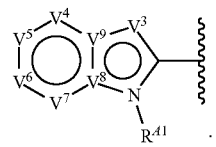

In certain embodiments, Ring A is of the formula:

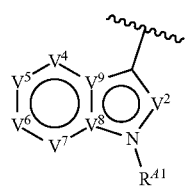

In certain embodiments, Ring A is of the formula:

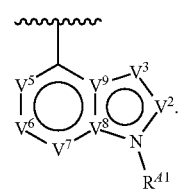

In certain embodiments, Ring A is of the formula:

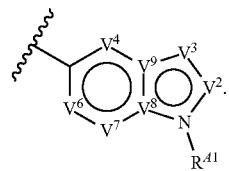

In certain embodiments, Ring A is of the formula:

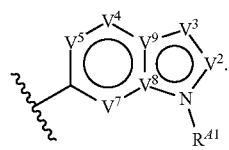

In certain embodiments, Ring A is of the formula:

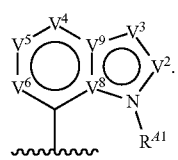

In certain embodiments, only one of $V^1$, $V^2$, $V^3$, $V^4$, $V^5$, $V^6$, $V^7$, $V^8$, and $V^9$ is selected from the group consisting of O, S, N, and $NR^{A1}$. In certain embodiments, only one of $V^1$, $V^2$, $V^3$, $V^4$, $V^5$, $V^6$, $V^7$, $V^8$, and $V^9$ is selected from the group consisting of N and $NR^{A1}$. In certain embodiments, $V^1$ is N or $NR^{A1}$; $V^2$, $V^3$, $V^4$, $V^5$, $V^6$, $V^7$, $V^8$, and $V^9$ are each independently C or $CR^{A2}$; and therefore, Ring A is a substituted or unsubstituted indole ring. In certain embodiments, Ring A is of Formula (A-i):

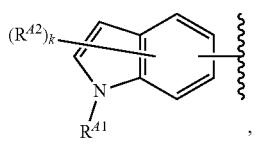

(A-i)

wherein $R^{A1}$, $R^{A2}$, and k are as defined herein. In certain embodiments, k is 0, 1, 2, 3, 4, or 5. In certain embodiments, Ring A is of Formula (iii-1):

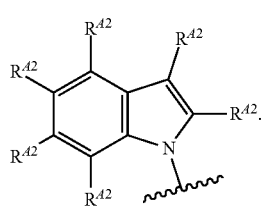

(iii-1)

In certain embodiments, Ring A is of Formula (iii-2):

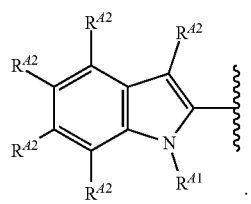

(iii-2)

In certain embodiments, Ring A is of Formula (iii-3):

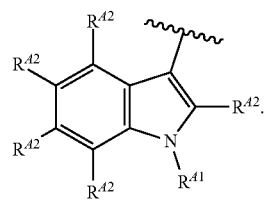

(iii-3)

In certain embodiments, Ring A is of the formula:

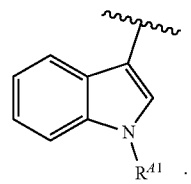

In certain embodiments, Ring A is of the formula:

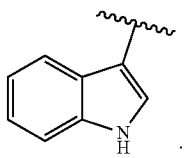 [SMILES: *c1c[nH]c2ccccc12]

In certain embodiments, Ring A is of Formula (iii-4):

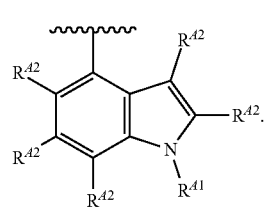

(iii-4)

In certain embodiments, Ring A is of Formula (iii-5):

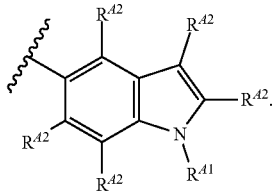
(iii-5)

In certain embodiments, Ring A is of Formula (iii-6):

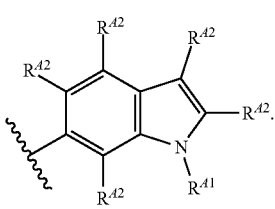
(iii-6)

In certain embodiments, Ring A is of Formula (iii-7):

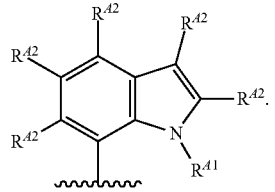
(iii-7)

In certain embodiments, only two of $V^1$, $V^2$, $V^3$, $V^4$, $V^5$, $V^6$, $V^7$, $V^8$, and $V^9$ are each independently selected from the group consisting of O, S, N, and $NR^{A1}$. In certain embodiments, only two of $V^1$, $V^2$, $V^3$, $V^4$, $V^5$, $V^6$, $V^7$, $V^8$, and $V^9$ are each independently selected from the group consisting of N and $NR^{A1}$. In certain embodiments, $V^1$ is N or $NR^{A1}$; and only one of $V^2$, $V^3$, $V^4$, $V^5$, $V^6$, $V^7$, $V^8$, and $V^9$ is N or $NR^{A1}$. In certain embodiments, V and $V^2$ are each independently N or $NR^{A1}$; $V^3$, $V^4$, $V^5$, $V^6$, $V^7$, $V^8$, and $V^9$ are each independently C or $CR^{A2}$; and therefore, Ring A is a substituted or unsubstituted indazole ring. In certain embodiments, Ring A is of Formula (A-ii):

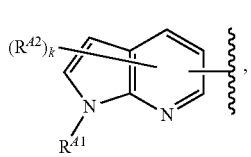
(A-ii)

wherein $R^{A1}$, $R^{A2}$, and k are as defined herein. In certain embodiments, k is 0, 1, 2, 3, or 4. In certain embodiments, Ring A is of the formula:

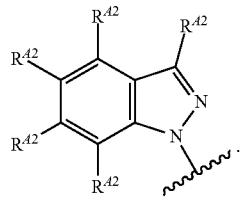

In certain embodiments, Ring A is of the formula:

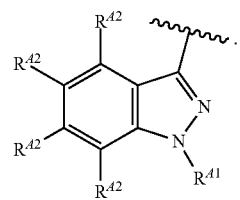

In certain embodiments, Ring A is of the formula:

In certain embodiments, Ring A is of the formula:

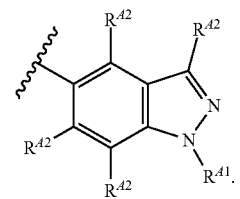

In certain embodiments, Ring A is of the formula:

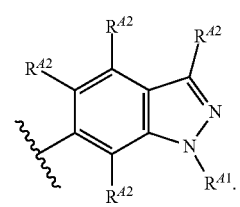

In certain embodiments, Ring A is of the formula:

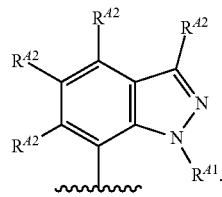

In certain embodiments, Ring A is of Formula (A-iii):

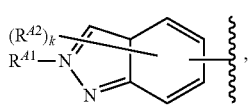 (A-iii)

wherein $R^{A1}$, $R^{A2}$, and k are as defined herein. In certain embodiments, k is 0, 1, 2, 3, or 4. In certain embodiments, Ring A is of the formula:

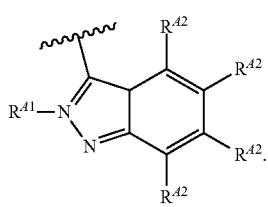

In certain embodiments, Ring A is of the formula:

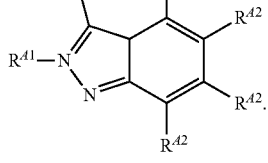

In certain embodiments, Ring A is of the formula:

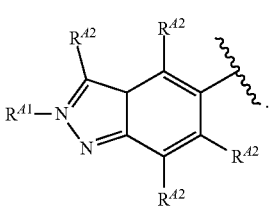

In certain embodiments, Ring A is of the formula:

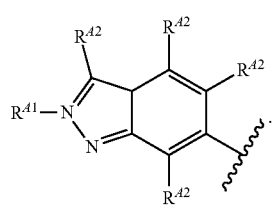

In certain embodiments, Ring A is of the formula:

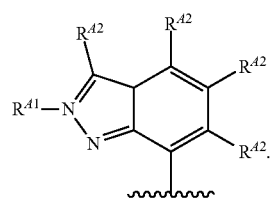

In certain embodiments, Ring A is of the formula:

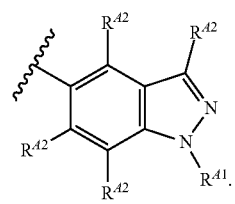

In certain embodiments, Ring A is of the formula:

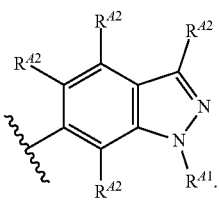

In certain embodiments, Ring A is of the formula:

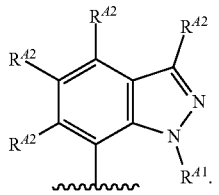

In certain embodiments, $V^1$ and $V^3$ are each independently N or $NR^{A1}$; $V^2$, $V^4$, $V^5$, $V^6$, $V^7$, $V^8$, and $V^9$ are each independently C or $CR^{A2}$; and therefore, Ring A is a substituted or unsubstituted benzimidazole ring. In certain embodiments, Ring A is of Formula (iv-1):

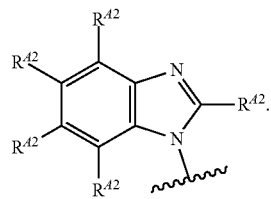

(iv-1)

In certain embodiments, Ring A is of Formula (iv-2):

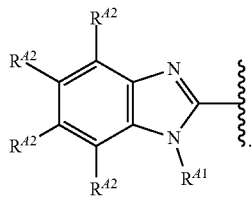

(iv-2)

In certain embodiments, Ring A is of Formula (iv-3):

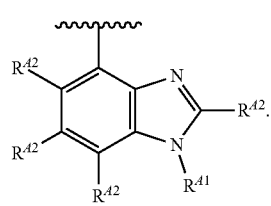

(iv-3)

In certain embodiments, Ring A is of Formula (iv-4):

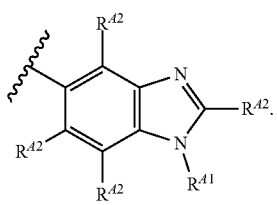

(iv-4)

In certain embodiments, Ring A is of Formula (iv-5):

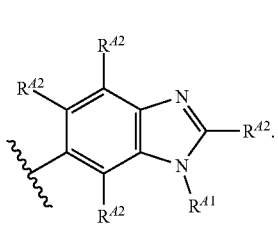

(iv-5)

In certain embodiments, Ring A is of Formula (iv-6):

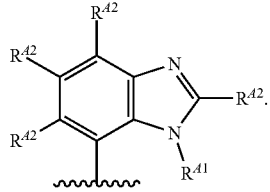

(iv-6)

In certain embodiments, $V^1$ and $V^4$ are each independently N or $NR^{A1}$; $V^2$, $V^3$, $V^5$, $V^6$, $V^7$, $V^8$, and $V^9$ are each independently C or $CR^{A2}$; and therefore, Ring A is a substituted or unsubstituted 4-azaindazole ring. In certain embodiments, Ring A is of the formula:

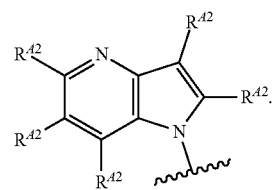

In certain embodiments, Ring A is of the formula:

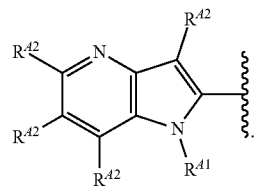

In certain embodiments, Ring A is of the formula:

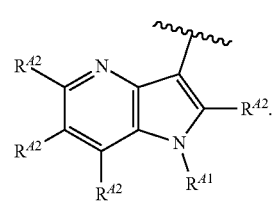

In certain embodiments, Ring A is of the formula:

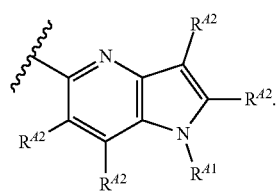

In certain embodiments, Ring A is of the formula:

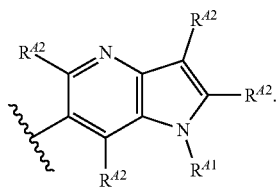

In certain embodiments, Ring A is of the formula:

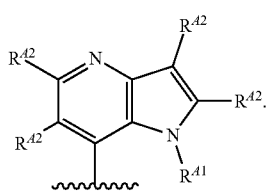

In certain embodiments, $V^1$ and $V^5$ are each independently N or $NR^{A1}$; $V^2$, $V^3$, $V^4$, $V^6$, $V^7$, $V^8$, and $V^9$ are each independently C or $CR^{A2}$; and therefore, Ring A is a substituted or unsubstituted 5-azaindazole ring. In certain embodiments, Ring A is of the formula:

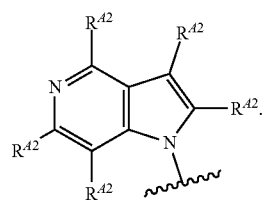

In certain embodiments, Ring A is of the formula:

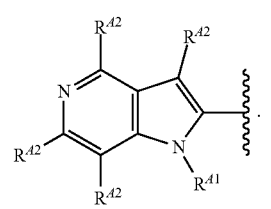

In certain embodiments, Ring A is of the formula:

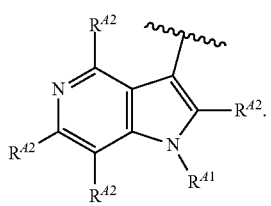

In certain embodiments, Ring A is of the formula:

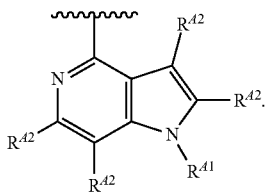

In certain embodiments, Ring A is of the formula:

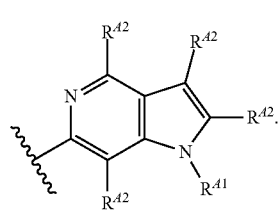

In certain embodiments, Ring A is of the formula:

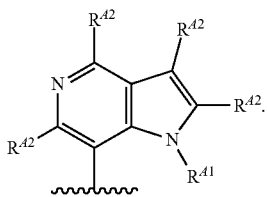

In certain embodiments, $V^1$ and $V^6$ are each independently N or $NR^{A1}$; $V^2$, $V^3$, $V^4$, $V^5$, $V^7$, $V^8$, and $V^9$ are each independently C or $CR^{A2}$; and therefore, Ring A is a substituted or unsubstituted 6-azaindole ring. In certain embodiments, Ring A is of the formula:

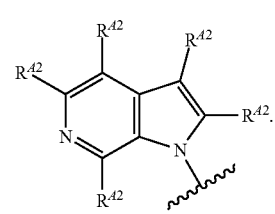

In certain embodiments, Ring A is of the formula:

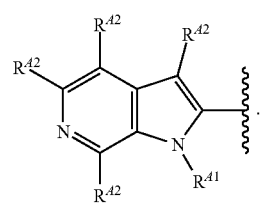

In certain embodiments, Ring A is of the formula:

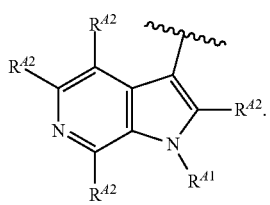

In certain embodiments, Ring A is of the formula:

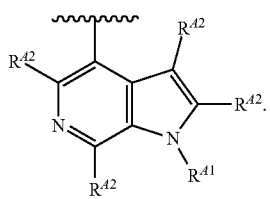

In certain embodiments, Ring A is of the formula:

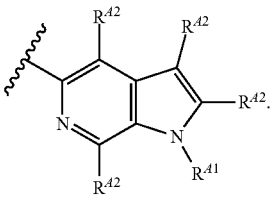

In certain embodiments, Ring A is of the formula:

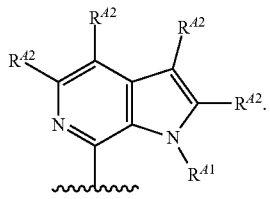

In certain embodiments, $V^1$ and $V^7$ are each independently N or $NR^{A1}$; $V^2$, $V^3$, $V^4$, $V^5$, $V^6$, $V^8$, and $V^9$ are each independently C or $CR^{A2}$; and therefore, Ring A is a substituted or unsubstituted 7-azaindole ring. In certain embodiments, Ring A is of Formula (v-1):

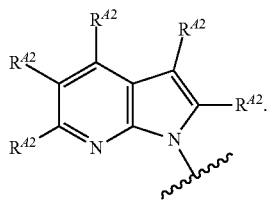

(v-1)

In certain embodiments, Ring A is of Formula (v-2):

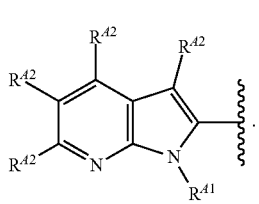

(v-2)

In certain embodiments, Ring A is of Formula (v-3):

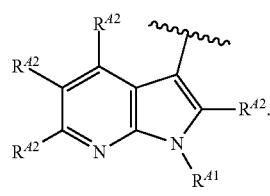

(v-3)

In certain embodiments, Ring A is of Formula (v-4):

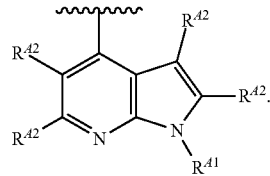

(v-4)

In certain embodiments, Ring A is of Formula (v-5):

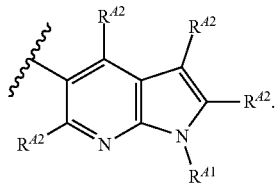

(v-5)

In certain embodiments, Ring A is of Formula (v-6):

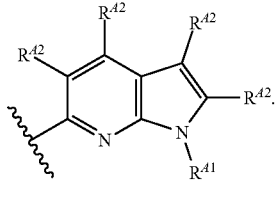

(v-6)

In certain embodiments, $V^1$ and $V^a$ are each independently N or $NR^{A1}$, $V^2$, $V^3$, $V^4$, $V^5$, $V^6$, $V^7$, and $V^9$ are each independently C or $CR^{A2}$; and therefore, Ring A is a substituted or unsubstituted 8-azaindole ring. In certain embodiments, Ring A is of Formula (vi-1):

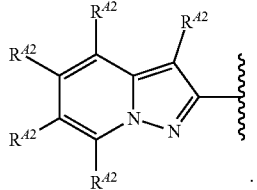
(vi-1)

In certain embodiments, Ring A is of Formula (vi-2):

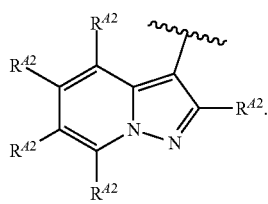
(vi-2)

In certain embodiments, Ring A is of Formula (vi-3):

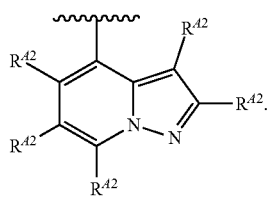
(vi-3)

In certain embodiments, Ring A is of Formula (vi-4):

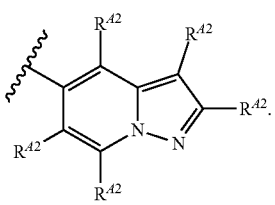
(vi-4)

In certain embodiments, Ring A is of Formula (vi-5):

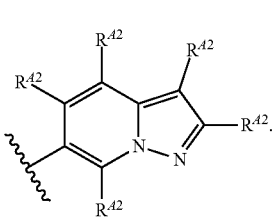
(vi-5)

In certain embodiments, Ring A is of Formula (vi-6):

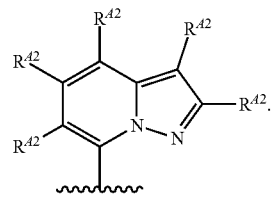
(vi-6)

In certain embodiments, $V^1$ and $V^9$ are each independently N or $NR^{A1}$; $V^2$, $V^3$, $V^4$, $V^5$, $V^6$, $V^7$, and $V^8$ are each independently C or $CR^{A2}$; and therefore, Ring A is a substituted or unsubstituted 9-azaindole ring. In certain embodiments, Ring A is of the formula:

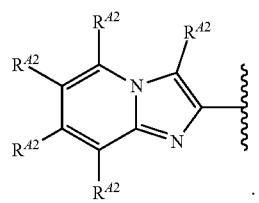

In certain embodiments, Ring A is of the formula:

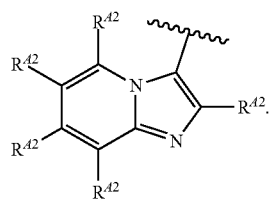

In certain embodiments, Ring A is of the formula:

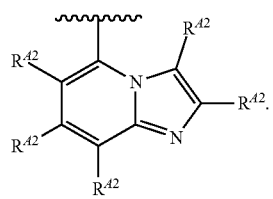

In certain embodiments, Ring A is of the formula:

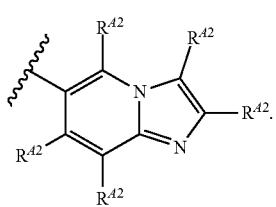

In certain embodiments, Ring A is of the formula:

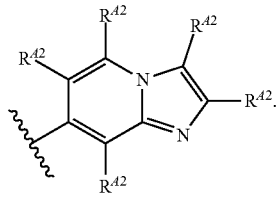

In certain embodiments, Ring A is of the formula:

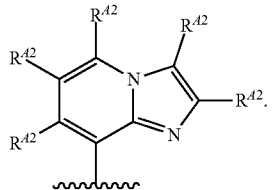

In certain embodiments, only three of $V^1$, $V^2$, $V^3$, $V^4$, $V^5$, $V^6$, $V^7$, $V^8$, and $V^9$ are each independently selected from the group consisting of O, S, N, and $NR^{A1}$. In certain embodiments, only three of $V^1$, $V^2$, $V^3$, $V^4$, $V^5$, $V^6$, $V^7$, $V^8$, and $V^9$ are each independently selected from the group consisting of N and $NR^{A1}$. In certain embodiments, $V^1$ is N or $NR^{A1}$; and only two of $V^2$, $V^3$, $V^4$, $V^5$, $V^6$, $V^7$, $V^8$, and $V^9$ are each independently N or $NR^{A1}$.

In compounds of Formula (I), Ring A may also be a substituted or unsubstituted monocyclic heteroaryl ring. In certain embodiments, Ring A is a substituted or unsubstituted, 5- or 6-membered, monocyclic heteroaryl ring, wherein one, two, three, or four atoms in the heteroaryl ring system are independently oxygen, nitrogen, or sulfur, as valency permits. In compounds of Formula (I), Ring A may also be a substituted or unsubstituted 5-membered heteroaryl ring. In certain embodiments, Ring A is of Formula (i-5):

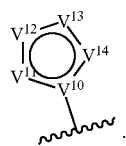

(i-5)

In compounds of Formula (I), $V^{10}$, $V^{11}$, $V^{12}$, $V^{13}$, and $V^{14}$ of Ring A may each independently be O, S, N, $NR^{A1}$, C, or $CR^{A2}$, as valency permits. In certain embodiments, only one of $V^{10}$, $V^{11}$, $V^{12}$, $V^{13}$, and $V^{14}$ is selected from the group consisting of O, S, N, and $NR^{A1}$. In certain embodiments, Ring A is of the formula:

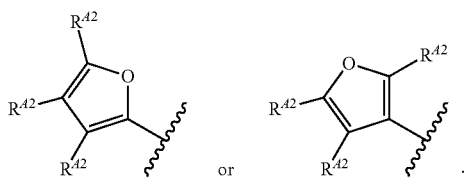

In certain embodiments, Ring A is of the formula:

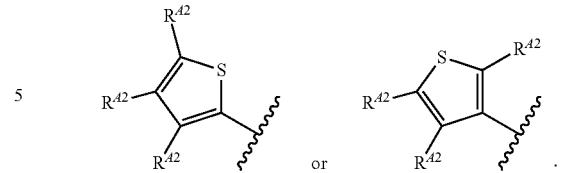

In compounds of Formula (I), Ring A may also be a substituted or unsubstituted monocyclic heteroaryl ring. In compounds of Formula (I), Ring A may also be a substituted or unsubstituted 5-membered heteroaryl ring. In certain embodiments, Ring A is of Formula (i-5):

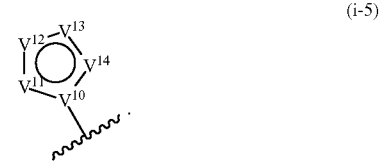

(i-5)

In certain embodiments, only two of $V^{10}$, $V^{11}$, $V^{12}$, $V^{13}$, and $V^{14}$ are each independently selected from the group consisting of O, S, N, and $NR^{A1}$. In certain embodiments, Ring A is of the formula:

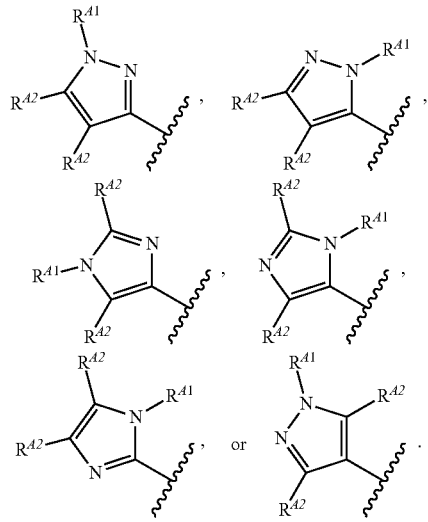

In certain embodiments, Ring A is of the formula:

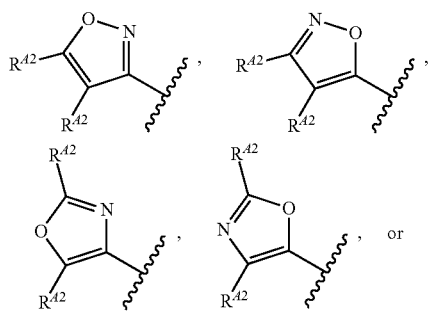

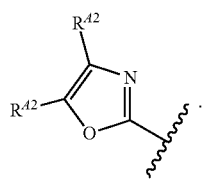

In certain embodiments, Ring A is of the formula:

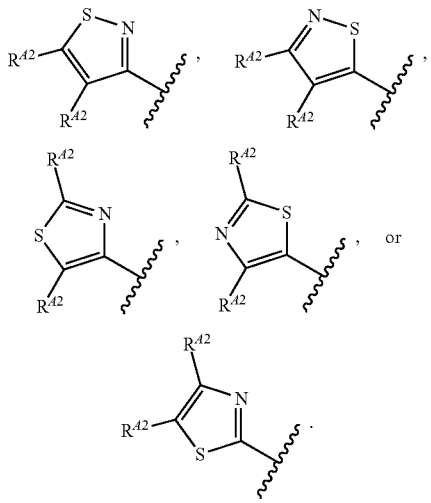

In certain embodiments, Ring A is of Formula (vii):

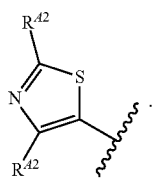

In certain embodiments, Ring A is of the formula:

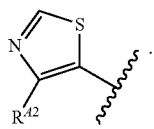

In certain embodiments, Ring A is of the formula:

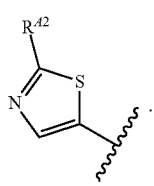

In certain embodiments, Ring A is of the formula:

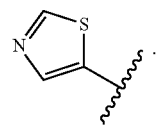

In certain embodiments, only three of $V^{10}$, $V^{11}$, $V^{12}$, $V^{13}$, and $V^{14}$ are each independently selected from the group consisting of O, S, N, and $NR^{A1}$. In certain embodiments, Ring A is of the formula:

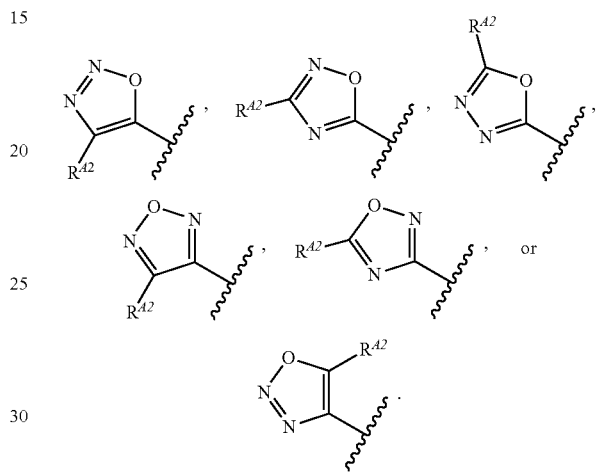

In certain embodiments, Ring A is of the formula:

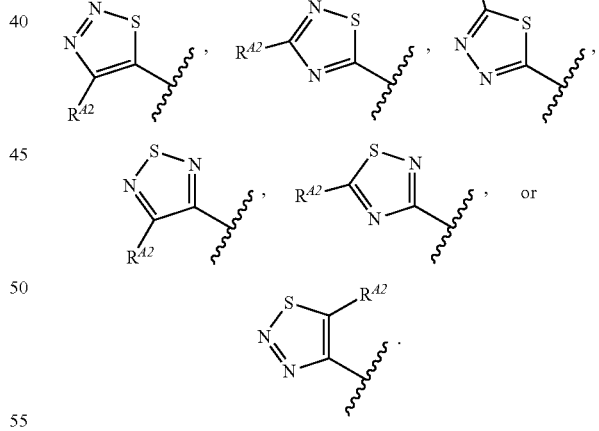

In certain embodiments, Ring A is of the formula:

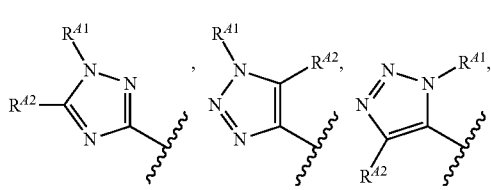

-continued

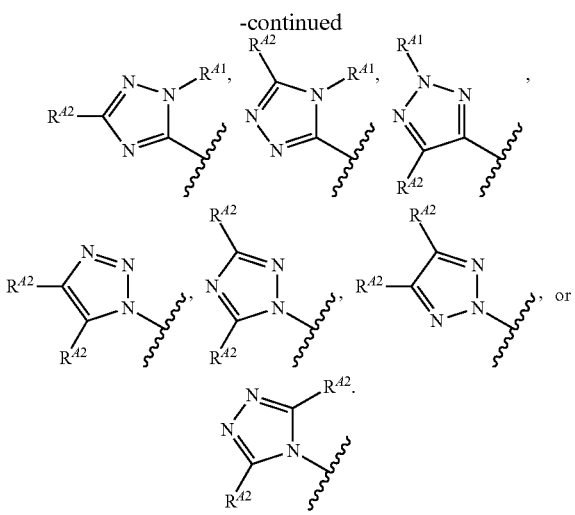

In certain embodiments, only four of $V^{10}$, $V^{11}$, $V^{12}$, $V^{13}$, and $V^{14}$ are each independently selected from the group consisting of N and $NR^{A1}$. In certain embodiments, Ring A is of the formula:

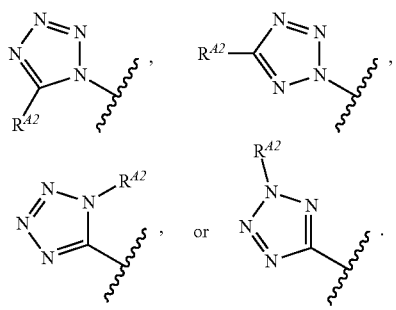

In compounds of Formula (I), Ring A may also be a substituted or unsubstituted 6-membered heteroaryl ring. In certain embodiments, Ring A is of Formula (i-6):

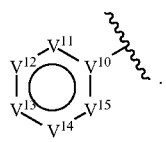
(i-6)

In compounds of Formula (I), $V^{10}$, $V^{11}$, $V^{12}$, $V^{13}$, $V^{14}$, and $V^{15}$ of Ring A may each independently be N, C, or $CR^{A2}$, as valency permits. In certain embodiments, only one of $V^{10}$, $V^{11}$, $V^{12}$, $V^{13}$, $V^{14}$, and $V^{15}$ is N. In certain embodiments, Ring A is of Formula (A-v):

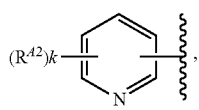
(A-v)

wherein $R^{A2}$ and k are as defined herein. In certain embodiments, k is 0, 1, 2, 3, or 4. In certain embodiments, Ring A is of the formula:

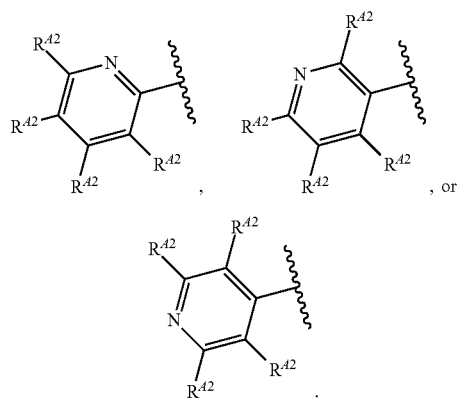

In certain embodiments, only two of $V^{10}$, $V^{11}$, $V^{12}$, $V^{13}$, $V^{14}$, and $V^{15}$ are N. In certain embodiments, Ring A is of the formula:

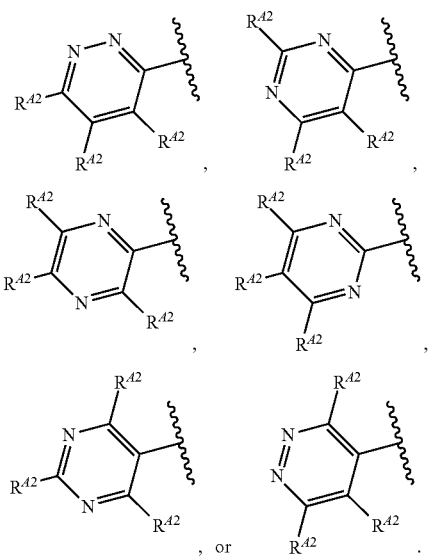

In certain embodiments, only three of $V^{10}$, $V^{11}$, $V^{12}$, $V^{13}$, $V^{14}$, and $V^{15}$ are N. In certain embodiments, Ring A is of the formula:

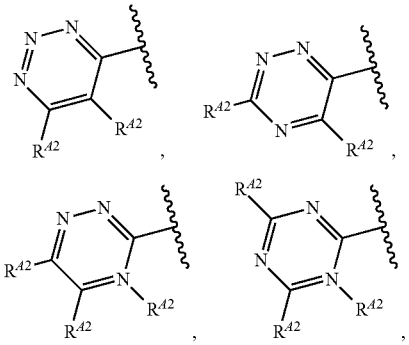

-continued

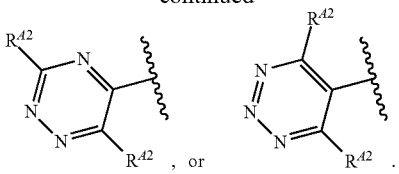

In certain embodiments, Ring A is of the formula:

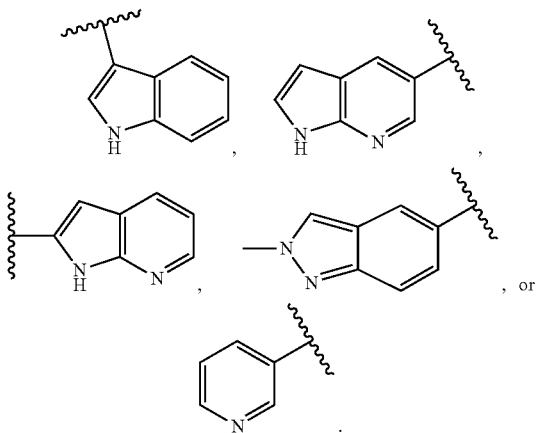

In certain embodiments, Ring A is a substituted or unsubstituted, monocyclic heterocyclic ring. In certain embodiments, Ring A is a substituted or unsubstituted, 3- to 7-membered, monocyclic heterocyclic ring, wherein one, two, or three atoms in the heterocyclic ring system are independently oxygen, nitrogen, or sulfur, as valency permits. In certain embodiments, Ring A is a substituted or unsubstituted 5-membered heterocyclic ring. In certain embodiments, Ring A is a substituted or unsubstituted 6-membered heterocyclic ring. In certain embodiments, Ring A is of Formula (A-vi):

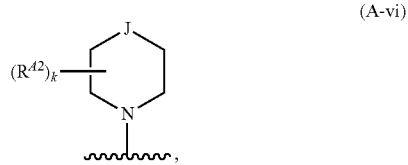

(A-vi)

wherein $R^{A2}$ is as defined herein;

J is $C(R^{CJ})_2$ or $NR^{NJ}$;

each instance of $R^{CJ}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$; and $R^{NJ}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, optionally substituted acyl, or a nitrogen protecting group.

In certain embodiments, k is 0, 1, 2, 3, 4, 5, or 6. In certain embodiments, Ring A is of the formula:

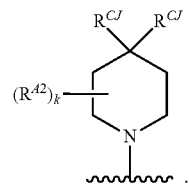

In certain embodiments, at least one $R^{CJ}$ is hydrogen. In certain embodiments, at least one $R^{CJ}$ is halogen. In certain embodiments, at least one $R^{CJ}$ is halogen. In certain embodiments, at least one $R^{CJ}$ is F. In certain embodiments, at least one $R^{CJ}$ is Cl. In certain embodiments, at least one $R^{CJ}$ is Br. In certain embodiments, at least one $R^{CJ}$ is I (iodine). In certain embodiments, at least one $R^{CJ}$ is substituted alkyl. In certain embodiments, at least one $R^{CJ}$ is unsubstituted alkyl. In certain embodiments, at least one $R^{CJ}$ is $C_{1-6}$ alkyl. In certain embodiments, at least one $R^{CJ}$ is methyl. In certain embodiments, at least one $R^{CJ}$ is ethyl. In certain embodiments, at least one $R^{CJ}$ is propyl. In certain embodiments, at least one $R^{CJ}$ is —$OR^a$, wherein $R^a$ is as defined herein. In certain embodiments, at least one $R^{CJ}$ is —$N(R^a)_2$, wherein $R^a$ is as defined herein. In certain embodiments, at least one $R^{CJ}$ is —$NHR^a$, wherein $R^a$ is as defined herein. In certain embodiments, at least one $R^{CJ}$ is —$N(R^a)_2$, wherein two $R^a$ are joined with the intervening nitrogen to form a substituted or unsubstituted heterocyclic ring. In certain embodiments, both instances of $R^{CJ}$ are hydrogen. In certain embodiments, one $R^{CJ}$ is hydrogen and one $R^{CJ}$ is halogen. In certain embodiments, one $R^{CJ}$ is hydrogen and one $R^{CJ}$ is halogen. In certain embodiments, one $R^{CJ}$ is hydrogen and one $R^{CJ}$ is F. In certain embodiments, one $R^{CJ}$ is hydrogen and one $R^{CJ}$ is Cl. In certain embodiments, one $R^{CJ}$ is hydrogen and one $R^{CJ}$ is Br. In certain embodiments, one $R^{CJ}$ is hydrogen and one $R^{CJ}$ is I (iodine). In certain embodiments, one $R^{CJ}$ is hydrogen and one $R^{CJ}$ is substituted alkyl. In certain embodiments, one $R^{CJ}$ is hydrogen and one $R^{CJ}$ is unsubstituted alkyl. In certain embodiments, one $R^{CJ}$ is hydrogen and one $R^{CJ}$ is $C_{1-6}$ alkyl. In certain embodiments, one $R^{CJ}$ is hydrogen and one $R^{CJ}$ is methyl. In certain embodiments, one $R^{CJ}$ is hydrogen and one $R^{CJ}$ is ethyl. In certain embodiments, one $R^{CJ}$ is hydrogen and one $R^{CJ}$ is propyl. In certain embodiments, one $R^{CJ}$ is hydrogen and one $R^{CJ}$ is —$N(R^a)_2$, wherein two $R^a$ are joined with the intervening nitrogen to form a substituted or unsubstituted 5-membered heterocyclic ring. In certain embodiments, one $R^{CJ}$ is hydrogen and one $R^{CJ}$ is —$N(R^a)_2$, wherein two $R^a$ are joined with the intervening nitrogen to form a substituted or unsubstituted 6-membered heterocyclic ring. In certain embodiments, one $R^{CJ}$ is hydrogen and one $R^{CJ}$ is substituted or unsubstituted morpholinyl. In certain embodiments, one $R^{CJ}$ is hydrogen and one $R^{CJ}$ is substituted or unsubstituted piperazinyl. In certain embodiments, one $R^{CJ}$ is hydrogen and one $R^{CJ}$ is substituted or unsubstituted piperidinyl. In certain embodiments, Ring A is of the formula:

In certain embodiments, Ring A is of the formula:

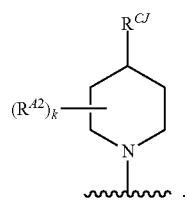

In certain embodiments, Ring A is of the formula:

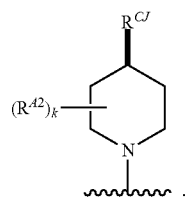

In certain embodiments, Ring A is of the formula:

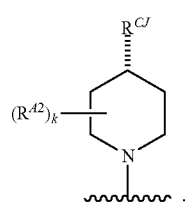

In certain embodiments, Ring A is of the formula:

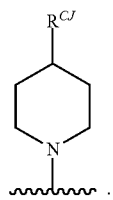

In certain embodiments, Ring A is of the formula:

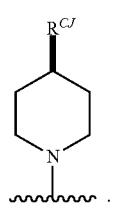

In certain embodiments, Ring A is of the formula:

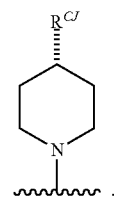

In certain embodiments, Ring A is of the formula:

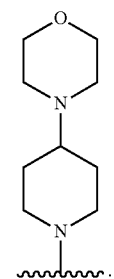

In certain embodiments, Ring A is of the formula:

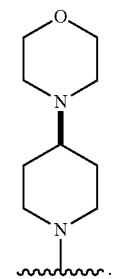

In certain embodiments, Ring A is of the formula:

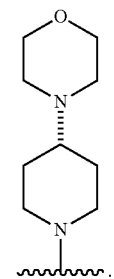

In certain embodiments, Ring A is of the formula:

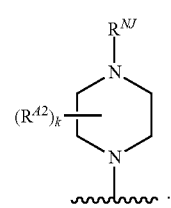

In certain embodiments, Ring A is of the formula:

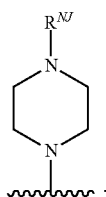

In certain embodiments, $R^{NJ}$ is hydrogen. In certain embodiments, $R^{NJ}$ is substituted alkyl. In certain embodiments, $R^{NJ}$ is unsubstituted alkyl. In certain embodiments, $R^{NJ}$ is $C_{1-6}$ alkyl. In certain embodiments, $R^{NJ}$ is methyl. In certain embodiments, $R^{NJ}$ is ethyl. In certain embodiments, $R^{NJ}$ is propyl. In certain embodiments, $R^{NJ}$ is ethyl. In certain embodiments, $R^{NJ}$ is a nitrogen protecting group. In certain embodiments, $R^{NJ}$ is ethyl. In certain embodiments, $R^{NJ}$ is Boc.

In compounds of Formula (I), Ring A may be substituted with one or more $R^A$ groups when the $R^A$ group is attached to a carbon atom. In certain embodiments, at least one $R^A$ is halogen. In certain embodiments, at least one $R^A$ is F. In certain embodiments, at least one $R^A$ is Cl. In certain embodiments, at least one $R^A$ is Br. In certain embodiments, at least one $R^A$ is I (iodine). In certain embodiments, at least one $R^A$ is substituted alkyl. In certain embodiments, at least one $R^A$ is unsubstituted alkyl. In certain embodiments, at least one $R^A$ is $C_{1-6}$ alkyl. In certain embodiments, at least one $R^A$ is methyl. In certain embodiments, at least one $R^A$ is ethyl. In certain embodiments, at least one $R^A$ is propyl. In certain embodiments, at least one $R^A$ is substituted alkenyl. In certain embodiments, at least one $R^A$ is unsubstituted alkenyl. In certain embodiments, at least one $R^A$ is vinyl. In certain embodiments, at least one $R^A$ is substituted alkynyl. In certain embodiments, at least one $R^A$ is unsubstituted alkynyl. In certain embodiments, at least one $R^A$ is ethynyl. In certain embodiments, at least one $R^A$ is substituted carbocyclyl. In certain embodiments, at least one $R^A$ is unsubstituted carbocyclyl. In certain embodiments, at least one $R^A$ is substituted heterocyclyl. In certain embodiments, at least one $R^A$ is unsubstituted heterocyclyl. In certain embodiments, at least one $R^A$ is substituted aryl. In certain embodiments, at least one $R^A$ is unsubstituted aryl. In certain embodiments, at least one $R^A$ is substituted phenyl. In certain embodiments, at least one $R^A$ is unsubstituted phenyl. In certain embodiments, at least one $R^A$ is substituted heteroaryl. In certain embodiments, at least one $R^A$ is —$OR^a$, wherein $R^a$ is as defined herein. In certain embodiments, at least one $R^A$ is —$OR^a$, wherein $R^{Aa}$ is hydrogen. In certain embodiments, at least one $R^A$ is —$OR^a$, wherein $R^a$ is hydrogen or substituted or unsubstituted $C_{1-6}$ alkyl. In certain embodiments, at least one $R^A$ is —$OR^a$, wherein $R^a$ is unsubstituted $C_{1-6}$ alkyl. In certain embodiments, at least one $R^A$ is —$OCH_3$. In certain embodiments, at least one $R^A$ is —$N(R^a)_2$, wherein $R^a$ is hydrogen or substituted or unsubstituted $C_{1-6}$ alkyl. In certain embodiments, at least one $R^A$ is —$NHR^a$. In certain embodiments, at least one $R^A$ is —$SR^a$.

In compounds of Formula (I), Ring A may be substituted with one or more $R^A$ groups as valency permits. In certain embodiments, k is 0. In certain embodiments, k is 1. In certain embodiments, k is 2. In certain embodiments, k is 3. In certain embodiments, k is 5. In certain embodiments, k is 6.

In certain embodiments, at least one instance of $R^{A1}$ is H (hydrogen). In certain embodiments, at least one instance of $R^{A1}$ is halogen. In certain embodiments, at least one instance of $R^{A1}$ is F (fluorine). In certain embodiments, at least one instance of $R^{A1}$ is Cl (chlorine). In certain embodiments, at least one instance of $R^{A1}$ is Br (bromine). In certain embodiments, at least one instance of $R^{A1}$ is I (iodine). In certain embodiments, at least one instance of $R^{A1}$ is substituted acyl. In certain embodiments, at least one instance of $R^{A1}$ is unsubstituted acyl. In certain embodiments, at least one instance of $R^{A1}$ is acetyl. In certain embodiments, at least one instance of $R^{A1}$ is substituted acetyl. In certain embodiments, at least one instance of $R^{A1}$ is substituted alkyl. In certain embodiments, at least one instance of $R^{A1}$ is unsubstituted alkyl. In certain embodiments, at least one instance of $R^{A1}$ is $C_{1-6}$ alkyl. In certain embodiments, at least one instance of $R^{A1}$ is methyl. In certain embodiments, at least one instance of $R^{A1}$ is ethyl. In certain embodiments, at least one instance of $R^{A1}$ is propyl. In certain embodiments, at least one instance of $R^{A1}$ is butyl. In certain embodiments, at least one instance of $R^{A1}$ is substituted alkenyl. In certain embodiments, at least one instance of $R^{A1}$ is unsubstituted alkenyl. In certain embodiments, at least one instance of $R^{A1}$ is vinyl. In certain embodiments, at least one instance of $R^{A1}$ is substituted alkynyl. In certain embodiments, at least one instance of $R^{A1}$ is unsubstituted alkynyl. In certain embodiments, at least one instance of $R^{A1}$ is ethynyl. In certain embodiments, at least one instance of $R^{A1}$ is substituted carbocyclyl. In certain embodiments, at least one instance of $R^{A1}$ is unsubstituted carbocyclyl. In certain embodiments, at least one instance of $R^{A1}$ is substituted heterocyclyl. In certain embodiments, at least one instance of $R^{A1}$ is unsubstituted heterocyclyl. In certain embodiments, at least one instance of $R^{A1}$ is substituted aryl. In certain embodiments, at least one instance of $R^{A1}$ is unsubstituted aryl. In certain embodiments, at least one instance of $R^{A1}$ is substituted phenyl. In certain embodiments, at least one instance of $R^{A1}$ is unsubstituted phenyl. In certain embodiments, at least one instance of $R^{A1}$ is substituted heteroaryl. In certain embodiments, at least one instance of $R^{A1}$ is unsubstituted heteroaryl. In certain embodiments, at least one instance of $R^{A1}$ is substituted pyridyl. In certain embodiments, at least one instance of $R^{A1}$ is unsubstituted pyridyl. In certain embodiments, at least one instance of $R^{A1}$ is a nitrogen protecting group. In certain embodiments, at least one instance of $R^{A1}$ is Bn, BOC, Cbz, Fmoc, trifluoroacetyl, triphenylmethyl, acetyl, or Ts.

In certain embodiments, at least one $R^{A1}$ is hydrogen, substituted or unsubstituted $C_{1-6}$ alkyl, or a nitrogen protecting group. In certain embodiments, all instances of $R^{A1}$ are each independently hydrogen, substituted or unsubstituted $C_{1-6}$ alkyl, or a nitrogen protecting group. In certain embodiments, all instances of $R^{A1}$ are hydrogen.

In certain embodiments, at least one $R^{A2}$ is H. In certain embodiments, at least one $R^{A2}$ is halogen. In certain embodiments, at least one $R^{A2}$ is F. In certain embodiments, at least one $R^{A2}$ is Cl. In certain embodiments, at least one $R^{A2}$ is Br. In certain embodiments, at least one $R^{A2}$ is I (iodine). In certain embodiments, at least one $R^{A2}$ is substituted acyl. In certain embodiments, at least one $R^{A2}$ is unsubstituted acyl. In certain embodiments, at least one $R^{A2}$ is acetyl. In certain embodiments, at least one $R^{A2}$ is substituted acetyl. In certain embodiments, at least one $R^{A2}$ is substituted alkyl. In certain embodiments, at least one $R^{A2}$ is unsubstituted alkyl. In certain embodiments, at least one $R^{A2}$ is $C_{1-6}$ alkyl. In certain embodiments, at least one $R^{A2}$ is methyl. In certain embodiments, at least one $R^{A2}$ is ethyl. In certain embodiments, at least one $R^{A2}$ is propyl. In certain embodiments, at least one $R^{A2}$ is butyl. In certain embodiments, at least one $R^{A2}$ is substituted alkenyl. In certain embodiments, at least one $R^{A2}$ is unsubstituted alkenyl. In certain embodiments, at least one $R^{A2}$ is vinyl. In certain embodiments, at least one $R^{A2}$ is substituted alkynyl. In certain embodiments, at least one $R^{A2}$ is unsubstituted alkynyl. In certain embodiments, at least one $R^{A2}$ is ethynyl. In certain embodiments, at least one $R^{A2}$ is substituted carbocyclyl. In certain embodiments, at least one $R^{A2}$ is unsubstituted carbocyclyl. In certain embodiments, at least one $R^{A2}$ is substituted heterocyclyl. In certain embodiments, at least one $R^{A2}$ is unsubstituted heterocyclyl. In certain embodiments, at least one $R^{A2}$ is substituted aryl. In certain embodiments, at least one $R^{A2}$ is unsubstituted aryl. In certain embodiments, at least one $R^{A2}$ is substituted phenyl. In certain embodiments, at least one $R^{A2}$ is unsubstituted phenyl. In certain embodiments, at least one $R^{A2}$ is substituted heteroaryl. In certain embodiments, at least one $R^{A2}$ is unsubstituted heteroaryl. In certain embodiments, at least one $R^{A2}$ is substituted pyridyl. In certain embodiments, at least one $R^{A2}$ is unsubstituted pyridyl. In certain embodiments, at least one $R^{A2}$ is $-OR^{A2a}$, wherein $R^{A2a}$ is as defined herein. In certain embodiments, at least one $R^{A2}$ is $-OR^{A2a}$, wherein $R^{A2a}$ is hydrogen. In certain embodiments, at least one $R^{A2}$ is $-OR^{A2a}$, wherein $R^{A2a}$ is substituted or unsubstituted $C_{1-6}$ alkyl. In certain embodiments, at least one $R^{A2}$ is $-OR^{A2a}$, wherein $R^{A2a}$ is unsubstituted $C_{1-6}$ alkyl. In certain embodiments, at least one $R^{A2}$ is $-OCH_3$. In certain embodiments, at least one $R^{A2}$ is $-N(R^{A2a})_2$. In certain embodiments, at least one $R^{A2}$ is $-SR^{A2a}$. In certain embodiments, all instances of $R^{A2}$ are hydrogen.

In certain embodiments, all $R^{A1}$ and $R^{A2}$ are hydrogen. In certain embodiments, $R^{A1}$ is hydrogen; and at least one $R^{A2}$ is substituted or unsubstituted alkyl. In certain embodiments, $R^{A1}$ is hydrogen; and at least one $R^{A2}$ is unsubstituted alkyl. In certain embodiments, $R^{A1}$ is hydrogen; and at least one $R^{A2}$ is methyl, ethyl, or n-propyl. In certain embodiments, $R^{A1}$ is hydrogen; and at least one $R^{A2}$ is $-OR^{A2a}$, wherein $R^{A2a}$ is as defined herein. In certain embodiments, $R^{A1}$ is hydrogen; and at least one $R^{A2}$ is $-OR^{A2a}$, wherein $R^{A2a}$ is substituted or unsubstituted $C_{1-6}$ alkyl. In certain embodiments, $R^{A1}$ is hydrogen; and at least one $R^{A2}$ is $-OR^{A2a}$, wherein $R^{A2a}$ is unsubstituted $C_{1-6}$ alkyl. In certain embodiments, $R^{A1}$ is hydrogen; and at least one $R^{A2}$ is $-OCH_3$.

In certain embodiments, $R^a$ is H. In certain embodiments, $R^a$ is halogen. In certain embodiments, $R^a$ is F. In certain embodiments, $R^a$ is Cl. In certain embodiments, $R^a$ is Br. In certain embodiments, $R^a$ is I (iodine). In certain embodiments, $R^a$ is substituted $C_{1-6}$ alkyl. In certain embodiments, $R^a$ is unsubstituted $C_{1-6}$ alkyl. In certain embodiments, $R^a$ is methyl. In certain embodiments, $R^a$ is ethyl. In certain embodiments, at least one $R^a$ is H. In certain embodiments, each $R^a$ is H. In certain embodiments, at least one $R^a$ is halogen (e.g., F, Cl, Br, or I (iodine)). In certain embodiments, at least one $R^a$ is substituted or unsubstituted alkyl. In certain embodiments, at least one $R^a$ is substituted $C_{1-6}$ alkyl. In certain embodiments, at least one $R^a$ is unsubstituted $C_{1-6}$ alkyl. In certain embodiments, at least one $R^a$ is Me. In certain embodiments, at least one $R^a$ is substituted methyl (e.g., $-CF_3$ or Bn), Et, substituted ethyl (e.g., fluorinated ethyl), Pr, substituted propyl (e.g., fluorinated propyl), Bu, or substituted butyl (e.g., fluorinated butyl). In certain embodiments, at least one $R^a$ is substituted or unsubstituted alkenyl or substituted or unsubstituted alkynyl. In certain embodiments, at least one $R^a$ is substituted or unsubstituted carbocyclyl, substituted or unsubstituted heterocyclyl, substituted or unsubstituted aryl, or substituted or unsubstituted heteroaryl. In certain embodiments, at least one $R^a$ is a nitrogen protecting group when attached to a nitrogen atom, an oxygen protecting group when attached to an oxygen atom, or a sulfur protecting group when attached to a sulfur atom. In certain embodiments, two instances of $R^a$ are joined to form a substituted or unsubstituted, heterocyclic ring, or substituted or unsubstituted, heteroaryl ring.

As generally defined herein, $R^{B1}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$, wherein $R^a$ is as defined herein. In certain embodiments, $R^{B1}$ is H. In certain embodiments, $R^{B1}$ is halogen. In certain embodiments, $R^{B1}$ is F. In certain embodiments, $R^{B1}$ is Cl. In certain embodiments, $R^{B1}$ is Br. In certain embodiments, $R^{B1}$ is I (iodine). In certain embodiments, $R^{B1}$ is substituted alkyl. In certain embodiments, $R^{B1}$ is unsubstituted alkyl. In certain embodiments, $R^{B1}$ is $C_{1-6}$ alkyl. In certain embodiments, $R^{B1}$ is methyl. In certain embodiments, $R^{B1}$ is ethyl. In certain embodiments, $R^{B1}$ is propyl. In certain embodiments, $R^{B1}$ is butyl. In certain embodiments, $R^{B1}$ is $-OR^{B1a}$, wherein $R^{B1a}$ is hydrogen or substituted or unsubstituted alkyl. In certain embodiments, $R^{B1}$ is $-N(R^{B1a})_2$, wherein each instance of $R^{B1a}$ is independently H or substituted or unsubstituted alkyl. In certain embodiments, $R^{B1}$ is $-NHR^{B1a}$, wherein $R^{B1a}$ is independently H or substituted or unsubstituted alkyl. In certain embodiments, $R^{B1}$ is $-NH_2$, As generally defined herein, $R^{B2}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$, wherein $R^a$ is as defined herein. In certain embodiments, $R^{B2}$ is H. In certain embodiments, $R^{B2}$ is halogen. In certain embodiments, $R^{B2}$ is F. In certain embodiments, $R^{B2}$ is Cl. In certain embodiments, $R^{B2}$ is Br. In certain embodiments, $R^{B2}$ is I (iodine). In certain embodiments, $R^{B2}$ is substituted alkyl. In certain embodiments, $R^{B2}$ is unsubstituted alkyl. In certain embodiments, $R^{B2}$ is $C_{1-6}$ alkyl. In certain embodiments, $R^{B2}$ is methyl. In certain embodiments, $R^{B2}$ is ethyl. In certain embodiments, $R^{B2}$ is propyl.

In certain embodiments, $R^{B1}$ and $R^{B2}$ are the same. In certain embodiments, $R^{B1}$ and $R^{B2}$ are different. In certain embodiments, both $R^{B1}$ and $R^{B2}$ are hydrogen. In certain embodiments, $R^{B1}$ is hydrogen and $R^{B2}$ is hydrogen, halogen, substituted or unsubstituted alkyl, $-OR^a$, or $-N(R^a)_2$, wherein each instance of $R^a$ is independently hydrogen or substituted or unsubstituted alkyl. In certain embodiments, $R^{B1}$ is hydrogen and $R^{B2}$ is halogen. In certain embodiments, $R^{B1}$ is hydrogen and $R^{B2}$ is substituted or unsubstituted alkyl. In certain embodiments, $R^{B1}$ is hydrogen and $R^{B2}$ is unsubstituted alkyl. In certain embodiments, $R^{B1}$ is hydrogen and $R^{B2}$ is methyl or ethyl. In certain embodiments, $R^{B2}$ is hydrogen and $R^{B1}$ is hydrogen, halogen, substituted or unsubstituted alkyl, —OR$^a$, or —N(R$^a$)$_2$, wherein each instance of R$^a$ is independently hydrogen, substituted or unsubstituted alkyl, an oxygen protecting group when attached to oxygen, or a nitrogen protecting group when attached to nitrogen. In certain embodiments, R$^{B2}$ is hydrogen and R$^{B1}$ is halogen. In certain embodiments, R$^{B2}$ is hydrogen and R$^{B1}$ is substituted or unsubstituted alkyl. In certain embodiments, R$^{B2}$ is hydrogen and R$^{B1}$ is unsubstituted alkyl. In certain embodiments, R$^{B2}$ is hydrogen and R$^{B1}$ is methyl or ethyl. In certain embodiments, R$^{B2}$ is hydrogen and R$^{B1}$ is —OR$^a$, wherein R$^a$ is independently hydrogen, substituted or unsubstituted alkyl, or an oxygen protecting group. In certain embodiments, R$^{B2}$ is hydrogen and R$^{B1}$ is —N(R$^a$), wherein each instance of R$^a$ is independently hydrogen, substituted or unsubstituted alkyl, or a nitrogen protecting group.

In compounds of Formula (I), L$^1$ is a divalent linker moiety connecting Ring A and Ring B. L$^1$ may be a bond, —C(R$^b$)$_2$—, —C(=O)—, —O—, —S—, —S(=O)—, —S(=O)$_2$—, or —NR$^c$—; wherein R$^b$ and R$^c$ are as defined herein. In certain embodiments, L$^1$ is a bond. In certain embodiments, L$^1$ is —O— or —S—. In certain embodiments, L$^1$ is —O—. In certain embodiments, L$^1$ is —S—. In certain embodiments, L$^1$ is —NR$^c$—. In certain embodiments, L$^1$ is —NH—. In certain embodiments, L$^1$ is —C(R$^b$)$_2$—. In certain embodiments, L$^1$ is —CH$_2$—.

In certain embodiments, R$^b$ is H. In certain embodiments, R$^b$ is halogen. In certain embodiments, R$^b$ is F. In certain embodiments, R$^b$ is Cl. In certain embodiments, R$^b$ is Br. In certain embodiments, R$^b$ is I (iodine). In certain embodiments, R$^b$ is substituted C$_{1-6}$ alkyl. In certain embodiments, R$^b$ is unsubstituted C$_{1-6}$ alkyl. In certain embodiments, R$^b$ is methyl. In certain embodiments, R$^b$ is ethyl. In certain embodiments, at least one R$^b$ is H. In certain embodiments, each R$^b$ is H. In certain embodiments, at least one R$^b$ is halogen (e.g., F, Cl, Br, or I (iodine)). In certain embodiments, at least one R$^b$ is substituted C$_{1-6}$ alkyl. In certain embodiments, at least one R$^b$ is unsubstituted C$_{1-6}$ alkyl. In certain embodiments, at least one R$^b$ is Me. In certain embodiments, at least one R$^b$ is substituted methyl (e.g., —CF$_3$ or Bn), Et, substituted ethyl (e.g., fluorinated ethyl), Pr, substituted propyl (e.g., fluorinated propyl), Bu, or substituted butyl (e.g., fluorinated butyl).

In certain embodiments, R$^c$ is H. In certain embodiments, R$^c$ is substituted C$_{1-6}$ alkyl. In certain embodiments, R$^c$ is unsubstituted C$_{1-6}$ alkyl. In certain embodiments, R$^c$ is methyl. In certain embodiments, R$^c$ is ethyl. In certain embodiments, R$^c$ is a nitrogen protecting group. In certain embodiments, R$^c$ is BOC, acetyl, or Ts. In certain embodiments, at least one R$^c$ is H. In certain embodiments, each R$^c$ is H. In certain embodiments, at least one R$^c$ is halogen (e.g., F, Cl, Br, or I (iodine)). In certain embodiments, at least one R$^c$ is substituted C$_{1-6}$ alkyl. In certain embodiments, at least one R$^c$ is unsubstituted C$_{1-6}$ alkyl. In certain embodiments, at least one R$^c$ is Me. In certain embodiments, at least one R$^c$ is substituted methyl (e.g., —CF$_3$ or Bn), Et, substituted ethyl (e.g., fluorinated ethyl), Pr, substituted propyl (e.g., fluorinated propyl), Bu, or substituted butyl (e.g., fluorinated butyl). In certain embodiments, at least one R$^c$ is a nitrogen protecting group.

In compounds of Formula (I), X is a divalent linker moiety connecting Ring B and Ring C. As generally defined herein, X is —C(R$^b$)$_2$—, —C(=O)—, —O—, —S—, —S(=O)—, —S(=O)$_2$—, —NR$^c$—, —C(R$^b$)$_2$C(R$^b$)$_2$—, —C(R$^b$)$_2$C(=O)—, —C(=O)C(R$^b$)$_2$—, (E)-CR$^b$=CR$^b$—, (Z)—CR$^b$=CR$^b$—, —C≡C—, —OC(=O)—, —C(=O)O—, —SC(=O)—, —C(=O)S—, —NR$^c$C(=O)—, —C(=O)NR$^c$—, —OC(R$^b$)$_2$—, —C(R$^b$)$_2$O—, —SC(R$^b$)$_2$—, —C(R$^b$)$_2$S—, —NR$^c$C(R$^b$)$_2$—, —C(R$^b$)$_2$NR$^c$—, —S(=O)O—, —OS(=O)—, —S(=O)NR$^c$—, —NR$^c$S(=O)—, —S(=O)$_2$O—, —OS(=O)$_2$—, —S(=O)$_2$NR$^c$—, or —NR$^c$S(=O)$_2$—. In certain embodiments, X is —O—. In certain embodiments, X is —S—. In certain embodiments, X is —NR$^c$—, wherein R$^c$ is hydrogen, substituted or unsubstituted C$_{1-6}$ alkyl, or a nitrogen protecting group. In certain embodiments, X is —NH—. In certain embodiments, X is —C(R$^b$)$_2$—. In certain embodiments, X is —CH$_2$—.

In certain embodiments, L$^1$ is a bond, —O—, —S—, or —NR$^c$—; and X is —C(R$^b$)$_2$—, —C(=O)—, —O—, —S—, —S(=O)—, —S(=O)$_2$—, or —NR$^c$—, wherein R$^b$ and R$^c$ are as defined herein. In certain embodiments, L$^1$ is a bond and X is —C(R$^b$)$_2$—, —C(=O)—, —O—, —S—, —S(=O)—, —S(=O)$_2$—, or —NR$^c$—, wherein R$^b$ and R$^c$ are as defined herein. In certain embodiments, L$^1$ is a bond and X is —O—. In certain embodiments, L$^1$ is a bond and X is —S—. In certain embodiments, L$^1$ is a bond and X is —NR$^c$—, wherein R$^c$ is as defined herein. In certain embodiments, L$^1$ is a bond and X is —NH—. In certain embodiments, L$^1$ is —O— and X is —C(R$^b$)$_2$—, —C(=O)—, —O—, —S—, —S(=O)—, —S(=O)$_2$—, or —NR$^c$—, wherein R$^b$ and R$^c$ are as defined herein. In certain embodiments, L$^1$ is —O— and X is —O—. In certain embodiments, L$^1$ is —O— and X is —S—. In certain embodiments, L$^1$ is —O— and X is —NR$^c$—, wherein R$^c$ is as defined herein. In certain embodiments, L$^1$ is —O— and X is-NH—. In certain embodiments, L$^1$ is —NR$^c$— and X is —O—. In certain embodiments, L$^1$ is —NR$^c$— and X is —S—. In certain embodiments, L$^1$ is —NR$^c$— and X is independently —NR$^c$—, wherein R$^c$ is as defined herein. In certain embodiments, L$^1$ and X are —NH—.

In compounds of Formula (I), L$^2$ is a divalent linker moiety connecting Ring C and Ring D. L$^2$ may be —C(R$^b$)$_2$—, —C(=O)—, —O—, —S—, —S(=O)—, —S(=O)$_2$—, —NR$^c$—, —C(R$^b$)$_2$C(R$^b$)$_2$—, —C(R$^b$)$_2$C(=O)—, —C(=O)C(R$^b$)$_2$—, (E)-CR$^b$=CR$^b$—, (Z)—CR$^b$=CR$^b$—, —C≡C—, —OC(=O)—, —C(=O)O—, —SC(=O)—, —C(=O)S—, —NR$^c$C(=O)—, —C(=O)NR$^c$—, —OC(R$^b$)$_2$—, —C(R$^b$)$_2$O—, —SC(R$^b$)$_2$—, —C(R$^b$)$_2$S—, —NR$^c$C(R$^b$)$_2$—, —C(R$^b$)$_2$NR$^c$—, —S(=O)O—, —OS(=O)—, —S(=O)NR$^c$—, —NR$^c$S(=O)—, —S(=O)$_2$O—, —OS(=O)$_2$—, —S(=O)$_2$NR$^c$—, —NR$^c$S(=O)$_2$—, —OC(=O)O—, —NR$^c$C(=O)O—, —OC(=O)NR$^c$—, —NR$^c$C(=O)NR$^c$—, —C(R$^b$)$_2$C(=O)C(R$^b$)$_2$—, —OC(=O)C(R$^b$)$_2$—, —C(R$^b$)$_2$C(=O)O—, —NR$^c$C(=O)C(R$^b$)$_2$—, —C(R$^b$)$_2$C(=O)NR$^c$—, or a substituted or unsubstituted C$_{1-4}$ hydrocarbon chain, optionally wherein one or more carbon units of the hydrocarbon chain are independently replaced with —C(=O)—, —O—, —S—, —S(=O)—, —S(=O)$_2$—, or —NR$^c$—, wherein R$^b$ and R$^c$ are as defined herein. In certain embodiments, L$^2$ is —NR$^c$C(=O)—, —C(=O)NR$^c$—, —C(=O)—, —C(R$^b$)$_2$—, —C(R$^b$)$_2$C(=O)—, or —C(R$^b$)$_2$C(=O)NR$^c$—, wherein each instance of R$^b$ is independently hydrogen, halogen, or substituted or unsubstituted C$_{1-6}$ alkyl; and each instance of R$^c$ is independently hydrogen, substituted or unsubstituted C$_{1-6}$ alkyl, or a nitrogen protecting group. In certain embodiments, L$^2$ is —C(=O)—. In certain embodiments, L$^2$ is —C(R$^b$)$_2$—. In certain embodiments, L$^2$ is —CH$_2$—. In certain embodiments, L$^2$ is —NR$^c$—. In certain embodiments, L$^2$ is —NH—. In certain embodiments, L$^2$ is —NR$^c$C(=O)— or —C(=O)NR$^c$—. In certain embodiments, L$^2$ is —NHC(=O)— or —C(=O)NH—. In certain embodiments, L$^2$ is of the formula: —C(=O)NR$^c$—. In certain embodiments, $L^2$ is of the formula: —C(=O)NH—. In certain embodiments, $L^2$ is of the formula: —NR$^c$C(=O)—. In certain embodiments, $L^2$ is of the formula: —NHC(=O)—. In certain embodiments, $L^2$ is of the formula: —C(=O)NH— or —NH(=O)—. In certain embodiments, $L^2$ is of the formula: —C(R$^b$)$_2$C(=O)—. In certain embodiments, $L^2$ is of the formula: —CH$_2$C(=O)—. In certain embodiments, $L^2$ is of the formula: —C(R$^b$)$_2$C(=O)NR$^c$—. In certain embodiments, $L^2$ is of the formula: —CH$_2$C(=O)NR$^c$—. In certain embodiments, $L^2$ is of the formula: —CH$_2$C(=O)NH—.

As generally defined herein, Ring C is a substituted or unsubstituted phenyl ring. In certain embodiments, Ring C is a substituted phenyl ring. In certain embodiments, Ring C is an unsubstituted phenyl ring. In certain embodiments, Ring C is a substituted or unsubstituted 1,2-phenylene moiety. In certain embodiments, Ring C is a substituted or unsubstituted 1,3-phenylene moiety. In certain embodiments, Ring C is a substituted or unsubstituted 1,4-phenylene moiety. Ring C may be unsubstituted or may be substituted with one or more $R^C$ groups. In certain embodiments, at least one $R^C$ is halogen. In certain embodiments, at least one $R^C$ is F. In certain embodiments, at least one $R^C$ is Cl. In certain embodiments, at least one $R^C$ is Br. In certain embodiments, at least one $R^C$ is I (iodine). In certain embodiments, at least one $R^c$ is substituted alkyl. In certain embodiments, at least one $R^C$ is unsubstituted alkyl. In certain embodiments, at least one $R^C$ is $C_{1-6}$ alkyl. In certain embodiments, at least one $R^C$ is methyl. In certain embodiments, at least one $R^C$ is ethyl. In certain embodiments, at least one $R^C$ is propyl. In certain embodiments, at least one $R^C$ is substituted alkenyl. In certain embodiments, at least one $R^C$ is unsubstituted alkenyl. In certain embodiments, at least one $R^C$ is vinyl. In certain embodiments, at least one $R^C$ is substituted alkynyl. In certain embodiments, at least one $R^C$ is unsubstituted alkynyl. In certain embodiments, at least one $R^C$ is ethynyl. In certain embodiments, at least one $R^C$ is substituted carbocyclyl. In certain embodiments, at least one $R^C$ is unsubstituted carbocyclyl. In certain embodiments, at least one $R^C$ is substituted heterocyclyl. In certain embodiments, at least one $R^C$ is unsubstituted heterocyclyl. In certain embodiments, at least one $R^C$ is substituted aryl. In certain embodiments, at least one $R^C$ is unsubstituted aryl. In certain embodiments, at least one $R^C$ is substituted phenyl. In certain embodiments, at least one $R^C$ is unsubstituted phenyl. In certain embodiments, at least one $R^C$ is substituted heteroaryl. In certain embodiments, at least one $R^C$ is unsubstituted heteroaryl. In certain embodiments, each instance of $R^C$ is independently halogen, substituted or unsubstituted $C_{1-6}$ alkyl, or —OR$^a$ (e.g., —OH or —O(substituted or unsubstituted $C_{1-6}$ alkyl)).

In certain embodiments, Ring C is a substituted phenyl ring and at least one $R^C$ is independently halogen or substituted or unsubstituted $C_{1-6}$ alkyl. In certain embodiments, Ring C is a substituted phenyl ring and at least one $R^C$ is independently halogen. In certain embodiments, Ring C is a substituted phenyl ring and at least one $R^C$ is substituted or unsubstituted $C_{1-6}$ alkyl. In certain embodiments, Ring C is a substituted phenyl ring and one $R^C$ is substituted or unsubstituted $C_{1-6}$ alkyl. In certain embodiments, Ring C is a substituted phenyl ring and one $R^C$ is unsubstituted $C_{1-6}$ alkyl (e.g. methyl or ethyl).

Ring C may be unsubstituted or substituted with one or more $R^C$ groups as valency permits. In certain embodiments, Ring C is a substituted or unsubstituted phenyl ring and n is 0, 1, 2, 3, or 4. In certain embodiments, Ring C is unsubstituted, and thus n is 0. In certain embodiments, n is 1. In certain embodiments, n is 2. In certain embodiments, n is 3. In certain embodiments, n is 4.

As generally defined herein, Ring D is a substituted or unsubstituted phenyl ring. In certain embodiments, Ring D is a substituted phenyl ring. In certain embodiments, Ring D is an unsubstituted phenyl ring. In certain embodiments, Ring D is a substituted or unsubstituted 1,2-phenylene moiety. In certain embodiments, Ring D is a substituted or unsubstituted 1,3-phenylene moiety. In certain embodiments, Ring D is a substituted or unsubstituted 1,4-phenylene moiety.

In certain embodiments, Ring C is an unsubstituted phenyl ring and Ring D is a substituted or unsubstituted phenyl ring. In certain embodiments, Ring C is an unsubstituted phenyl ring and Ring D is an unsubstituted phenyl ring. In certain embodiments, Ring C is an unsubstituted phenyl ring and Ring D is a substituted phenyl ring. In certain embodiments, Ring C is a substituted phenyl ring and Ring D is a substituted phenyl ring. In certain embodiments, Ring C is a substituted phenyl ring and Ring D is an unsubstituted phenyl ring.

In compounds of Formula (I), Ring D is substituted with $R^E$ and may also be substituted with one or more $R^D$ groups. In certain embodiments, at least one $R^D$ is H. In certain embodiments, at least one $R^D$ is halogen. In certain embodiments, at least one $R^D$ is F. In certain embodiments, at least one $R^D$ is Cl. In certain embodiments, at least one $R^D$ is Br. In certain embodiments, at least one $R^D$ is I (iodine). In certain embodiments, at least one $R^D$ is substituted alkyl. In certain embodiments, at least one $R^D$ is unsubstituted alkyl. In certain embodiments, at least one $R^D$ is $C_{1-6}$ alkyl. In certain embodiments, at least one $R^D$ is methyl. In certain embodiments, at least one $R^D$ is ethyl. In certain embodiments, at least one $R^D$ is propyl. In certain embodiments, each instance of $R^c$ is independently halogen, substituted or unsubstituted $C_{1-6}$ alkyl, or —OR$^a$ (e.g., —OH or —O(substituted or unsubstituted $C_{1-6}$ alkyl)).

Ring D may be unsubstituted or substituted with one or more $R^D$ groups. In certain embodiments, Ring D is unsubstituted, and thus p is 0. In certain embodiments, p is 1. In certain embodiments, p is 2. In certain embodiments, p is 3. In certain embodiments, p is 4.

In certain embodiments, $R^D$ is halogen; and p is 1. In certain embodiments, $R^D$ is F; and p is 1. In certain embodiments, $R^D$ is Cl; and p is 1. In certain embodiments, $R^D$ is Br; and p is 1. In certain embodiments, $R^D$ is I (iodine); and p is 1. In certain embodiments, $R^D$ is substituted alkyl; and p is 1. In certain embodiments, $R^D$ is unsubstituted alkyl; and p is 1. In certain embodiments, $R^D$ is $C_{1-6}$ alkyl; and p is 1. In certain embodiments, $R^D$ is methyl; and p is 1. In certain embodiments, $R^D$ is ethyl, propyl, or butyl; and p is 1. In certain embodiments, each instance of $R^D$ is independently halogen or substituted or unsubstituted alkyl; and p is 2. In certain embodiments, each instance of $R^D$ is independently halogen or $C_{1-6}$ alkyl; and p is 2.

In compounds of Formula (I), Ring D also includes a substituent $R^E$. In certain embodiments, $R^E$ comprises a Michael acceptor moiety. This Michael acceptor moiety may react with a cysteine residue of a kinase (e.g., PIP4K) to allow covalent attachment of the compound to the kinase. In certain embodiments, the covalent attachment is irreversible. In other embodiments, the covalent attachment is reversible.

As generally defined herein in Formula (I), $R^E$ may be any one of Formulae (i-1)-(i-41). In certain embodiments, $R^E$ is of Formula (i-1):

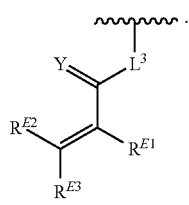

(i-1)

In certain embodiments, $R^E$ is of Formula (i-2):

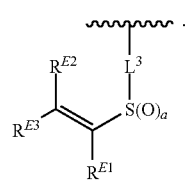

(i-2)

In certain embodiments, $R^E$ is of Formula (i-3):

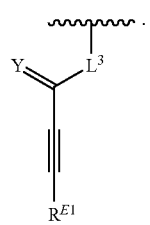

(i-3)

In certain embodiments, $R^E$ is of Formula (i-4):

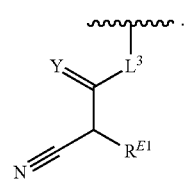

(i-4)

4). In certain embodiments, $R^E$ is of Formula (i-5):

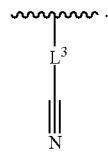

(i-5)

In certain embodiments, $R^E$ is of Formula (i-6):

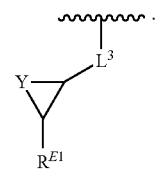

(i-6)

In certain embodiments, $R^E$ is of Formula (i-7):

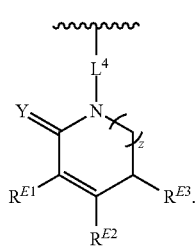

(i-7)

In certain embodiments, $R^E$ is of Formula (i-8):

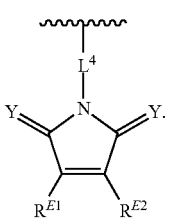

(i-8)

In certain embodiments, $R^E$ is of Formula (i-9):

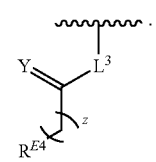

(i-9)

In certain embodiments, $R^E$ is of Formula (i-10):

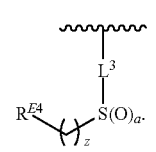

(i-10)

In certain embodiments, $R^E$ is of Formula (i-11):

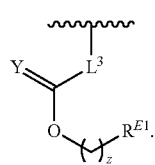

(i-11)

In certain embodiments, $R^E$ is of Formula (i-12):

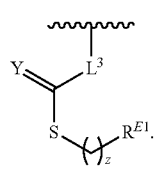

(i-12)

In certain embodiments, $R^E$ is of Formula (i-13):

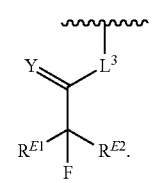

(i-13)

In certain embodiments, $R^E$ is of Formula (i-14):

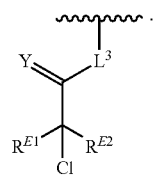

(i-14)

In certain embodiments, $R^E$ is of Formula (i-15):

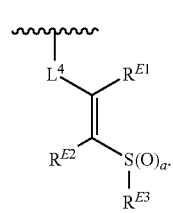

(i-15)

In certain embodiments, R is of Formula (i-16):

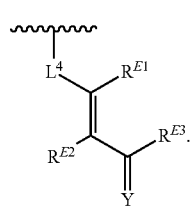

(i-16)

certain embodiments, $R^E$ is of Formula (i-17):

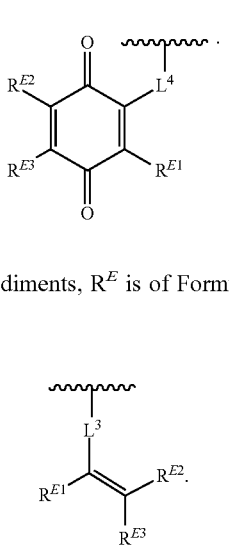

(i-17)

In certain embodiments, $R^E$ is of Formula (i-18):

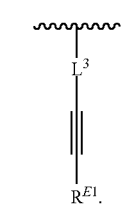

(i-18)

In certain embodiments, $R^E$ is of Formula (i-19):

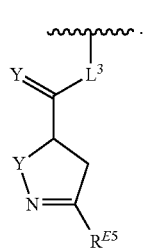

(i-19)

In certain embodiments, $R^E$ is of Formula (i-20):

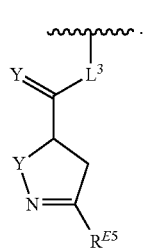

(i-20)

In certain embodiments, $R^E$ is of Formula (i-21):

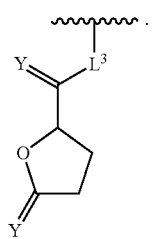
(i-21)

In certain embodiments, $R^E$ is of Formula (i-22):

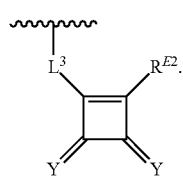
(i-22)

In certain embodiments, $R^E$ is of Formula (i-23):

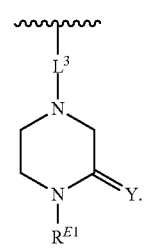
(i-23)

In certain embodiments, $R^E$ is of Formula (i-24):

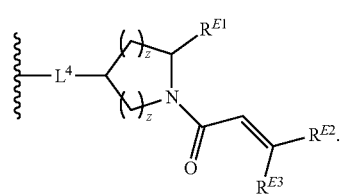
(i-24)

In certain embodiments, $R^E$ is of Formula (i-25):

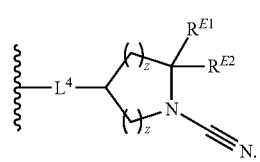
(i-25)

In certain embodiments, $R^E$ is of Formula (i-26):

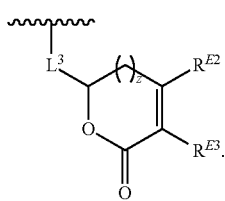
(i-26)

In certain embodiments, $R^E$ is of Formula (i-27):

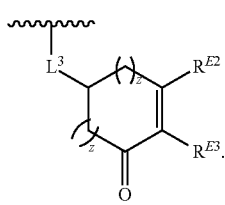
(i-27)

In certain embodiments, $R^E$ is of Formula (i-28):

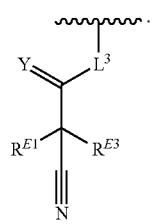
(i-28)

In certain embodiments, $R^E$ is of Formula (i-29):

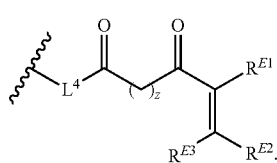
(i-29)

In certain embodiments, $R^E$ is of Formula (i-30):

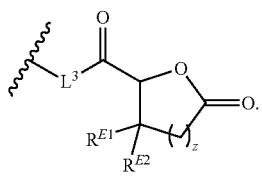
(i-30)

In certain embodiments, $R^E$ is of Formula (i-31):

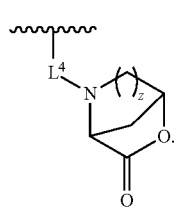

(i-31)

In certain embodiments, $R^E$ is of Formula (i-32):

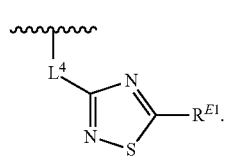

(i-32)

In certain embodiments, $R^E$ is of Formula (i-33):

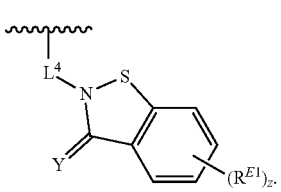

(i-33)

In certain embodiments, $R^E$ is of Formula (i-34):

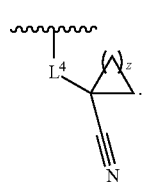

(i-34)

certain embodiments, $R^E$ is of Formula (i-3):

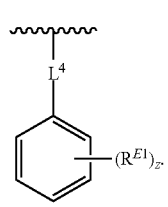

(i-35)

In certain embodiments, $R^E$ is of Formula (i-36):

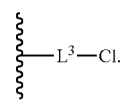

(i-36)

In certain embodiments, $R^E$ is of Formula (i-37):

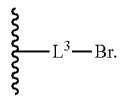

(i-37)

In certain embodiments, $R^E$ is of Formula (i-38):

(i-38)

$$\xi\!-\!L^3\!-\!F.$$

In certain embodiments, $R^E$ is of Formula (i-39):

(i-39)

$$\xi\!-\!L^3\!-\!CF_3.$$

In certain embodiments, $R^E$ is of Formula (i-40):

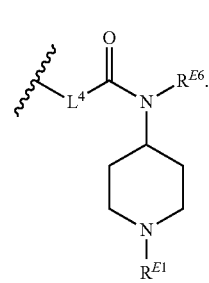

(i-40)

In certain embodiments, $R^E$ is of Formula (i-41):

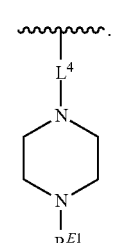

(i-41)

In certain embodiments, $R^E$ is of Formula (i-1a):

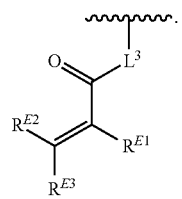
(i-1a)

In certain embodiments, $R^E$ is of Formula (i-1b):

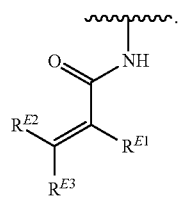
(i-1b)

In certain embodiments, $R^E$ is of Formula (i-1c):

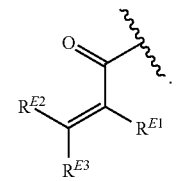
(i-1c)

In certain embodiments, $R^E$ is of Formula (i-1d):

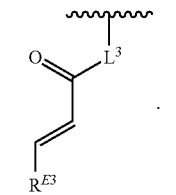
(i-1d)

In certain embodiments, $R^E$ is of Formula (i-1e):

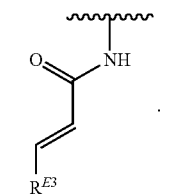
(i-1e)

In certain embodiments, $R^E$ s of Formula (i-1f):

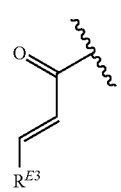
(i-1f)

In certain embodiments, $R^E$ is of Formula (i-1g):

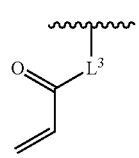
(i-1g)

In certain embodiments, $R^E$ is

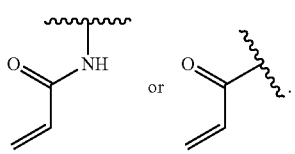

In certain embodiments, $R^E$ is of the formula:

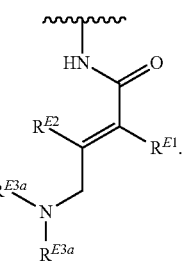

In certain embodiments, $R^E$ is of Formula (i-1h):

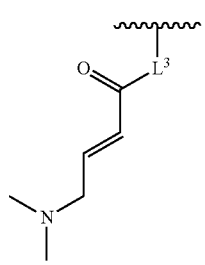
(i-1h)

In certain embodiments, $R^E$ is

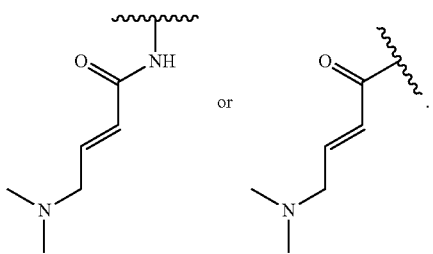 or 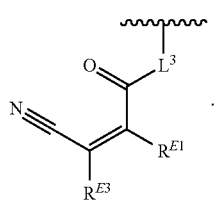.

In certain embodiments, $R^E$ is of Formula (i-1a):

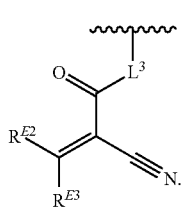

(i-1a)

In certain embodiments, $R^E$ is of Formula (i-1b):

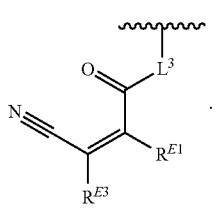

(i-1b)

In certain embodiments, $R^E$ is of Formula (i-1c):

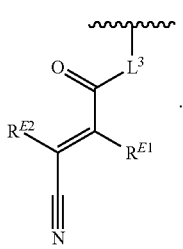

(i-1c)

In certain embodiments, $R^E$ is of Formula (i-18a):

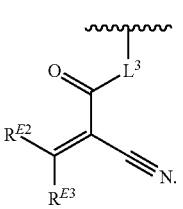

(i-18a)

In certain embodiments, $R^E$ is of Formula (i-18b):

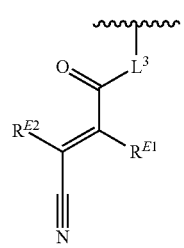

(i-18b)

In certain embodiments, $R^E$ is of Formula (i-18c):

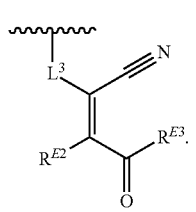

(i-18c)

In certain embodiments, $R^E$ is of Formula (i-15a):

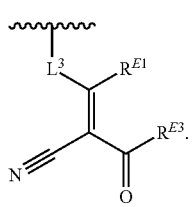

(i-15a)

In certain embodiments, $R^E$ is of Formula (i-15b):

(i-15b)

In certain embodiments, $R^E$ is of Formula (i-15c):

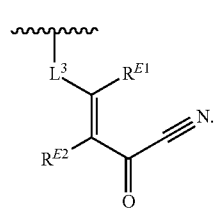

(i-15c)

In certain embodiment, X and $L^2$ are para or meta to each other. In certain embodiment, X and $L^2$ are para to each other. In certain embodiments, X and $L^2$ are meta to each other. In certain embodiment, $R^E$ and $L^2$ are para or meta to each other. In certain embodiments, $R^E$ and $L^2$ are para to each other. In certain embodiments, $R^E$ and $L^2$ are meta to each other. In certain embodiments, Ring D is of the formula:

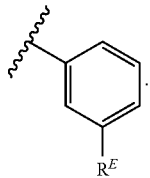

In certain embodiments, Ring D is of the formula:

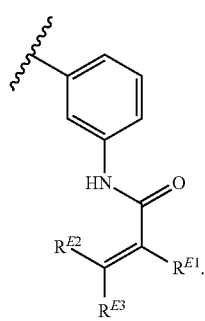

In certain embodiments, Ring D is of the formula:

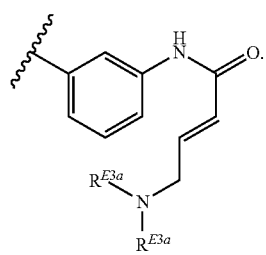

In certain embodiments, Ring D is of the formula:

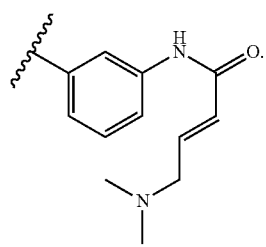 [SMILES: *c1cccc(NC(=O)/C=C/CN(C)C)c1]

In certain embodiments, Ring D is of the formula:

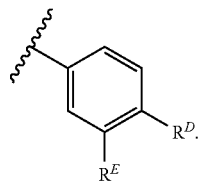

In certain embodiments, Ring D is of the formula:

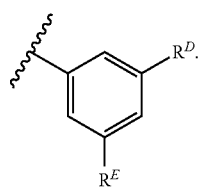

In certain embodiments, Ring D is of the formula:

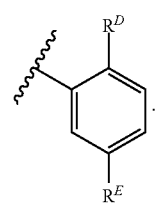

In certain embodiments, Ring D is of the formula:

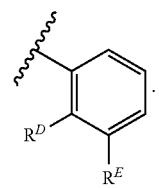

In certain embodiments, $R^E$ and $L^2$ are para to each other. In certain embodiments, Ring D is of the formula:

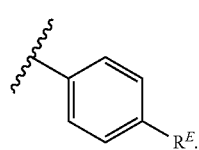

In certain embodiments, Ring D is of the formula:

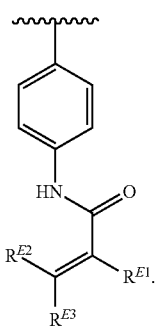

In certain embodiments, Ring D is of the formula:

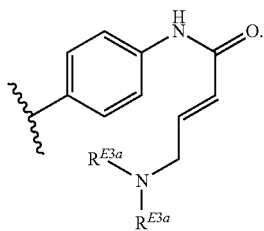

In certain embodiments, Ring D is of the formula:

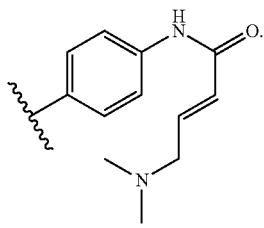 [SMILES: *c1ccc(NC(=O)/C=C/CN(C)C)cc1]

In certain embodiments, Ring D is of the formula:

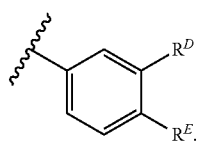

In certain embodiments, Ring D is of the formula:

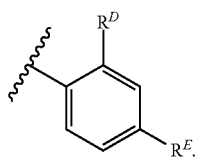

In compounds of Formula (I), $L^3$ is a divalent linker moiety. $L^3$ may contain 0-4 carbon or hetero atoms in the backbone of $L^3$. $L^3$ may be saturated or unsaturated. $L^3$ may be substituted or unsubstituted. $L^3$ may be branched or unbranched. In certain embodiments, $L^3$ is a bond. In certain embodiments, $L^3$ is —O—. In certain embodiments, $L^3$ is —S—. In certain embodiments, $L^3$ is —$NR^{L3a}$—. In certain embodiments, $L^3$ is —NH—. In certain embodiments, $L^3$ is a substituted $C_{1-4}$ hydrocarbon chain. In certain embodiments, $L^3$ is an unsubstituted $C_{1-4}$ hydrocarbon chain. In certain embodiments, $L^3$ is —$C(R^{L3b})_2$—. In certain embodiments, $L^3$ is —$CHR^{L3b}$—. In certain embodiments, $L^3$ is —$CH_2$—. In certain embodiments, $L^3$ is a substituted $C_2$ hydrocarbon chain. In certain embodiments, $L^3$ is an unsubstituted $C_2$ hydrocarbon chain. In certain embodiments, $L^3$ is —$C(R^{L3b})_2C(R^{L3b})_2$—. In certain embodiments, $L^3$ is —$CH_2CH_2$—. In certain embodiments, $L^3$ is trans-$CR^{L3b}$=$CR^{L3b}$—. In certain embodiments, $L^3$ is trans-CH=CH—. In certain embodiments, $L^3$ is cis-$CR^{L3b}$=$CR^{L3b}$—. In certain embodiments, $L^3$ is cis-CH=CH—. In certain embodiments, $L^3$ is —C≡C—. In certain embodiments, $L^3$ is a substituted $C_3$ hydrocarbon chain. In certain embodiments, $L^3$ is an unsubstituted $C_3$ hydrocarbon chain. In certain embodiments, $L^3$ is —$(CH_2)_3$—. In certain embodiments, $L^3$ is —CH=CH—$CH_2$—, wherein CH=CH is trans or cis. In certain embodiments, $L^3$ is —$CH_2$—CH=CH—, wherein CH=CH is trans or cis. In certain embodiments, $L^3$ is —C≡C—$CH_2$—. In certain embodiments, $L^3$ is —$CH_2$—C≡C—. In certain embodiments, $L^3$ is a substituted $C_4$ hydrocarbon chain. In certain embodiments, $L^3$ is an unsubstituted $C_4$ hydrocarbon chain. In certain embodiments, $L^3$ is —$(CH_2)_4$—. In certain embodiments, $L^3$ is —CH=CH—CH=CH—, wherein each instance of CH=CH is independently trans or cis. In certain embodiments, $L^3$ is —CH=CH—C≡C—, wherein CH=CH is trans or cis. In certain embodiments, $L^3$ is —C≡C—CH=CH—, wherein CH=CH is trans or cis. In certain embodiments, $L^3$ is —C≡C—C≡C—. In certain embodiments, $L^3$ is a substituted or unsubstituted $C_{1-4}$ hydrocarbon chain, wherein one or more carbon units of the hydrocarbon chain is replaced with —O—, —S—, —$NR^{L3a}$—, —$NR^{L3a}$C(=O)—, —C(=O)$NR^{L3a}$—, —SC(=O)—, —C(=O)S—, —OC(=O)—, —C(=O)O—, —$NR^{L3a}$C(=S)—, —C(=S)$NR^{L3a}$—, trans-$CR^{L3b}$=$CR^{L3b}$—, cis-$CR^{L3b}$=$CR^{L3b}$—, —C≡C—, —S(=O)$_2$O—, —OS(=O)$_2$—, —S(=O)$_2NR^{L3a}$—, or —$NR^{L3a}$S(=O)$_2$—.

In certain embodiments, $R^{L3a}$ is H. In certain embodiments, $R^{L3a}$ is substituted alkyl. In certain embodiments, $R^{L3a}$ is unsubstituted alkyl. In certain embodiments, $R^{L3a}$ is $C^{1-6}$ alkyl. In certain embodiments, $R^{L3a}$ is methyl. In certain embodiments, $R^{L3a}$ is ethyl. In certain embodiments, $R^{L3a}$ is propyl. In certain embodiments, $R^{L3a}$ is butyl. In certain embodiments, $R^{L3a}$ is a nitrogen protecting group. In certain embodiments, $R^{L3a}$ is Bn, BOC, Cbz, Fmoc, trifluoroacetyl, triphenylmethyl, acetyl, or Ts.

In certain embodiments, at least one $R^{L3b}$ is H. In certain embodiments, at least one $R^{L3b}$ is halogen. In certain embodiments, at least one $R^{L3b}$ is F. In certain embodiments, at least one $R^{L3b}$ is Cl. In certain embodiments, at least one $R^{L3b}$ is Br. In certain embodiments, at least one $R^{L3b}$ is I (iodine). In certain embodiments, at least one $R^{L3b}$ is substituted alkyl. In certain embodiments, at least one $R^{L3b}$ is unsubstituted alkyl. In certain embodiments, at least one $R^{L3b}$ is $C_{1-6}$ alkyl. In certain embodiments, at least one $R^{L3b}$ is methyl. In certain embodiments, at least one $R^{L3b}$ is ethyl. In certain embodiments, at least one $R^{L3b}$ is propyl. In certain embodiments, at least one $R^{L3b}$ is butyl. In certain embodiments, at least one $R^{L3b}$ is substituted alkenyl. In certain embodiments, at least one $R^{L3b}$ is unsubstituted alkenyl. In certain embodiments, at least one $R^{L3b}$ is vinyl. In certain embodiments, at least one $R^{L3b}$ is substituted alkynyl. In certain embodiments, at least one $R^{L3b}$ is unsubstituted alkynyl. In certain embodiments, at least one $R^{L3b}$ is ethynyl. In certain embodiments, at least one $R^{L3b}$ is substituted carbocyclyl. In certain embodiments, at least one $R^{L3b}$ is unsubstituted carbocyclyl. In certain embodiments, at least one $R^{L3b}$ is substituted heterocyclyl. In certain embodiments, at least one $R^{L3b}$ is unsubstituted heterocyclyl. In certain embodiments, at least one $R^{L3b}$ is substituted aryl. In certain embodiments, at least one $R^{L3b}$ is unsubstituted aryl. In certain embodiments, at least one $R^{L3b}$ is substituted phenyl. In certain embodiments, at least one $R^{L3b}$ is unsubstituted phenyl. In certain embodiments, at least one $R^{L3b}$ is substituted heteroaryl. In certain embodiments, at least one $R^{L3b}$ is unsubstituted heteroaryl. In certain embodiments, at least one $R^{L3b}$ is substituted pyridyl. In certain embodiments, at least one $R^{L3b}$ is unsubstituted pyridyl. In certain embodiments, two $R^{L3b}$ groups are joined to form a substituted carbocyclic ring. In certain embodiments, two $R^{L3b}$ groups are joined to form an unsubstituted carbocyclic ring. In certain embodiments, two $R^{L3b}$ groups are joined to form a substituted heterocyclic ring. In certain embodiments, two $R^{L3b}$ groups are joined to form an unsubstituted heterocyclic ring.

In compounds of Formula (I), $L^4$ is a divalent linker moiety. $L^4$ may contain 0-4 carbon or hetero atoms in the backbone of $L^4$. $L^4$ may be saturated or unsaturated. $L^4$ may be substituted or unsubstituted. $L^4$ may be branched or unbranched. In certain embodiments, $L^4$ is a bond. In certain embodiments, $L^4$ is a substituted $C_1$ hydrocarbon chain. In certain embodiments, $L^4$ is an unsubstituted $C_{1-4}$ hydrocarbon chain. In certain embodiments, $L^4$ is —C($R^{L4b}$)$_2$—. In certain embodiments, $L^4$ is —CHR$^{L4b}$—. In certain embodiments, $L^4$ is —CH$_2$—. In certain embodiments, $L^4$ is a substituted $C_2$ hydrocarbon chain. In certain embodiments, $L^4$ is a unsubstituted $C_2$ hydrocarbon chain. In certain embodiments, $L^4$ is —C($R^{L4b}$)$_2$C($R^{L4b}$)$_2$—. In certain embodiments, $L^4$ is —CH$_2$CH$_2$—. In certain embodiments, $L^4$ is trans-CR$^{L4b}$=CR$^{L4b}$—. In certain embodiments, $L^4$ is trans-CH=CH—. In certain embodiments, $L^4$ is cis-CR$^{L4b}$=CR$^{L4b}$—. In certain embodiments, $L^4$ is cis-CH=CH—. In certain embodiments, $L^4$ is —C≡C—. In certain embodiments, $L^4$ is a substituted $C_3$ hydrocarbon chain. In certain embodiments, $L^4$ is an unsubstituted $C_3$ hydrocarbon chain. In certain embodiments, $L^4$ is —(CH$_2$)$_3$—. In certain embodiments, $L^4$ is —CH=CH—CH$_2$—, wherein CH=CH is trans or cis. In certain embodiments, $L^4$ is —CH$_2$—CH=CH—, wherein CH=CH is trans or cis. In certain embodiments, $L^4$ is —C≡C—CH$_2$—. In certain embodiments, $L^4$ is —CH$_2$—C≡C—. In certain embodiments, $L^4$ is a substituted $C_4$ hydrocarbon chain. In certain embodiments, $L^4$ is an unsubstituted $C_4$ hydrocarbon chain. In certain embodiments, $L^4$ is —(CH$_2$)$_4$—. In certain embodiments, $L^4$ is —CH=CH—CH=CH—, wherein each instance of CH=CH is independently trans or cis. In certain embodiments, $L^4$ is —CH=CH—C≡C—, wherein CH=CH is trans or cis. In certain embodiments, $L^4$ is —C≡C—CH=CH—, wherein CH=CH is trans or cis. In certain embodiments, $L^4$ is —C≡C—C≡C—.

In compounds of Formula (I), $R^E$ may include a substituent $R^{E1}$. In certain embodiments, $R^{E1}$ is H. In certain embodiments, $R^{E1}$ is halogen. In certain embodiments, $R^{E1}$ is F. In certain embodiments, $R^{E1}$ is Cl. In certain embodiments, $R^{E1}$ is Br. In certain embodiments, $R^{E1}$ is I (iodine). In certain embodiments, $R^{E1}$ is substituted acyl. In certain embodiments, $R^{E1}$ is unsubstituted acyl. In certain embodiments, $R^{E1}$ is acetyl. In certain embodiments, $R^{E1}$ is substituted acetyl. In certain embodiments, $R^{E1}$ is substituted alkyl. In certain embodiments, $R^{E1}$ is unsubstituted alkyl. In certain embodiments, $R^{E1}$ is $C_{1-6}$ alkyl. In certain embodiments, $R^{E1}$ is methyl. In certain embodiments, $R^{E1}$ is ethyl. In certain embodiments, $R^{E1}$ is propyl. In certain embodiments, $R^{E1}$ is butyl. In certain embodiments, $R^{E1}$ is substituted alkenyl. In certain embodiments, $R^{E1}$ is unsubstituted alkenyl. In certain embodiments, $R^{E1}$ is vinyl. In certain embodiments, $R^{E1}$ is substituted alkynyl. In certain embodiments, $R^{E1}$ is unsubstituted alkynyl. In certain embodiments, $R^{E1}$ is ethynyl. In certain embodiments, $R^{E1}$ is substituted carbocyclyl. In certain embodiments, $R^{E1}$ is unsubstituted carbocyclyl. In certain embodiments, $R^{E1}$ is substituted heterocyclyl. In certain embodiments, $R^{E1}$ is unsubstituted heterocyclyl. In certain embodiments, $R^{E1}$ is substituted aryl. In certain embodiments, $R^{E1}$ is unsubstituted aryl. In certain embodiments, $R^{E1}$ is substituted phenyl. In certain embodiments, $R^{E1}$ is unsubstituted phenyl. In certain embodiments, $R^{E1}$ is substituted heteroaryl. In certain embodiments, $R^{E1}$ is unsubstituted heteroaryl. In certain embodiments, $R^{E1}$ is substituted pyridyl. In certain embodiments, $R^{E1}$ is unsubstituted pyridyl. In certain embodiments, $R^{E1}$ is —CN. In certain embodiments, $R^{E1}$ is —OR$^{E1a}$. In certain embodiments, $R^{E1}$ is —N(R$^{E1a}$)$_2$. In certain embodiments, $R^{E1}$ is —SR$^{E1a}$. In certain embodiments, $R^{E1}$ is —CH$_2$OR$^{E1a}$. In certain embodiments, $R^{E1}$ is —CH$_2$N(R$^{E1a}$)$_2$. In certain embodiments, $R^{E1}$ is —CH$_2$SR$^{E1a}$.

In certain embodiments, when $R^{E1}$ is —OR$^{E1a}$, —N(R$^{E1a}$)$_2$, —SR$^{E1a}$, —CH$_2$OR$^{E1a}$, —CH$_2$N(R$^{E1a}$)$_2$, or —CH$_2$SR$^{E1a}$, $R^{E1a}$ is H. In certain embodiments, $R^{E1}$ is —Si(R$^{E1a}$)$_3$, optionally wherein each instance of $R^{E1a}$ is independently unsubstituted $C_{1-6}$ alkyl or unsubstituted phenyl. In certain embodiments, $R^{E1}$ is —Si(Me)$_3$). In certain embodiments, $R^{E1a}$ is substituted acyl. In certain embodiments, $R^{E1a}$ is unsubstituted acyl. In certain embodiments, $R^{E1a}$ is acetyl. In certain embodiments, $R^{E1a}$ is substituted acetyl. In certain embodiments, $R^{E1a}$ is substituted alkyl. In certain embodiments, $R^{E1a}$ is unsubstituted alkyl. In certain embodiments, $R^{E1a}$ is $C_{1-6}$ alkyl. In certain embodiments, $R^{E1a}$ is methyl. In certain embodiments, $R^{E1a}$ is ethyl. In certain embodiments, $R^{E1a}$ is propyl. In certain embodiments, $R^{E1a}$ is butyl. In certain embodiments, $R^{E1a}$ is substituted alkenyl. In certain embodiments, $R^{E1a}$ is unsubstituted alkenyl. In certain embodiments, $R^{E1a}$ is vinyl. In certain embodiments, $R^{E1a}$ is substituted alkynyl. In certain embodiments, $R^{E1a}$ is unsubstituted alkynyl. In certain embodiments, $R^{E1a}$ is ethynyl. In certain embodiments, $R^{E1a}$ is substituted carbocyclyl. In certain embodiments, $R^{E1a}$ is unsubstituted carbocyclyl. In certain embodiments, $R^{E1a}$ is substituted heterocyclyl. In certain embodiments, $R^{E1a}$ is unsubstituted heterocyclyl. In certain embodiments, $R^{E1a}$ is substituted aryl. In certain embodiments, $R^{E1a}$ is unsubstituted aryl. In certain embodiments, $R^{E1a}$ is substituted phenyl. In certain embodiments, $R^{E1a}$ is unsubstituted phenyl. In certain embodiments, $R^{E1a}$ is substituted heteroaryl. In certain embodiments, $R^{E1a}$ is unsubstituted heteroaryl. In certain embodiments, $R^{E1a}$ is substituted pyridyl. In certain embodiments, $R^{E1a}$ is unsubstituted pyridyl. In certain embodiments, $R^{E1a}$ is a nitrogen protecting group when attached to a nitrogen atom. In certain embodiments, $R^{E1a}$ is Bn, BOC, Cbz, Fmoc, trifluoroacetyl, triphenylmethyl, acetyl, or Ts when attached to a nitrogen atom. In certain embodiments, $R^{E1a}$ is an oxygen protecting group when attached to an oxygen atom. In certain embodiments, $R^{E1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E1a}$ is a sulfur protecting group when attached to a sulfur atom. In certain embodiments, $R^{E1a}$ is acetamidomethyl, t-Bu, 3-nitro-2-pyridine sulfenyl, 2-pyridine-sulfenyl, or triphenylmethyl when attached to a sulfur atom. In certain embodiments, two $R^{E1a}$ groups are joined to form a substituted heterocyclic ring. In certain embodiments, two $R^{E1a}$ groups are joined to form an unsubstituted heterocyclic ring.

In compounds of Formula (I), $R^E$ may include a substituent $R^{E2}$. In certain embodiments, $R^{E2}$ is H. In certain embodiments, $R^{E2}$ is halogen. In certain embodiments, $R^{E2}$ is F. In certain embodiments, $R^{E2}$ is Cl. In certain embodiments, $R^{E2}$ is Br. In certain embodiments, $R^{E2}$ is I (iodine). In certain embodiments, $R^{E2}$ is substituted acyl. In certain embodiments, $R^{E2}$ is unsubstituted acyl. In certain embodiments, $R^{E2}$ is acetyl. In certain embodiments, $R^{E2}$ is substituted acetyl. In certain embodiments, $R^{E2}$ is substituted alkyl. In certain embodiments, $R^{E2}$ is unsubstituted alkyl. In certain embodiments, $R^{E2}$ is $C_{1-6}$ alkyl. In certain embodiments, $R^{E2}$ is methyl. In certain embodiments, $R^{E2}$ is ethyl. In certain embodiments, $R^{E2}$ is propyl. In certain embodiments, $R^{E2}$ is butyl. In certain embodiments, $R^{E2}$ is substituted alkenyl. In certain embodiments, $R^{E2}$ is unsubstituted alkenyl. In certain embodiments, $R^{E2}$ is vinyl. In certain embodiments, $R^{E2}$ is substituted alkynyl. In certain embodiments, $R^{E2}$ is unsubstituted alkynyl. In certain embodiments, $R^{E2}$ is ethynyl. In certain embodiments, $R^{E2}$ is substituted carbocyclyl. In certain embodiments, $R^{E2}$ is unsubstituted carbocyclyl. In certain embodiments, $R^{E2}$ is substituted heterocyclyl. In certain embodiments, $R^{E2}$ is unsubstituted heterocyclyl. In certain embodiments, $R^{E2}$ is substituted aryl. In certain embodiments, $R^{E2}$ is unsubstituted aryl. In certain embodiments, $R^{E2}$ is substituted phenyl. In certain embodiments, $R^{E2}$ is unsubstituted phenyl. In certain embodiments, $R^{E2}$ is substituted heteroaryl. In certain embodiments, $R^{E2}$ is unsubstituted heteroaryl. In certain embodiments, $R^{E2}$ is substituted pyridyl. In certain embodiments, $R^{E2}$ is unsubstituted pyridyl. In certain embodiments, $R^{E2}$ is —CN. In certain embodiments, $R^{E2}$ is —$OR^{E2a}$. In certain embodiments, $R^{E2}$ is —$N(R^{E2a})_2$. In certain embodiments, $R^{E2}$ is —$SR^{E2a}$. In certain embodiments, $R^{E2}$ is —$CH_2OR^{E2a}$. In certain embodiments, $R^{E2}$ is —$CH_2N(R^{E2a})_2$. In certain embodiments, $R^{E2}$ is —$CH_2SR^{E2a}$.

In certain embodiments, when $R^{E2}$ is —$OR^{E2a}$, —$N(R^{E2a})_2$, —$SR^{E2a}$, —$CH_2OR^{E2a}$, —$CH_2N(R^{E2a})_2$, or —$CH_2SR^{E2a}$, $R^{E2a}$ is H. In certain embodiments, $R^{E2a}$ is substituted acyl. In certain embodiments, $R^{E2a}$ is unsubstituted acyl. In certain embodiments, $R^{E2a}$ is acetyl. In certain embodiments, $R^{E2a}$ is substituted acetyl. In certain embodiments, $R^{E2a}$ is substituted alkyl. In certain embodiments, $R^{E2a}$ is unsubstituted alkyl. In certain embodiments, $R^{E2a}$ is $C_{1-6}$ alkyl. In certain embodiments, $R^{E2a}$ is methyl. In certain embodiments, $R^{E2a}$ is ethyl. In certain embodiments, $R^{E2a}$ is propyl. In certain embodiments, $R^{E2a}$ is butyl. In certain embodiments, $R^{E2a}$ is substituted alkenyl. In certain embodiments, $R^{E2a}$ is unsubstituted alkenyl. In certain embodiments, $R^{E2a}$ is vinyl. In certain embodiments, $R^{E2a}$ is substituted alkynyl. In certain embodiments, $R^{E2a}$ is unsubstituted alkynyl. In certain embodiments, $R^{E2a}$ is ethynyl. In certain embodiments, $R^{E2a}$ is unsubstituted carbocyclyl. In certain embodiments, $R^{E2a}$ is unsubstituted carbocyclyl. In certain embodiments, $R^{E2a}$ is substituted heterocyclyl. In certain embodiments, $R^{E2a}$ is unsubstituted heterocyclyl. In certain embodiments, $R^{E2a}$ is substituted aryl. In certain embodiments, $R^{E2a}$ is unsubstituted aryl. In certain embodiments, $R^{E2a}$ is substituted phenyl. In certain embodiments, $R^{E2a}$ is unsubstituted phenyl. In certain embodiments, $R^{E2a}$ is substituted heteroaryl. In certain embodiments, $R^{E2a}$ is unsubstituted heteroaryl. In certain embodiments, $R^{E2a}$ is substituted pyridyl. In certain embodiments, $R^{E2a}$ is unsubstituted pyridyl. In certain embodiments, $R^{E2a}$ is a nitrogen protecting group when attached to a nitrogen atom. In certain embodiments, $R^{E2a}$ is Bn, BOC, Cbz, Fmoc, trifluoroacetyl, triphenylmethyl, acetyl, or Ts when attached to a nitrogen atom. In certain embodiments, $R^{E2a}$ is an oxygen protecting group when attached to an oxygen atom. In certain embodiments, $R^{E2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E2a}$ is a sulfur protecting group when attached to a sulfur atom. In certain embodiments, $R^{E2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{E2a}$ groups are joined to form a substituted heterocyclic ring. In certain embodiments, two $R^{E2a}$ groups are joined to form an unsubstituted heterocyclic ring.

In compounds of Formula (I), $R^E$ may include a substituent $R^{E3}$. In certain embodiments, $R^{E3}$ is H. In certain embodiments, $R^{E3}$ is halogen. In certain embodiments, $R^{E3}$ is F. In certain embodiments, $R^{E3}$ is Cl. In certain embodiments, $R^{E3}$ is Br. In certain embodiments, $R^{E3}$ is I (iodine). In certain embodiments, $R^{E3}$ is substituted acyl. In certain embodiments, $R^{E3}$ is unsubstituted acyl. In certain embodiments, $R^{E3}$ is acetyl. In certain embodiments, $R^{E3}$ is substituted acetyl. In certain embodiments, $R^{E3}$ is substituted alkyl. In certain embodiments, $R^{E3}$ is unsubstituted alkyl. In certain embodiments, $R^{E3}$ is $C_{1-6}$ alkyl. In certain embodiments, $R^{E3}$ is methyl. In certain embodiments, $R^{E3}$ is ethyl. In certain embodiments, $R^{E3}$ is propyl. In certain embodiments, $R^{E3}$ is butyl. In certain embodiments, $R^{E3}$ is substituted alkenyl. In certain embodiments, $R^{E3}$ is unsubstituted alkenyl. In certain embodiments, $R^{E3}$ is vinyl. In certain embodiments, $R^{E3}$ is substituted alkynyl. In certain embodiments, $R^{E3}$ is unsubstituted alkynyl. In certain embodiments, $R^{E3}$ is ethynyl. In certain embodiments, $R^{E3}$ is substituted carbocyclyl. In certain embodiments, $R^{E3}$ is unsubstituted carbocyclyl. In certain embodiments, $R^{E3}$ is substituted heterocyclyl. In certain embodiments, $R^{E3}$ is unsubstituted heterocyclyl. In certain embodiments, $R^{E3}$ is substituted aryl. In certain embodiments, $R^{E3}$ is unsubstituted aryl. In certain embodiments, $R^{E3}$ is substituted phenyl. In certain embodiments, $R^{E3}$ is unsubstituted phenyl. In certain embodiments, $R^{E3}$ is substituted heteroaryl. In certain embodiments, $R^{E3}$ is unsubstituted heteroaryl. In certain embodiments, $R^{E3}$ is substituted pyridyl. In certain embodiments, $R^{E3}$ is unsubstituted pyridyl. In certain embodiments, $R^{E3}$ is —CN. In certain embodiments, $R^{E3}$ is —$OR^{E3a}$. In certain embodiments, $R^{E3}$ is —$N(R^{E3a})_2$. In certain embodiments, $R^{E3}$ is —$SR^{E3a}$. In certain embodiments, $R^{E3}$ is —$CH_2OR^{E3a}$. In certain embodiments, $R^{E3}$ is —$CH_2N(R^{E3a})_2$. In certain embodiments, $R^{E3}$ is —$CH_2SR^{E3a}$.

In certain embodiments, when $R^{E3}$ is —$OR^{E3a}$, —$N(R^{E3a})_2$, —$SR^{E3a}$, —$CH_2OR^{E3a}$, —$CH_2N(R^{E3a})_2$, or —$CH_2SR^{E3a}$, $R^{E3a}$ is H. In certain embodiments, $R^{E3a}$ is substituted acyl. In certain embodiments, $R^{E3a}$ is unsubstituted acyl. In certain embodiments, $R^{E3a}$ is acetyl. In certain embodiments, $R^{E3a}$ is substituted acetyl. In certain embodiments, $R^{E3a}$ is substituted alkyl. In certain embodiments, $R^{E3a}$ is unsubstituted alkyl. In certain embodiments, $R^{E3a}$ is $C_{1-6}$ alkyl. In certain embodiments, $R^{E3a}$ is methyl. In certain embodiments, $R^{E3a}$ is ethyl. In certain embodiments, $R^{E3a}$ is propyl. In certain embodiments, $R^{E3a}$ is butyl. In certain embodiments, $R^{E3a}$ is substituted alkenyl. In certain embodiments, $R^{E3a}$ is unsubstituted alkenyl. In certain embodiments, $R^{E3a}$ is vinyl. In certain embodiments, $R^{E3a}$ is substituted alkynyl. In certain embodiments, $R^{E3a}$ is unsubstituted alkynyl. In certain embodiments, $R^{E3a}$ is ethynyl. In certain embodiments, $R^{E3a}$ is substituted carbocyclyl. In certain embodiments, $R^{E3a}$ is unsubstituted carbocyclyl. In certain embodiments, $R^{E3a}$ is substituted heterocyclyl. In certain embodiments, $R^{E3a}$ is unsubstituted heterocyclyl. In certain embodiments, $R^{E3a}$ is substituted substituted aryl. In certain embodiments, $R^{E3a}$ is unsubstituted aryl. In certain embodiments, $R^{E3a}$ is substituted phenyl. In certain embodiments, $R^{E3a}$ is unsubstituted phenyl. In certain embodiments, $R^{E3a}$ is substituted heteroaryl. In certain embodiments, $R^{E3a}$ is unsubstituted heteroaryl. In certain embodiments, $R^{E3a}$ is substituted pyridyl. In certain embodiments, $R^{E3a}$ is unsubstituted pyridyl. In certain embodiments, $R^{E3a}$ is a nitrogen aryl. In deprotecting group when attached to a nitrogen atom. In certain embodiments, $R^{E3a}$ is Bn, BOC, Cbz, Fmoc, trifluoroacetyl, triphenylmethyl, acetyl, or Ts when attached to a nitrogen atom. In certain embodiments, $R^{E3a}$ is an oxygen protecting group when attached to an oxygen atom. In certain embodiments, $R^{E3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E3a}$ is a sulfur protecting group when attached to a sulfur atom. In certain embodiments, $R^{E3a}$ is acetamidomethyl, t-Bu, 3-nitro-2-pyridine sulfenyl, 2-pyridine-sulfenyl, or triphenylmethyl when attached to a sulfur atom. In certain embodiments, two $R^{E3a}$ groups are joined to form a substituted heterocyclic ring. In certain embodiments, two $R^{E3a}$ groups are joined to form an unsubstituted heterocyclic ring.

In compounds of Formula (I), $R^{E1}$ and $R^{E3}$, or $R^{E2}$ and $R^{E3}$, or $R^{E1}$ and $R^{E2}$ may be joined to form a substituted or unsubstituted carbocyclic or substituted or unsubstituted heterocyclic ring. In certain embodiments, $R^{E1}$ and $R^{E3}$ are joined to form a substituted or unsubstituted carbocyclic ring. In certain embodiments, $R^{E1}$ and $R^{E3}$ are joined to form a substituted or unsubstituted heterocyclic ring. In certain embodiments, $R^{E2}$ and $R^{E3}$ are joined to form a substituted or unsubstituted carbocyclic ring. In certain embodiments, $R^{E2}$ and $R^{E3}$ are joined to form a substituted or unsubstituted heterocyclic ring. In certain embodiments, $R^{E1}$ and $R^{E2}$ are joined to form a substituted or unsubstituted carbocyclic ring. In certain embodiments, $R^{E1}$ and $R^{E2}$ are joined to form a substituted or unsubstituted heterocyclic ring.

In compounds of Formula (I), $R^E$ may include a substituent $R^{E4}$. In certain embodiments, $R^{E4}$ is a leaving group. In certain embodiments, $R^{E4}$ is halogen. In certain embodiments, $R^{E4}$ is F. In certain embodiments, $R^{E4}$ is Cl. In certain embodiments, $R^{E4}$ is Br. In certain embodiments, $R^{E4}$ is I (iodine). In certain embodiments, $R^E$ is —OS(=O)$_w$R$^{E4a}$. In certain embodiments, w is 1. In certain embodiments, w is 2. In certain embodiments, $R^E$ is —OMs. In certain embodiments, $R^{E4}$ is —OTf. In certain embodiments, $R^{E4}$ is —OTs. In certain embodiments, $R^{E4}$ is —OBs. In certain embodiments, $R^{E4}$ is 2-nitrobenzenesulfonyloxy. In certain embodiments, $R^{E4}$ is —OR$^{E4a}$. In certain embodiments, $R^{E4}$ is —OMe. In certain embodiments, $R^{E4}$ is —OCF$_3$. In certain embodiments, $R^{E4}$ is —OPh. In certain embodiments, $R^{E4}$ is —OC(=)R$^{E4a}$. In certain embodiments, $R^{E4}$ is —OC(=O) Me. In certain embodiments, $R^{E4}$ is —OC(=O)CF$_3$. In certain embodiments, $R^{E4}$ is —OC(=O)Ph. In certain embodiments, $R^{E4}$ is —OC(=O)Cl. In certain embodiments, $R^{E4}$ is —OC(=O)OR$^{E4a}$. In certain embodiments, $R^{E4}$ is —OC(=O)OMe. In certain embodiments, $R^{E4}$ is —OC(=O)O(t-Bu).

In certain embodiments, $R^{E4a}$ is substituted alkyl. In certain embodiments, $R^{E4a}$ is unsubstituted alkyl. In certain embodiments, $R^{E4a}$ is $C_{1-6}$ alkyl. In certain embodiments, $R^{E4a}$ is methyl. In certain embodiments, $R^{E4a}$ is ethyl. In certain embodiments, $R^{E4a}$ is propyl. In certain embodiments, $R^{E4a}$ is butyl. In certain embodiments, $R^{E4a}$ is substituted alkenyl. In certain embodiments, $R^{E4a}$ is unsubstituted alkenyl. In certain embodiments, $R^{E4a}$ is vinyl. In certain embodiments, $R^{E4a}$ is substituted alkynyl. In certain embodiments, $R^{E4a}$ vinyl. In unsubstituted alkynyl. In certain embodiments, $R^{E4a}$ is ethynyl. In certain embodiments, $R^{E4a}$ is substituted carbocyclyl. In certain embodiments, $R^{E4a}$ is unsubstituted carbocyclyl. In certain embodiments, $R^{E4a}$ is substituted heterocyclyl. In certain embodiments, $R^{E4a}$ is unsubstituted heterocyclyl. In certain embodiments, $R^{E4a}$ is substituted aryl. In certain embodiments, $R^{E4a}$ is unsubstituted aryl. In certain embodiments, $R^{E4a}$ is substituted phenyl. In certain embodiments, $R^{E4a}$ is unsubstituted phenyl. In certain embodiments, $R^{E4a}$ is substituted heteroaryl. In certain embodiments, $R^{E4a}$ is unsubstituted heteroaryl. In certain embodiments, $R^{E4a}$ is substituted pyridyl. In certain embodiments, $R^{E4a}$ is unsubstituted pyridyl.

In compounds of Formula (I), $R^E$ may include a Y group. In certain embodiments, Y is =O. In certain embodiments, Y is —O—. In certain embodiments, Y is =S. In certain embodiments, Y is —S—. In certain embodiments, Y is =NR$^{E6}$. In certain embodiments, Y is —NR$^{E6}$—. In certain embodiments, Y is =NH. In certain embodiments, Y is —NH—. In certain embodiments, $R^{E6}$ is H. In certain embodiments, $R^{E6}$ is substituted or unsubstituted $C_{1-6}$ alkyl (e.g., —CH$_3$). In certain embodiments, $R^{E6}$ is a nitrogen protecting group (e.g., Bn, BOC, Cbz, Fmoc, trifluoroacetyl, triphenylmethyl, acetyl, or Ts).

In compounds of Formula (I), $R^E$ may include a substituent $R^{E5}$, which is halogen. In certain embodiments, $R^{E5}$ is F, Cl, Br, or I (iodine).

In certain embodiments, a is 1. In certain embodiments, a is 2.

In certain embodiments, z is 0. In certain embodiments, z is 1. In certain embodiments, z is 2. In certain embodiments, z is 3. In certain embodiments, z is 4. In certain embodiments, z is 5. In certain embodiments, z is 6.

In certain embodiments, $R^E$ is of Formula (i-1); and $R^{E1}$ is hydrogen. In certain embodiments, $R^E$ is of Formula (i-1); and $R^{E2}$ is hydrogen. In certain embodiments, $R^E$ is of Formula (i-1); and $R^{E3}$ is hydrogen. In certain embodiments, $R^E$ is of Formula (i-1); and $R^{E2}$ and $R^{E3}$ are each hydrogen. In certain embodiments, $R^E$ is of Formula (i-1); and $R^{E1}$, $R^{E2}$ and $R^{E3}$ are each hydrogen. In certain embodiments, $R^E$ is of Formula (i-1); and $R^{E1}$ is —CH$_2$N(R$^{E1a}$). In certain embodiments, $R^E$ is of Formula (i-1); $R^{E1}$ is —CH$_2$N(R$^{E1a}$); and $R^{E1a}$ is $C_{1-6}$ alkyl. In certain embodiments, $R^E$ is of Formula (i-1); $R^{E1}$ is —CH$_2$N(R$^{E1a}$); and $R^{E1a}$ is methyl. In certain embodiments, $R^E$ is of Formula (i-1); and $R^{E2}$ is —CH$_2$N (R$^{E2a}$). In certain embodiments, $R^E$ is of Formula (i-1); $R^{E2}$ is —CH$_2$N(R$^{E2a}$); and $R^{E2a}$ is $C_{1-6}$ alkyl. In certain embodiments, $R^E$ is of Formula (i-1); $R^{E2}$ is —CH$_2$N(R$^{E2a}$); and $R^{E2a}$ is methyl. In certain embodiments, $R^E$ is of Formula (i-1); and $R^{E3}$ is —CH$_2$N(R$^{E3a}$). In certain embodiments, $R^E$ is of Formula (i-1); $R^{E3}$ is —CH$_2$N(R$^{E3a}$); and $R^{E3a}$ is $C_{1-6}$ alkyl. In certain embodiments, $R^E$ is of Formula (i-1); $R^{E3}$ is —CH$_2$N(R$^{E3a}$); and $R^{E3a}$ is methyl. In certain embodiments, $R^E$ is of Formula (i-1); and Y is =O. In certain embodiments, $R^E$ is of Formula (i-1); and $L^3$ is —NR$^{L3a}$—. In certain embodiments, $R^E$ is of Formula (i-1); and $L^3$ is —NH—. In certain embodiments, $R^E$ is of the formula:

111

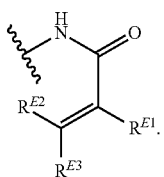

In certain embodiments, $R^E$ is of the formula:

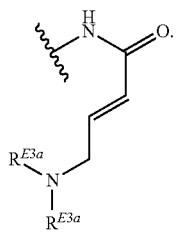

In certain embodiments, $R^E$ is of the formula:

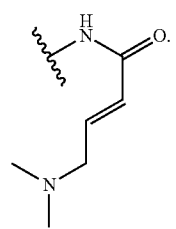 [SMILES: *NC(=O)/C=C/CN(C)C]

In certain embodiments, $R^E$ is of the formula:

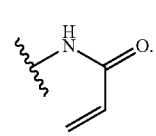 [SMILES: *NC(=O)C=C]

In certain embodiments, $R^E$ is of the formula:

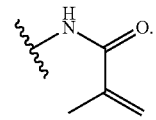

In certain embodiments, $R^E$ is of the formula:

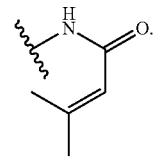 [SMILES: *NC(=O)C=C(C)C]

In certain embodiments, $R^E$ is of the formula:

112

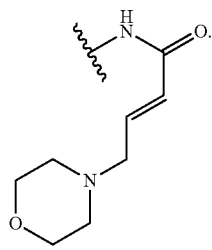 [SMILES: *NC(=O)/C=C/CN1CCOCC1]

In certain embodiments, $R^E$ is of the formula:

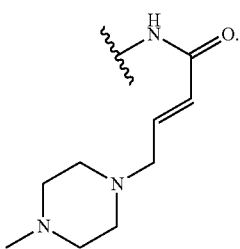 [SMILES: *NC(=O)/C=C/CN1CCN(C)CC1]

In certain embodiments, $R^E$ is of the formula:

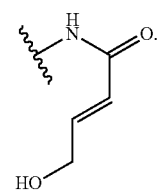

In certain embodiments, $R^E$ is of the formula:

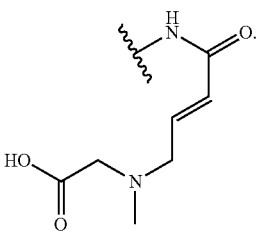 [SMILES: *NC(=O)/C=C/CN(C)CC(=O)O]

In certain embodiments, $R^E$ is of the formula:

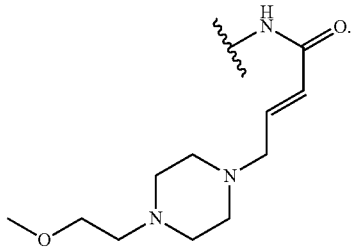 [SMILES: *NC(=O)/C=C/CN1CCN(CCOC)CC1]

In certain embodiments, $R^E$ is of the formula:

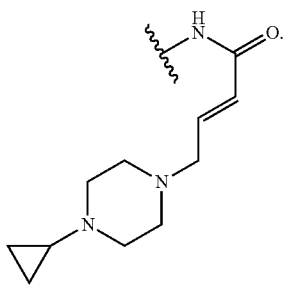 [SMILES: *NC(=O)/C=C/CN1CCN(C2CC2)CC1]

In certain embodiments, $R^E$ is of the formula:

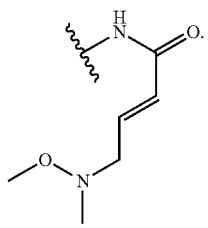 [SMILES: *NC(=O)/C=C/CN(C)OC]

In certain embodiments, $R^E$ is of the formula:

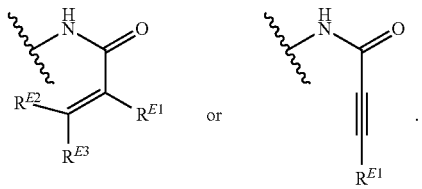

In certain embodiments, $R^E$ is of the formula:

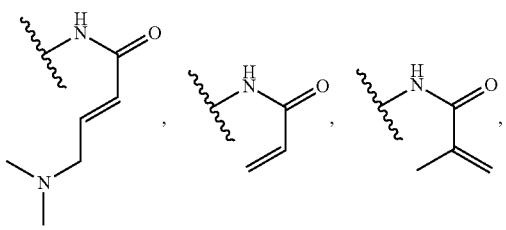

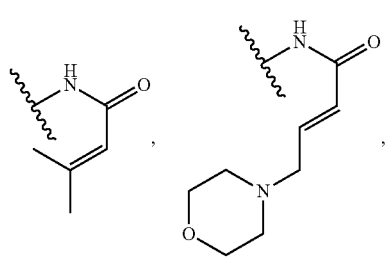

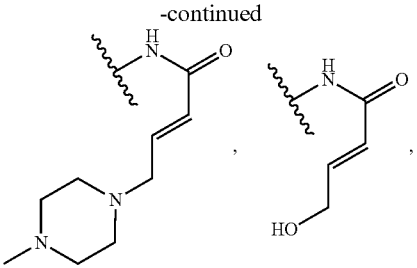

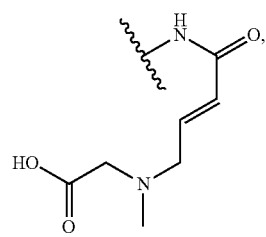

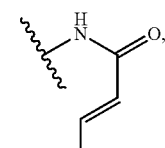

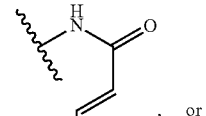

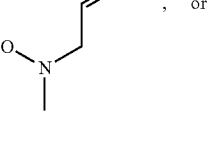

In certain embodiments, $R^E$ is of Formula (i-3); and $R^{E1}$ is hydrogen. In certain embodiments, $R^E$ is of Formula (i-3); and $R^{E1}$ is —CH$_2$N(R$^{E1a}$). In certain embodiments, $R^E$ is of Formula (i-3); and $R^{E1}$ is —Si(R$^{E1a}$)$_3$ (e.g., —Si(Me)$_3$). In certain embodiments, $R^E$ is of Formula (i-3); $R^{E1}$ is —CH$_2$N(R$^{E1a}$); and $R^{E1a}$ is C$_{1-6}$ alkyl. In certain embodiments, $R^E$ is of Formula (i-3); $R^{E1}$ is —CH$_2$N(R$^{E1a}$); and $R^{E1a}$ is methyl. In certain embodiments, $R^E$ is of Formula (i-3); and Y is =O. In certain embodiments, $R^E$ is of Formula (i-3); and $L^3$ is —NR$^{L3a}$—. In certain embodiments, $R^E$ is of Formula (i-3); and $L^3$ is —NH—.

In certain embodiments, $R^E$ is of the formula:

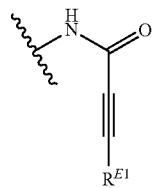

In certain embodiments, $R^E$ is of the formula:

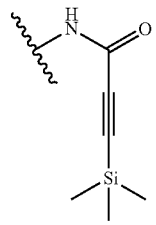

In certain embodiments, $R^E$ is not of the formula:

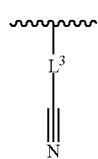
(i-5)

In certain embodiments, $R^E$ is of the formula: (i-36), (i-37), or (i-38).
In certain embodiments, $R^E$ is of the formula:

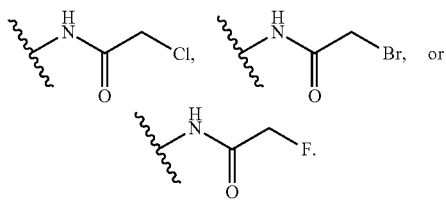

In certain embodiments, $R^E$ is of the formula:

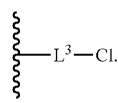
(i-36)

In certain embodiments, $R^E$ is of the formula:

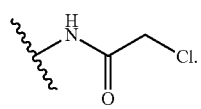 [SMILES: *NC(=O)CCl]

In certain embodiments, the compound of Formula (I) is of Formula (I-a):

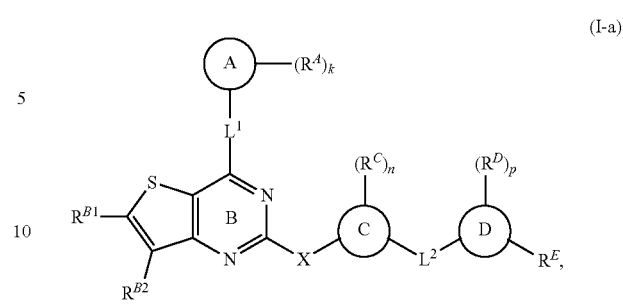
(I-a)

or a pharmaceutically acceptable salt thereof.

In certain embodiments, the compound of Formula (I) is of Formula (I-a-i):

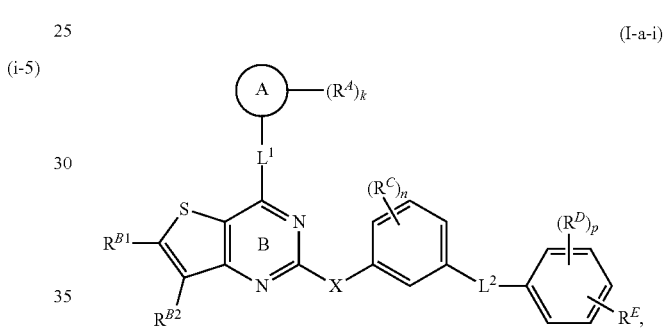
(I-a-i)

or a pharmaceutically acceptable salt thereof.

In certain embodiments, the compound of Formula (I) is of Formula (I-a-ii):

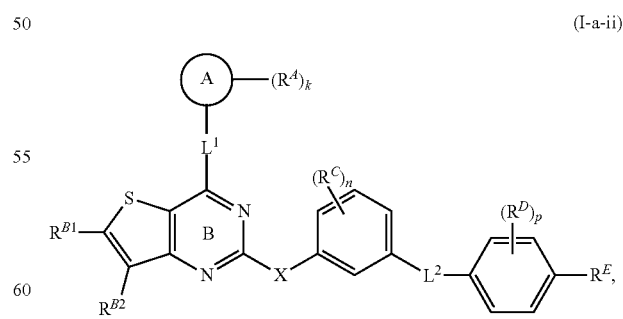
(I-a-ii)

or a pharmaceutically acceptable salt thereof.

In certain embodiments, the compound of Formula (I) is of Formula (I-a-iii):

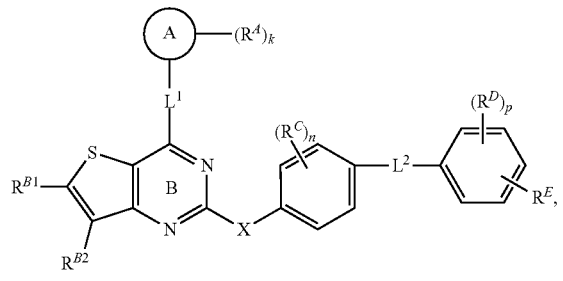

(I-a-iii)

or a pharmaceutically acceptable salt thereof.

In certain embodiments, the compound of Formula (I) is of Formula (I-a-iv):

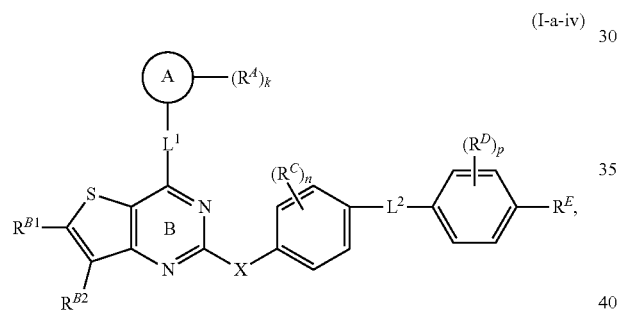

(I-a-iv)

or a pharmaceutically acceptable salt thereof.

In certain embodiments, the compound of Formula (I) is of Formula (I-b):

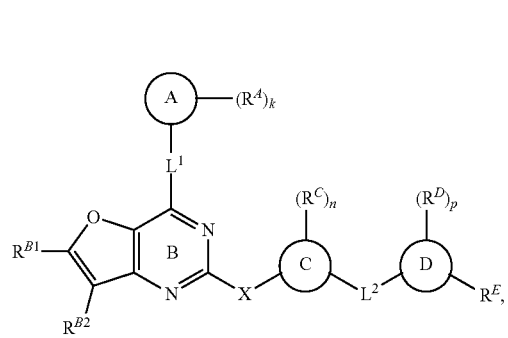

(I-b)

or a pharmaceutically acceptable salt thereof.

In certain embodiments, the compound of Formula (I) is of Formula (I-b-i):

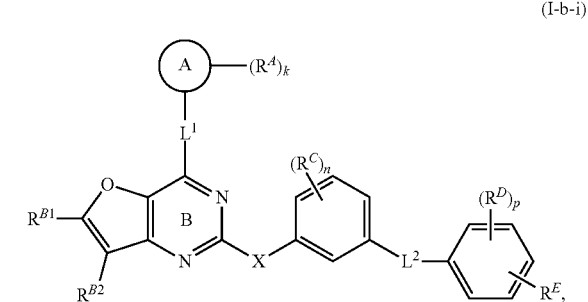

(I-b-i)

or a pharmaceutically acceptable salt thereof.

In certain embodiments, the compound of Formula (I) is of Formula (I-b-ii):

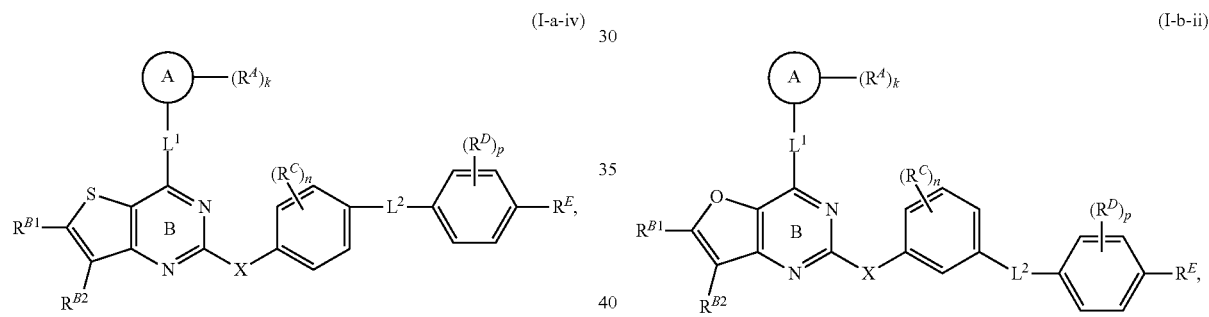

(I-b-ii)

or a pharmaceutically acceptable salt thereof.

In certain embodiments, the compound of Formula (I) is of Formula (I-b-iii):

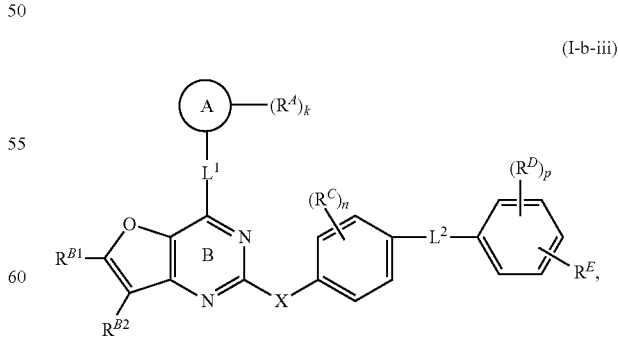

(I-b-iii)

or a pharmaceutically acceptable salt thereof.

In certain embodiments, the compound of Formula (I) is of Formula (I-b-iv):

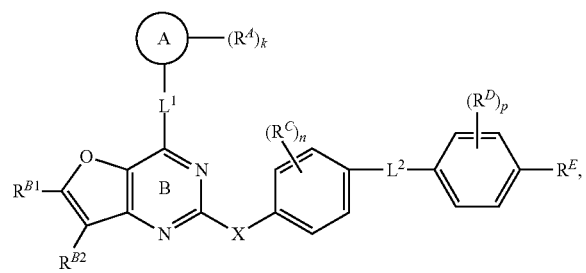

(I-b-iv)

or a pharmaceutically acceptable salt thereof.

In certain embodiments of Formulae (I), and (I-a)-(I-c), $R^E$ is of Formula (i-1); and $L^3$ is —$NR^{L3a}$—. In certain embodiments of Formulae (I)-(VI), $R^E$ is of Formula (i-1); and $L^3$ is —NH—. In certain embodiments of Formulae (I)-(VI), $R^E$ is of the formula:

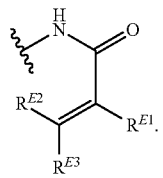

In certain embodiments of Formulae (I)-(VI), $R^E$ is of the formula:

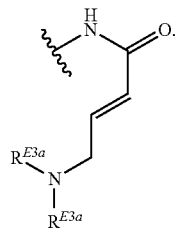

In certain embodiments, $R^E$ is of the formula:

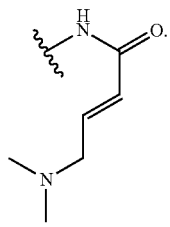 [SMILES: *NC(=O)/C=C/CN(C)C]

In certain embodiments, the compound of Formula (I) is of the formula:

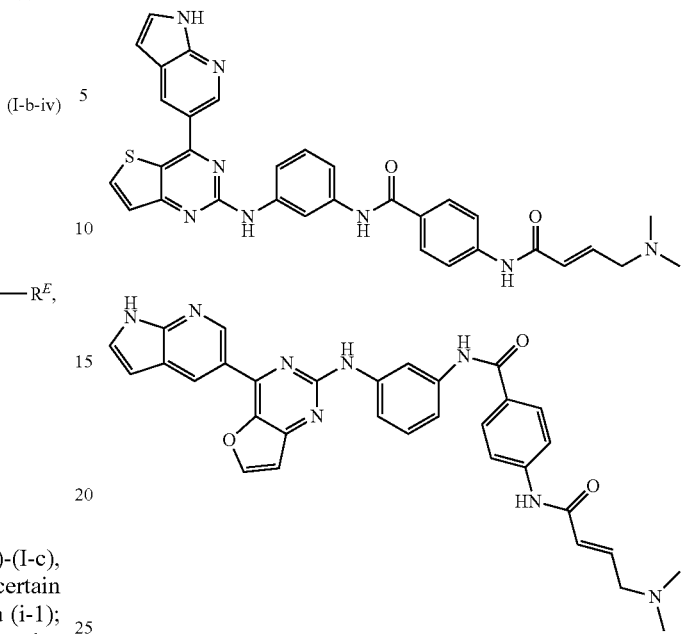

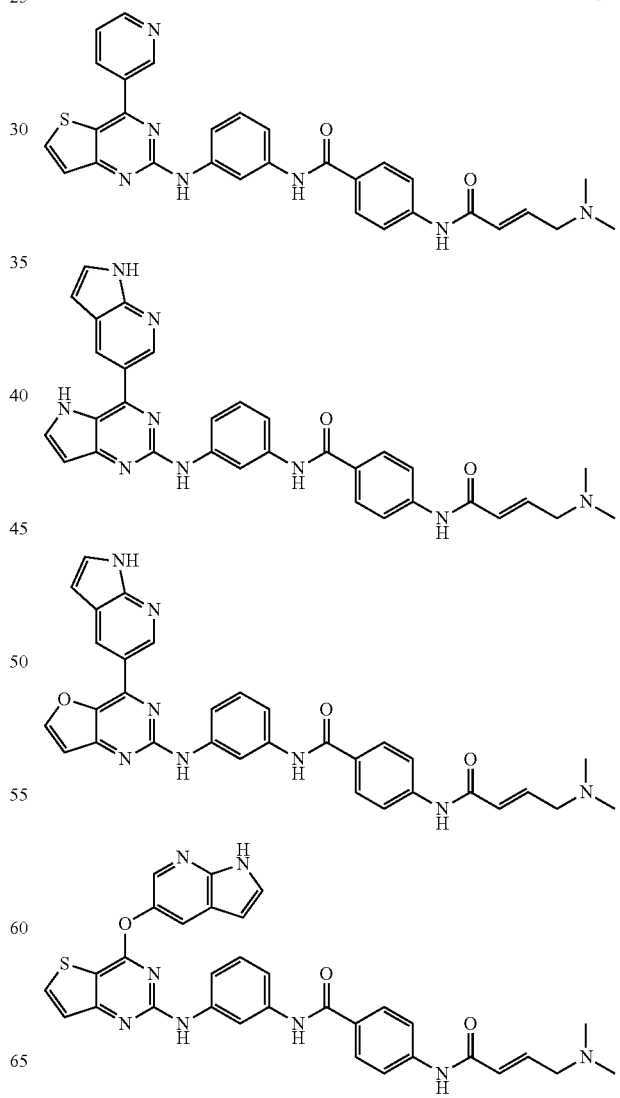

121
-continued
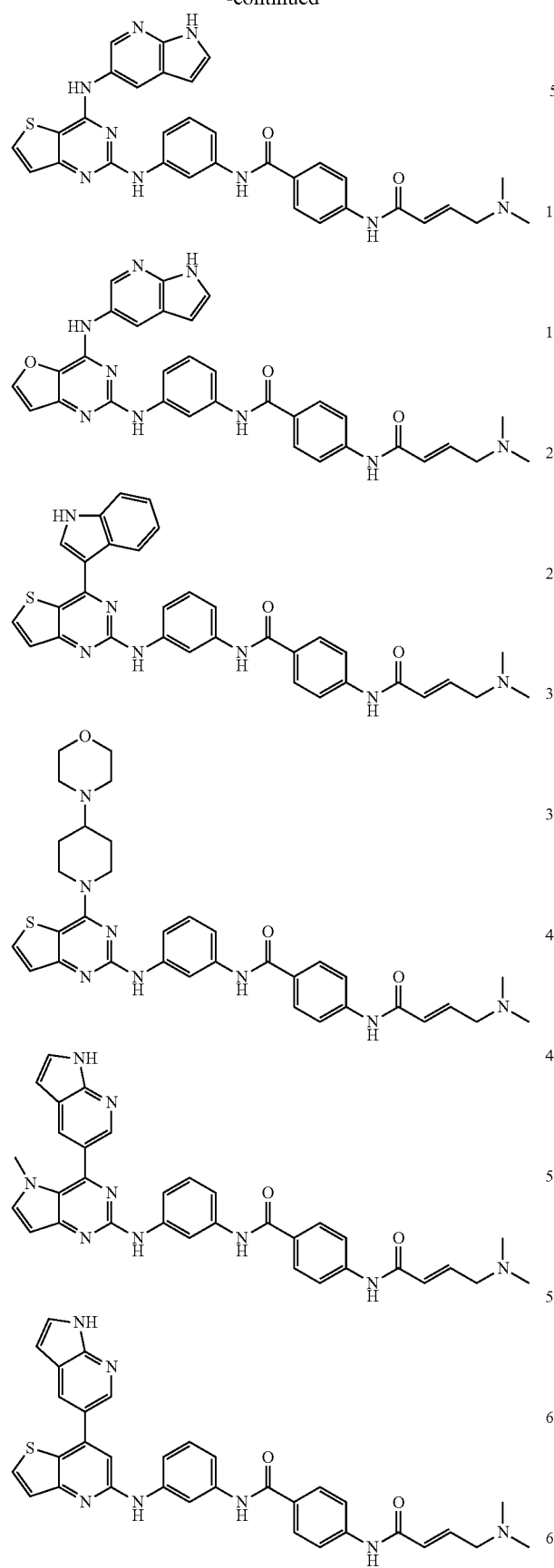
122
-continued
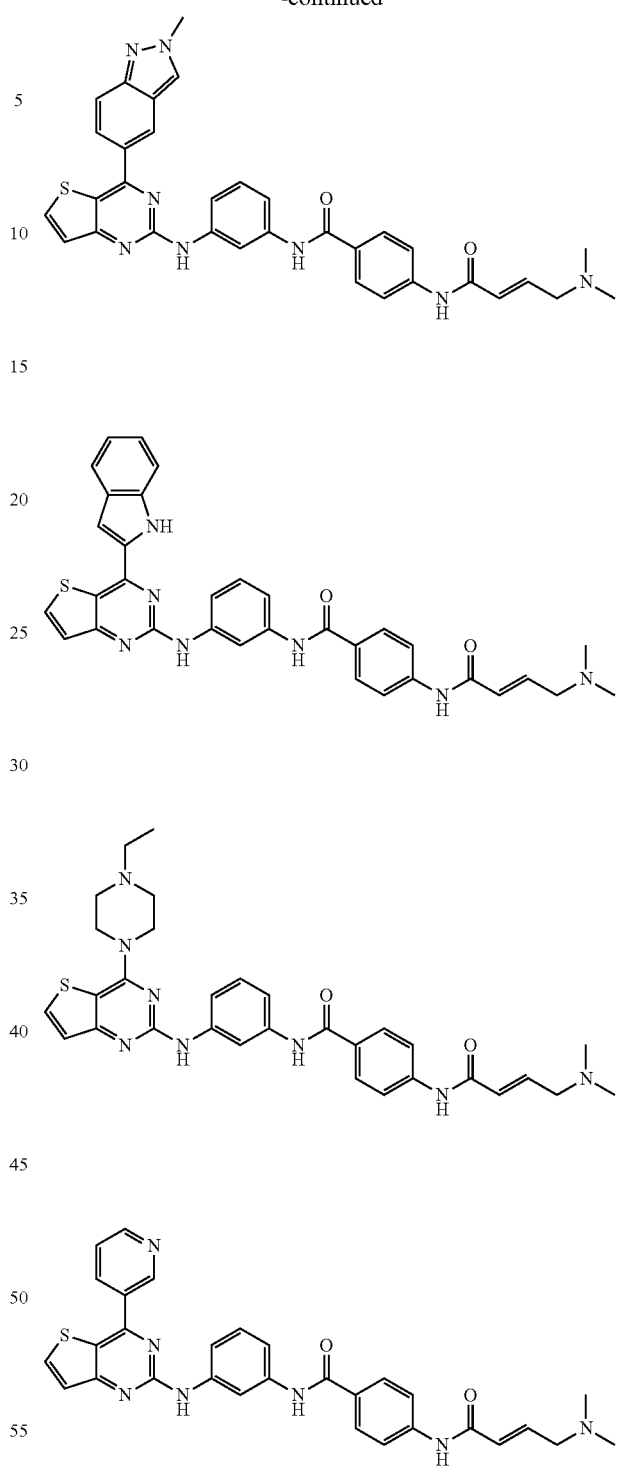
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:

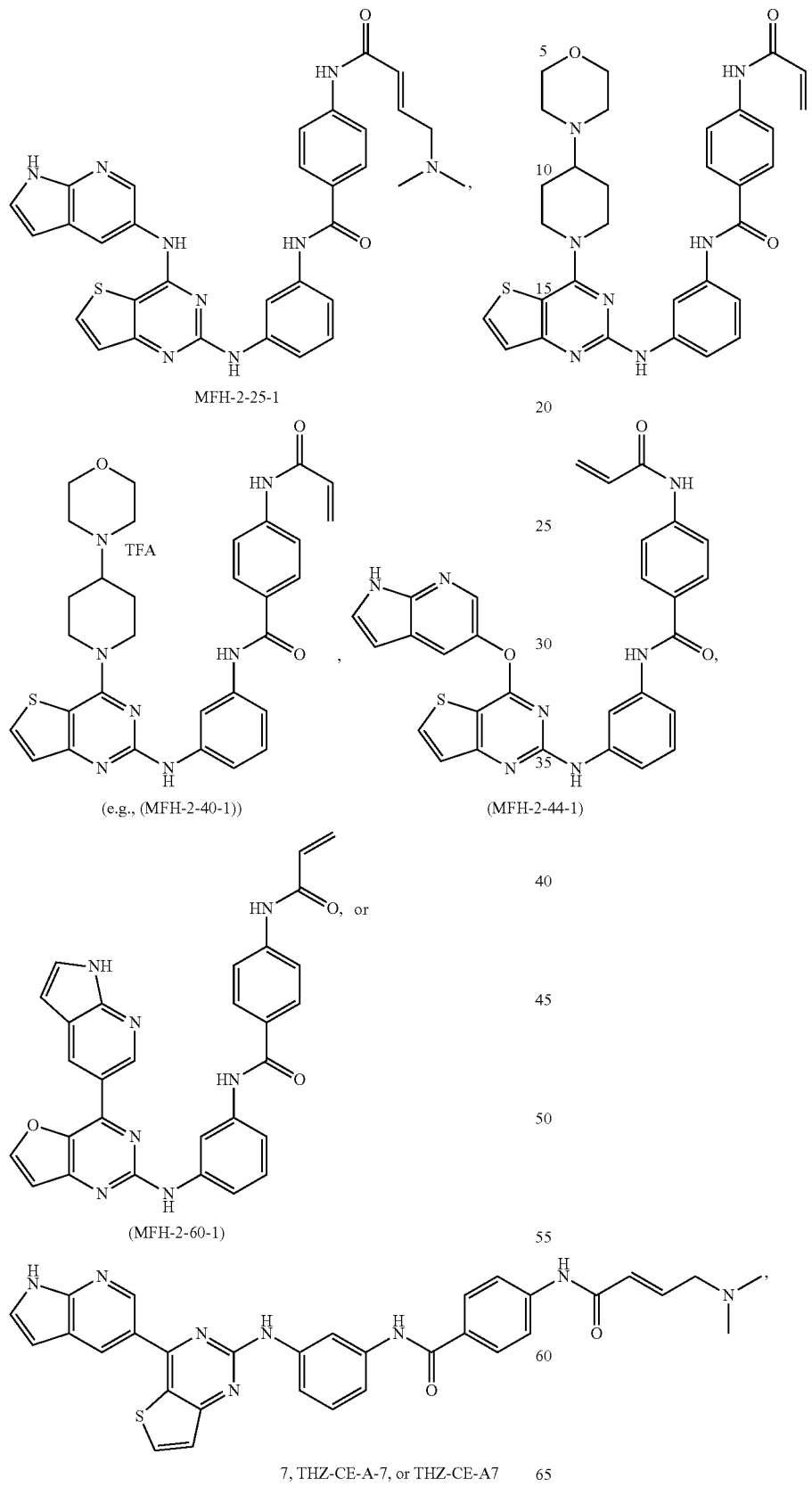

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

(FMF-3-27-1)

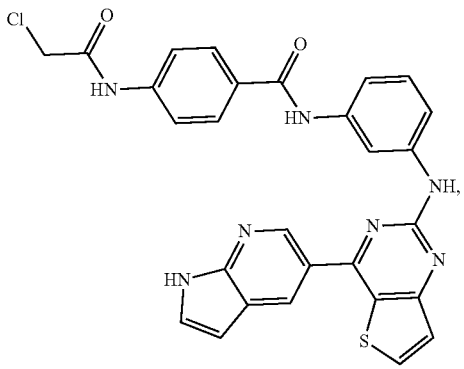

or a pharmaceutically acceptable salt, solvate, hydrate, polymorph, co-crystal, tautomer, stereoisomer, isotopically labeled derivative, or prodrug thereof.

In certain embodiments, a compound of Formula (I) is substantially pure. In certain embodiments, a compound of Formula (I) is a substantially pure stereoisomer. In certain embodiments, the compounds of the present invention are compounds of Formula (I), and pharmaceutically acceptable salts, solvates, hydrates, polymorphs, co-crystals, tautomers, stereoisomers, isotopically labeled derivatives, and prodrugs thereof. In certain embodiments, the compounds of the present invention are compounds of Formula (I), and pharmaceutically acceptable salts and stereoisomers thereof. In certain embodiments, the compounds of the present invention are compounds of Formula (I), and pharmaceutically acceptable salts thereof. In certain embodiments, the compounds of the present invention are a stereoisomeric mixture of compounds of Formula (I), and pharmaceutically acceptable salts thereof. In certain embodiments, the compounds of the present invention are a racemic stereoisomeric mixture of compounds of Formula (I), and pharmaceutically acceptable salts thereof.

The compounds of the present invention may bear multiple binding motifs for binding to a kinase. The compounds of the present invention may also inhibit a kinase. In certain embodiments, the kinase is a protein kinase. In certain embodiments, the protein kinase is a CDK (e.g., CDK7, CDK12, and/or CDK13). In certain embodiments, the kinase is a lipid kinase. In certain embodiments, the protein kinase is a PIP4K. In certain embodiments, the PIP4K is a PIP4K2. In certain embodiments, the PIP4K2 is PIP4K2A protein. In certain embodiments, the PIP4K2 is PIP4K2B protein. In certain embodiments, the PIP4K2 is PIPK2C protein. Ring A of the inventive compounds may be accommodated by a hydrophobic pocket in the ATP-binding site of the kinase (e.g., a lipid kinase such as PIP4K2 enzyme). Functionalities on Rings A and B may bind to residues of the kinase (e.g., a lipid kinase such as PIP4K2 enzyme). For example, Ring A may form a hydrogen bond with a Cys residue of PIP4K (e.g. Cys293 of PIP4K2A enzyme or Cys307 and/or Cys318 of PIP4K2B enzyme). Functional groups of $R^E$ may form one or more hydrogen bonds with the kinase (e.g., a lipid kinase such as PIP4K2 enzyme). Moreover, the Michael acceptor moiety of $R^E$ may react with a cysteine residue of the kinase (e.g., a lipid kinase such as PIP4K2 enzyme) to allow covalent attachment of the compound to the kinase (e.g., a lipid kinase such as a PIP4K2 enzyme).

In certain embodiments, the provided compound is capable of covalently modifying Cys293 of PI5P4Kα. In certain embodiments, the provided compound is capable of covalently modifying Cys307 and/or Cys318 of PI5P4Kβ. In certain embodiments, the provided compound is capable of covalently modifying Cys313 of PI5P4Kγ while Cys313 is based on the sequence alignment.

The compounds of the present invention are thought to be kinase inhibitors. In certain embodiments, the inventive compounds are inhibitors of protein kinases. In certain embodiments, the inventive compounds are CDK inhibitors. In certain embodiments, the inventive compounds are CDK7 inhibitors. In certain embodiments, the inventive compounds are CDK12 inhibitors. In certain embodiments, the inventive compounds are CDK13 inhibitors. In certain embodiments, the inventive compounds are inhibitors of lipid kinases. In certain embodiments, the inventive compounds are PIPK inhibitors. In certain embodiments, the inventive compounds are PIP4K2 inhibitors. In certain embodiments, the inventive compounds are PIP4K2A inhibitors. In certain embodiments, the inventive compounds are PIP4K2B inhibitors. In certain embodiments, the inventive compounds are PIP4K2C inhibitors. In certain embodiments, the inventive compounds are selective CDK inhibitors (e.g., being more active in inhibiting a CDK than a non-CDK kinase). In certain embodiments, the inventive compounds are selective CDK7 inhibitors (e.g., being more active in inhibiting CDK7 than a non-CDK7 kinase). In certain embodiments, the inventive compounds are selective CDK12 inhibitors. In certain embodiments, the inventive compounds are selective CDK13 inhibitors. In certain embodiments, the inventive compounds are selective PIPK inhibitors (e.g., being more active in inhibiting a PIPK than a non-PIPK kinase). In certain embodiments, the inventive compounds are selective PIP4K2 inhibitors (e.g., being more active in inhibiting PIP4K2 than a non-PIP4K2 kinase). In certain embodiments, the inventive compounds are selective PIP4K2A inhibitors. In certain embodiments, the inventive compounds are selective PIP4K2B inhibitors. In certain embodiments, the inventive compounds are selective PIP4K2C inhibitors.

The selectivity of an inventive compound for a first kinase (e.g., lipid kinase) over a second kinase (e.g., a non-lipid kinase) may be measured by the quotient of the $IC_{50}$ (half maximal inhibitory concentration) value of the inventive compound in inhibiting the activity of the second kinase over the $IC_{50}$ value of the inventive compound in inhibiting the activity of the first kinase. The selectivity of an inventive compound for a first kinase over a second kinase may also be measured by the quotient of the $K_d$ (dissociation constant) value of an adduct (covalent or non-covalent) of the inventive compound and the second kinase over the $K_d$ value of an adduct of the inventive compound and the first kinase. In certain embodiments, the selectivity is at least about 1-fold, at least about 2-fold, at least about 5-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold. In certain embodiments, $IC_{50}$ values are measured by a functional antagonist assay. In certain embodiments, $IC_{50}$ values are measured by a competition binding assay. In certain embodiments, $IC_{50}$ values are measured by a method described herein. In certain embodiments, $K_d$ values are measured by a nuclear magnetic resonance method (e.g., a linearization method and a curve fitting method). In certain embodiments, $K_d$ values are measured by a mass spectrometry method (e.g., a one-ligand one-binding-site ESI-MS method).

Pharmaceutical Compositions, Kits, and Administration

The present invention provides pharmaceutical compositions comprising a compound of Formula (I), e.g., a compound of Formula (I), or a pharmaceutically acceptable salt, solvate, hydrate, polymorph, co-crystal, tautomer, stereoisomer, isotopically labeled derivative, or prodrug thereof, as described herein, and optionally a pharmaceutically acceptable excipient. In certain embodiments, the pharmaceutical composition of the invention comprises a compound of Formula (I), or a pharmaceutically acceptable salt thereof, and optionally a pharmaceutically acceptable excipient. In certain embodiments, the compound of Formula (I), or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

In certain embodiments, a dose described herein is a dose to an adult human whose body weight is 70 kg. In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is selected from the group consisting of cytotoxic agents, epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the invention are kits (e.g., pharmaceutical packs). The inventive kits may be useful for preventing and/or treating a proliferative disease (e.g., cancer (e.g., leukemia, lymphoma, melanoma, multiple myeloma, breast cancer, Ewing's sarcoma, osteosarcoma, brain cancer, neuroblastoma, lung cancer), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, and prodrug thereof, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, polymorph, co-crystal, tautomer, stereoisomer, isotopically labeled derivative, and prodrug thereof, or a pharmaceutical composition thereof, to a subject to prevent and/or treat a proliferative disease.

Methods of Treatment and Uses

The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The proliferative disease to be treated or prevented using the compounds of Formula (I) may be associated with overexpression of a kinase. The proliferative disease to be treated or prevented using the compounds of Formula (I) may be associated with aberrant activity of a kinase. In certain embodiments, the kinase is a lipid kinase. In certain embodiments, the lipid kinase is a PIP kinase. In certain embodiments, the PIPK is PIP4K, catalyzing phosphorylation of lipid phosphatidylinositol-5-phosphate (PI-5-P) at the 4-position to generate phosphatidylinositol-4,5-bisphosphate (PI-4,5-$P_2$). In some embodiments, the PIP4K is class I PIP4K, i.e. PIP4K1. In some embodiments, the PIP4K is class II PIP4K, i.e. PIP4K2. In some embodiments, the PIP4K2 is PIP4K2A protein. In some embodiments, the PIP4K2 is PIP4K2B protein. In some embodiments, the PIP4K2 is PIP4K2C protein.

In certain embodiments, the kinase is a protein kinase. In certain embodiments, the protein kinase is a cyclin-dependent kinase (CDK). The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as cyclin dependent kinases (CDKs) and a diverse set of their cognate protein partners termed cyclins. CDKs are CDC2 (also known as CDK1) homologous serine-threonine kinase proteins that are able to utilize ATP as a substrate in the phosphorylation of diverse polypeptides in a sequence-dependent context. Cyclins are a family of proteins characterized by a homology region, containing approximately 100 amino acids, termed the "cyclin box" which is used in binding to, and defining selectivity for, specific CDK partner proteins. In certain embodiments, the CDK is CDK7. In certain embodiments, the CDK is CDK12. In certain embodiments, the CDK is CDK13.

In certain embodiments, a proliferative disease may be associated with aberrant activity of a CDK (e.g., CDK7). Aberrant activity of a CDK (e.g., CDK7) may be an elevated and/or an inappropriate activity of the CDK. Deregulation of cell cycle progression is a characteristic of a proliferative disease, and a majority of proliferative diseases have abnormalities in some component of CDK (e.g., CDK7) activity, frequently through elevated and/or inappropriate CDK activation. Inhibition of the catalytic activity of CDK7 would be expected to inhibit cell cycle progression by blocking the phosphorylation of cell cycle CDKs, and would additionally inhibit transcription of effectors of cell division. In certain embodiments, CDK7 is not overexpressed, and the activity of CDK7 is elevated and/or inappropriate. In certain other embodiments, CDK7 is overexpressed, and the activity of CDK7 is elevated and/or inappropriate. The compounds of Formula (I), and pharmaceutically acceptable salts, solvates, hydrates, polymorphs, co-crystals, tautomers, stereoisomers, isotopically labeled derivatives, prodrugs, and compositions thereof, may inhibit the activity of CDK7 and be useful in treating and/or preventing proliferative diseases.

In other embodiments, the proliferative disease to be treated or prevented using the compounds of Formula (I) will typically be associated with aberrant activity of CDK12. Aberrant activity of CDK12 may be an elevated and/or an inappropriate (e.g., abnormal) activity of CDK12. In certain embodiments, CDK12 is not overexpressed, and the activity of CDK12 is elevated and/or inappropriate. In certain other embodiments, CDK12 is overexpressed, and the activity of CDK12 is elevated and/or inappropriate. The compounds of Formula (I), and pharmaceutically acceptable salts, solvates, hydrates, tautomers, stereoisomers, isotopically labeled derivatives, and compositions thereof, may inhibit the activity of CDK12 and be useful in treating and/or preventing proliferative diseases.

In other embodiments, the proliferative disease to be treated or prevented using the compounds of Formula (I) will typically be associated with aberrant activity of CDK13. Aberrant activity of CDK13 may be an elevated and/or an inappropriate (e.g., abnormal) activity of CDK13. In certain embodiments, CDK13 is not overexpressed, and the activity of CDK13 is elevated and/or inappropriate. In certain other embodiments, CDK13 is overexpressed, and the activity of CDK13 is elevated and/or inappropriate. The compounds of Formula (I), and pharmaceutically acceptable salts, solvates, hydrates, tautomers, stereoisomers, isotopically labeled derivatives, and compositions thereof, may inhibit the activity of CDK13 and be useful in treating and/or preventing proliferative diseases.

In certain embodiments, the proliferative disease to be treated or prevented using the compounds of Formula (I) is cancer. All types of cancers disclosed herein or known in the art are contemplated as being within the scope of the invention. In some embodiments, the cancer has one or more mutations. In certain embodiments, the cancer has EGFR mutation. In certain embodiments, the cancer has TP53 mutation. In certain embodiments, the cancer has loss of TP53 mutation. In certain embodiments, the cancer has KRAS mutation. In certain embodiments, the cancer has ALK mutation. In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of MYC (a gene that codes for a transcription factor). In certain embodiments, the proliferative disease is a hematological malignancy. In certain embodiments, the proliferative disease is a blood cancer. In certain embodiments, the proliferative disease is a hematological malignancy. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is acute monocytic leukemia (AMoL). In certain embodiments, the proliferative disease is lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is breast cancer. In certain embodiments, the proliferative disease is triple-negative breast cancer (TNBC). In certain embodiments, the proliferative disease is a bone cancer. In certain embodiments, the proliferative disease is osteosarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the lung cancer has one or more mutations. In certain embodiments, the lung cancer has EGFR mutation. In certain embodiments, the lung cancer has TP53 mutation. In certain embodiments, the lung cancer has loss of TP53 mutation. In certain embodiments, the lung cancer has KRAS mutation. In certain embodiments, the lung cancer has ALK mutation. In some embodiments, the proliferative disease is small cell lung cancer (SCLC). In some embodiments, the proliferative disease is non-small cell lung cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

In certain embodiments, the infectious disease to be treated or prevented using the compounds of Formula (I) is a viral disease. Such viral infections are described in U.S. Provisional patent application, U.S. Ser. No. 61/622,828, filed Apr. 11, 2012, and international PCT application, PCT/US2013/032488, filed Mar. 15, 2013 and published on Oct. 17, 2011, each of which is incorporated herein in its entirety by reference.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a B-cell. In certain embodiments, the cell is a T-cell. In certain embodiments, the cell is a cancer cell. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

In another aspect, the present invention provides methods of modulating the activity of a kinase (e.g. a lipid kinase such as PIPK (e.g. PIP4K2A, PIP4K2B, or PIP4K2C protein) enzyme or a protein kinase such as CDK (e.g., CDK7, CDK1, CDK2, CDK5, CDK8, CDK9, CDK12, CDK13) enzyme) in a biological sample or subject. In certain embodiments, the activity of the kinase is aberrant activity of the kinase. In certain embodiments, the inhibition of the activity of the kinase is irreversible. In other embodiments, the inhibition of the activity of the kinase is reversible. In certain embodiments, the methods of inhibiting the activity of the kinase include attaching a compound of Formula (I) to the kinase.

Also provided in the present invention are methods of inhibiting transcription in a biological sample or subject.

The present invention also provides methods of inhibiting cell growth in a biological sample or subject.

In certain embodiments, the methods described herein include administering to a subject or contacting a biological sample with an effective amount of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound of Formula (I), or a pharmaceutically acceptable salt thereof, or a pharmaceutical composition thereof. In certain embodiments, the compound is contacted with a biological sample. In certain embodiments, the compound is administered to a subject.

In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is an anti-myelodysplasia agent. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), or a combination thereof.

In certain embodiments, the additional pharmaceutical agent is an anti-macroglobulinemia agent.

In certain embodiments, the additional pharmaceutical agent is LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is a histone deacetylase inhibitor. In certain embodiments, the histone deacetylase inhibitor is a hydroxamic acid such as Vorinostat (SAHA), ITF2357, or PXD-101, a cyclic peptide such as depsipeptide, a benzamide such as MS-275, or an aliphatic acid such as valproic acid or AN-9.

In certain embodiments, the additional pharmaceutical agent is an inhibitor of a lipid kinase. In certain embodiments, the additional pharmaceutical agent is an inhibitor of a PIP4K. In certain embodiments, the additional pharmaceutical agent is an inhibitor of a PIP4K2. In certain embodiments, the additional pharmaceutical agent is an inhibitor of a PIP4K2A. In certain embodiments, the additional pharmaceutical agent is an inhibitor of a PIP4K2B. In certain embodiments, the additional pharmaceutical agent is an inhibitor of a PIP4K2C. In certain embodiments, the additional pharmaceutical agent is an inhibitor of a protein kinase. In certain embodiments, the additional pharmaceutical agent is an inhibitor of a CDK. In certain embodiments, the additional pharmaceutical agent is an inhibitor of CDK7. In certain embodiments, the additional pharmaceutical agent is an inhibitor of CDK12. In certain embodiments, the additional pharmaceutical agent is an inhibitor of CDK13. In certain embodiments, the additional pharmaceutical agent is flavopiridol, triptolide, SNS-032 (BMS-387032), PHA-767491, PHA-793887, BS-181, (S)-CR8, (R)-CR8, or NU6140. In certain embodiments, the additional pharmaceutical agent is an inhibitor of a mitogen-activated protein kinase (MAPK). In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a CaM kinase. In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase. In certain embodiments, the additional pharmaceutical agent is an inhibitor of one or more protein kinases selected from the group consisting of IRAK1, IRAK4, BMX, and PI3K. In certain embodiments, the additional pharmaceutical agent is an inhibitor of one or more protein kinases selected from the group consisting of BUB1B, CDK2, CDK9, CHEK2, FGR, HIPK4, PRKCQ, RET, SRC, or MELK. In certain embodiments, the additional pharmaceutical agent is an inhibitor of one or more protein kinases selected from the group consisting of ABL, ARG, BLK, CSK, EphB1, EphB2, FGR, FRK, FYN, SRC, YES, LCK, LYN, MAP2K5, NLK, p38a, SNRK, and TEC. In certain embodiments, the additional pharmaceutical agent is an inhibitor of one or more protein kinases selected from the group consisting of ABL1(H396P)-phosphorylated, ABL1-phosphorylated, BLK, EPHA4, EPHB2, EPHB3, EPHB4, FGR, JAK3(JH1 domain-catalytic), KIT, KIT(L576P), KIT(V559D), PDGFRB, SRC, YES, ABL1(H396P)-nonphosphorylated, ABL1(Y253F)-phosphorylated, ABL1-nonphosphorylated, FRK, LYN, ABL1(Q252H)-nonphosphorylated, DDR1, EPHB1, ERBB4, p38-alpha, ABL2, ABL1(Q252H)-phosphorylated, SIK, EPHA8, MEK5, ABL1(E255K)-phosphorylated, ABL1(F317L)-nonphosphorylated, FYN, LCK, EPHA2, ABL(M351T)-phosphorylated, TXK, EGFR(L858R), EGFR(L861Q), ERBB2, ERBB3, EPHA5, ABL1(F317I)-nonphosphorylated, EGFR(L747-E749del, A750P), CSK, EPHA1, ABL1(F317L)-phosphorylated, BRAF(V600E), EGFR, KIT-autoinhibited, and EGFR(E746-A750del). In certain embodiments, the additional pharmaceutical agent is an inhibitor of one or more protein kinases selected from the group consisting of ABL1(F317L)-nonphosphorylated, ABL1(H396P)-nonphosphorylated, AB L1(H396P)-phosphorylated, ABL1-phosphorylated, BLK, EPHA4, EPHB2, EPHB3, EPHB4, JAK3(JH1domain-catalytic), KIT, KIT(L576P), KIT(V559D), LYN, PDGFRB, SRC, YES, ABL1-nonphosphorylated, ABL1(Y253F)-phosphorylated, ERBB3, FGR, FRK, p38-alpha, ABL1(F317I)-nonphosphorylated, DDR1, EPHA2, ABL1(Q252H)-phosphorylated, MEK5, ABL1(Q252H)-nonphosphorylated, ABL2, FYN, EPHB1, ABL1(E255K)-phosphorylated, ABL1(F317L)-phosphorylated, EPHA1, ABL1(M351T)-phosphorylated, ERBB4, TXK, LCK, EPHA8, SIK, EPHA5, EGFR(L861Q), CSF1R-autoinhibited, BRAF(V600E), BRK, CSK, KIT(D816V), KIT-autoinhibited, EGFR(L747-T751del,Sins), EGFR(L858R), EGFR(L747-E749del, A750P), and CSF1R. In certain embodiments, the additional pharmaceutical agent is an anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the compounds described herein or pharmaceutical compositions can be administered in combination with an anti-cancer therapy including, but not limited to, transplantation (e.g., bone marrow transplantation, stem cell transplantation), surgery, radiation therapy, immunotherapy, and chemotherapy.

Another aspect of the invention relates to methods of screening a library of compounds to identify one or more compounds that are useful in the treatment of a proliferative disease, in inhibiting a kinase (e.g., PIPK or CDK (e.g CDK7, CDK12, CDK13) enzyme), in inhibiting cell growth. In certain embodiments, the library of compounds is a library of compounds of Formula (I). The methods of screening a library include providing at least two different compounds of Formula (I), or pharmaceutically acceptable salts, solvates, hydrates, polymorphs, co-crystals, tautomers, stereoisomers, isotopically labeled derivatives, or prodrugs thereof, or pharmaceutical compositions thereof; and performing at least one assay using the different compounds of Formula (I), or pharmaceutically acceptable salts, solvates, hydrates, polymorphs, co-crystals, tautomers, stereoisomers, isotopically labeled derivatives, or prodrugs thereof, or pharmaceutical compositions thereof, to detect one or more characteristics associated with the proliferative disease. In certain embodiments, the methods of screening a library include providing at least two different compounds of Formula (I), or pharmaceutically acceptable salts thereof, or pharmaceutical compositions thereof; and performing at least one assay using the different compounds of Formula (I), or pharmaceutically acceptable salts thereof, or pharmaceutical compositions thereof, to detect one or more characteristics associated with the proliferative disease. The characteristic to be detected may be a desired characteristic associated with the proliferative disease. In certain embodiments, the desired characteristic is anti-proliferation. In certain embodiments, the desired characteristic is anti-cancer. In certain embodiments, the desired characteristic is inhibition of a kinase. In certain embodiments, the desired characteristic is inhibition of a lipid kinase. In certain embodiments, the desired characteristic is inhibition of PIPK. In certain embodiments, the desired characteristic is inhibition of PIP4K. In certain embodiments, the desired characteristic is inhibition of class II PIP4K, i.e. PIP4K2. In certain embodiments, the desired characteristic is inhibition of PIP4K2A. In certain embodiments, the desired characteristic is inhibition of PIP4K2B. In certain embodiments, the desired characteristic is inhibition of PIP4K2C. In certain embodiments, the desired characteristic is inhibition of a protein kinase. In certain embodiments, the desired characteristic is inhibition of CDK. In certain embodiments, the desired characteristic is inhibition of CDK7. In certain embodiments, the desired characteristic is inhibition of CDK12. In certain embodiments, the desired characteristic is inhibition of CDK13. In certain embodiments, the desired characteristic is down-regulation of a kinase such as PIPK or CDK.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthesis of the Compounds

The compounds provided herein can be prepared from readily available starting materials using the following general methods and procedures. See, e.g., Scheme 1 below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Figure 2:
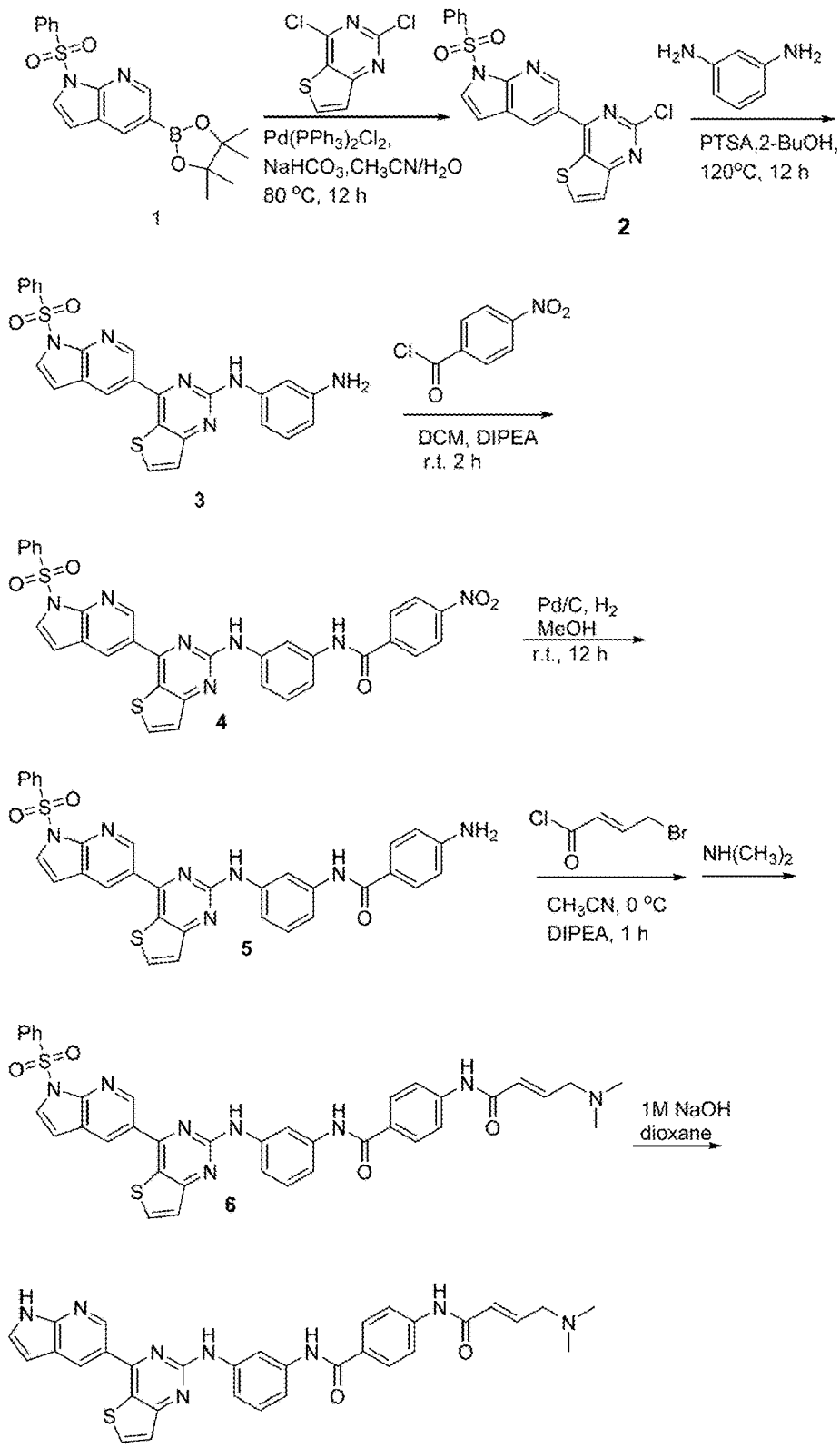
FIG. 2 shows an exemplary synthesis of Compound 7.
Figure 3A:
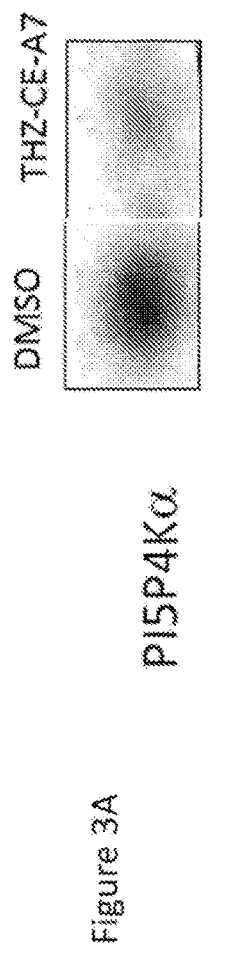
FIGS. 3A and 3B show the inhibition of PI5P4Kα/β by compound THZ-CE-A7.
Figure 3B:
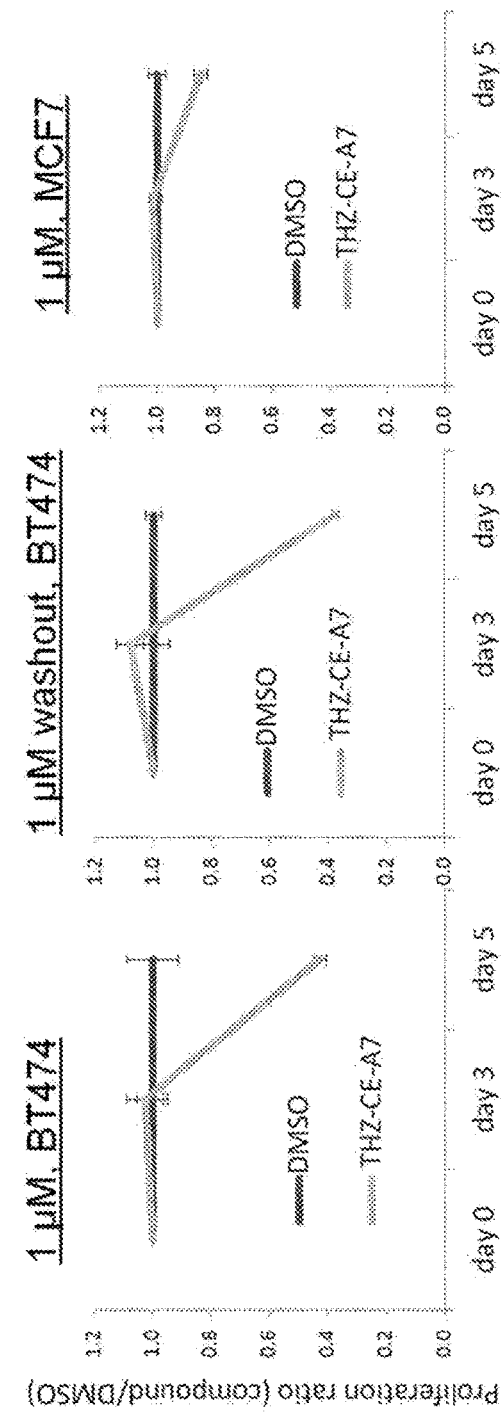

Example 1. Synthesis of Compound 7 (FIG. 2)

2-chloro-4-(1-(phenylsulfonyl)-1H-pyrrolo[2,3-b]pyridin-5-yl)thieno[3,2-d]pyrimidine (Compound 2)

To a solution of 1 (1.0 g, 2.6 mmol) in MeCN and H$_2$O(20 mL, 4/1, v/v) was added 2,4-dichlorothieno[3,2-d]pyrimidine (0.53 g, 2.6 mmol), NaHCO$_3$ (0.21 g, 2.6 mmol) and Pd(PPh$_3$)$_2$Cl$_2$(91 mg, 0.013 mmol). The reaction mixture was heated to 80° C. for 12 h. Then the mixture was diluted with EtOAc (100 mL) at room temperature, washed with water and brine, dried (Na$_2$SO$_4$), and concentrated. The residue was purified by a silica gel column to afford the title compound 2(0.83 g, 75%). MS(ESI): m/z 427.15 (M+H)$^+$.

N1-(4-(1-(phenylsulfonyl)-1H-pyrrolo[2,3-b]pyridin-5-yl)thieno[3,2-d]pyrimidin-2-yl)benzene-1,3-diamine (Compound 3)

To a solution of 2 (0.83 g, 1.95 mmol) in 2-BuOH (5.0 mL) was added benzene-1,3-diamine (0.21 g, 1.95 mmol) and PTSA (0.33 mg, 1.95 mmol). The reaction mixture was heated to 120° C. for 12 h. Then the resulting mixture was diluted with EtOAc (150 mL) at room temperature, washed with water and brine, dried (Na$_2$SO$_4$), and concentrated. The residue was purified by a silica gel column to afford the title compound 3 (0.31 g, 32%). MS(ESI): m/z 499.21 (M+H)$^+$.

4-nitro-N-(3-(4-(1-(phenylsulfonyl)-1H-pyrrolo[2,3-b]pyridin-5-yl)thieno[3,2-d]pyrimidin-2-ylamino)phenyl)benzamide (Compound 4)

To a solution of 3 (0.31 g, 0.62 mmol) in DCM (5.0 mL) was added 4-nitrobenzoyl chloride (0.47 g, 0.93 mmol) and DIPEA (0.20 mL). The reaction mixture was stirred at room temperature for 2 h. Then the resulting mixture was concentrated and purified by a silica gel column to afford the title compound 4 (0.32 g, 81%). MS(ESI): m/z 648.30 (M+H)$^+$.

4-amino-N-(3-(4-(1-(phenylsulfonyl)-1H-pyrrolo[2,3-b]pyridin-5-yl)thieno[3,2-d]pyrimidin-2-ylamino)phenyl)benzamide (Compound 5)

To a solution of 4 (0.32 g, 0.5 mmol) in MeOH (8.0 mL) was added 10% Pd/C (120 mg) and protected by a balloon of H$_2$. The reaction mixture was stirred at 25° C. for 12 h. Then the resulting mixture was filtered through a pad of celite. The crude product was purified by a silica gel column to afford the title compound 5 (0.25 g, 80%). MS(ESI): m/z 618.24 (M+H)$^+$.

(E)-4-(4-(dimethylamino)but-2-enamido)-N-(3-(4-(1-(phenylsulfonyl)-1H-pyrrolo[2,3-b]pyridin-5-yl)thieno[3,2-d]pyrimidin-2-ylamino)phenyl)benzamide (Compound 6)

To a solution of 5 (0.25 g, 0.4 mmol) in CH$_3$CN (8.0 mL) was added (E)-4-bromobut-2-enoyl chloride (0.10 g, 0.6 mmol) and DIPEA (0.12 mL). The reaction mixture was stirred at 0° C. for 0.5 h. Then 1 mL of 2.0 M dimethylamine (in THF) was added. The resulting mixture was concentrated and purified by a silica gel column to afford the title compound 6 (0.12 g, 42%). MS(ESI): m/z 729.11 (M+H)$^+$.

(E)-N-(4-(5-chloro-4-(1H-pyrrolo[2,3-b]pyridin-5-yl)pyrimidin-2-ylamino)phenyl)-3-(4-(dimethylamino)but-2-enamido)benzamide (Compound 7)

To a solution of 6 (100 mg, 0.13 mmol) in dioxane (4.0 mL) was IM NaOH (1 mL). The reaction mixture was stirred at room temperature for 2 h. Then resulting mixture was concentrated and purified by a silica gel column to afford the title compound 7 (18.4 mg). MS m/z 589.18 (M+H)$^+$. $^1$H NMR (400 MHz, DMSO-d$_6$) δ 12.00 (s, 1H), 10.69 (s, 1H), 10.13 (s, 1H), 9.73 (s, 1H), 9.02 (s, 1H), 8.76 (s, 1H), 8.37 (s, 2H), 7.96 (d, J=7.8 Hz, 2H), 7.80 (d, J=7.8 Hz, 2H), 7.55-7.43 (m, 2H), 7.42 (s, 1H), 7.28-7.00 (m, 2H), 6.81-6.77 (m, 1H), 6.48 (d, J=15.2 Hz, 1H), 3.86 (d, J=15.2 Hz, 2H), 2.71 (s, 6H).
Example 2. Synthesis of Compound MFH-2-25-1
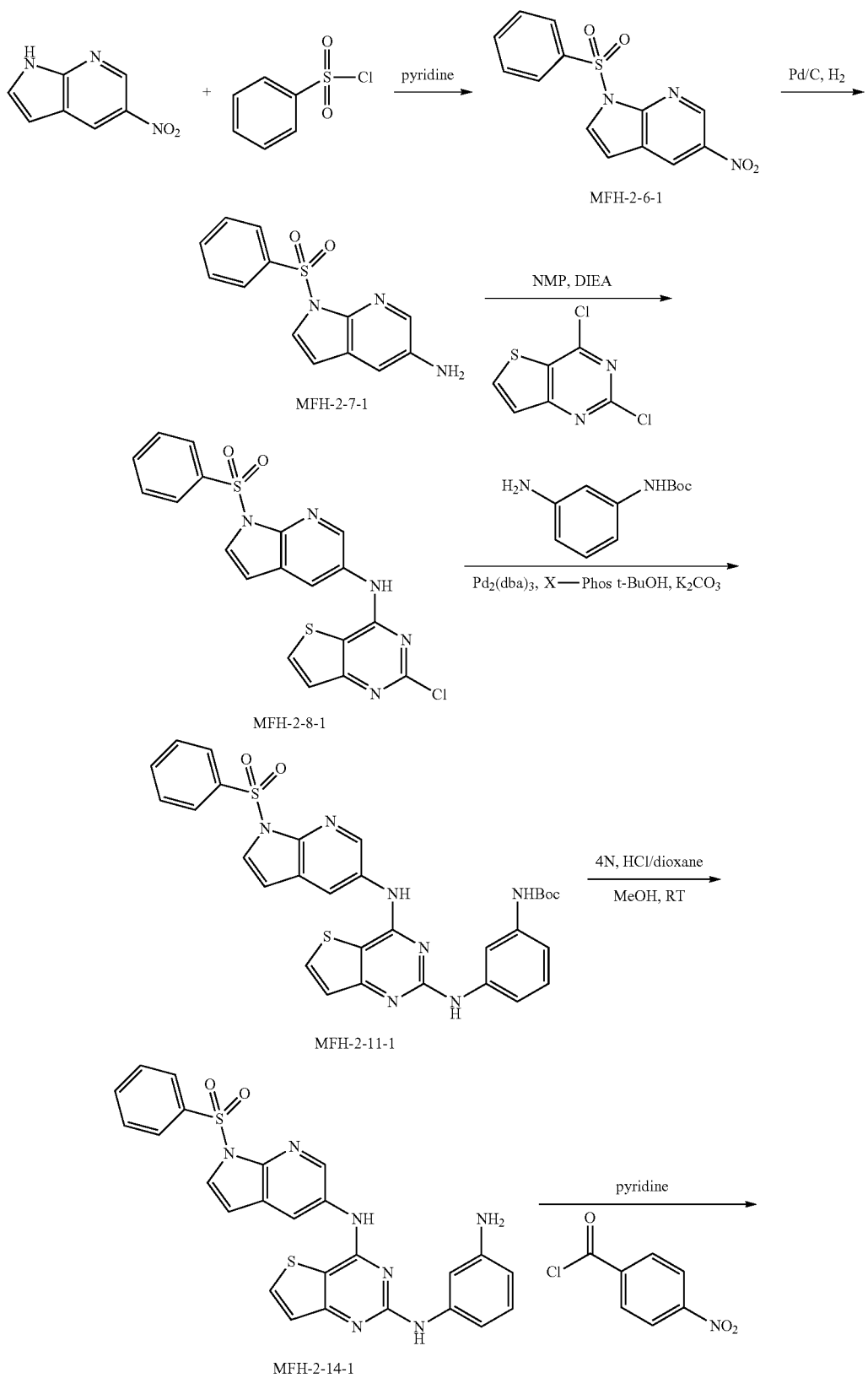

-continued
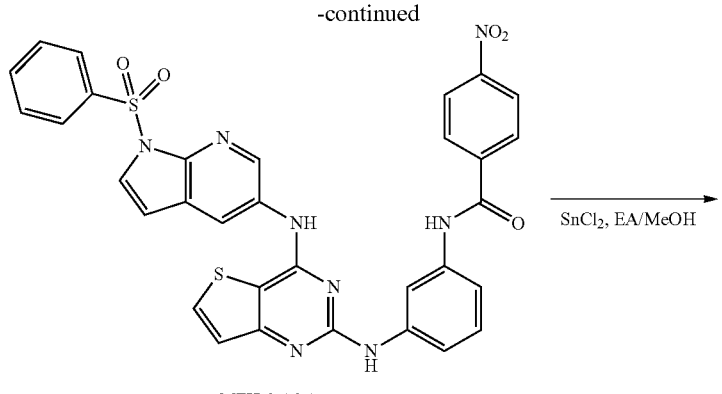
MFH-2-16-1
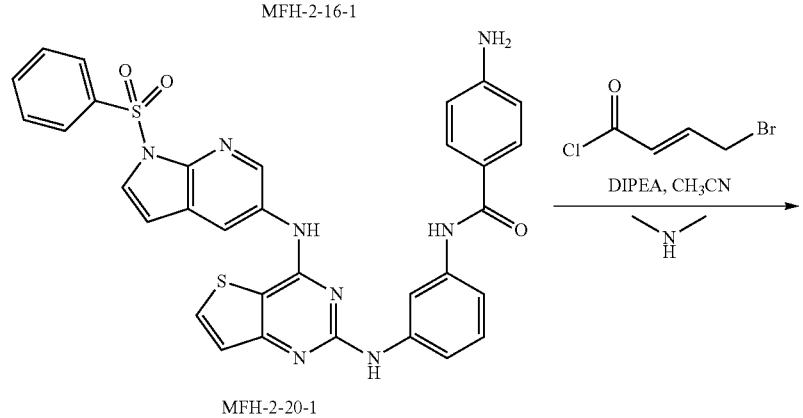
MFH-2-20-1
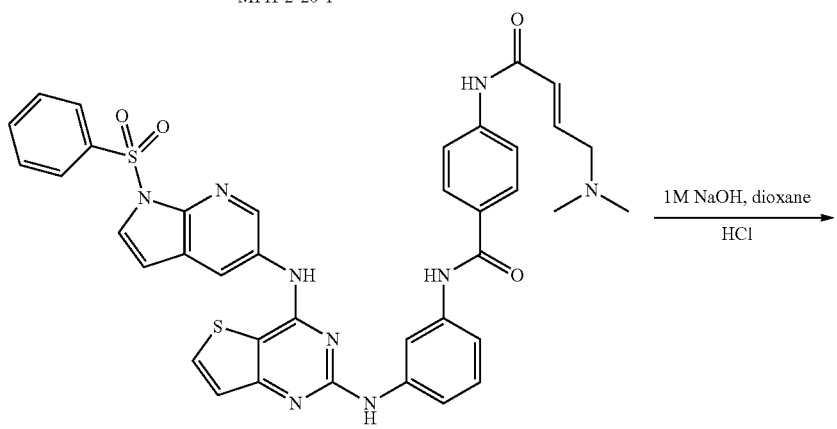
MFH-2-23-1
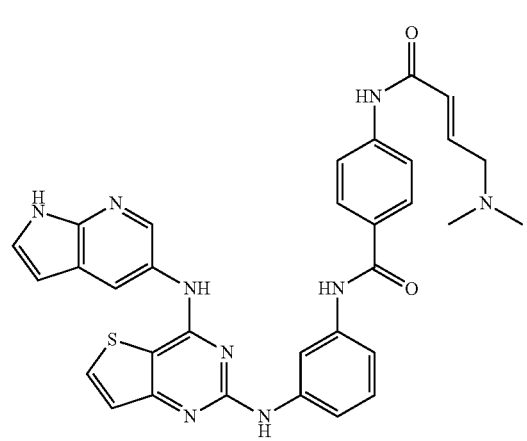
MFH-2-25-1

5-nitro-1-(phenylsulfonyl)-1H-pyrrolo[2,3-b]pyridine (MFH-2-6-1)

A mixture of 5-nitro-1H-pyrrolo[2,3-b]pyridine (300 mg, 1.84 mmol) and benzenesulfonyl chloride (812 mg, 4.6 mmol) in pyridine (3 mL) was refluxed for 6 hours. Then the reaction mixture was concentrated under reduced pressure, and the residue was purified by silica gel (PE/EA=0-50%) to obtain MFH-2-6-1 (530 mg, yield 95%). LCMS (m/z): 304 [M+H]$^+$.

1-(phenylsulfonyl)-1H-pyrrolo[2,3-b]pyridin-5-amine (MFH-2-7-1)

A mixture of MFH-2-6-1 (530 mg, 1.75 mmol) and 10% Pd/C (50 mg) in MeOH (20 mL) was stirred overnight at room temperature with an H$_2$ balloon. The mixture was filtered through CELITE, and solvent was removed to give MFH-2-7-1 (230 mg, yield 48%). LCMS (m/z): 274 [M+H]$^+$.

2-chloro-N-(1-(phenylsulfonyl)-1H-pyrrolo[2,3-b]pyridin-5-yl)thieno[3,2-d]pyrimidin-4-amine (MFH-2-8-1)

A solution of MFH-2-7-1 (230 mg, 0.84 mmol), 2,4-dichlorothieno[3,2-d]pyrimidine (173 mg, 0.84 mmol) and DIEA (163 mg, 1.26 mmol) in NMP (1 mL) was stirred at 100° C. for 10 hours. The mixture was then extracted with chloroform and iso-propanol (4:1). The organic phase was washed with brine (50 mL×2) and dried over Na$_2$SO$_4$. The removal of the solvent to provide the residue which was purified by silica gel (MeOH/DCM=0-20%) to give MFH-2-8-1 (259 mg, yield 70%). LCMS (m/z): 442 [M+H]$^+$.

tert-butyl 3-(4-(1-(phenylsulfonyl)-1H-pyrrolo[2,3-b]pyridin-5-ylamino)thieno[3,2-d]pyrimidin-2-ylamino)phenylcarbamate (MFH-2-11-1)

A mixture of MFH-2-8-1 (259 mg, 0.57 mmol), tert-butyl 3-aminophenylcarbamate (147 mg, 0.7 mmol), 2-dicyclohexylphosphino-2',4',6'-triisopropylbiphenyl (48 mg, 0.1 mmol), K$_2$CO$_3$ (118 mg, 0.86 mmol), and Pd$_2$(dba)$_3$ (91 mg, 0.1 mmol) in tert-Butanol (8 mL) was refluxed for 5 hours under N$_2$ atmosphere. After cooling down to room temperature, the reaction mixture was diluted with water (20 mL) and extracted with chloroform and iso-propanol (4:1). The organic phase was washed with brine (50 mL×2), dried over Na$_2$SO$_4$, filtered, and concentrated under reduced pressure. The residue was purified by silica gel column chromatography (MeOH/DCM, 0-20%) to give MFH-2-11-1 (170 mg, yield 49%). LCMS (m/z): 614 [M+H]$^+$.

N2-(3-aminophenyl)-N4-(1-(phenylsulfonyl)-1H-pyrrolo[2,3-b]pyridin-5-yl)thieno[3,2-d]pyrimidine-2,4-diamine (MFH-2-14-1)

To a mixture of compound MFH-2-11-1 (170 mg, 0.28 mmol) in methanol (5 mL) was added 4 N HCl/dioxane (6 mL) and the resulted solution was stirred for 3 hours. The mixture was concentrated under reduced pressure to provide the crude which was directly used in the next step. LCMS (m/z): 514 [M+H]$^+$.

4-nitro-N-(3-(4-(1-(phenylsulfonyl)-1H-pyrrolo[2,3-b]pyridin-5-ylamino)thieno[3,2-d]pyrimidin-2-ylamino)phenyl)benzamide (MFH-2-16-1)

A mixture of MFH-2-14-1 (140 mg, 0.27 mmol) and 4-nitrobenzoyl chloride (61 mg, 0.33 mmol) in pyridine (2 mL) was refluxed overnight. Then the reaction mixture was concentrated under reduced pressure, and the residue was directly used in the next step. LCMS (m/z): 663 [M+H]$^+$.

4-amino-N-(3-(4-(1-(phenylsulfonyl)-1H-pyrrolo[2,3-b]pyridin-5-ylamino)thieno[3,2-d]pyrimidin-2-ylamino)phenyl)benzamide (MFH-2-20-1)

To a solution of MFH-2-16-1 (179 mg, 0.27 mmol) in ethyl acetate and methanol (1:1) were added Tin(II) chloride dehydrate (183 mg, 0.81 mmol) and conc. HCl (0.1 mL). After stirring for 3 hours at 80° C., the reaction mixture was diluted with chloroform and iso-propanol (4:1), neutralized with saturated NaHCO$_3$, and filtered. The filtrate was extracted with chloroform and iso-propanol (4:1) and concentrated under reduced pressure, and the resulting residue was purified by silica gel column chromatography (MeOH/DCM=0-20%) to give MFH-2-20-1 (90 mg, yield 53%). LCMS (m/z): 633 [M+H]$^+$.

(E)-4-(4-bromobut-2-enamido)-N-(3-(4-(1-(phenylsulfonyl)-1H-pyrrolo[2,3-b]pyridin-5-ylamino)thieno[3,2-d]pyrimidin-2-ylamino)phenyl)benzamide (MFH-2-23-1)

A solution of (E)-4-bromobut-2-enoic acid (12 mg, 0.07 mmol) in SOCl$_2$ (0.2 mL) was stirred at 70° C. for 1 hour under N$_2$ atmosphere. The mixture was cooled to room temperature and then was concentrated under reduced pressure. The residue was diluted with dichloromethane, and the resulted solution was added dropwise to a solution of MFH-2-20-1 (30 mg, 0.05 mmol) and DIPEA (0.2 mL) in CH$_3$CN (2 mL) at 0° C. After stirring for 1 hour at 0° C., a solution of dimethylamine in THF (2 mol/L, 0.05 ml, 0.1 mmol) was added, and the reaction mixture was stirred at room temperature for 1 hour. The removal of the solvent under reduced pressure provided the residue which was purified by HPLC (MeOH/H$_2$O, 0.05% TFA) to obtain MFH-2-23-1 (30 mg, yield 86%). LCMS (m/z): 744 [M+H]$^+$.

(E)-N-(3-(4-(1H-pyrrolo[2,3-b]pyridin-5-ylamino)thieno[3,2-d]pyrimidin-2-ylamino)phenyl)-4-(4-(dimethylamino)but-2-enamido)benzamide (MFH-2-25-1)

A solution of MFH-2-23-1 (30 mg, 0.04 mmol) in 1 M NaOH (5 ml) and dioxane (5 mL) was stirred at room temperature for 2 hours. The solution was then neutralized (1 M HCl) and concentrated under reduced pressure. The residue was purified by prep-HPLC (MeOH/H$_2$O, 0.05% TFA) to obtain MFH-2-25-1 (off-white solid, 6.8 mg, yield 28%). LCMS (m/z): 604 [M+H]; $^1$H NMR (500 MHz, DMSO-d6) δ 11.78 (s, 1H), 10.77 (s, 1H), 10.64 (s, 1H), 10.32 (s, 1H), 10.22 (s, 1H), 10.05 (s, 1H), 8.37 (s, 1H), 8.27 (s, 2H), 7.93 (t, J=10.6 Hz, 3H), 7.80 (d, J=8.8 Hz, 2H), 7.51 (d, J=8.3 Hz, 2H), 7.40 (s, 1H), 7.31 (d, J=5.2 Hz, 1H), 7.19 (s, 1H), 6.84-6.73 (m, 1H), 6.50 (d, J=15.3 Hz, 1H), 6.46 (s, 1H), 3.18 (d, 2H) 2.81 (s, 6H).

Example 3. Synthesis of Compound MFH-2-40-1

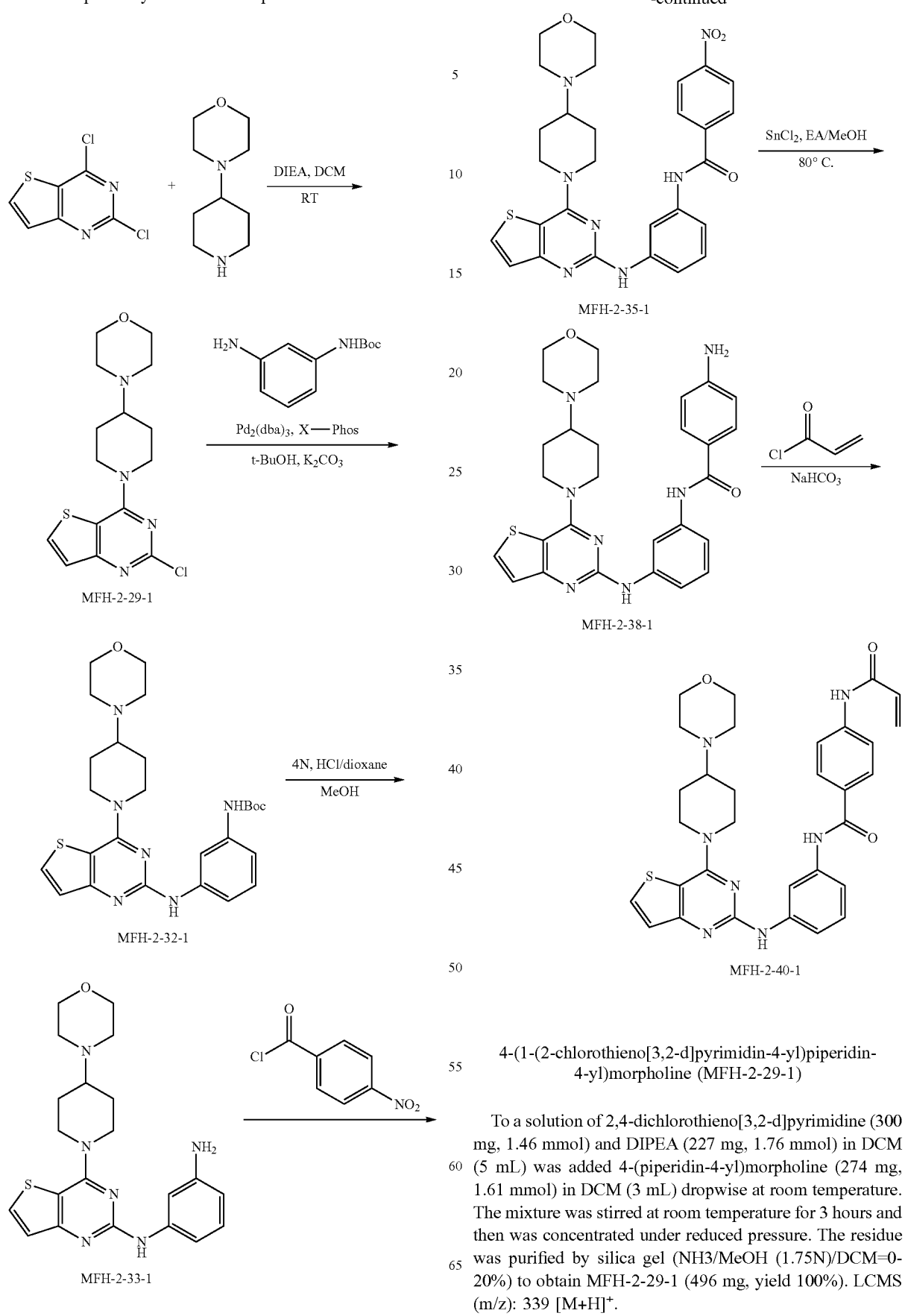

4-(1-(2-chlorothieno[3,2-d]pyrimidin-4-yl)piperidin-4-yl)morpholine (MFH-2-29-1)

To a solution of 2,4-dichlorothieno[3,2-d]pyrimidine (300 mg, 1.46 mmol) and DIPEA (227 mg, 1.76 mmol) in DCM (5 mL) was added 4-(piperidin-4-yl)morpholine (274 mg, 1.61 mmol) in DCM (3 mL) dropwise at room temperature. The mixture was stirred at room temperature for 3 hours and then was concentrated under reduced pressure. The residue was purified by silica gel (NH3/MeOH (1.75N)/DCM=0-20%) to obtain MFH-2-29-1 (496 mg, yield 100%). LCMS (m/z): 339 [M+H]$^+$.

tert-butyl3-(4-(4-morpholinopiperidin-1-yl)thieno[3,2-d]pyrimidin-2-ylamino)phenylcarbamate (MFH-2-32-1)

A solution of MFH-2-29-1 (496 mg, 1.46 mmol), tert-butyl 3-aminophenylcarbamate (335 mg, 1.61 mmol), 2-Dicyclohexylphosphino-2',4',6'-triisopropylbiphenyl (105 mg, 0.22 mmol), K$_2$CO$_3$ (243 mg, 1.76 mmol), and Pd$_2$(dba)$_3$ (201 mg, 0.22 mmol) in tert-Butanol (10 mL) was refluxed for 5 hours under N$_2$ atmosphere. The mixture was cooled to room temperature, diluted with water (20 mL), and extracted with chloroform and iso-propanol (4:1). The organic phase was washed with brine (50 mL×2), dried over Na$_2$SO$_4$, and filtered, and the solvent was removed under reduced pressure. The residue was purified by silica gel column chromatography (NH$_3$/MeOH (1.75N)/DCM 20%) to give MFH-2-32-1 (700 mg, yield 94%). LCMS (m/z): 511 [M+H]$^+$.

N1-(4-(4-morpholinopiperidin-1-yl)thieno[3,2-d]pyrimidin-2-yl)benzene-1,3-diamine (MFH-2-33-1)

To a mixture of compound MFH-2-32-1 (700 mg, 1.37 mmol) in methanol (6 mL) was added 4 N HCl/dioxane (12 mL), and the reaction was stirred for 3 hours at room temperature. The solution was concentrated under reduced pressure, and the residue was used directly in the next step. LCMS (m/z): 411 [M+H]$^+$.

N-(3-(4-(4-morpholinopiperidin-1-yl)thieno[3,2-d]pyrimidin-2-ylamino)phenyl)-4-nitrobenzamide (MFH-2-35-1)

A mixture of MFH-2-33-1 (570 mg, 1.39 mmol), 4-nitrobenzoyl chloride (322 mg, 1.74 mmol), and pyridine (3 mL) was refluxed overnight. Then the reaction mixture was concentrated under reduced pressure, and the residue was directly used in the next step. LCMS (m/z): 560 [M+H]$^+$.

4-amino-N-(3-(4-(4-morpholinopiperidin-1-yl)thieno[3,2-d]pyrimidin-2-ylamino)phenyl)benzamide (MFH-2-38-1)

To a solution of MFH-2-35-1 (430 mg, 0.77 mmol) in ethyl acetate and methanol (1:1) were added Tin(II) chloride dehydrate (522 mg, 2.31 mmol) and conc. HCl (0.2 mL). After stirring for 3 hours at 80° C., the reaction mixture was diluted with chloroform and iso-propanol (4:1) and neutralized with saturated NaHCO$_3$. The solution was then filtered, and the filtrate was extracted with chloroform and iso-propanol (4:1). Concentration under reduced pressure provided the crude which was purified by silica gel column chromatography (NH$_3$/MeOH (1.75N)/DCM=0-20%) to give MFH-2-38-1 (200 mg, yield 49%). LCMS (m/z): 530 [M+H]$^+$.

4-acrylamido-N-(3-(4-(4-morpholinopiperidin-1-yl)thieno[3,2-d]pyrimidin-2-ylamino)phenyl)benzamide (MFH-2-40-1)

To a solution of MFH-2-38-1 (50 mg, 0.09 mmol) in sat. NaHCO$_3$ (3 mL) and THF (3 mL) was added acryloyl chloride (11 mg, 0.12 mmol) in DCM (0.5 mL) dropwise at 0° C. The mixture was stirred for 1 hour and then was concentrated under reduced pressure. The residue was purified by prep-HPLC (MeOH/H$_2$O, 0.05% TFA) to obtain MFH-2-40-1 (off-white solid, 14 mg, yield 25%). LCMS (m/z): 584 [M+H]$^+$; $^1$H NMR (500 MHz, DMSO-d6) δ 10.47 (s, 1H), 10.13 (s, 1H), 9.95 (s, 1H), 9.46 (s, 1H), 8.32 (s, 1H), 8.17 (d, J=5.4 Hz, 1H), 7.98 (d, J=8.7 Hz, 2H), 7.82 (d, J=8.8 Hz, 2H), 7.39 (d, J=7.3 Hz, 1H), 7.28 (s, 1H), 7.26 (d, J=1.0 Hz, 1H), 7.24 (s, 1H), 6.49 (dd, J=17.0, 10.2 Hz, 1H), 6.32 (dd, J=17.0, 1.9 Hz, 1H), 5.82 (dd, J=10.1, 1.9 Hz, 1H), 3.97 (s, 4H), 3.08 (s, 4H), 3.03 (s, 1H), 2.21 (d, J=10.8 Hz, 4H), 1.71 (d, J=9.1 Hz, 4H).

Example 4. Synthesis of Compound MFH-2-44-1

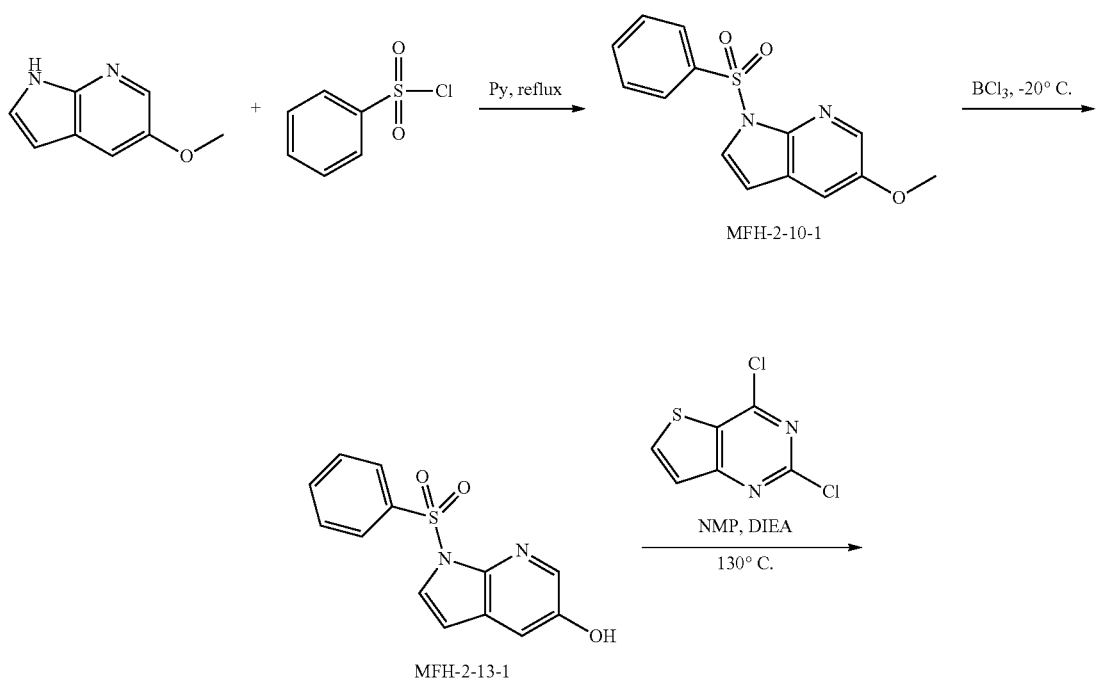

-continued
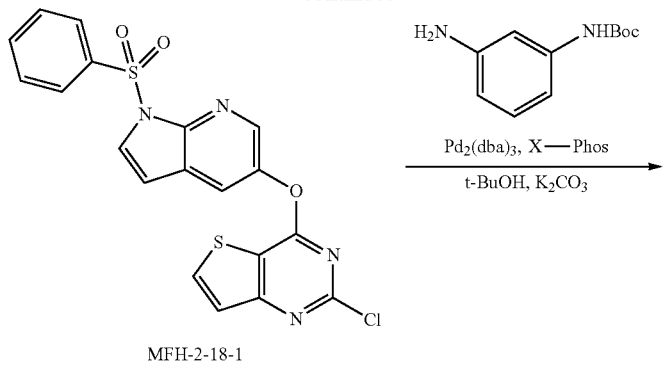
MFH-2-18-1
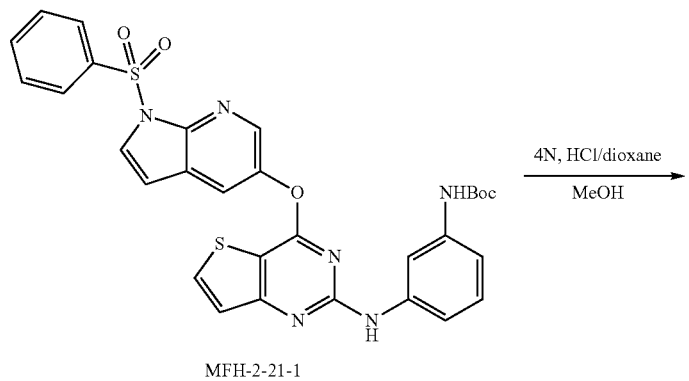
MFH-2-21-1
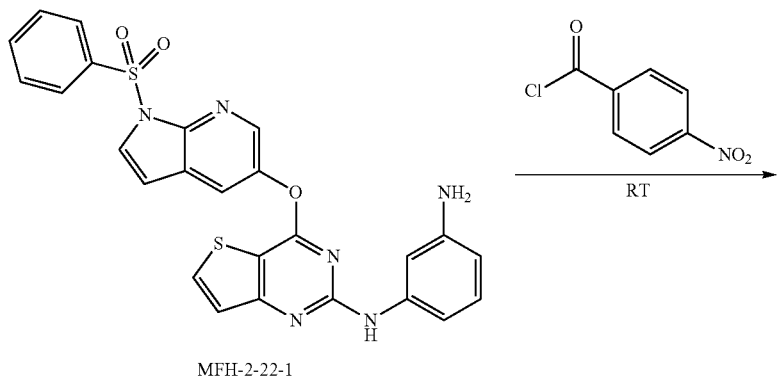
MFH-2-22-1
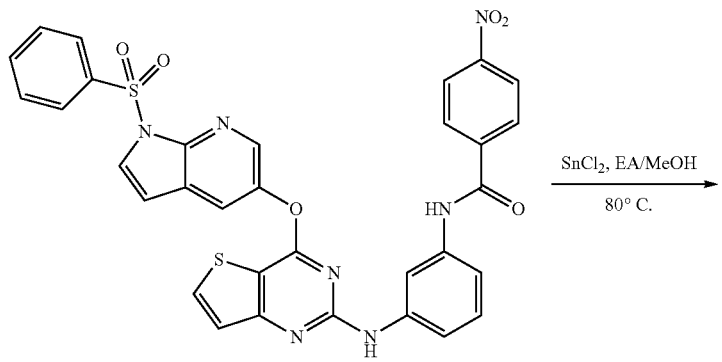
MFH-2-37-1

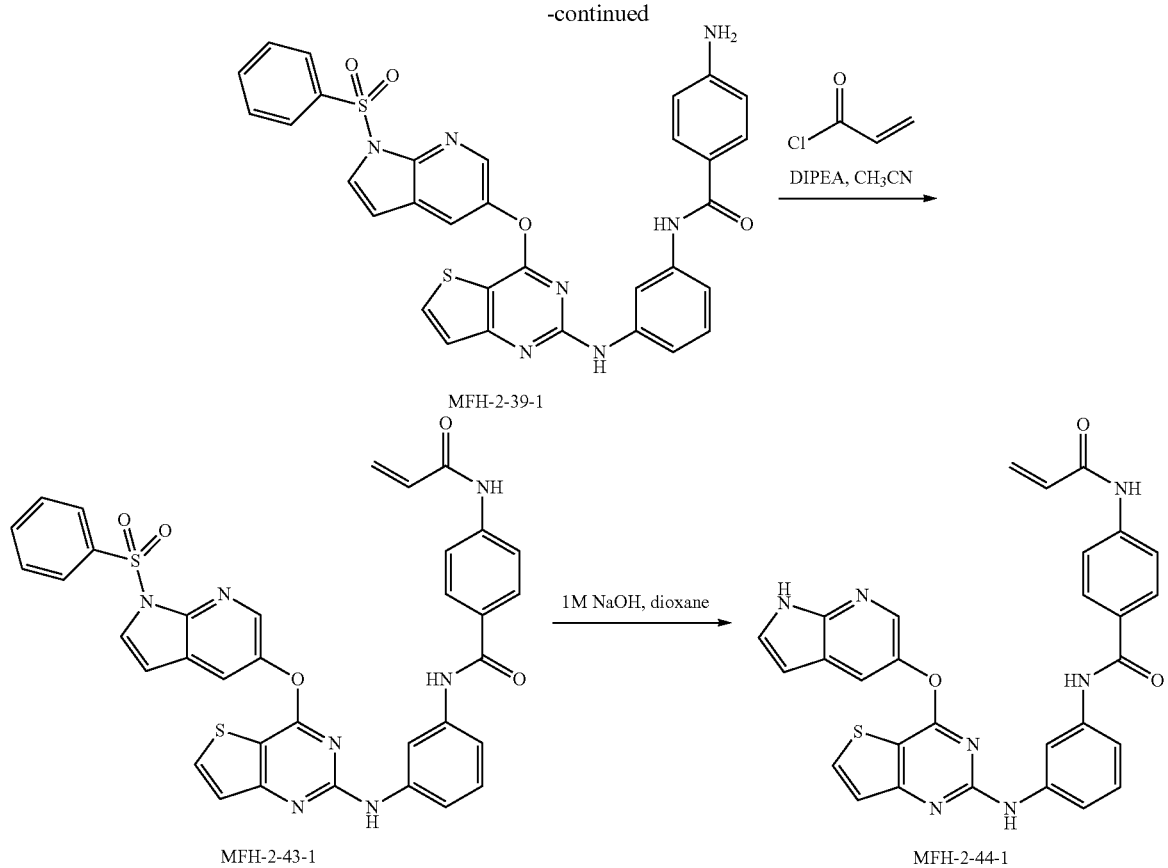

5-methoxy-1-(phenylsulfonyl)-1H-pyrrolo[2,3-b]pyridine (MFH-2-10-1)

A mixture of 5-methoxy-1H-pyrrolo[2,3-b]pyridine (800 mg, 5.4 mmol) and benzenesulfonyl chloride (1.9 g, 10.8 mmol) in pyridine (8 mL) was refluxed overnight. Then the reaction mixture was concentrated under reduced pressure, and the residue was purified by silica gel (PE/EA=0-50%) to obtain MFH-2-10-1 (646 mg, yield 42%). LCMS (m/z): 289 [M+H]$^+$.

1-(phenylsulfonyl)-1H-pyrrolo[2,3-b]pyridin-5-ol (MFH-2-13-1)

To a solution of MFH-2-10-1 (646 mg, 2.25 mmol) in DCM (20 mL) was added boron trichloride in hexane (1 mol/L, 22.5 ml, 22.5 mmol) dropwise at −15° C. The mixture was warmed to room temperature and the mixture was stirred overnight. After completion, water (50 ml) was added at 0° C. and the aqueous layer was extracted with DCM. The combined organic layers was washed with brine, dried over Na$_2$SO$_4$, filtered, and concentrated. The residue was purified by silica gel column chromatography (PE/EA=0-50%) to give MFH-2-13-1 (353 mg, yield 57%). LCMS (m/z): 275 [M+H]$^+$.

2-chloro-4-(1-(phenylsulfonyl)-1H-pyrrolo[2,3-b]pyridin-5-yloxy)thieno[3,2-d]pyrimidine (MFH-2-18-1)

A mixture of MFH-2-13-1 (353 mg, 1.29 mmol), 2,4-dichlorothieno[3,2-d]pyrimidine (205 mg, 1.00 mmol), and DIEA (259 mg, 2.00 mmol) in NMP (2 mL) was stirred at 130° C. for 10 hours. The residue was extracted with chloroform and iso-propanol (4:1). The organic phase was washed with brine (50 mL×2) and dried over Na$_2$SO$_4$. After removal of the solvent, the residue was purified by silica gel (MeOH/DCM=0-20%) to obtain MFH-2-18-1 (290 mg, yield 51%). LCMS (m/z): 443 [M+H]$^+$.

tert-butyl3-(4-(1-(phenylsulfonyl)-1H-pyrrolo[2,3-b]pyridin-5-yloxy)thieno[3,2-d]pyrimidin-2-ylamino)phenylcarbamate (MFH-2-21-1)

A mixture of MFH-2-18-1 (290 mg, 0.66 mmol), tert-butyl 3-aminophenylcarbamate (164 mg, 0.79 mmol), 2-Dicyclohexylphosphino-2',4',6'-triisopropylbiphenyl (63 mg, 0.13 mmol), K$_2$CO$_3$ (109 mg, 0.79 mmol), and Pd$_2$(dba)$_3$ (120 mg, 0.13 mmol) in tert-Butanol (8 mL). The mixture was stirred at reflux for 5 hours under N$_2$ atmosphere. The mixture was cooled to room temperature and diluted with water (20 ml) and extracted with chloroform and iso-propanol (4:1). The organic phase was washed with brine (50 mL×2). The organic layer was dried over Na$_2$SO$_4$, filtered, and concentrated to give the crude which was purified by silica gel column chromatography (MeOH/DCM=0-20%) to give MFH-2-21-1 (400 mg, yield 99%). LCMS (m/z): 615 [M+H]$^+$.

N1-(4-(1-(phenylsulfonyl)-1H-pyrrolo[2,3-b]pyridin-5-yloxy)thieno[3,2-d]pyrimidin-2-yl)benzene-1,3-diamine (MFH-2-22-1)

To a solution of MFH-2-21-1 (400 mg, 0.65 mmol) in methanol (5 mL) was added 4 N HCl/dioxane (12 mL). The solution was then stirred for 3 hours at room temperature, and the solvent was removed under reduced pressure to provide a crude which was directly used in the next step. LCMS (m/z): 515 [M+H]+.

4-nitro-N-(3-(4-(1-(phenylsulfonyl)-1H-pyrrolo[2,3-b]pyridin-5-yloxy)thieno[3,2-d]pyrimidin-2-ylamino)phenyl)benzamide (MFH-2-37-1)

The mixture of MFH-2-22-1 (200.0 mg, 0.39 mmol) and 4-nitrobenzoyl chloride (72.0 mg, 0.39 mmol) in pyridine (3.0 mL) was refluxed overnight. Then the reaction mixture was concentrated under reduced pressure, and the residue was directly used in the next step. LCMS (m/z): 664 [M+H]+.

4-amino-N-(3-(4-(1-(phenylsulfonyl)-1H-pyrrolo[2,3-b]pyridin-5-yloxy)thieno[3,2-d]pyrimidin-2-ylamino)phenyl)benzamide (MFH-2-39-1)

To a solution of MFH-2-37-1 (258 mg, 0.39 mmol) in ethyl acetate and methanol (1:1) was added Tin(II) chloride dehydrate (271 mg, 1.2 mmol). After stirring for 3 hours at 80° C., the reaction mixture was diluted with chloroform and iso-propanol (4:1) and neutralized with saturated NaHCO$_3$. The mixture was then filtered, and the filtrate was extracted with chloroform and iso-propanol (4:1). The solvent was then removed under reduced pressure, and the resulting residue was purified by silica gel column chromatography (MeOH/DCM=0-20%) to give MFH-2-39-1 (120 mg, yield 48%). LCMS (m/z): 634 [M+H]+.

4-acrylamido-N-(3-(4-(1-(phenylsulfonyl)-1H-pyrrolo[2,3-b]pyridin-5-yloxy)thieno[3,2-d]pyrimidin-2-ylamino)phenyl)benzamide (MFH-2-43-1)

To a solution of MFH-2-39-1 (25 mg, 0.04 mmol) and DIPEA (0.2 mL) in CH$_3$CN (2 mL) was added acryloyl chloride (5 mg, 0.05 mmol) in DCM (0.2 mL) dropwise. The mixture was then stirred at 0° C. for 1 hour. The solution was then concentrated under reduced pressure, and the residue was purified by prep-HPLC (MeOH/H$_2$O, 0.05% TFA) to provide MFH-2-43-1 (22 mg, yield 80%). LCMS (m/z): 688 [M+H]+.

N-(3-(4-(1H-pyrrolo[2,3-b]pyridin-5-yloxy)thieno[3,2-d]pyrimidin-2-ylamino)phenyl)-4-acrylamidobenzamide (MFH-2-44-1)

To a solution of MFH-2-43-1 (22 mg, 0.03 mmol) in IM NaOH (3 ml) and dioxane (3 mL) was stirred at room temperature for 2 hours. The solution was neutralized (1 M HCl) and concentrated under reduced pressure. The residue was purified by prep-HPLC (MeOH/H$_2$O, 0.05% TFA) to obtain MFH-2-44-1 (3.8 mg, yield 22%). LCMS (m/z): 548 [M+H]+; $^1$H NMR (500 MHz, DMSO-d6) δ 11.82 (s, 1H), 10.44 (d, J=10.0 Hz, 1H), 10.05 (s, 1H), 9.44 (s, 1H), 8.30 (d, J=5.4 Hz, 1H), 8.26 (d, J=2.5 Hz, 1H), 8.03 (t, J=4.9 Hz, 1H), 7.99 (d, J=7.0 Hz, 1H), 7.97-7.91 (m, 2H), 7.80 (d, J=8.8 Hz, 2H), 7.61-7.55 (m, 1H), 7.38 (dd, J=13.7, 6.8 Hz, 2H), 7.28-7.19 (m, 1H), 6.93 (t, J=8.1 Hz, 1H), 6.51 (dd, J=3.4, 1.8 Hz, 1H), 6.49-6.43 (m, 1H), 6.31 (dd, J=17.0, 1.9 Hz, 1H), 5.81 (dd, J=10.1, 1.9 Hz, 1H).

Example 5. Synthesis of Compound MFH-2-60-1

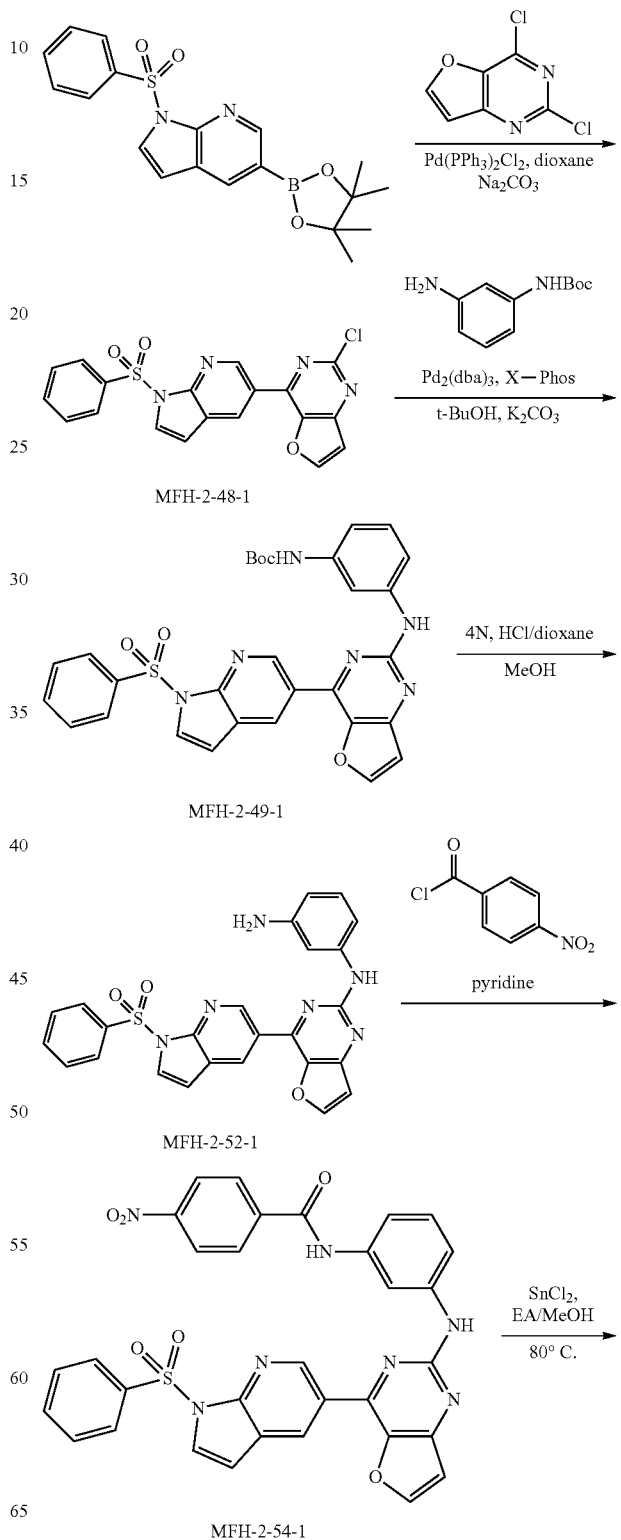

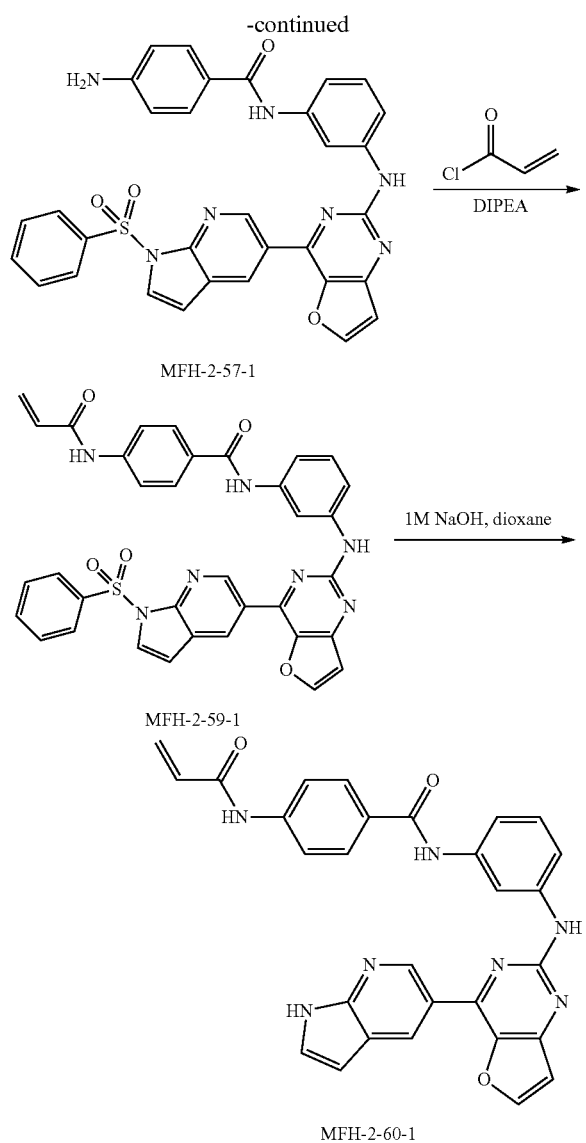

2-chloro-4-(1-(phenylsulfonyl)-1H-pyrrolo[2,3-b]pyridin-5-yl)furo[3,2-d]pyrimidine (MFH-2-48-1)

A mixture of 2,4-dichlorofuro[3,2-d]pyrimidine (300 mg, 1.59 mmol), 1-(phenylsulfonyl)-5-(4,4,5,5-tetramethyl-1,3,2-dioxaborolan-2-yl)-1H-pyrrolo[2,3-b]pyridine (640 mg, 1.67 mmol), Sat. Na₂CO₃ (3 mL), and Pd(PPh₃)₂Cl₂ (167 mg, 0.24 mmol) in dioxane (6 mL) was stirred at 80° C. for 2 hours under N₂ atmosphere. The mixture was then cooled to room temperature and diluted with water (30 mL). The residue was extracted with chloroform and iso-propanol (4:1), and the organic phase was washed with brine (50 mL×2) and dried with Na₂SO₄. The solvent was then removed, and the residue was purified by silica gel (MeOH/DCM=0-10%) to obtain MFH-2-48-1 (520 mg, yield 79%). LCMS (m/z): 411 [M+H]⁺.

tert-butyl3-(4-(1-(phenylsulfonyl)-1H-pyrrolo[2,3-b]pyridin-5-yl)furo[3,2-d]pyrimidin-2-ylamino)phenylcarbamate (MFH-2-49-1)

A mixture of MFH-2-48-1 (520 mg, 1.27 mmol), tert-butyl 3-aminophenylcarbamate (277 mg, 1.33 mmol), 2-Di-cyclohexylphosphino-2',4',6'-triisopropylbiphenyl (91 mg, 0.19 mmol) K₂CO₃ (210 mg, 1.52 mmol), and Pd₂(dba)₃ (174 mg, 0.19 mmol) in tert-Butanol (8 mL) was refluxed for 5 hours under N₂ atmosphere. The mixture was cooled to room temperature and diluted with water (20 mL) and extracted with chloroform and iso-propanol (4:1). The organic phase was washed with brine (50 mL×2) and dried over Na₂SO₄, filtered, and concentrated under reduced pressure. The residue was purified by silica gel column chromatography (MeOH/DCM=0-20%) to give MFH-2-49-1 (310 mg, yield 42%). LCMS (m/z): 583 [M+H]⁺.

N1-(4-(1-(phenylsulfonyl)-1H-pyrrolo[2,3-b]pyridin-5-yl)furo[3,2-d]pyrimidin-2-yl)benzene-1,3-diamine (MFH-2-52-1)

To a mixture of compound MFH-2-49-1 (310 mg, 0.53 mmol) in methanol (5 mL) was added 4 N HCl/dioxane (8 mL). The mixture was stirred for 3 hours at room temperature and then was concentrated under reduced pressure to give a crude which was used directly in the next step. LCMS (m/z): 483 [M+H]⁺.

4-nitro-N-(3-(4-(1-(phenylsulfonyl)-1H-pyrrolo[2,3-b]pyridin-5-yl)furo[3,2-d]pyrimidin-2-ylamino)phenyl)benzamide (MFH-2-54-1)

A mixture of MFH-2-52-1 (220 mg, 0.46 mmol), 4-nitrobenzoyl chloride (101 mg, 0.55 mmol), and pyridine (2 mL) was refluxed for overnight. Then the reaction mixture was concentrated under reduced pressure, and the residue was used directly in the next step. LCMS (m/z): 632 [M+H]⁺.

4-amino-N-(3-(4-(1-(phenylsulfonyl)-1H-pyrrolo[2,3-b]pyridin-5-yl)furo[3,2-d]pyrimidin-2-ylamino)phenyl)benzamide (MFH-2-57-1)

To a solution of MFH-2-54-1 (290 mg, 0.46 mmol) in ethyl acetate and methanol (1:1) were added tin(II) chloride dehydrate (312 mg, 1.38 mmol) and conc. HCl (0.1 mL). After stirring for 3 hours at 80° C., the reaction mixture was diluted with chloroform and iso-propanol (4:1), neutralized with saturated NaHCO₃, and filtered. The filtrate was extracted with chloroform and iso-propanol (4:1) and concentrated under reduced pressure, and the resulting residue was purified by silica gel column chromatography (MeOH/DCM=0-20%) to give MFH-2-57-1 (140 mg, yield 51%). LCMS (m/z): 602 [M+H]⁺.

4-acrylamido-N-(3-(4-(1-(phenylsulfonyl)-1H-pyrrolo[2,3-b]pyridin-5-yl)furo[3,2-d]pyrimidin-2-ylamino)phenyl)benzamide (MFH-2-59-1)

To a solution of MFH-2-57-1 (40 mg, 0.07 mmol) and DIPEA (0.2 mL) in CH₃CN (2 mL) was added acryloyl chloride (8 mg, 0.09 mmol) in DCM (0.2 mL) dropwise. The mixture was then stirred at 0° C. for 1 hour and then was concentrated under reduced pressure. The residue was purified by prep-HPLC (C18 column, MeOH/H₂O, containing 0.05% TFA) to obtain MFH-2-59-1 (off-white solid, 40 mg, yield 87%). LCMS (m/z): 656 [M+H]⁺.

N-(3-(4-(1H-pyrrolo[2,3-b]pyridin-5-yl)furo[3,2-d]pyrimidin-2-ylamino)phenyl)-4-acrylamidobenzamide (MFH-2-60-1)

To a solution of MFH-2-59-1 (40 mg, 0.06 mmol) in 1 M NaOH (4 mL) and dioxane (4 mL) was stirred at room temperature for 2 hours. The reaction solution was neutralized (1 M HCl), concentrated under reduced pressure. The residue was purified by prep-HPLC ($C_{18}$ column, MeOH/$H_2O$, containing 0.05% TFA) to obtain MFH-2-60-1 (off-white solid, 6.8 mg, yield 22%), LCMS (m/z): 516 [M+H]$^+$. $^1$H NMR (500 MHz, DMSO-d6) δ 12.02 (s, 1H), 10.44 (s, 1H), 10.14 (d, J=15.8 Hz, 1H), 9.61 (s, 1H), 9.35 (s, 1H), 9.09 (d, J=1.7 Hz, 1H), 8.48 (d, J=2.2 Hz, 1H), 8.43 (s, 1H), 7.99 (dd, J=18.6, 8.6 Hz, 2H), 7.82 (t, J=12.7 Hz, 2H), 7.62-7.59 (m, 1H), 7.58-7.55 (m, 1H), 7.33-7.26 (m, 2H), 7.06 (d, J=2.2 Hz, 1H), 6.62 (dd, J=3.3, 1.7 Hz, 1H), 6.49 (dd, J=16.9, 10.1 Hz, 1H), 6.33 (dd, J=17.0, 1.8 Hz, 1H), 5.83 (dd, J=10.1, 1.8 Hz, 1H).

Example 6. Synthesis of Compound FMF-3-27-1

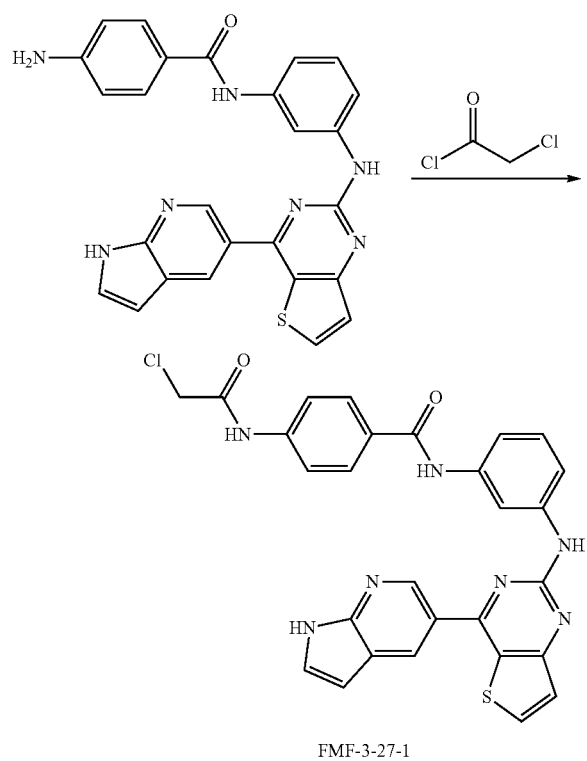

FMF-3-27-1

N-(3-((4-(1H-pyrrolo[2,3-b]pyridin-5-yl)thieno[3,2-d]pyrimidin-2-yl)amino)phenyl)-4-(2-chloroacetamido)benzamide N-(3-((4-(1H-pyrrolo[2,3-b]pyridin-5-yl)thieno[3,2-d]pyrimidin-2-yl)amino)phenyl)-4-aminobenzamide (30 mg, 0.06 mmol) was dissolved in 5 mL THF and 5 mL saturated aqueous solution of $NaHCO_3$. The reaction mixture was cooled to 0° C. A 1.3 mM solution of 2-chloroacetyl chloride in THF was added drop-wise until the reaction was complete as analyzed by LC/MS. The reaction mixture was diluted with water and extracted with dichloromethane (3×20 mL), dried over $MgSO_4$, concentrated, and purified by HPLC to give the title compound (10 mg, 0.02 mmol) as a TFA salt. $^1$H NMR (500 MHz, DMSO-d$_6$) δ 12.04 (s, 1H), 10.60 (s, 1H), 10.17 (s, 1H), 9.77 (s, 1H), 9.07 (d, J=2.0 Hz, 1H), 8.82 (d, J=2.0 Hz, 1H), 8.48-8.29 (m, 2H), 8.01 (d, J=8.7 Hz, 2H), 7.75 (d, J=8.7 Hz, 2H), 7.66-7.58 (m, 2H), 7.47 (d, J=5.5 Hz, 1H), 7.34 (d, J=8.4 Hz, 1H), 7.29 (t, J=8.0 Hz, 1H), 6.64 (dd, J=3.4, 1.8 Hz, 1H), 4.32 (s, 2H). MS (ESI) m/z: 555 Da (M+H)$^+$.

Biological Evaluation

Example 7. Kinase Assay

PIP4K in vitro kinase assay was carried out as described in Rameh et al (Nature, 1997). Briefly, 0.1 ug of GST-PI5P4Ka or 0.4 ug of GST-PI5P4Ka resuspended in 70 uL of kinase buffer containing 20 mM HEPES pH 7.4, 100 mM NaCl, 0.5 mM EGTA was stabilized at room temperature for 10 minutes and incubated with 1 uM of DMSO or indicated compound for 30 minutes. Then the kinase reaction was carried out in a total volume of 100 ul for 10 minutes by adding 20 uL of lipid substrates (4 ug of phosphatidylserine and 2 ug of PI5P) in buffer containing 30 mM HEPES pH7.4 and 1 mM EGTA, and 10 uL of ATP mix (500 uM non-radiolabeled ATP, 10 uCi [g-$^{32}$P]-ATP, 65 mM HEPES pH7.4 and 100 mM $MgCl_2$). The reaction was terminated by adding 50 uL of HCl. Phosphoinositides were extracted by adding 100 uL methanol/chloroform (1:1, vol:vol) mix and subjected to thin layer chromatography separation using heat-activated 1% potassium oxalate-coated silica gel 60 plates (EMD Chemicals Inc., Billerica, Mass., USA) and a 1-propanol/2 M acetic acid (65:35, vol:vol) solvent system. The radiolabeled PI(4,5)P$_2$ was quantified with a Phosphorimager (Molecular Dynamics, STORM840, GE Healthcare, Waukesha, Wis., USA).

Example 8. Cell Proliferation Assay

To determine cell proliferation, cells were plated at 2×10 cells per well of 96-well plate. Cells were incubated and assayed at indicated times using Cell Titer-Glo Luminescent Cell Viability assay (Promega). Cells were allowed to equilibrate to room temperature for 15 minutes, then an equal volume of the Cell Titer-Glo reagent was added to wells and incubated for 15 minutes on an orbital shaker. Luminescence was recorded according to the manufacturer's protocol.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

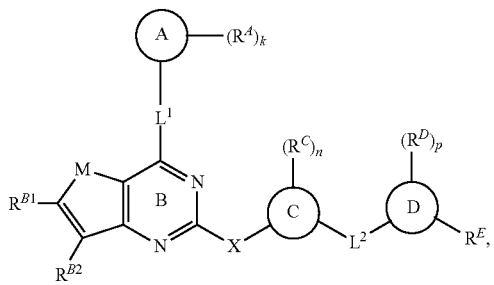

(I)

or a pharmaceutically acceptable salt thereof, wherein:

Ring A is a substituted or unsubstituted, monocyclic or bicyclic heteroaryl ring or a substituted or unsubstituted, monocyclic heterocyclic ring;

each instance of $R^A$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

k is 0, 1, 2, 3, 4, 5, or 6;

M is $NR^M$, O, or S;

$R^M$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$L^1$ is a bond, —C($R^b$)$_2$—, —C(=O)—, —O—, —S—, —S(=O)—, —S(=O)$_2$—, or —$NR^c$—;

each instance of $R^b$ is independently hydrogen, halogen, or substituted or unsubstituted $C_{1-6}$ alkyl;

each instance of $R^c$ is independently hydrogen, substituted or unsubstituted $C_{1-6}$ alkyl, or a nitrogen protecting group;

$R^{B1}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$;

$R^{B2}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$;

X is —C($R^b$)$_2$—, —C(=O)—, —O—, —S—, —S(=O)—, —S(=O)$_2$—, —$NR^c$—, —C($R^b$)$_2$C($R^b$)$_2$—, —C($R^b$)$_2$C(=O)—, —C(=O)C($R^b$)$_2$—, (E)-C$R^b$=C$R^b$—, (Z)—C$R^b$=C$R^b$—, —C≡C—, —OC(=O)—, —C(=O)O—, —SC(=O)—, —C(=O)S—, —$NR^cC$(=O)—, —C(=O)$NR^c$—, —OC($R^b$)$_2$—, —C($R^b$)$_2$O—, —SC($R^b$)$_2$—, —C($R^b$)$_2$S—, —$NR^cC$($R^b$)$_2$—, —C($R^b$)$_2$$NR^c$, —S(=O)O—, —OS(=O)—, —S(=O)$NR^c$—, —$NR^cS$(=O)—, —S(=O)$_2$O—, —OS(=O)$_2$—, —S(=O)$_2$$NR^c$—, or —$NR^cS$(=O)$_2$—;

Ring C is a substituted or unsubstituted phenyl ring;

Ring D is a substituted or unsubstituted phenyl ring;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$;

n is 0, 1, 2, 3, or 4;

$L^2$ is —C($R^b$)$_2$—, —C(=O)—, —O—, —S—, —S(=O)—, —S(=O)$_2$—, —$NR^c$—, —C($R^b$)$_2$C($R^b$)$_2$—, —C($R^b$)$_2$C(=O)—, —C(=O)C($R^b$)$_2$—, (E)-C$R^b$=C$R^b$—, (Z)—C$R^b$=C$R^b$—, —C≡C—, —OC(=O)—, —C(=O)O—, —SC(=O)—,

—C(=O)S—, —NR$^c$C(=O)—, —C(=O)NR$^c$—, —OC(R$^b$)$_2$—, —C(R$^b$)$_2$O—, —SC(R$^b$)$_2$—, —C(R$^b$)$_2$S—, —NR$^c$C(R$^b$)$_2$—, —C(R$^b$)$_2$NR$^c$—, —S(=O)O—, —OS(=O)—, —S(=O)NR$^c$—, —NR$^c$s(=O)—, —S(=O)$_2$O—, —OS(=O)$_2$—, —S(=O)$_2$NR$^c$—, —NR$^c$(=O)$_2$—, —OC(=O)O—, —NR$^c$C(=O)O—, —OC(=O)NR$^c$—, NR$^c$C(=O)NR$^c$—, —C(R$^b$)$_2$C(=O)C(R$^b$)$_2$—, —OC(=O)C(R$^b$)$_2$—, —C(R$^b$)$_2$C(=O)O—, —NR$^c$C(=O)C(R$^b$)$_2$—, —C(R$^b$)$_2$C(=O)NR$^c$—, or a substituted or unsubstituted C$_{1-4}$ hydrocarbon chain, optionally wherein one or more carbon units of the hydrocarbon chain are independently replaced with —C(=O)—, —O—, —S—, —S(=O)—, —S(=O)$_2$—, or —NR$^c$—;

each instance of R$^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

p is 0, 1, 2, 3, or 4;

R$^E$ is of the formula:

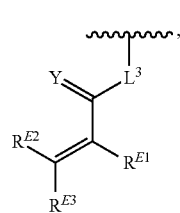
(i-1)

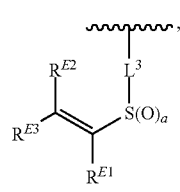
(i-2)

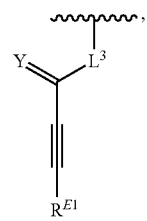
(i-3)

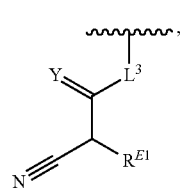
(i-4)

-continued

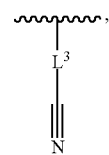
(i-5)

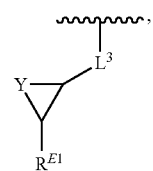
(i-6)

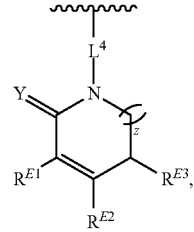
(i-7)

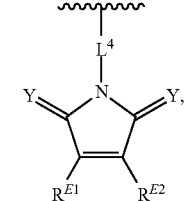
(i-8)

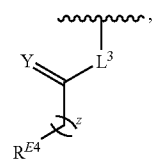
(i-9)

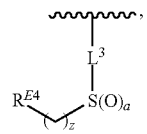
(i-10)

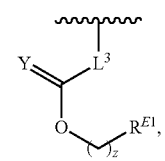
(i-11)

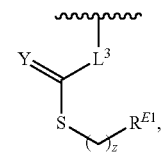
(i-12)

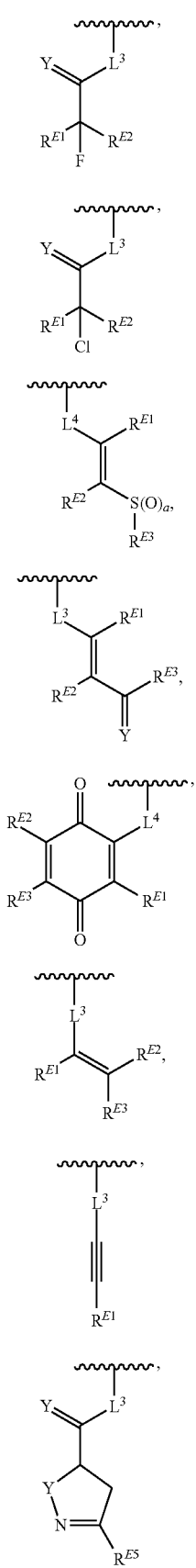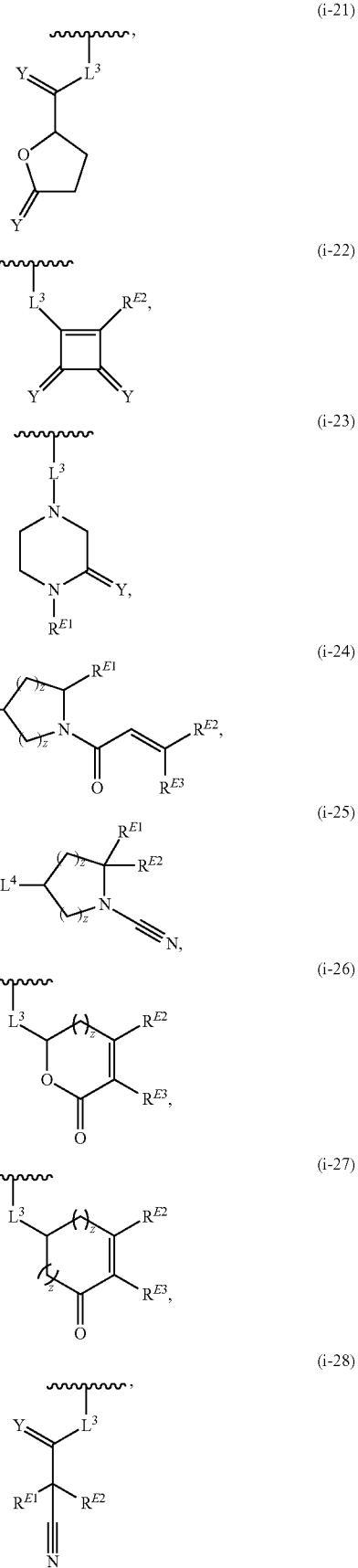

201
-continued

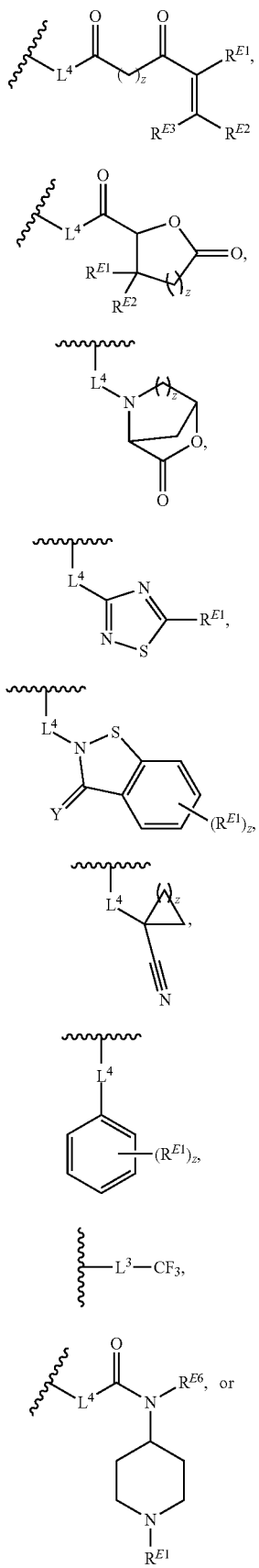

(i-29)
(i-30)
(i-31)
(i-32)
(i-33)
(i-34)
(i-35)
(i-39)
(i-40)

202
-continued

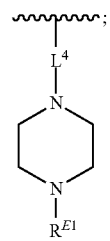

(i-41)

$L^3$ is —C($R^b$)$_2$—, —C(=O)—, —O—, —S—, —S(=O)—, —S(=O)$_2$—, —$NR^c$—, —C($R^b$)$_2$C($R^b$)$_2$—, —C($R^b$)$_2$C(=O)—, —C(=O)C($R^b$)$_2$—, (E)-C$R^b$=C$R^b$—, (Z)—C$R^b$=C$R^b$—, —C≡C—, —OC(=O)—, —C(=O)O—, —SC(=O)—, —C(=O)S—, —$NR^c$C(=O)—, —C(=O)$NR^c$—, —OC($R^b$)$_2$—, —C($R^b$)$_2$O—, —SC($R^b$)$_2$—, —C($R^b$)$_2$S—, —$NR^c$C($R^b$)$_2$—, —C($R^b$)$_2$$NR^c$—, —S(=O)O—, —OS(=O)—, —S(=O)$NR^c$—, —$NR^c$S(=O)—, —S(=O)$_2$O—, —OS(=O)$_2$—, —S(=O)$_2$$NR^c$—, —$NR^c$S(=O)$_2$—, —OC(=O)O—, —$NR^c$C(=O)O—, —OC(=O)$NR^c$—, —$NR^c$C(=O)$NR^c$—, —C($R^b$)$_2$C(=O)C($R^b$)$_2$—, —OC(=O)C($R^b$)$_2$—, —C($R^b$)$_2$C(=O)O—, —$NR^c$C(=O)C($R^b$)$_2$—, —C($R^b$)$_2$C(=O)$NR^c$—, or a substituted or unsubstituted $C_{1-4}$ hydrocarbon chain, optionally wherein one or more carbon units of the hydrocarbon chain are independently replaced with —C(=O)—, —O—, —S—, —S(=O)—, —S(=O)$_2$—, or —$NR^c$—;

$L^4$ is a bond or substituted or unsubstituted $C_{1-6}$ hydrocarbon chain;

each of $R^{E1}$, $R^{E2}$, and $R^{E3}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —CH$_2$O$R^a$, —CH$_2$N($R^a$)$_2$, —CH$_2$S$R^a$, —O$R^a$, —N($R^a$)$_2$, —S$R^a$, or —Si($R^a$)$_3$; or $R^{E1}$ and $R^{E3}$, or $R^{E2}$ and $R^{E3}$, or $R^{E1}$ and $R^{E2}$ are joined to form a substituted or unsubstituted, carbocyclic ring, or substituted or unsubstituted, heterocyclic ring;

$R^{E4}$ is a leaving group;

$R^{E5}$ is halogen;

$R^{E6}$ is hydrogen, substituted or unsubstituted $C_{1-6}$ alkyl, or a nitrogen protecting group;

each instance of Y is independently O, S, or $NR^c$;

a is 1 or 2; and each instance of z is independently 0, 1, 2, 3, 4, 5, or 6.

2. The compound of claim 1, wherein the compound is of the formula:

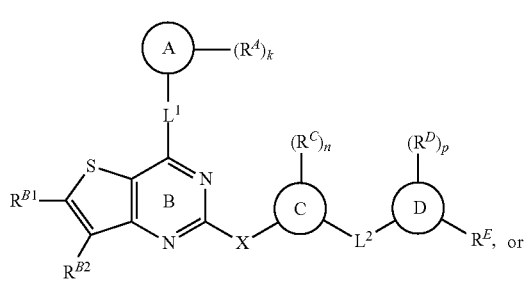

(I-a)

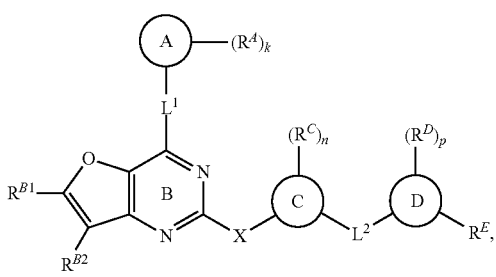

(I-b)

or a pharmaceutically acceptable salt thereof.

3. The compound of claim 1, wherein the compound is of the formula:

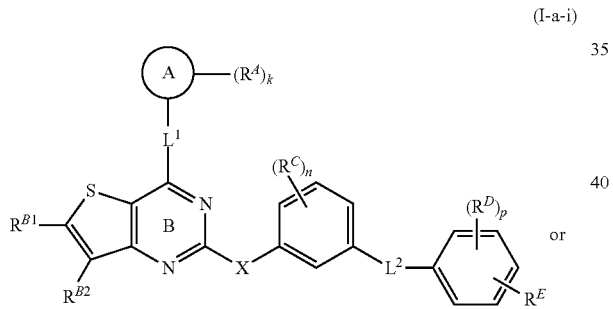

(I-a-i)

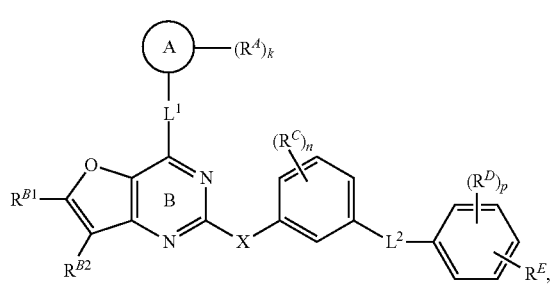

(I-b-i)

or a pharmaceutically acceptable salt thereof.

4. The compound of claim 1, or a pharmaceutically acceptable salt thereof, wherein Ring A is a substituted or unsubstituted, bicyclic heteroaryl ring.

5. The compound of claim 4, or a pharmaceutically acceptable salt thereof, wherein Ring A is of Formula (A-i):

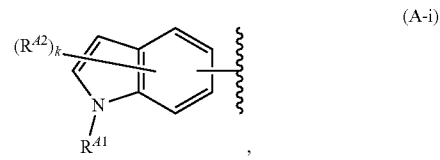

(A-i)

wherein:
R$^{A1}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; and each instance of R$^{A2}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —OR$^{A2a}$, —N(R$^{A2a}$)$_2$, or —SR$^{A2a}$, wherein each occurrence of R$^{A2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A2a}$ groups are joined to form a substituted or unsubstituted heterocyclic ring.

6. The compound of claim 4, or a pharmaceutically acceptable salt thereof, wherein Ring A is of Formula (A-ii):

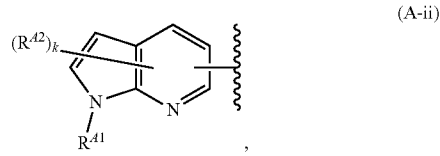

(A-ii)

wherein:
R$^{A1}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; and each instance of R$^{A2}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —OR$^{A2a}$, —N(R$^{A2a}$)$_2$, or —SR$^{A2a}$, wherein each occurrence of R$^{A2}$a is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2a}$ groups are joined to form a substituted or unsubstituted heterocyclic ring.

7. The compound of claim 4, or a pharmaceutically acceptable salt thereof, wherein Ring A is of Formula (A-iii):

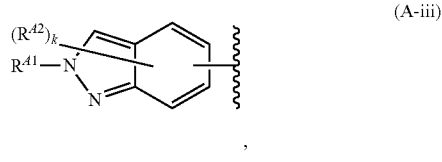

(A-iii)

wherein:
R$^{A1}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; and each instance of $R^{A2}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —OR$^{A2a}$, —N(R$^{A2a}$)$_2$, or —SR$^{A2a}$, wherein each occurrence of R$^{A2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A2a}$ groups are joined to form a substituted or unsubstituted heterocyclic ring.

8. The compound of claim 1, or a pharmaceutically acceptable salt thereof, wherein Ring A is a substituted or unsubstituted, monocyclic heteroaryl ring.

9. The compound of claim 8, or a pharmaceutically acceptable salt thereof, wherein Ring A is of Formula (A-v):

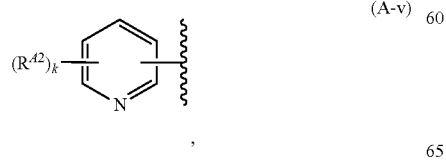

(A-v)

wherein:
each instance of R$^{A2}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —OR$^{A2a}$, —N(R$^{A2a}$)$_2$, or —SR$^{A2a}$, wherein each occurrence of R$^{A2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A2a}$ groups are joined to form a substituted or unsubstituted heterocyclic ring.

10. The compound of claim 1, or a pharmaceutically acceptable salt thereof, wherein Ring A is a substituted or unsubstituted, monocyclic heterocyclic ring.

11. The compound of claim 10, or a pharmaceutically acceptable salt thereof, wherein Ring A is of Formula (A-vi):

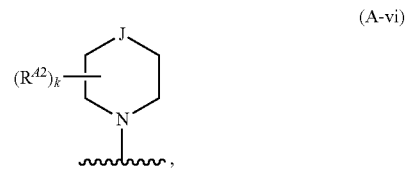

(A-vi)

wherein:
J is C(R$^{CJ}$)$_2$ or NR$^{NJ}$;
each instance of R$^{CJ}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and R$^{NJ}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, optionally substituted acyl, or a nitrogen protecting group; and
each instance of R$^{A2}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —OR$^{A2a}$, —N(R$^{A2a}$)$_2$, or —SR$^{A2a}$, wherein each occurrence of $R^{A2a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2a}$ groups are joined to form a substituted or unsubstituted heterocyclic ring.

12. The compound of claim 1, or a pharmaceutically acceptable salt thereof, wherein $L^1$ is a bond.

13. The compound of claim 1, or a pharmaceutically acceptable salt thereof, wherein $L^1$ is —O—.

14. The compound of claim 1, or a pharmaceutically acceptable salt thereof, wherein $L^1$ is —$NR^c$—.

15. The compound of claim 1, or a pharmaceutically acceptable salt thereof, wherein X is —$NR^c$—.

16. The compound of claim 1, or a pharmaceutically acceptable salt thereof, wherein $L^2$ is —$NR^cC$(=O)— or —C(=O)$NR^c$—.

17. The compound of claim 1, or a pharmaceutically acceptable salt thereof, wherein $R^E$ is of Formula (i-18):

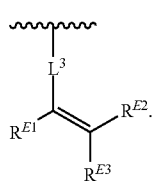

(i-18)

18. The compound of claim 17, or a pharmaceutically acceptable salt thereof, wherein $R^E$ is of the formula:

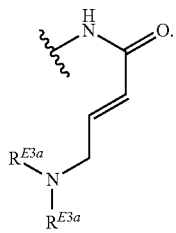

19. The compound of claim 1, wherein the compound is of the formula:

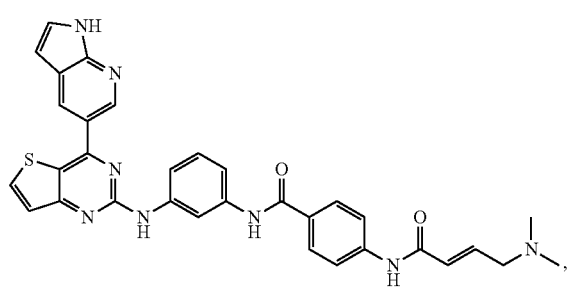 [SMILES: CN(C)C/C=C/C(=O)Nc1ccc(C(=O)Nc2cccc(Nc3cc(-c4cnc5[nH]ccc5c4)c4sccc4n3)c2)cc1]

-continued

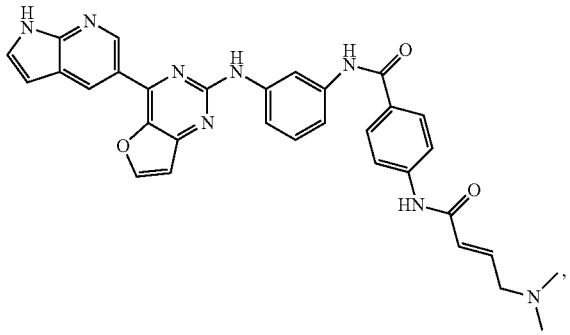

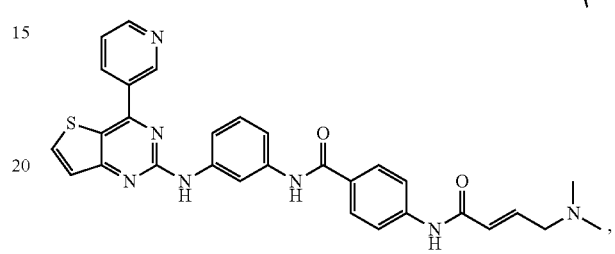

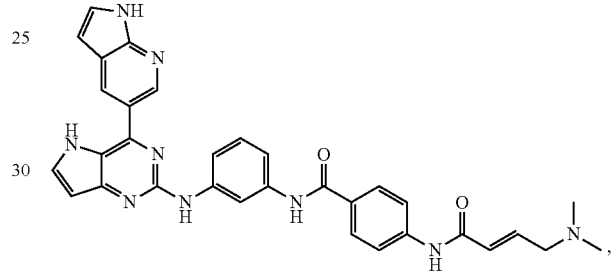

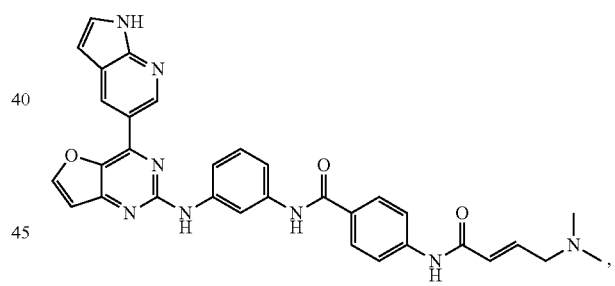

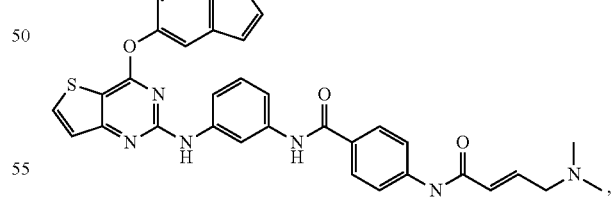

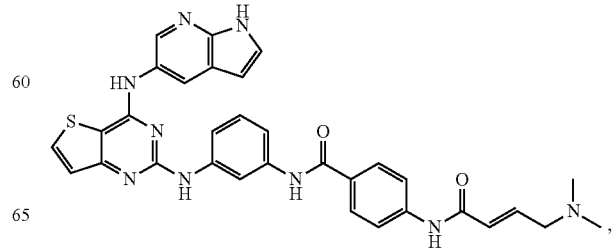

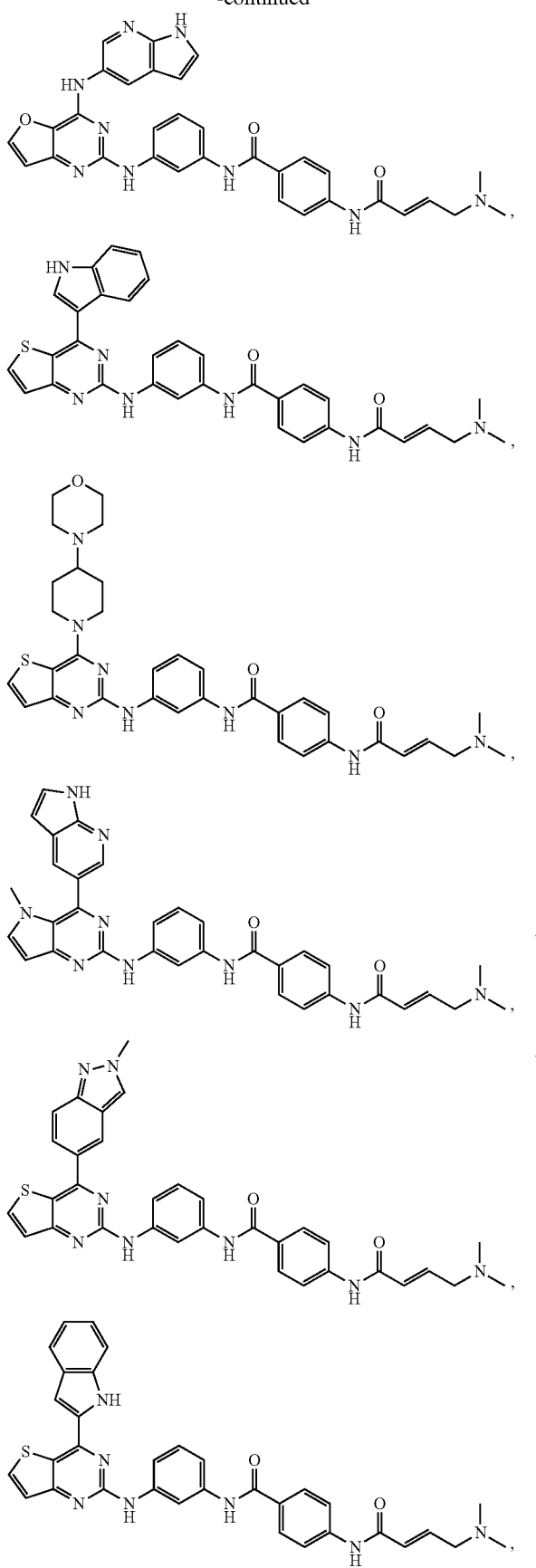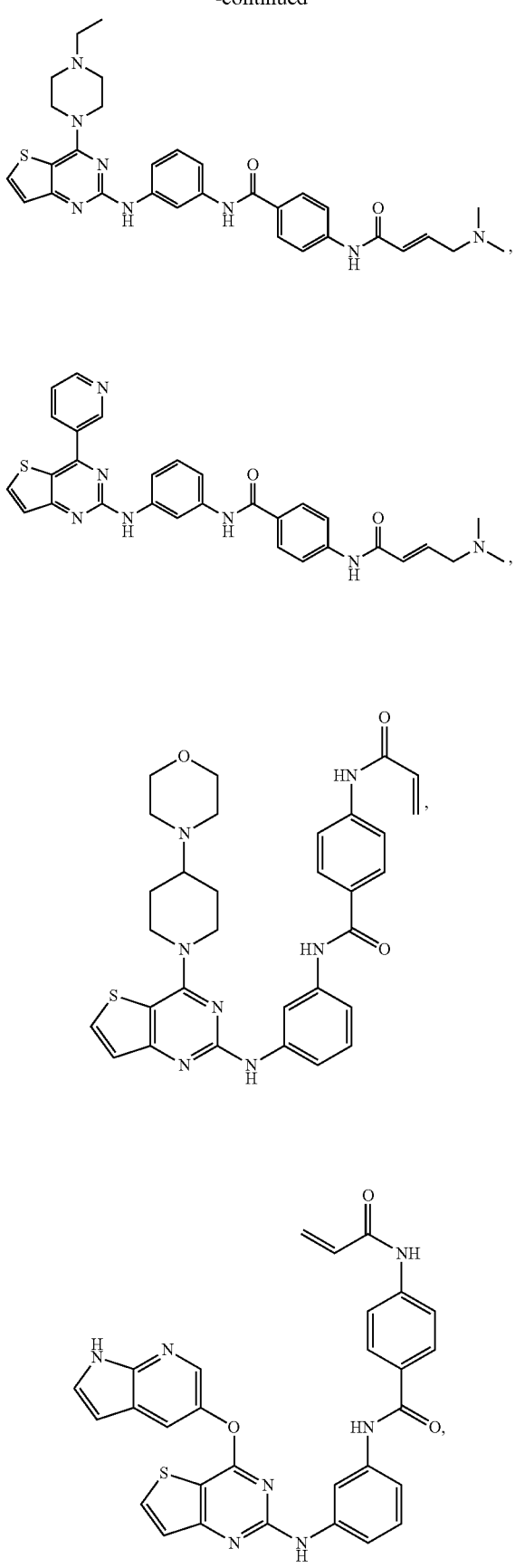

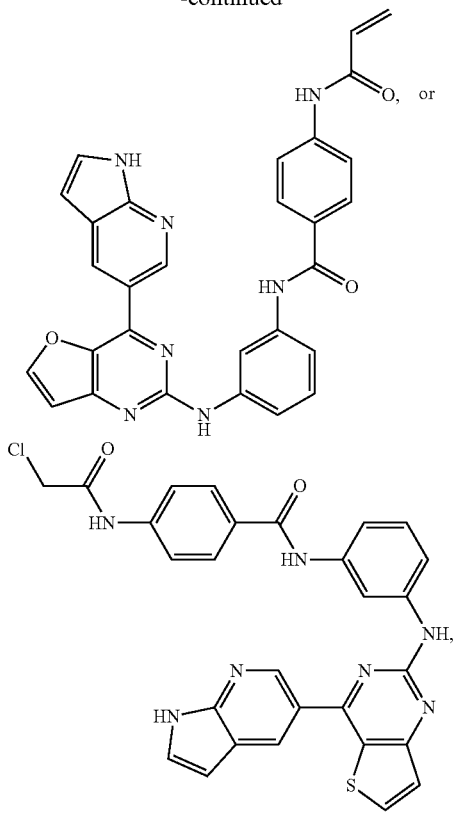

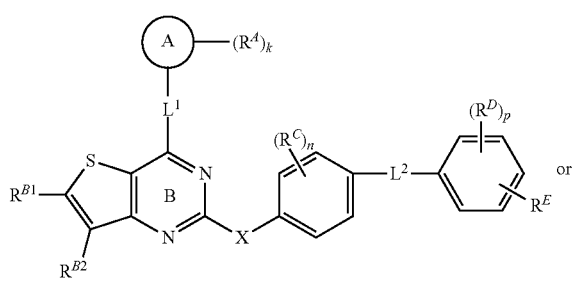

or a pharmaceutically acceptable salt thereof.

20. A pharmaceutical composition comprising a compound of claim 1, or a pharmaceutically acceptable salt thereof, and optionally a pharmaceutically acceptable excipient.

21. A method of treating a proliferative disease in a subject in need thereof, the method comprising administering to the subject in need thereof a therapeutically effective amount of a compound of claim 1, or a pharmaceutically acceptable salt thereof.

22. A method of modulating the activity of a kinase in a biological sample or subject, the method comprising administering to the subject or contacting the biological sample with an effective amount of a compound of claim 1, or a pharmaceutically acceptable salt thereof.

23. The compound of claim 1, wherein the compound is of the formula:

(I-a-iii)

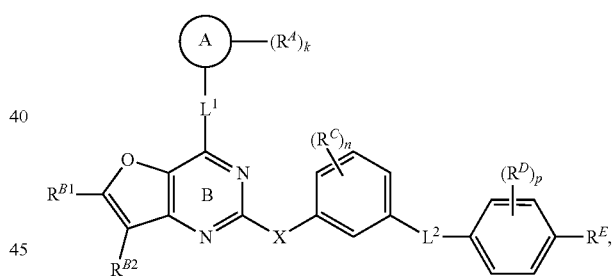

or

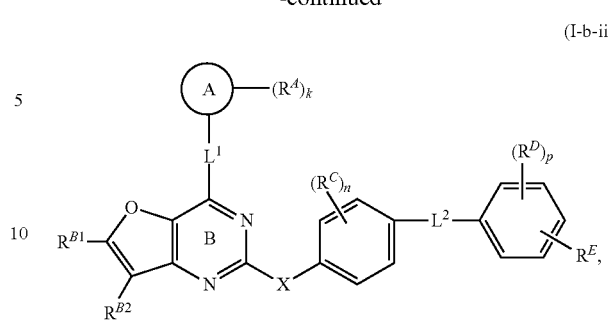

(I-b-iii)

or a pharmaceutically acceptable salt thereof.

24. The compound of claim 1, wherein the compound is of the formula:

(I-a-ii)

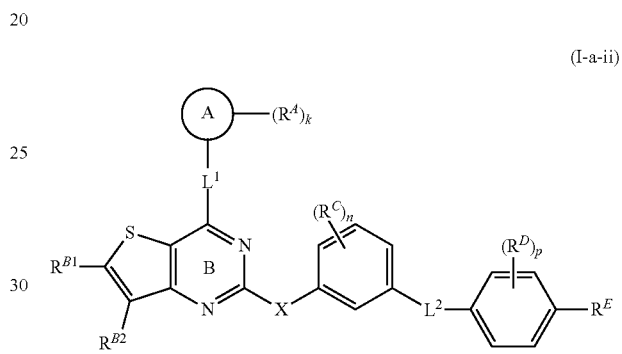

or (I-b-ii)

or a pharmaceutically acceptable salt thereof.

25. The compound of claim 1, wherein the compound is of the formula:

(I-a-iv)

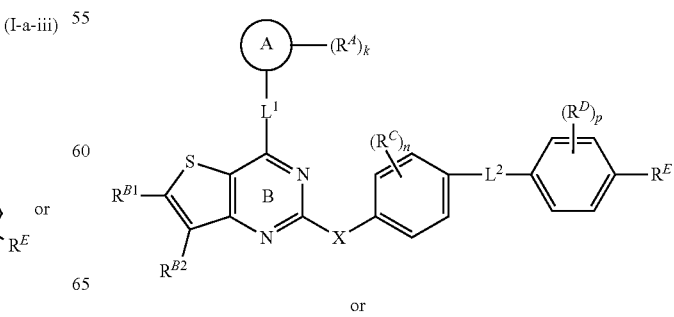

or

-continued

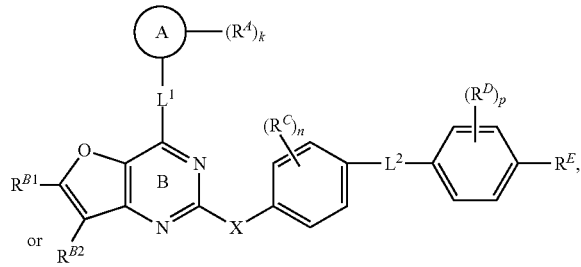
(I-b-iv)

or a pharmaceutically acceptable salt thereof.

26. The compound of claim 1, or a pharmaceutically acceptable salt thereof, wherein X is —NH—.

27. The compound of claim 1, or a pharmaceutically acceptable salt thereof, wherein $L^2$ is —NHC(=O)—.

28. The compound of claim 1, or a pharmaceutically acceptable salt thereof, wherein $R^E$ is of the formula:

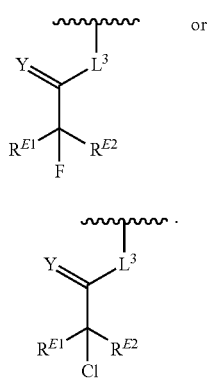

29. The compound of claim 1, wherein the compound is of the formula:

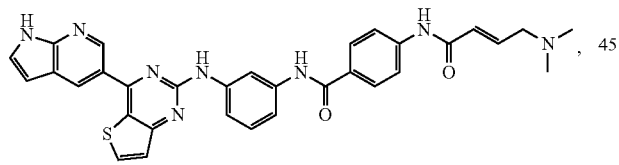

or a pharmaceutically acceptable salt thereof.

30. The method of claim 21, wherein the compound is of the formula:

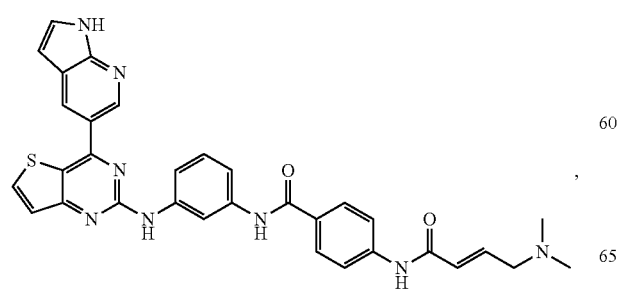

-continued

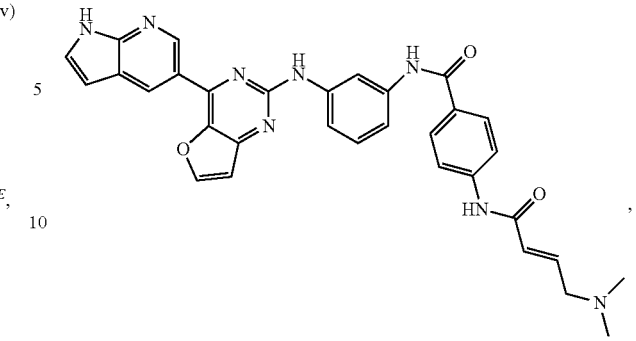

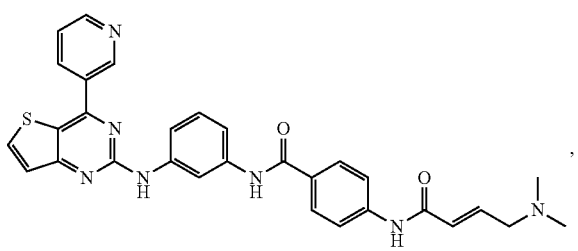

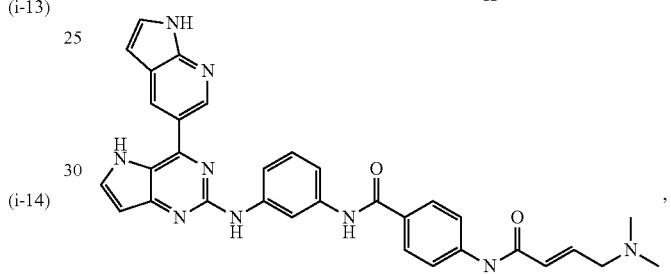

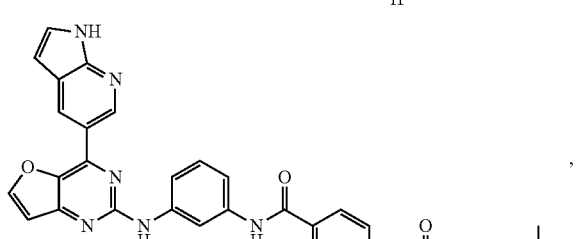

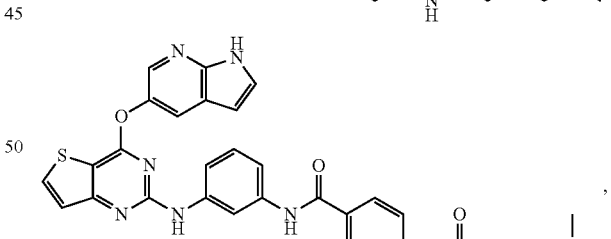

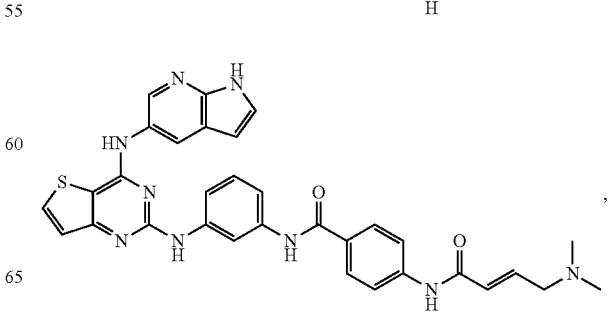

215
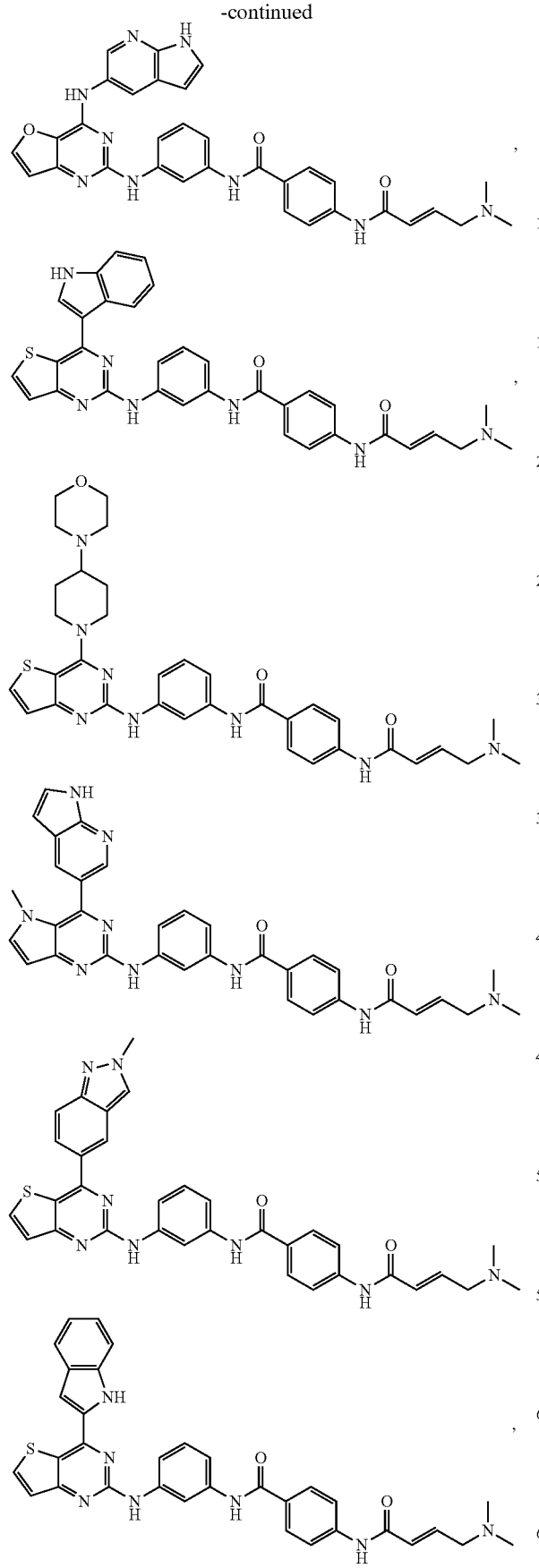
216
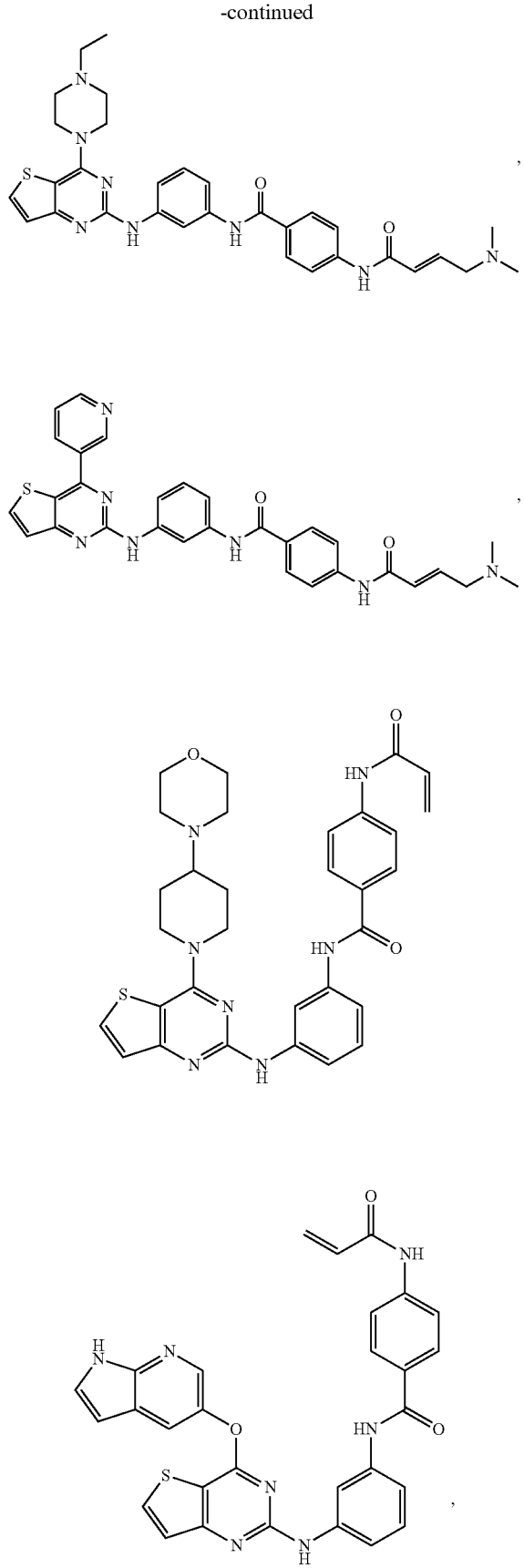

-continued

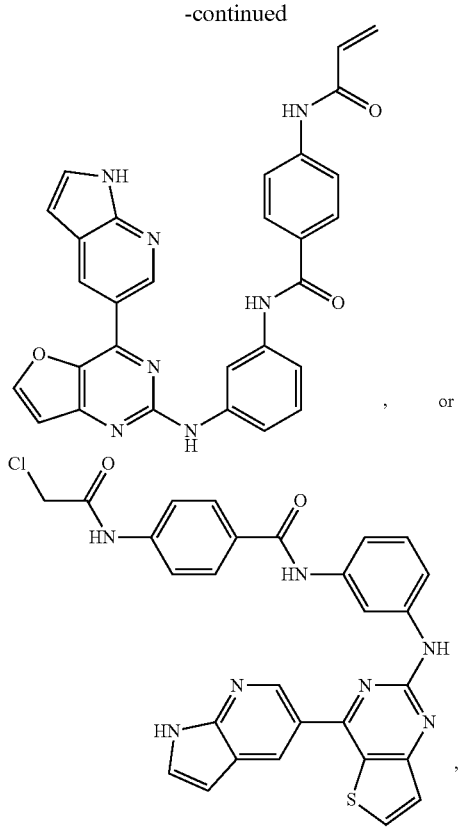

, or

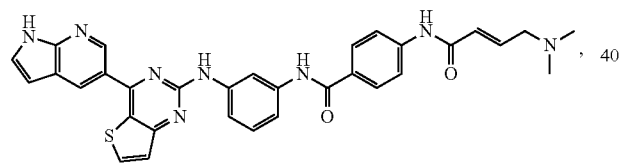

, or a pharmaceutically acceptable salt thereof.

31. The method of claim 21, wherein the compound is of the formula:

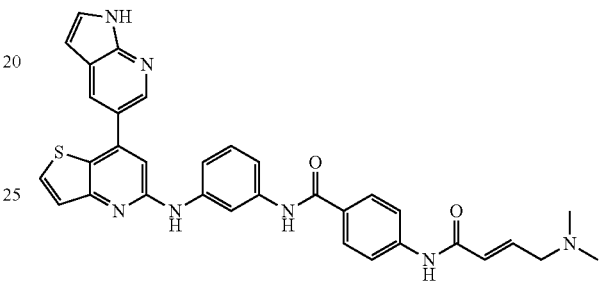

, or a pharmaceutically acceptable salt thereof.

32. The method of claim 21, wherein the proliferative disease is cancer.

33. The method of claim 21, wherein the proliferative disease is breast cancer.

34. The method of claim 21, wherein the proliferative disease is lung cancer.

35. A kit comprising:
a compound of claim 1, or a pharmaceutically acceptable salt thereof; and
instructions for administering to a subject or contacting a biological sample with the compound, or a pharmaceutically acceptable salt thereof.

36. A method of inhibiting the growth of an abnormally proliferative cell in a subject or biological sample, the method comprising administering to the subject or contacting the biological sample with an effective amount of a compound of claim 1, or a pharmaceutically acceptable salt thereof.

37. A method of inhibiting transcription in a biological sample or subject, the method comprising administering to the subject or contacting the biological sample with an effective amount of a compound of claim 1, or a pharmaceutically acceptable salt thereof.

38. A compound of the formula:

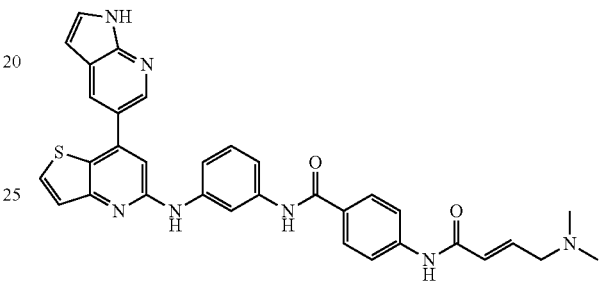

, or a pharmaceutically acceptable salt thereof.

39. A pharmaceutical composition comprising a compound of claim 38, or a pharmaceutically acceptable salt thereof, and optionally a pharmaceutically acceptable excipient.

40. A kit comprising:
a compound of claim 38, or a pharmaceutically acceptable salt thereof; and
instructions for administering to a subject or contacting a biological sample with the compound, or a pharmaceutically acceptable salt thereof.

41. A method of treating a proliferative disease in a subject in need thereof, the method comprising administering to the subject in need thereof a therapeutically effective amount of a compound of claim 38, or a pharmaceutically acceptable salt thereof.

42. A method of modulating the activity of a kinase in a biological sample or subject, inhibiting the growth of an abnormally proliferative cell in a biological sample or subject, or inhibiting transcription in a biological sample or subject, the method comprising administering to the subject or contacting the biological sample with an effective amount of a compound of claim 38, or a pharmaceutically acceptable salt thereof.

* * * * *

UNITED STATES PATENT AND TRADEMARK OFFICE
CERTIFICATE OF CORRECTION

PATENT NO. : 10,342,798 B2  
APPLICATION NO. : 15/737683  
DATED : July 9, 2019  
INVENTOR(S) : Nathanael S. Gray et al.

Page 1 of 1

It is certified that error appears in the above-identified patent and that said Letters Patent is hereby corrected as shown below:

In the Claims

In Claim 1, at Column 197, Line 5, the text: "–NR$^c$s(=O)–" should be replaced with:
-- –NR$^c$S(=O)– --.

In Claim 1, at Column 201, Lines 9-15, the formula: " 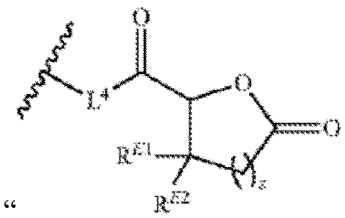 " should be replaced with the formula: -- 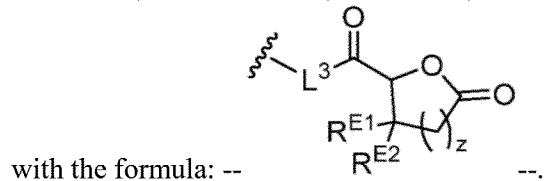 --.

Signed and Sealed this  
Twenty-fifth Day of February, 2020

Andrei Iancu  
*Director of the United States Patent and Trademark Office*